(12) United States Patent
Cooper et al.

(10) Patent No.: US 11,059,816 B2
(45) Date of Patent: Jul. 13, 2021

(54) ETHER LINKED TRIAZOLES AS NRF2 ACTIVATORS

(71) Applicants: GLAXOSMITHKLINE INTELLECTUAL PROPERTY DEVELOPMENT LIMITED, Brentford (GB); ASTEX THERAPEUTICS LIMITED, Cambridge (GB)

(72) Inventors: Anthony William James Cooper, Stevenage (GB); Nicole Cathleen Goodwin, King of Prussia, PA (US); Charlotte Mary Griffiths-Jones, Cambridge (GB); Thomas Daniel Heightman, Cambridge (GB); Jeffrey K. Kerns, King of Prussia, PA (US); Hendrika Maria Gerarda Willems, Cambridge (GB); Hongxing Yan, King of Prussia, PA (US)

(73) Assignees: GLAXOSMITHKLINE INTELLECTUAL PROPERTY DEVELOPMENT LIMITED, Brentford (GB); ASTEX THERAPEUTICS LIMITED, Cambridge (GB)

( * ) Notice: Subject to any disclaimer, the term of this patent is extended or adjusted under 35 U.S.C. 154(b) by 0 days.

(21) Appl. No.: 16/468,777

(22) PCT Filed: Dec. 11, 2017

(86) PCT No.: PCT/IB2017/057807
§ 371 (c)(1),
(2) Date: Jun. 12, 2019

(87) PCT Pub. No.: WO2018/109649
PCT Pub. Date: Jun. 21, 2018

(65) Prior Publication Data
US 2020/0071317 A1     Mar. 5, 2020

Related U.S. Application Data

(60) Provisional application No. 62/434,500, filed on Dec. 15, 2016.

(51) Int. Cl.
| | | |
|---|---|---|
| *A61K 31/553* | (2006.01) | |
| *A61P 9/04* | (2006.01) | |
| *A61P 11/00* | (2006.01) | |
| *C07D 498/04* | (2006.01) | |
| *C07D 419/12* | (2006.01) | |
| *C07D 249/04* | (2006.01) | |
| *C07D 401/12* | (2006.01) | |
| *C07D 419/14* | (2006.01) | |
| *C07D 513/04* | (2006.01) | |

(52) U.S. Cl.
CPC ......... *C07D 419/12* (2013.01); *C07D 249/04* (2013.01); *C07D 401/12* (2013.01); *C07D 419/14* (2013.01); *C07D 498/04* (2013.01); *C07D 513/04* (2013.01)

(58) Field of Classification Search
CPC .......... A61K 31/553; A61P 9/04; A61P 11/00; C07D 498/04
See application file for complete search history.

(56) References Cited

FOREIGN PATENT DOCUMENTS

| | | | |
|---|---|---|---|
| WO | WO 2015/092713 A1 | 6/2015 | |
| WO | WO 2016/202253 A1 | 12/2016 | |

*Primary Examiner* — Brenda L Coleman
(74) *Attorney, Agent, or Firm* — Nora L. Stein; Fang Qian; Duke M. Fitch

(57) ABSTRACT

The present invention relates to ether-linked triazole compounds, methods of making them, pharmaceutical compositions containing them and their use as NRF2 activators. In particular, the invention relates to compounds of Formula (I), and pharmaceutically acceptable salts thereof:

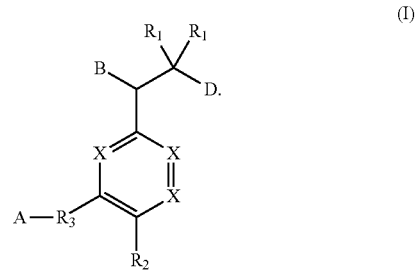

4 Claims, No Drawings

ETHER LINKED TRIAZOLES AS NRF2 ACTIVATORS

This application is a § 371 national stage entry of International Application No. PCT/IB2017/057807, filed 11 Dec. 2017, which claims the benefit of U.S. Provisional Application No. 62/434,500, filed 15 Dec. 2016.

FIELD OF THE INVENTION

The present invention relates to ether-linked triazole compounds, methods of making them, pharmaceutical compositions containing them and their use as NRF2 activators.

BACKGROUND OF THE INVENTION

NRF2 (NF-E2 related factor 2) is a member of the cap-n-collar family of transcription factors containing a characteristic basic-leucine zipper motif. Under basal conditions, NRF2 levels are tightly controlled by the cytosolic actin-bound repressor, KEAP1 (Kelch-like ECH associating protein 1), which binds to NRF2 and targets it for ubiquitylation and proteasomal degradation via the Cul3-based E3-ubiquitin ligase complex. Under conditions of oxidative stress, DJ1 (PARK7) is activated and stabilizes NRF2 protein by preventing NRF2 from interacting with KEAP1. Also, modification of reactive cysteines on KEAP1 can cause a conformational change in KEAP1 that alters NRF2 binding and promotes NRF2 stabilization. Thus, the levels of NRF2 in the cell are usually kept low in normal conditions but the system is designed to respond quickly to environmental stress by increasing NRF2 levels and thus downstream NRF2 activity.

Inappropriately low NRF2 activity in the face of on-going oxidative stress appears to be a pathological mechanism underlying chronic obstructive pulmonary disease (COPD). Yamada, K., et al. *BMC Pulmonary Medicine*, 2016, 16: 27. This may be a result of an altered equilibrium between NRF2 activators with both inappropriate lack of positive activators such as DJ1, and overabundance of negative activators such as Keap1 and Bach1. Therefore, restoration of NRF2 activity in the lungs of COPD patients should result in repair of the imbalance and mitigation of deleterious processes such as apoptosis of structural cells (including alveolar epithelial and endothelial cells) and inflammation. The results of these effects would be enhanced cytoprotection, preservation of lung structure, and structural repair in the COPD lung, thus slowing disease progression. Therefore, NRF2 activators may treat COPD (Boutten, A., et al. 2011. *Trends Mol. Med.* 17:363-371) and other respiratory diseases, including asthma, Acute Lung Injury (ALI) (Cho, H. Y., and Kleeberger, S. R., 2015, *Arch Toxicol.* 89:1931-1957; Zhao, H. et al., 2017, *Am J Physiol Lung Clee Mol Physiol* 312: L155-L162, first published Nov. 18, 2016; doi:10.1152/ajplung.00449.2016), Acute Respiratory Distress Syndrome (ARDS) and pulmonary fibrosis (Cho, H. Y., and Kleeberger, S. R. 2010. *Toxicol. Appl. Pharmacol.* 244:43-56).

The therapeutic potential of an NRF2 activator is exemplified in pulmonary macrophages from COPD patients where NRF2 pathway appears maladaptive. These cells have impaired bacterial phagocytosis compared with similar cells from control patients, and this effect is reversed by the addition of NRF2 activators in vitro. Therefore, in addition to the effects mentioned above, restoration of appropriate NRF2 activity could also rescue COPD exacerbations by reducing lung infection.

This is demonstrated by the NRF2 activator, Sulforaphane, which increases the expression of Macrophage Receptor with Collagenous structure (MARCO) by COPD macrophages and alveolar macrophages from cigarette smoke-exposed mice, thereby improving in these cells bacterial phagocytosis (*Pseudomonas aeruginosa*, non-typable *Haemophilus influenzae*) and bacterial clearance both ex vivo and in vivo. (Harvey, C. J., et al. 2011. *Sci. Transl. Med.* 3:78ra32).

The therapeutic potential of targeting NRF2 in the lung is not limited to COPD. Rather, targeting the NRF2 pathway could provide treatments for other human lung and respiratory diseases that exhibit oxidative stress components such as chronic asthma and acute asthma, lung disease secondary to environmental exposures including but not limited to ozone, diesel exhaust and occupational exposures, fibrosis, acute lung infection (e.g., viral (Noah, T. L. et al. 2014. *PLoS ONE* 9(6): e98671), bacterial or fungal), chronic lung infection, al antitrypsin disease, ALI, ARDS and cystic fibrosis (CF, Chen, J. et al. 2008. *PLoS One.* 2008; 3 (10): e3367).

A therapy that targets the NRF2 pathway also has many potential uses outside the lung and respiratory system. Many of the diseases for which an NRF2 activator may be useful are autoimmune diseases (psoriasis, IBD, MS), suggesting that an NRF2 activator may be useful in autoimmune diseases in general.

In the clinic, a drug targeting the NRF2 pathway (bardoxolone methyl) has shown efficacy in diabetic patients with diabetic nephropathy/chronic kidney disease (CKD) (Aleksunes, L. M., et al. 2010. *J. Pharmacol. Exp. Ther.* 335:2-12), though phase III trials with this drug in patients with the most severe stage of CKD were terminated. Furthermore, there is evidence to suspect that such a therapy would be effective in sepsis-induced acute kidney injury, other acute kidney injury (AKI) (Shelton, L. M., et al. 2013. *Kidney International.* June 19. doi: 10.1038/ki.2013.248), and kidney disease or malfunction seen during kidney transplantation.

In the cardiac area, bardoxolone methyl is currently under investigation in patients 30 with Pulmonary Arterial Hypertension and so a drug targeting NRF2 by other mechanisms may also be useful in this disease area. Oxidative stress is increased in the diseased myocardium, resulting in accumulation of reactive oxygen species (ROS) which impairs cardiac function [*Circ* (1987) 76(2); 458-468] and increases susceptibility to arrhythmia [*J of Mol & Cell Cardio* (1991) 23(8); 899-918] by a direct toxic effect of increased necrosis and apoptosis [*Circ Res* (2000) 87(12); 1172-1179]. In a mouse model of pressure overload (TAC), NRF2 gene and protein expression is increased during the early stage of cardiac adaptive hypertrophy, but decreased in the later stage of maladaptive cardiac remodeling associated with systolic dysfunction [*Arterioscler Thromb Vasc Biol* (2009) 29(11); 1843-5 1850; *PLOS ONE* (2012) 7 (9); e44899]. In addition, NRF2 activation has been shown to suppress myocardial oxidative stress as well as cardiac apoptosis, fibrosis, hypertrophy, and dysfunction in mouse models of pressure overload [*Arterioscler Thromb Vasc Biol* (2009) 29 (11); *J of Mol & Cell Cardio* (2014) 72; 305-315; and 1843-1850; *PLOS ONE* (2012) 7 (9); e44899]. NRF2 activation has also been shown to protect against cardiac I/R injury in mice 10 [*Circ Res* (2009) 105(4); 365-374; *J of Mol & Cell Cardio* (2010) 49(4); 576-586] and reduce myocardial oxidative damage following cardiac I/R injury in rat. Therefore, a drug targeting NRF2 by other mechanisms may be useful in a variety of cardiovascular diseases including but not limited to atherosclerosis, hypertension, and heart failure (Oxidative Medicine and Cellular Longevity Volume 2013 (2013), Article ID 104308, 10 pages), acute coronary 15 syndrome, myocardial infarction, myocardial repair, cardiac remodeling, cardiac arrhythmias, heart failure with preserved ejection fraction, heart failure with reduced ejection fraction and diabetic cardiomyopathy.

A drug activating the NRF2 pathway could also be useful for treatment of several neurodegenerative diseases including Parkinson's disease (PD), Alzheimer's disease (AD), amyotrophic lateral sclerosis (ALS) (*Brain Res.* 2012 Mar. 29; 1446:109-18.2011.12.064. Epub 2012 Jan. 12) and multiple sclerosis (MS). Multiple in vivo models have shown that NRF2 KO mice are more sensitive to neurotoxic insults than their wild-type counterparts. Treatment of rats with the NRF2 activator tert-butylhydroquinone (tBHQ) reduced cortical damage in rats in a cerebral ischemia-reperfusion model, and cortical glutathione levels were increased in NRF2 wild-type but not KO mice after administration of tBHQ (Shih, A. Y., et al. 2005. *J. Neurosci.* 25: 10321-10335). Tecfidera™ (dimethyl fumarate), which activates NRF2 among other targets, is approved in the U.S. to treat relapsing-remitting multiple sclerosis (MS). Activation of NRF2 may also help treat cases of Friedreich's Ataxia, where increased sensitivity to oxidative stress and impaired NRF2 activation has been reported (Paupe V., et al, 2009. *PLoS One;* 4 (1): e4253. Omaveloxolone (RTA-408) is also in clinical trials for Friedreich's Ataxia.

There is preclinical evidence of the specific protective role of the NRF2 pathway in models of inflammatory bowel disease (IBD, Crohn's Disease and Ulcerative Colitis) and/or colon cancer (Khor, T. O., et al 2008. *Cancer Prev. Res.* (*Phila*) 1:187-191).

Age-related macular degeneration (AMD) is a common cause of vision loss in people over the age of 50. Cigarette smoking is a major risk factor for the development of non-neovascular (dry) AMD and perhaps also neovascular (wet) AMD. Findings in vitro and in preclinical species support the notion that the NRF2 pathway is involved in the anti-oxidant response of retinal epithelial cells and modulation of inflammation in pre-clinical models of eye injury (Schimel, et al. 2011. *Am. J. Pathol.* 178:2032-2043). Fuchs Endothelial Corneal Dystrophy (FECD) is a progressive, blinding disease characterized by corneal endothelial cells apoptosis. It is a disease of aging and increased oxidative stress related to low levels of NRF2 expression and/or function (Bitar, M. S., et al. 2012. *Invest Ophthalmol. Vis.* Aug. 24, 2012 vol. 53 no. 9 5806-5813). In addition, an NRF2 activator may be useful in uveitis or other inflammatory eye condtions.

Non-alcoholic steatohepatitis (NASH) is a disease of fat deposition, inflammation, and damage in the liver that occurs in patients who drink little or no alcohol. In preclinical models, development of NASH is greatly accelerated in KO mice lacking NRF2 when challenged with a methionine- and choline-deficient diet (Chowdhry S., et al. 2010. *Free Rad. Biol. & Med.* 48:357-371). Administration of the NRF2 activators oltipraz and NK-252 in rats on a choline-deficient L-amino acid-defined diet significantly attenuated progression of histologic abnormalities, especially hepatic fibrosis (Shimozono R. et al. 2012. *Molecular Pharmacology.* 84:62-70). Other liver diseases that may be amenable to NRF2 modulation are toxin-induced liver disease (e.g., acetaminophen-induced hepatic disease), viral hepatitis, and cirrhosis (Oxidative Medicine and Cellular Longevity Volume 2013 (2013), Article ID 763257, 9 page).

Recent studies have also begun to elucidate the role of ROS in skin diseases such as psoriasis. A study in psoriasis patients showed an increase in serum malondialdehyde and nitric oxide end products and a decrease in erythrocyte-superoxide dismutase activity, catalase activity, and total antioxidant status that correlated in each case with disease severity index (Dipali P. K., et al. *Indian J Clin Biochem.* 2010 October; 25(4): 388-392). Also, an NRF2 activator may be useful in treating the dermatitis/topical effects of radiation (Schafer, M. et al. 2010. *Genes & Devl.* 24:1045-1058), and the immunosuppression due to radiation exposure (Kim, J. H. et al., *J. Clin. Invest.* 2014 Feb. 3; 124(2): 730-41).

There are also data suggesting that an NRF2 activator may be beneficial in preeclampsia, a disease that occurs in 2-5% of pregnancies and involves hypertension and proteinuria (*Annals of Anatomy—Anatomischer Anzeicier Volume* 196, Issue 5, September 2014, Pages 268-277).

Preclinical data has shown that compounds with NRF2 activating activity are better at reversing high altitude-induced damage than compounds without NRF2 activity, using animal and cellular models of Acute Mountain Sickness (Lisk C. et al, 2013, Free Radic Biol Med. October 2013; 63: 264-273.)

SUMMARY OF THE INVENTION

In one aspect, this invention provides for ether-linked triazole analogs, or a salt, particularly a pharmaceutically acceptable salt thereof, and pharmaceutical compositions containing them. In particular, the compounds of this invention include a compound of Formula (I):

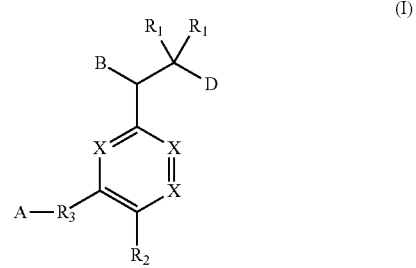

wherein:
B is —O($CH_2$)-triazolyl, —O($CH_2$)$_m$, —O($CH_2$)$_m$-oxazolyl, —O($CH_2$)$_m$-oxadiazolyl and —O($CH_2$)$_m$-isoxazolyl, wherein each of the —O($CH_2$)-triazolyl, —O($CH_2$)$_m$, —O($CH_2$)$_m$, —O($CH_2$)$_m$-oxazolyl, —O($CH_2$)$_m$-oxadiazolyl or —O($CH_2$)$_m$-isoxazolyl is unsubstituted or substituted by 1 or 2 substituents independently selected from —$C_{1-6}$ alkyl, —($CH_2$)$_m$—O—$C_{1-3}$alkyl, —($CH_2$)$_n$—$C_{3-7}$ cycloalkyl, —($CH_2$)$_m$—$C_{4-7}$ heterocycloalkyl, —($CH_2$)$_n$-phenyl, —($CH_2$)$_n$-phenyl-($CH_2$)$_n$-aryl, —($CH_2$)$_n$-phenyl-($CH_2$)$_n$-heteroaryl, —($CH_2$)$_n$—$C_{3-7}$cycloalkyl, —($CH_2$)$_n$—$C_{3-7}$heterocycloalkyl, —($CH_2$)$_n$—$C_{3-7}$heterocycloalkyl-($CH_2$)$_n$—$C_{3-7}$heterocycloalkyl, —($CH_2$)$_n$—$C_{3-7}$heterocycloalkyl-C(O)R', —($CH_2$)$_n$—$C_{3-7}$ heterocycloalkyl-C(O)—$C_{3-7}$ heterocycloalkyl, —($CH_2$)$_n$—$C_{3-7}$heterocycloalkyl-C(O)—$C_{3-7}$cycloalkyl, —($CH_2$)$_n$—$C_{3-7}$heterocycloalkyl-C(O)aryl, —($CH_2$)$_n$-phenyl-($CH_2$)$_n$—$C_{4-7}$heterocycloalkyl, —($CH_2$)$_2$—O—($CH_2$)$_2$—OR$_4$, CN, $C_{1-6}$alkylNR$_4$R$_5$, $C_{1-6}$alkylNC(O)R$_7$, $C_{1-6}$alkylNC(O)OR$_4$ and halo and wherein each of the moieties —($CH_2$)$_n$-phenyl, —($CH_2$)$_n$-phenyl-($CH_2$)$_n$-aryl, —($CH_2$)$_n$-phenyl-($CH_2$)$_n$-heteroaryl, —($CH_2$)$_n$—$C_{3-7}$ cycloalkyl, —($CH_2$)$_n$—$C_{3-7}$heterocycloalkyl, —($CH_2$)$_n$—$C_{3-7}$heterocycloalkyl-($CH_2$)$_n$—$C_{3-7}$heterocycloalkyl, —(CH$_2$)$_n$—C$_{3-7}$heterocycloalkyl-C(O)R', —(CH$_2$)$_n$—C$_{3-7}$ heterocycloalkyl-C(O) C$_{3-7}$heterocycloalkyl, —(CH$_2$)$_n$—C$_{3-7}$heterocycloalkyl-C(O)—C$_{3-7}$cycloalkyl, —(CH$_2$)$_n$—C$_{3-7}$heterocycloalkyl-C(O)aryl, —(CH$_2$)$_n$-phenyl-(CH$_2$)$_n$—C$_{4-7}$ heterocycloalkyl, —(CH$_2$)$_2$—O(CH$_2$)$_2$—OR$_4$ are unsubstituted or further substituted by 1, 2 or 3 substituents independently selected from C$_{1-4}$alkyl, —SO$_2$R$_4$, halo, —(CH$_2$)$_n$, —(CH$_2$)$_n$C(O)OR$_4$, —(CH$_2$)$_m$OH, —C(O)R$_D$;

D is —C(O)OH, —C(O)CR', —C(O)NHSO$_2$CH$_3$, —SO$_2$NHC(O)CH$_3$, 5-(trifluoromethyl)-4H-1,2,4-triazol-2-yl, or tetrazolyl;

R$_1$ is independently hydrogen, —OH, —C$_{1-3}$alkyl, —C$_{1-3}$alkylOR', F, —C$_{3-6}$spirocycloalkyl, oxetane, or the two R$_1$ groups together with the carbon to which they are attached form a cyclopropyl group;

R' is hydrogen, —C$_{1-4}$alkyl or —NH$_2$;

R$_2$ is hydrogen, —C$_{1-4}$alkyl, —CF$_3$, or halo;

R$_3$ is —(CH$_2$)$_m$;

R$_4$ is hydrogen or —C$_{1-3}$alkyl;

or, when R$_2$ is —C$_{1-4}$alkyl, R$_3$ is —(CH$_2$)$_m$—, and m is 2 or 3, R$_2$ and R$_3$ together form a cycloalkyl ring fused to the phenyl ring to which they are attached;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

wherein each of tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, CN, —O—C$_{1-3}$alkyl, —CH$_2$—O—CH$_3$, and OH;

and wherein the piperidinyl is further unsubstituted or substituted by a substituent independently selected from pyrazolyl, —CH$_2$pyrazolyl, and oxadiazolyl each of which is unsubstituted or substituted by —C$_{1-3}$alkyl, or, when A is piperidinyl, it is unsubstituted or substituted by —SO$_2$R, wherein R is C$_{1-3}$alkyl, phenyl or C$_{3-7}$cycloalkyl;

and wherein the oxazepane is further unsubstituted or substituted by 1 or 2 substituents independently selected from —C$_{1-3}$alkyl and C$_{3-7}$cycloalkyl;

and wherein the morpholinyl is further unsubstituted or substituted by phenyl which phenyl is unsubstituted or independently substituted by a substituent selected from C$_{1-3}$ alkyl and —O—C$_{1-3}$ alkyl;

and wherein the pyrrolidinyl is further optionally substituted by a triazolyl group which is optionally substituted by —C$_{1-3}$alkyl;

and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$ heterocycloalkyl, —CH$_2$-azabicycloheptanyl, —CH$_2$-oxepane, and —CH$_2$-azabicyclohexanyl, and wherein each of —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, including the —CH$_2$—, are further unsubstituted or substituted by 1 or 2 substituents independently selected from —C$_{1-3}$ alkyl and F;

or, A is,

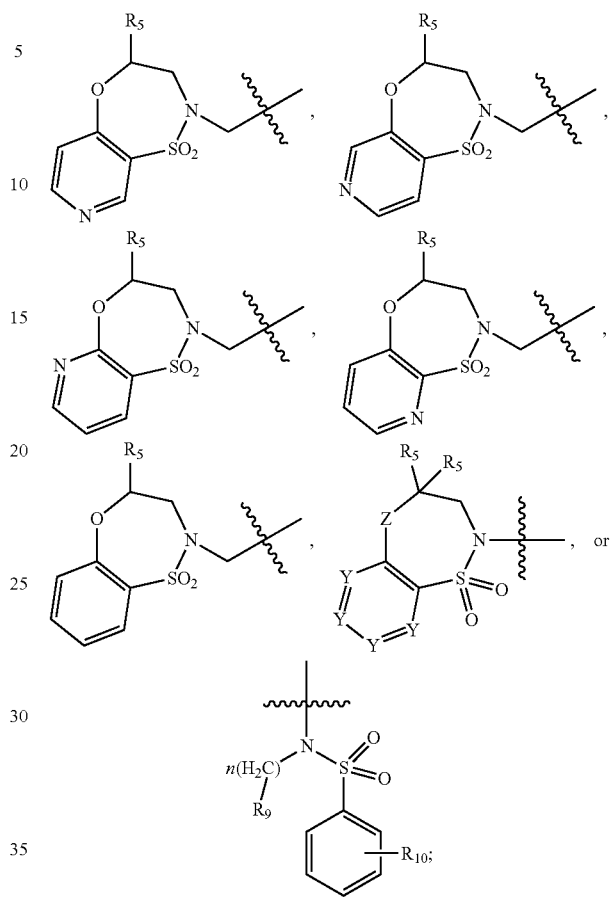

R$_5$ is independently hydrogen or C$_{1-5}$alkyl;
R$_6$ is hydrogen or —C$_{1-4}$alkyl;
R$_7$ is hydrogen, aryl, heteroaryl, C$_{5-10}$heterocycloalkyl, —C$_{1-4}$alkyl or —C$_{3-7}$cycloalkyl;
X is independently CH or N;
Y is independently CH or N;
Z is O, CH$_2$, NR$_5$, S, S(O), SO$_2$;
wherein, when A is,

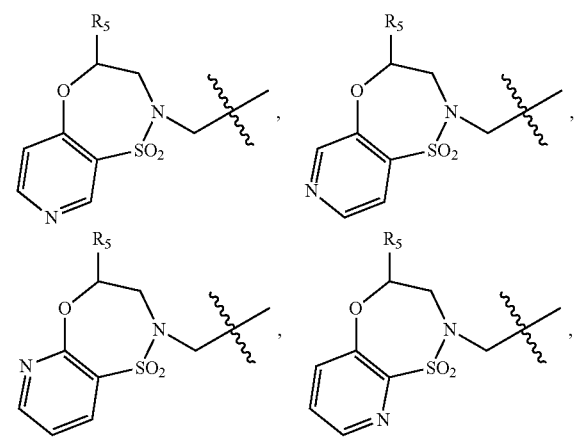

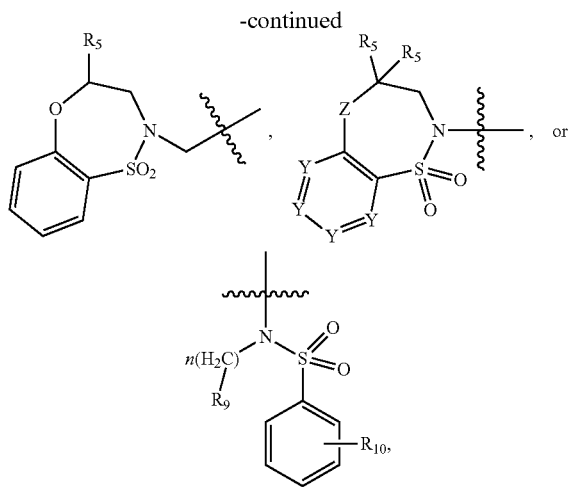

A is unsubstituted of substituted by one, two or three substituents independently selected from halo, —CF$_3$, —CN, —OMe, —C(O)NH$_2$, —OCF$_3$, and —C$_{1-4}$alkylNR$_6$R$_8$;
R$_8$ is hydrogen, —C$_{1-5}$ alkyl, —C$_{3-7}$cycloalkyl, —C$_{4-8}$heterocycloalkyl, —C$_{1-5}$ alkoxy, —C$_{1-3}$ alkyl-O—C$_{1-3}$alkyl, —C$_{1-3}$alkyl-NH—C$_{1-3}$alkyl, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_5$R$_6$, or heteroaryl, wherein each of —C$_{1-5}$ alkyl, —C$_{3-7}$cycloalkyl, —C$_{4-7}$heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_5$R$_6$, or heteroaryl is unsubstituted or substituted by one or two substituents independently selected from —OH, —CO$_2$H, —C(O)NR$_5$R$_6$, —C(O)OR$_5$, —N—C(O)—C$_{1-3}$ alkyl, F, —CN, —CH—F$_2$, —CF$_3$, —(CH$_2$)$_n$—O—(CH$_2$)$_m$—CH$_3$, and —C$_{3-7}$cycloalkyl, a 5-6-membered heteroaryl ring containing 1, 2 or 3 heteroatoms selected from O, N and S;
R$_9$ is -phenyl, —C$_{3-7}$cycloalkyl, —C$_{3-7}$heterocycloalkyl containing 1 or 2 heteroatoms selected from O, N and S, –5-10-membered aryl ring or a –5-10-membered heteroaryl ring, containing 1, 2 or 3 heteroatoms selected from O, N and S, wherein each of -phenyl, —C$_{3-7}$cycloalkyl, —C$_{3-7}$heterocycloalkyl containing 1 or 2 heteroatoms selected from O, N and S, –5-10-membered aryl ring or a –5-10-membered heteroaryl ring, containing 1, 2 or 3 heteroatoms selected from O, N and S is unsubstituted or independently substituted by one or two substituents selected from halo, —C(O)OH, —CF$_3$, —CN, —OMe, —C(O)NH$_2$, —OCF$_3$, and —C$_{1-4}$alkylNR$_6$R$_8$;
R$_{10}$ is independently selected from hydrogen, halo, —C(O)OH, —CF$_3$, —CN, —OMe, —C(O)NH$_2$, —OCF$_3$, and —C$_{1-4}$alkylNR$_6$R$_8$;
m is 1, 2, 3 or 4; and
n is 0, 1, 2 or 3;
or a pharmaceutically acceptable salt thereof.

In a second aspect, this invention provides for the use of the compounds of Formula (I) as NRF2 activators.

Accordingly, the present invention is also directed to a method of regulating NRF2 which method comprises contacting a cell with a compound according to Formula (I), or a salt, particularly a pharmaceutically acceptable salt, thereof.

In another aspect, this invention provides for the use of the compounds of Formula (I) for treating and preventing conditions associated with NRF2 imbalance.

In one aspect, the invention is provides a pharmaceutical composition comprising a compound of the invention according to Formula (I), or a salt, particularly a pharmaceutically acceptable salt thereof, and a pharmaceutically acceptable excipient. Particularly, this invention is directed to a pharmaceutical composition for the treatment of an NRF2 regulated disease or disorder, wherein the composition comprises a compound according to Formula (I), or a salt, particularly a pharmaceutically acceptable salt thereof, and a pharmaceutically acceptable excipient.

In a further aspect, this invention provides for a method of treating a respiratory or non-respiratory disorder, including COPD, asthma, ALI, ARDS, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness, which comprises administering to a human in need thereof, a compound of Formula (I).

In one aspect, this invention relates to a method of treating COPD, which comprises administering to a human in need thereof, a compound of Formula (I), or a salt, particularly a pharmaceutically acceptable salt thereof.

In one aspect, this invention relates to a method of treating heart failure, which comprises administering to a human in need thereof, a compound of Formula (I), or a salt, particularly a pharmaceutically acceptable salt thereof.

In yet another aspect, this invention provides for the use of a compound of Formula (I), or a salt, particularly a pharmaceutically acceptable salt thereof, for the treatment of a respiratory or non-respiratory disorder, including COPD, asthma, ALI, ARDS, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention relates to the use of a compound of Formula (I), or a salt, particularly a pharmaceutically acceptable salt thereof, for the treatment of COPD.

In one aspect, this invention relates to the use of a compound of Formula (I), or a salt, particularly a pharmaceutically acceptable salt thereof, for the treatment of heart failure.

In a further aspect, this invention relates to use of a compound of Formula (I), or a salt, particularly a pharmaceutically acceptable salt thereof, in the manufacture of a medicament for use in the treatment of a respiratory or non-respiratory disorder, including COPD, asthma, ALI, ARDS, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention relates to use of a compound of Formula (I), or a salt, particularly a pharmaceutically acceptable salt thereof, in the manufacture of a medicament for the treatment of COPD.

In one aspect, this invention relates to use of a compound of Formula (I), or a salt, particularly a pharmaceutically acceptable salt thereof, in the manufacture of a medicament for the treatment of heart failure.

In a further aspect, this invention relates to a compound of Formula (I), or a salt, particularly a pharmaceutically acceptable salt thereof, for use in medical therapy. This invention relates to a compound of Formula (I), or a salt, particularly a pharmaceutically acceptable salt thereof, for use in therapy, specifically for use in the treatment of a respiratory or non-respiratory disorder, including COPD, asthma, ALI, ARDS, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention relates to a compound of Formula (I), or a salt, particularly a pharmaceutically acceptable salt thereof, for use in the treatment of COPD.

In one aspect, this invention relates to a compound of Formula (I), or a salt, particularly a pharmaceutically acceptable salt thereof, for use in the treatment of heart failure.

Other aspects and advantages of the present invention are described further in the following detailed description of the embodiments thereof.

DETAILED DESCRIPTION OF THE INVENTION

The present invention provides for compounds of Formula (I):

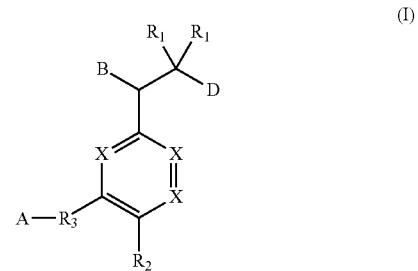

wherein:
B is —O(CH$_2$)-triazolyl, —O(CH$_2$)$_m$, —O(CH$_2$)$_m$-oxazolyl, —O(CH$_2$)$_m$-oxadiazolyl and —O(CH$_2$)$_m$-isoxazolyl, wherein each of the —O(CH$_2$)-triazolyl, —O(CH$_2$)$_m$, —O(CH$_2$)$_m$, —O(CH$_2$)$_m$-oxazolyl, —O(CH$_2$)$_m$-oxadiazolyl or —O(CH$_2$)$_m$-isoxazolyl is unsubstituted or substituted by 1 or 2 substituents independently selected from —C$_{1-6}$ alkyl, —(CH$_2$)$_m$—O—C$_{1-3}$alkyl, —(CH$_2$)$_n$—C$_{3-7}$ cycloalkyl, —(CH$_2$)$_m$—C$_{4-7}$ heterocycloalkyl, —(CH$_2$)$_n$-phenyl, —(CH$_2$)$_n$-phenyl-(CH$_2$)$_n$-aryl, —(CH$_2$)$_n$-phenyl-(CH$_2$)$_n$-heteroaryl, —(CH$_2$)$_n$—C$_{3-7}$cycloalkyl, —(CH$_2$)$_n$—C$_{3-7}$heterocycloalkyl, —(CH$_2$)$_n$—C$_{3-7}$heterocycloalkyl-(CH$_2$)$_n$—C$_{3-7}$heterocycloalkyl, —(CH$_2$)$_n$—C$_{3-7}$heterocycloalkyl-C(O)R', —(CH$_2$)$_n$—C$_{3-7}$ heterocycloalkyl-C(O) C$_{3-7}$ heterocycloalkyl, —(CH$_2$)$_n$—C$_{3-7}$heterocycloalkyl-C(O)—C$_{3-7}$cycloalkyl, —(CH$_2$)$_n$—C$_{3-7}$heterocycloalkyl-C(O)aryl, —(CH$_2$)$_n$-phenyl-(CH$_2$)$_n$—C$_{4-7}$heterocycloalkyl, —(CH$_2$)$_2$—O—(CH$_2$)$_2$—OR$_4$, CN, C$_{1-6}$alkylNR$_4$R$_5$, C$_{1-6}$alkylNC(O)R$_7$, C$_{1-6}$alkylNC(O)OR$_4$ and halo and wherein each of the moieties —(CH$_2$)$_n$-phenyl, —(CH$_2$)$_n$-phenyl-(CH$_2$)$_n$-aryl, —(CH$_2$)$_n$-phenyl-(CH$_2$)$_n$-heteroaryl, —(CH$_2$)$_n$—C$_{3-7}$ cycloalkyl, —(CH$_2$)$_n$—C$_{3-7}$heterocycloalkyl, —(CH$_2$)$_n$—C$_{3-7}$heterocycloalkyl-(CH$_2$)$_n$—C$_{3-7}$heterocycloalkyl, —(CH$_2$)$_n$—C$_{3-7}$heterocycloalkyl-C(O)R', —(CH$_2$)$_n$—C$_{3-7}$ heterocycloalkyl-C(O) C$_{3-7}$heterocycloalkyl, —(CH$_2$)$_n$—C$_{3-7}$heterocycloalkyl-C(O)—C$_{3-7}$cycloalkyl, —(CH$_2$)$_n$—C$_{3-7}$heterocycloalkyl-C(O)aryl, —(CH$_2$)$_n$-phenyl-(CH$_2$)$_n$—C$_{4-7}$ heterocycloalkyl, —(CH$_2$)$_2$—O—(CH$_2$)$_2$—OR$_4$ are unsubstituted or further substituted by 1, 2 or 3 substituents independently selected from —C$_{1-4}$alkyl, —SO$_2$R$_4$, halo, —(CH$_2$)$_n$, —(CH$_2$)$_n$C(O)OR$_4$, —(CH$_2$)$_m$OH, —C(O)R$_7$;

D is —C(O)OH, —C(O)CR', —C(O)NHSO$_2$CH$_3$, —SO$_2$NHC(O)CH$_3$, 5-(trifluoromethyl)-4H-1,2,4-triazol-2-yl, or tetrazolyl;

R$_1$ is independently hydrogen, —OH, —C$_{1-3}$alkyl, —C$_{1-3}$alkylOR', F, —C$_{3-6}$spirocycloalkyl, oxetane, or the two R$_1$ groups together with the carbon to which they are attached form a cyclopropyl group;

R' is hydrogen, —C$_{1-4}$alkyl or —NH$_2$;

R$_2$ is hydrogen, —C$_{1-4}$alkyl, —CF$_3$, or halo;

R$_3$ is —(CH$_2$)$_m$;

R$_4$ is hydrogen or —C$_{1-3}$alkyl;

or, when R$_2$ is —C$_{1-4}$alkyl, R$_3$ is —(CH$_2$)$_m$—, and m is 2 or 3, R$_2$ and R$_3$ together form a cycloalkyl ring fused to the phenyl ring to which they are attached;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

wherein each of tetrahydrobenzoxazepinyl, tetrahydropyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, CN, —O—C$_{1-3}$alkyl, —CH$_2$—O—CH$_3$, and OH;

and wherein the piperidinyl is further unsubstituted or substituted by a substituent independently selected from pyrazolyl, —CH$_2$pyrazolyl, and oxadiazolyl each of which is unsubstituted or substituted by —C$_{1-3}$alkyl, or, when A is piperidinyl, it is unsubstituted or substituted by —SO$_2$R, wherein R is C$_{1-3}$alkyl, phenyl or C$_{3-7}$cycloalkyl;

and wherein the oxazepane is further unsubstituted or substituted by 1 or 2 substituents independently selected from —C$_{1-3}$alkyl and C$_{3-7}$cycloalkyl;

and wherein the morpholinyl is further unsubstituted or substituted by phenyl which phenyl is unsubstituted or independently substituted by a substituent selected from C$_{1-3}$ alkyl and —O—C$_{1-3}$ alkyl;

and wherein the pyrrolidinyl is further optionally substituted by a triazolyl group which is optionally substituted by —C$_{1-3}$ alkyl;

and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$ heterocycloalkyl, —CH$_2$-azabicycloheptanyl, —CH$_2$-oxepane, and —CH$_2$-azabicyclohexanyl, and wherein each of —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, including the CH$_2$—, are further unsubstituted or substituted by 1 or 2 substituents independently selected from —C$_{1-3}$ alkyl and F;

or, A is,

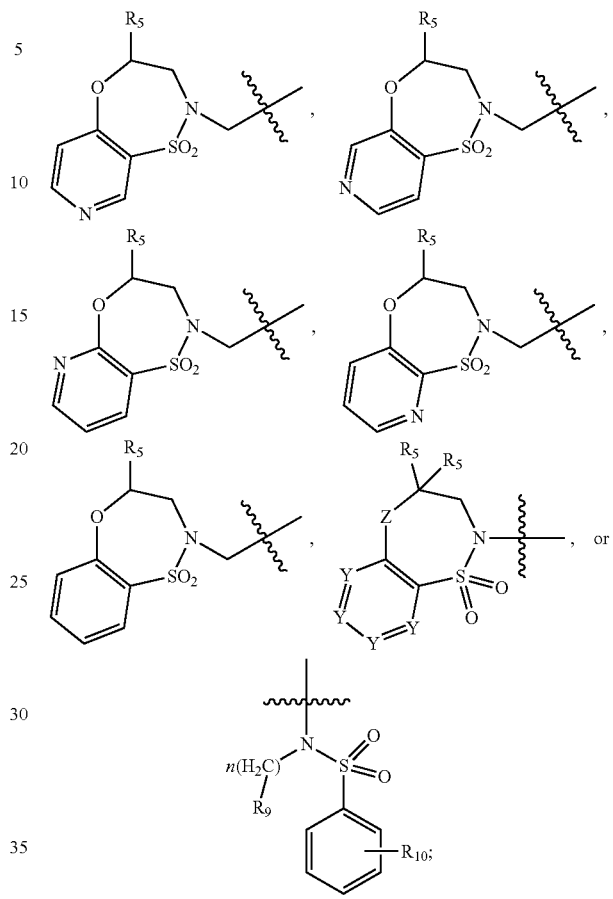

R$_5$ is independently hydrogen or C$_{1-5}$alkyl;
R$_6$ is hydrogen or —C$_{1-4}$alkyl;
R$_7$ is hydrogen, aryl, heteroaryl, C$_{5-10}$heterocycloalkyl, —C$_{1-4}$alkyl or —C$_{3-7}$cycloalkyl;
X is independently CH or N;
Y is independently CH or N;
Z is O, CH$_2$, NR$_5$, S, S(O), SO$_2$;
wherein, when A is,

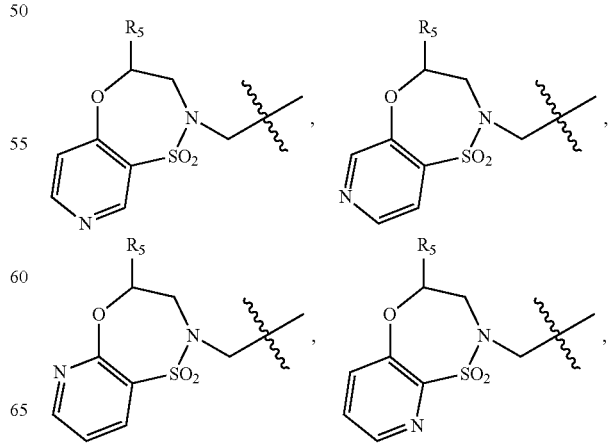

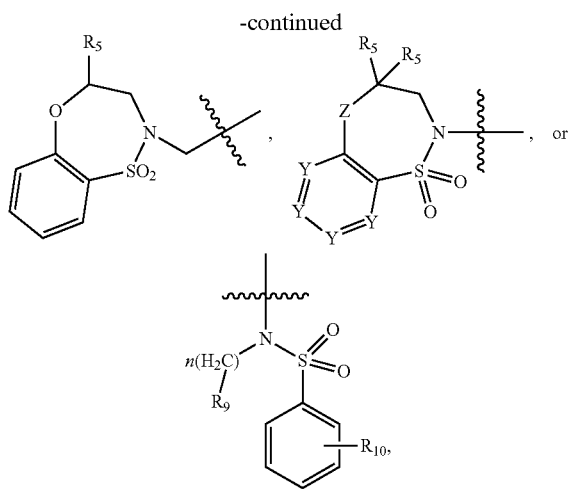

A is unsubstituted of substituted by one, two or three substituents independently selected from halo, —CF$_3$, —CN, —OMe, —C(O)NH$_2$, —OCF$_3$, and —C$_{1-4}$alkylNR$_6$R$_8$;

R$_8$ is hydrogen, —C$_{1-5}$ alkyl, —C$_{3-7}$cycloalkyl, —C$_{4-8}$heterocycloalkyl, —C$_{1-5}$ alkoxy, —C$_{1-3}$ alkyl-O—C$_{1-3}$alkyl, —C$_{1-3}$alkyl-NH—C$_{1-3}$alkyl, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_5$R$_6$, or heteroaryl, wherein each of —C$_{1-5}$ alkyl, —C$_{3-7}$cycloalkyl, —C$_{4-7}$heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_5$R$_6$, or heteroaryl is unsubstituted or substituted by one or two substituents independently selected from —OH, —CO$_2$H, —C(O)NR$_5$R$_6$, —C(O)OR$_5$, —N—C(O)—C$_{1-3}$ alkyl, F, —CN, —CH—F$_2$, —CF$_3$, —(CH$_2$)$_n$—O—(CH$_2$)$_m$—CH$_3$, and —C$_{3-7}$cycloalkyl, a 5-6-membered heteroaryl ring containing 1, 2 or 3 heteroatoms selected from O, N and S;

R$_9$ is -phenyl, —C$_{3-7}$cycloalkyl, —C$_{3-7}$heterocycloalkyl containing 1 or 2 heteroatoms selected from O, N and S, –5-10-membered aryl ring or a –5-10-membered heteroaryl ring, containing 1, 2 or 3 heteroatoms selected from O, N and S, wherein each of -phenyl, —C$_{3-7}$cycloalkyl, —C$_{3-7}$heterocycloalkyl containing 1 or 2 heteroatoms selected from O, N and S, –5-10-membered aryl ring or a –5-10-membered heteroaryl ring, containing 1, 2 or 3 heteroatoms selected from O, N and S is unsubstituted or independently substituted by one or two substituents selected from halo, —C(O)OH, —CF$_3$, —CN, —OMe, —C(O)NH$_2$, —OCF$_3$, and —C$_{1-4}$alkylNR$_6$R$_8$;

R$_{10}$ is independently selected from hydrogen, halo, —C(O)OH, —CF$_3$, —CN, —OMe, —C(O)NH$_2$, —OCF$_3$, and —C$_{1-4}$alkylNR$_6$R$_8$;

m is 1, 2, 3 or 4; and n is 0, 1, 2 or 3;

or a pharmaceutically acceptable salt thereof.

"Alkyl" refers to a monovalent saturated hydrocarbon chain having the specified number of carbon member atoms. For example, C$_{1-4}$ alkyl refers to an alkyl group having from 1 to 4 carbon member atoms. Alkyl groups may be straight or branched. Representative branched alkyl groups have one, two, or three branches. Alkyl includes methyl, ethyl, propyl, (n-propyl and isopropyl), butyl (n-butyl, isobutyl, s-butyl, and t-butyl), pentyl (n-pentyl, tert-pentyl, iso-pentyl), and hexyl (n-hexyl, isohexyl, ter-hexyl).

"Cycloalkyl" refers to a monovalent saturated or unsaturated hydrocarbon ring having the specified number of carbon member atoms. For example, C$_{3-7}$cycloalkyl refers to a cycloalkyl group having from 3- to 7-carbon member atoms, unless otherwise limited. Unsaturated cycloalkyl groups have one or more carbon-carbon double bonds within the ring. Cycloalkyl groups are not aromatic. Cycloalkyl includes cyclopropyl, cyclopropenyl, cyclobutyl, cyclobutenyl, cyclopentyl, cyclopentenyl, cyclohexyl, and cyclohexenyl.

"C$_{3-8}$heterocycloalkyl" refers to a 3- to 8-membered ring, unless otherwise limited, containing from 1 to 4 heteroatoms, generally 1 or 2 heteroatoms, independently selected from nitrogen, oxygen, and sulfur. Examples are azetidine, thietane, thietane 1-oxide, thietane 1,1-dioxide, tetrahydrofuran, pyrrolidine, tetrahydrothiophene, tetrahydrothiophene 1-oxide, tetrahydrothiophene 1,2-dioxide, piperidine, piperazine, morpholine, thiomorpholine, thiomorpholine 1-oxide, thiomorpholine 1,1-dioxide, tetrahydropyran, tetrahydrothiopyran, tetrahydrothiopyran 1-oxide, tetrahydrothiopyran 1-1 dioxide, piperidine-2-one, azepan-2-one, pyrrolidin-2-one, azepane, oxepane, oxazepane, thiepane, thiepane 1-oxide, thiepane 1,1-dioxide, and thiazepane.

A heterocyclic group is a cyclic group having, as ring members, atoms of at least two different elements, which cyclic group may be saturated, partially unsaturated (non-aromatic) or fully unsaturated (aromatic). The terms "heterocyclic" or "heterocyclyl" includes heterocycloalkyl and heteroaryl groups. It is to be understood that the terms heterocyclic, heterocyclyl, heteroaryl, and heterocycloalkyl, are intended to encompass stable groups where a ring nitrogen heteroatom is optionally oxidized (e.g., heteroaryl groups containing an N-oxide, such as oxo-pyridyl (pyridyl-N-oxide) and oxo-oxadiazolyl (oxo-4,5-dihydro-1,3,4-oxadiazolyl) or where a ring sulfur heteroatom is optionally oxidized (e.g., heterocycloalkyl groups containing sulfones or sulfoxide moieties, such as tetrahydrothienyl-1-oxide (tetrahydrothienyl sulfoxide, tetrahydrothiophenyl sulfoxide) and tetrahydrothienyl-1,1-dioxide (tetrahydrothienyl sulfone)).

"Aryl" refers to a group or moiety comprising an aromatic, monocyclic or bicyclic hydrocarbon radical containing from 6- to 10-carbon ring atoms and having at least one aromatic ring. Examples of "aryl" groups are phenyl, naphthyl, indenyl, and dihydroindenyl (indanyl). Generally, in the compounds of this invention, aryl is phenyl.

"Heteroaryl" represents a group or moiety comprising an aromatic monocyclic or bicyclic radical, containing 5- to 10-ring atoms, including 1- to 4-heteroatoms independently selected from nitrogen, oxygen and sulfur. This term also encompasses bicyclic heterocyclic-aryl groups containing either an aryl ring moiety fused to a heterocycloalkyl ring moiety or a heteroaryl ring moiety fused to a cycloalkyl ring moiety.

When used herein, the terms 'halogen' and 'halo' include fluorine, chlorine, bromine and iodine, and fluoro, chloro, bromo, and iodo, respectively.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e., one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

The term "independently" means that where more than one substituent is selected from a number of possible substituents, those substituents may be the same or different. That is, each substituent is separately selected from the entire group of recited possible substituents.

The invention also includes various isomers of the compounds of Formula (I) and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers). The compounds according to Formula (I) contain one or more asymmetric centers, also referred to as chiral centers, and may, therefore, exist as individual enantiomers, diastereomers, or other stereoisomeric forms, or as mixtures thereof. All such isomeric forms are included within the present invention, including mixtures thereof.

Chiral centers may also be present in a substituent such as an alkyl group. Where the stereochemistry of a chiral center present in Formula (I), or in any chemical structure illustrated herein, is not specified the structure is intended to encompass any stereoisomer and all mixtures thereof. Thus, compounds according to Formula (I) containing one or more chiral centers may be used as racemic mixtures, enantiomerically enriched mixtures, or as enantiomerically pure individual stereoisomers.

Individual stereoisomers of a compound according to Formula (I) which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

For compounds falling within the scope of the invention, the structural conventions used in the Examples are as follows: (a) absolute stereochemistry is defined by the structure; (b) when annotated by "or", then stereochemistry is unknown but resolved; and (c) when annotated by "&" or "and", then stereochemistry is relative, but racemic.

It is to be understood that the references herein to a compound of Formula (I) or a salt thereof includes a compound of Formula (I) as a free base [or acid, as appropriate], or as a salt thereof, for example as a pharmaceutically acceptable salt thereof. Thus, in one embodiment, the invention is directed to a compound of Formula (I). In another embodiment, the invention is directed to a salt of a compound of Formula (I). In a further embodiment, the invention is directed to a pharmaceutically acceptable salt of a compound of Formula (I). In another embodiment, the invention is directed to a compound of Formula (I) or a salt thereof. In a further embodiment, the invention is directed to a compound of Formula (I) or a pharmaceutically acceptable salt thereof.

Compounds of Formula (I) have both a basic amine group and a carboxylic acid group and can consequently be in the form of a zwitterion, also known as an inner salt. Therefore, in an embodiment the compound of Formula (I) is in a zwitterion form.

As used herein, "pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Pharmaceutically acceptable salts include, amongst others, those described in Berge, J. Pharm. Sci., 1977, 66, 1-19, or those listed in P H Stahl and C G Wermuth, editors, *Handbook of Pharmaceutical Salts; Properties, Selection and Use, Second Edition* Stahl/Wermuth: VCH/VHCA, 2011 (see http://www.wiley.com/WileyCDA/WileyTitle/productCd-3906390519.html).

The skilled artisan will appreciate that pharmaceutically acceptable salts of the compounds according to Formula (I) may be prepared. These pharmaceutically acceptable salts may be prepared in situ during the final isolation and purification of the compound, or by separately treating the purified compound in its free acid or free base form with a suitable base or acid, respectively.

It will be understood that if a compound of Formula (I) contains two or more basic moieties, the stoichiometry of salt formation may include 1, 2 or more equivalents of acid. Such salts would contain 1, 2 or more acid counterions, for example, a dihydrochloride salt.

Stoichiometric and non-stoichiometric forms of a pharmaceutically acceptable salt of a compound of Formula (I) are included within the scope of the invention, including sub-stoichiometric salts, for example where a counterion contains more than one acidic proton.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl)amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e., the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formula (I) and following of this invention can generally be prepared by carrying out the procedures disclosed in the Schemes and/or in the Examples below, by substituting a readily available isotopically labeled reagent for a non-isotopically labeled reagent.

Representative Embodiments

In one embodiment, the compound of Formula (I) is:

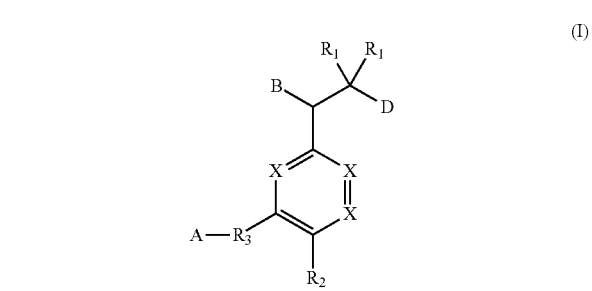

wherein:
B is —O(CH$_2$)-triazolyl, —O(CH$_2$)$_m$, —O(CH$_2$)$_m$-oxazolyl, —O(CH$_2$)$_m$-oxadiazolyl and —O(CH$_2$)$_m$-isoxazolyl, wherein each of the —O(CH$_2$)-triazolyl, —O(CH$_2$)$_m$, —O(CH$_2$)$_m$, —O(CH$_2$)$_m$-oxazolyl, —O(CH$_2$)$_m$-oxadiazolyl or —O(CH$_2$)$_m$-isoxazolyl is unsubstituted or substituted by 1 or 2 substituents independently selected from —C$_{1-6}$ alkyl, —(CH$_2$)$_m$—O—C$_{1-3}$alkyl, —(CH$_2$)$_n$—C$_{3-7}$ cycloalkyl, —(CH$_2$)$_m$—C$_{4-7}$ heterocycloalkyl, —(CH$_2$)$_n$-phenyl, —(CH$_2$)$_n$-phenyl-(CH$_2$)$_n$-aryl, —(CH$_2$)$_n$-phenyl-(CH$_2$)$_n$-heteroaryl, —(CH$_2$)$_n$—C$_{3-7}$cycloalkyl, —(CH$_2$)$_n$—C$_{3-7}$heterocycloalkyl, —(CH$_2$)$_n$—C$_{3-7}$heterocycloalkyl-(CH$_2$)$_n$—C$_{3-7}$heterocycloalkyl, —(CH$_2$)$_n$—C$_{3-7}$heterocycloalkyl-C(O)R', —(CH$_2$)$_n$—C$_{3-7}$heterocycloalkyl-C(O)—C$_{3-7}$heterocycloalkyl, —(CH$_2$)$_n$—C$_{3-7}$heterocycloalkyl-C(O)—C$_{3-7}$cycloalkyl,
—(CH$_2$)$_n$—C$_{3-7}$ heterocycloalkyl-C(O)aryl, —(CH$_2$)$_n$-phenyl-(CH$_2$)$_n$—C$_{4-7}$ heterocycloalkyl, —(CH$_2$)$_2$—O—(CH$_2$)$_2$—OR$_4$, CN, C$_{1-6}$alkylNR$_4$R$_6$, C$_{1-6}$alkylNC(O)R$_7$, C$_{1-6}$alkylNC(O)OR$_4$ and halo and wherein each of the moieties —(CH$_2$)$_n$-phenyl, —(CH$_2$)$_n$-phenyl-(CH$_2$)$_n$-aryl, —(CH$_2$)$_n$-phenyl-(CH$_2$)$_n$-heteroaryl, —(CH$_2$)$_n$—C$_{3-7}$cycloalkyl, —(CH$_2$)$_n$—C$_{3-7}$heterocycloalkyl, —(CH$_2$)$_n$—C$_{3-7}$heterocycloalkyl-(CH$_2$)$_n$—C$_{3-7}$heterocycloalkyl, —(CH$_2$)$_n$—C$_{3-7}$heterocycloalkyl-C(O)R', —(CH$_2$)$_n$—C$_{3-7}$ heterocycloalkyl-C(O) C$_{3-7}$ heterocycloalkyl, —(CH$_2$)$_n$—C$_{3-7}$ heterocycloalkyl-C(O)—C$_{3-7}$cycloalkyl, —(CH$_2$)$_n$—C$_{3-7}$ heterocycloalkyl-C(O)aryl, —(CH$_2$)$_n$-phenyl-(CH$_2$)$_n$—C$_{4-7}$ heterocycloalkyl, —(CH$_2$)$_2$—O—(CH$_2$)$_2$—OR$_4$ are unsubstituted or further substituted by 1, 2 or 3 substituents independently selected from
—C$_{1-4}$alkyl, —SO$_2$R$_4$, halo, —(CH$_2$)$_m$, —(CH$_2$)$_n$C(O)OR$_4$, —(CH$_2$)$_m$OH, —C(O)R$_7$;
D is —C(O)OH, —C(O)CR', —C(O)NHSO$_2$CH$_3$, —SO$_2$NHC(O)CH$_3$, 5-(trifluoromethyl)-4H-1,2,4-triazol-2-yl, or tetrazolyl;
R$_1$ is independently hydrogen, —OH, —C$_{1-3}$alkyl, —C$_{1-3}$alkylOR', F, —C$_{3-6}$spirocycloalkyl, oxetane, or the two R$_1$ groups together with the carbon to which they are attached form a cyclopropyl group;
R' is hydrogen, —C$_{1-4}$alkyl or —NH$_2$;
R$_2$ is hydrogen, —C$_{1-4}$alkyl, —CF$_3$, or halo;
R$_3$ is —(CH$_2$)$_m$;
R$_4$ is hydrogen or —C$_{1-3}$alkyl;
or, when R$_2$ is —C$_{1-4}$alkyl, R$_3$ is —(CH$_2$)$_m$—, and m is 2 or 3, R$_2$ and R$_3$ together form a cycloalkyl ring fused to the phenyl ring to which they are attached;
A is tetrahydrobenzoxazepinyl, tetrahydro-pyrido-oxazepinyl, tetrahydrobenzazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;
wherein each of tetrahydrobenzoxazepinyl, tetrahydropyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, CN, —O—C$_{1-3}$alkyl, —CH$_2$—O—CH$_3$, and OH;
and wherein the piperidinyl is further unsubstituted or substituted by a substituent independently selected from pyrazolyl, —CH$_2$pyrazolyl, and oxadiazolyl each of which is unsubstituted or substituted by —C$_{1-3}$ alkyl, or, when A is piperidinyl, it is unsubstituted or substituted by —SO$_2$R, wherein R is C$_{1-3}$alkyl, phenyl or C$_{3-7}$cycloalkyl;
and wherein the oxazepane is further unsubstituted or substituted by 1 or 2 substituents independently selected from —C$_{1-3}$alkyl and C$_{3-7}$cycloalkyl;
and wherein the morpholinyl is further unsubstituted or substituted by phenyl which phenyl is unsubstituted or independently substituted by a substituent selected from C$_{1-3}$ alkyl and —O—C$_{1-3}$ alkyl;
and wherein the pyrrolidinyl is further optionally substituted by a triazolyl group which is optionally substituted by —C$_{1-3}$alkyl;
and wherein the imidazolyl, triazolyl, pyrazolyl, and tetrazolyl groups each are further unsubstituted or substituted by 1, 2 or 3 substituents independently selected from —CH$_2$—C$_{4-7}$cycloalkyl, —CH$_2$—C$_{5-7}$heterocycloalkyl, —CH$_2$-azabicycloheptanyl, —CH$_2$-oxepane, and —CH$_2$-azabicyclohexanyl, and wherein each of —CH$_2$—C$_{4-7}$cycloalkyl, —CH$_2$—CO$_{5-7}$heterocycloalkyl, —CH$_2$-azabicycloheptanyl, —CH$_2$-oxepane, or —CH$_2$-azabicyclohexanyl, including the CH$_2$—, are further unsubstituted or substituted by 1 or 2 substituents independently selected from —C$_{1-3}$ alkyl and F;

or, A is,

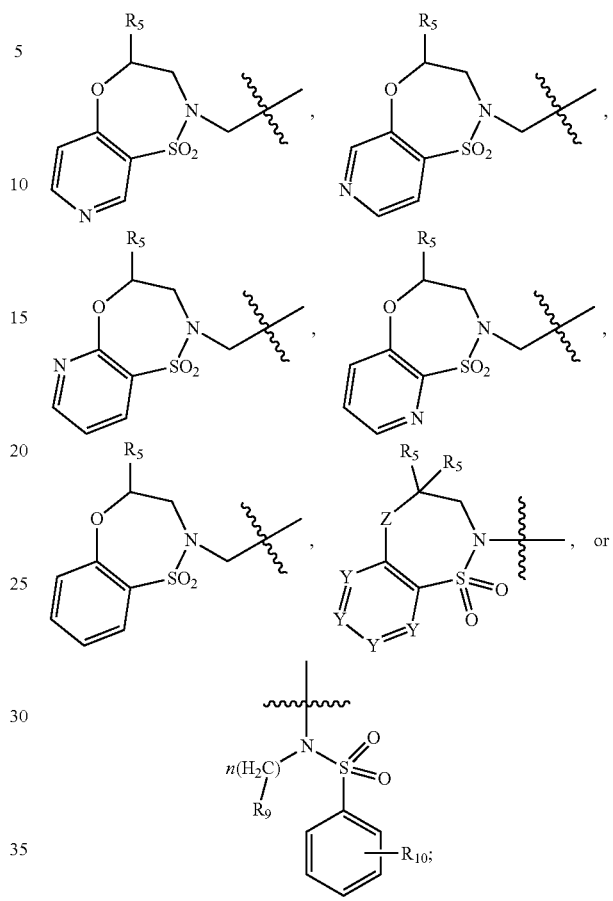

R$_5$ is independently hydrogen or C$_{1-5}$alkyl;
R$_6$ is hydrogen or —C$_{1-4}$alkyl;
R$_7$ is hydrogen, aryl, heteroaryl, C$_{5-10}$heterocycloalkyl, —C$_{1-4}$alkyl or —C$_{3-7}$cycloalkyl;
X is independently CH or N;
Y is independently CH or N;
Z is O, CH$_2$, NR$_5$, S, S(O), SO$_2$;
wherein, when A is,

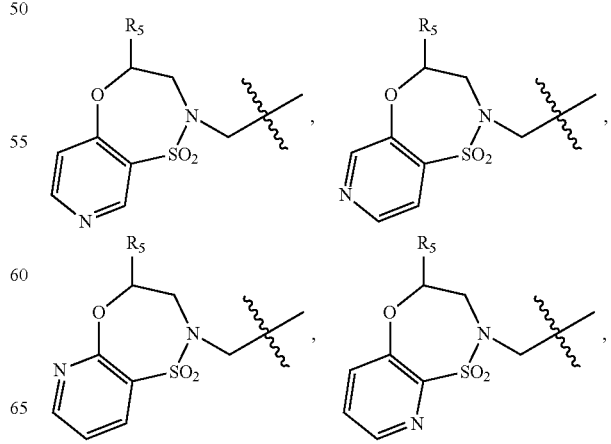

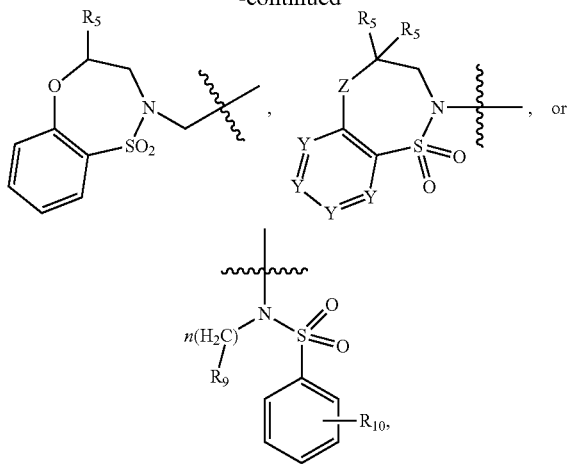

A is unsubstituted of substituted by one, two or three substituents independently selected from halo, —$CF_3$, —$C_{1-4}$ alkyl, —CN, —OMe, —$C(O)NH_2$, —$OCF_3$, and —$C_{1-4}$ alkylNR$_6$R$_8$;

R$_8$ is hydrogen, —$C_{1-5}$ alkyl, —$C_{3-7}$cycloalkyl, —$C_{4-8}$heterocycloalkyl, —$C_{1-5}$ alkoxy, —$C_{1-3}$ alkyl-O—$C_{1-3}$alkyl, —$C_{1-3}$alkyl-NH—$C_{1-3}$alkyl, —$C_{1-3}$alkyl-SO$_2$C$_{1-3}$alkyl, —$C_{1-3}$alkyl-C$_{4-8}$heterocycloalkyl, —$C_{1-3}$alkyl-C(O)NR$_5$R$_6$, or heteroaryl, wherein each of —$C_{1-5}$ alkyl, —$C_{3-7}$cycloalkyl, 7heterocycloalkyl, —$C_{1-5}$ alkoxy, —$C_{1-3}$ alkyl-O—$C_{1-3}$ alkyl, —$C_{1-3}$ alkyl-NH—$C_{1-3}$ alkyl, —$C_{1-3}$ alkyl-C(O)NR$_5$R$_6$, or heteroaryl is unsubstituted or substituted by one or two substituents independently selected from —OH, —$CO_2H$, —$C(O)NR_5R_6$, —$C(O)OR_5$, —N—C(O)—$C_{1-3}$ alkyl, F, —CN, —CH—F$_2$, —CF$_3$, —(CH$_2$)$_n$—O—(CH$_2$)$_m$—CH$_3$, and —$C_{3-7}$cycloalkyl, a 5-6-membered heteroaryl ring containing 1, 2 or 3 heteroatoms selected from O, N and S;

R$_9$ is -phenyl, —$C_{3-7}$ cycloalkyl, —$C_{3-7}$ heterocycloalkyl containing 1 or 2 heteroatoms selected from O, N and S, –5-10-membered aryl ring or a –5-10-membered heteroaryl ring, containing 1, 2 or 3 heteroatoms selected from O, N and S, wherein each of -phenyl, —$C_{3-7}$cycloalkyl, —$C_{3-7}$heterocycloalkyl containing 1 or 2 heteroatoms selected from O, N and S, –5-10-membered aryl ring or a –5-10-membered heteroaryl ring, containing 1, 2 or 3 heteroatoms selected from O, N and S is unsubstituted or independently substituted by one or two substituents selected from halo, —C(O)OH, —CF$_3$, —C$_{1-4}$alkyl, —CN, —OMe, —C(O)NH$_2$, —OCF$_3$, and —C$_{1-4}$ alkylNR$_6$R$_8$;

R$_{10}$ is independently selected from hydrogen, halo, —C(O)OH, —CF$_3$, —C$_{1-4}$alkyl, —CN, —OMe, —C(O)NH$_2$, —OCF$_3$, and —C$_{1-4}$ alkylNR$_6$R$_8$;

m is 1, 2, 3 or 4; and n is 0, 1, 2 or 3;

or a pharmaceutically acceptable salt thereof.

In another embodiment, the compound of Formula (I) is substituted as follows:

B is —O(CH$_2$)-triazolyl and —O(CH$_2$)$_m$, wherein each of the —O(CH$_2$)-triazolyl or —O(CH$_2$)$_n$, is unsubstituted or substituted by 1 or 2 substituents independently selected from —C$_{1-6}$alkyl, —(CH$_2$)$_n$—C$_{3-7}$ cycloalkyl, —(CH$_2$)$_m$—C$_{4-7}$ heterocycloalkyl, —(CH$_2$)$_n$-phenyl, —(CH$_2$)$_n$-phenyl-(CH$_2$)$_n$-aryl, —(CH$_2$)$_n$-phenyl-(CH$_2$)$_n$-heteroaryl, —(CH$_2$)$_n$—C$_{3-7}$ cycloalkyl, —(CH$_2$)$_n$—C$_{3-7}$heterocycloalkyl, —(CH$_2$)$_n$—C$_{3-7}$heterocycloalkyl-(CH$_2$)$_n$—C$_{3-7}$heterocycloalkyl, —(CH$_2$)$_n$—C$_{3-7}$heterocycloalkyl-C(O)R', —(CH$_2$)$_n$—C$_{3-7}$heterocycloalkyl-C(O) C$_{3-7}$heterocycloalkyl, —(CH$_2$)$_n$—C$_{3-7}$heterocycloalkyl-C(O)—C$_{3-7}$cycloalkyl, —(CH$_2$)$_n$—C$_{3-7}$heterocycloalkyl-C(O)aryl, —(CH$_2$)$_n$-phenyl-(CH$_2$)$_n$—C$_{4-7}$ heterocycloalkyl, —(CH$_2$)$_2$—O—(CH$_2$)$_2$—OR$_4$, CN, and halo and wherein each of the moieties —(CH$_2$)$_n$-phenyl, —(CH$_2$)$_n$-phenyl-(CH$_2$)$_n$-aryl, —(CH$_2$)$_n$-phenyl-(CH$_2$)$_n$-heteroaryl, —(CH$_2$)$_n$—C$_{3-7}$cycloalkyl, —(CH$_2$)$_n$—C$_{3-7}$heterocycloalkyl, —(CH$_2$)$_n$—C$_{3-7}$heterocycloalkyl-(CH$_2$)$_n$—C$_{3-7}$heterocycloalkyl, —(CH$_2$)$_n$—C$_{3-7}$heterocycloalkyl-C(O)R', —(CH$_2$)$_n$—C$_{3-7}$heterocycloalkyl-C(O)—C$_{3-7}$heterocycloalkyl, —(CH$_2$)$_n$—C$_{3-7}$heterocycloalkyl-C(O)—C$_{3-7}$cycloalkyl, —(CH$_2$)$_n$—C$_{3-7}$heterocycloalkyl-C(O)aryl, —(CH$_2$)$_n$-phenyl-(CH$_2$)$_n$—C$_{4-7}$ heterocycloalkyl, —(CH$_2$)$_2$—O(CH$_2$)$_2$—OR$_4$ are unsubstituted or further substituted by 1, 2 or 3 substituents independently selected from C$_{1-4}$alkyl, —SO$_2$R$_4$, halo, —(CH$_2$)$_n$, —(CH$_2$)$_n$C(O)OR$_4$, —(CH$_2$)$_m$OH, —C(O)R$_8$;

D is —C(O)OH, —C(O)CR', —C(O)NHSO$_2$CH$_3$, SO$_2$NHC(O)CH$_3$, 5-(trifluoromethyl)-4H-1,2,4-triazol-2-yl, or tetrazolyl;

R$_1$ is independently hydrogen, —OH, —C$_{1-3}$alkyl, —C$_{1-3}$alkylOR', F, —C$_{3-6}$spirocycloalkyl, oxetane, or the two R$_1$ groups together with the carbon to which they are attached form a cyclopropyl group;

R' is hydrogen or —C$_{1-4}$alkyl;

R$_2$ is hydrogen, —C$_{1-4}$alkyl, —CF$_3$, or halo;

R$_3$ is —(CH$_2$)$_m$;

R$_4$ is hydrogen or —C$_{1-3}$alkyl;

or, when R$_2$ is —C$_{3-4}$alkyl, R$_3$ is —(CH$_2$)$_m$—, and m is 2 or 3, R$_2$ and R$_3$ together form a cycloalkyl ring fused to the phenyl ring to which they are attached;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

wherein each of tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, CN, —O—C$_{1-3}$alkyl, —CH$_2$—O—CH$_3$, and OH;

and wherein the piperidinyl is further unsubstituted or substituted by a substituent independently selected from pyrazolyl, —CH$_2$pyrazolyl, and oxadiazolyl each of which is unsubstituted or substituted by —C$_{1-3}$alkyl, or, when A is piperidinyl, it is unsubstituted or substituted by —SO$_2$R, wherein R is C$_{1-3}$alkyl, phenyl or C$_{3-7}$cycloalkyl;

and wherein the oxazepane is further unsubstituted or substituted by 1 or 2 substituents independently selected from —C$_{1-3}$alkyl and C$_{3-7}$cycloalkyl;

and wherein the morpholinyl is further unsubstituted or substituted by phenyl which phenyl is unsubstituted or independently substituted by a substituent selected from C$_{1-3}$ alkyl and —O—C$_{1-3}$ alkyl;

and wherein the pyrrolidinyl is further optionally substituted by a triazolyl group which is optionally substituted by —C$_{1-3}$alkyl;

and wherein the imidazolyl, triazolyl, pyrazolyl, and tetrazolyl groups each are further unsubstituted or substituted by 1, 2 or 3 substituents independently selected from —CH$_2$—

C₄₋₇cycloalkyl, —CH₂—C₅₋₇ heterocycloalkyl, —CH₂-azabicycloheptanyl, —CH₂-oxepane, and —CH₂-azabicyclohexanyl, and wherein each of —CH₂—C₄₋₇ cycloalkyl, —CH₂—C₅₋₇ heterocycloalkyl, —CH₂-azabicycloheptanyl, —CH₂-oxepane, or —CH₂-azabicyclohexanyl, including the CH₂—, are further unsubstituted or substituted by 1 or 2 substituents independently selected from —C₁₋₃ alkyl and F;

or, A is,

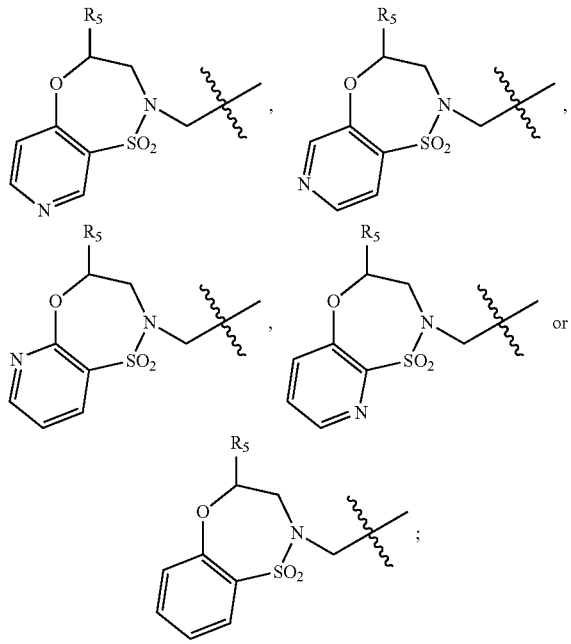

R₅ is hydrogen or —C₁₋₅alkyl;
R₆ is hydrogen or —C₁₋₄alkyl;
R₇ is hydrogen or —C₁₋₄alkyl;
R₈ is hydrogen, aryl, heteroaryl, C₅₋₁₀heterocycloalkyl, —C₁₋₄alkyl or —C₃₋₇cycloalkyl;
m is 1, 2, 3 or 4;
n is 0, 1, 2 or 3; and
X is independently CH or N;
or a pharmaceutically acceptable salt thereof.

In one embodiment, the compound of Formula (I) is substituted as follows:
B is —O(CH₂)-triazolyl wherein the —O(CH₂)₂triazolyl is unsubstituted or substituted by 1 or 2 substituents independently selected from C₁₋₆alkyl, —(CH₂)ₙ-phenyl, —(CH₂)ₙ—C₃₋₇heterocycloalkyl, —(CH₂)ₙ-phenyl-(CH₂)ₙ-aryl and —(CH₂)ₙ-phenyl-(CH₂)ₙ-heteroaryl, and wherein each of C₁₋₆ alkyl, —(CH₂)ₙ-phenyl, —(CH₂)ₙ—C₃₋₇ heterocycloalkyl, —(CH₂)ₙ-phenyl-(CH₂)ₙ-aryl and —(CH₂)ₙ-phenyl-(CH₂)ₙ-heteroaryl is unsubstituted or further substituted by 1, 2 or 3 substituents independently selected from C₁₋₄alkyl, —SO₂R₄, halo, —(CH₂)ₙ, —(CH₂)ₙC(O)OR₄, —(CH₂)ₘ OH, —C(O)R₇;
D is —C(O)OH;
R₁ is independently hydrogen or —C₁₋₃alkyl;
R₂ is —C₁₋₄alkyl or halo;
R₃ is —(CH₂);
R₄ is hydrogen or —C₁₋₃alkyl;
A is

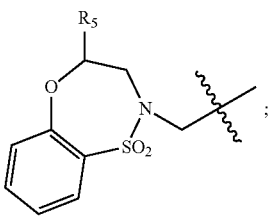

R₅ is hydrogen or —C₁₋₅alkyl;
R₇ is hydrogen, aryl, heteroaryl, C₁₋₁₀heterocycloalkyl, —C₁₋₄alkyl or —C₃₋₇cycloalkyl;
m is 1 or 2;
n is 0 or 1; and
X is independently CH or N;
or a pharmaceutically acceptable salt thereof.

In a second embodiment, the compound of Formula (I) is substituted as follows:
B is —O(CH₂)-triazolyl wherein the —O(CH₂)₂triazolyl is unsubstituted or substituted by 1 or 2 substituents independently selected from C₁₋₆alkyl, —(CH₂)ₙ-phenyl, —(CH₂)ₙ—C₃₋₇heterocycloalkyl, —(CH₂)ₙ-phenyl-(CH₂)ₙ-aryl and —(CH₂)ₙ-phenyl-(CH₂)ₙ-heteroaryl, and wherein each of C₁₋₆ alkyl, —(CH₂)ₙ-phenyl, —(CH₂)ₙ—C₃₋₇ heterocycloalkyl, —(CH₂)ₙ-phenyl-(CH₂)ₙ-aryl and —(CH₂)ₙ-phenyl-(CH₂)ₙ-heteroaryl is unsubstituted or further substituted by 1, 2 or 3 substituents independently selected from C₁₋₄alkyl, —SO₂R₄, halo, —(CH₂)ₙ, —(CH₂)ₙ C(O)OR₄, —(CH₂)ₘOH, —C(O)R₇;
D is —C(O)OH;
R₁ is independently hydrogen or methyl;
R₂ is methyl;
R₃ is —(CH₂);
R₄ is hydrogen or —C₁₋₃alkyl;
A is

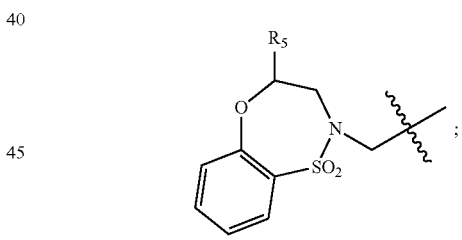

R₅ is methyl or ethyl;
R₇ is hydrogen, aryl, heteroaryl, C₁₋₁₀heterocycloalkyl, —C₁₋₄alkyl or —C₃₋₇cycloalkyl;
m is 1 or 2;
n is 0 or 1; and
X is CH;
or a pharmaceutically acceptable salt thereof.

In another embodiment, the compound of Formula (I) is substituted as follows:
B is —O(CH₂)-triazolyl, unsubstituted or substituted by 1 or 2 substituents independently selected from C₁₋₆alkyl, —(CH₂)ₙ—O—C₁₋₃alkyl, —(CH₂)ₙ—C₃₋₇cycloalkyl, —(CH₂)₂—O(CH₂)₂—OR₄, and wherein each of C₁₋₆ alkyl, —(CH₂)ₙ—C₃₋₇ cycloalkyl, —(CH₂)₂—O—(CH₂)₂—OR₄ are unsubstituted or further substituted by 1 or 2 substituents independently selected from C₁₋₄alkyl, —SO₂R₄, halo, —(CH₂)ₙ, —(CH₂)ₙC(O)OR₄, —(CH₂)ₘOH, —C(O)R₇;
D is —C(O)OH;

$R_1$ is independently —$C_{1-3}$alkyl;
$R_2$ is —$C_{1-4}$alkyl;
$R_3$ is —$(CH_2)_m$;
$R_4$ is hydrogen or —$C_{1-3}$alkyl;
A is tetrahydrobenzoxazepinyl, tetrahydro-pyrido-oxazepinyl or tetrahydrobenzazepinyl, each of which is unsubstituted or substituted by 1, 2, or 3 substituents independently selected from —$C_{1-3}$ alkyl, —$C_{3-6}$ spirocycloalkyl, halo, CN, —O—$C_{1-3}$ alkyl, —$CH_2$—O—$CH_3$, and OH;
or A is

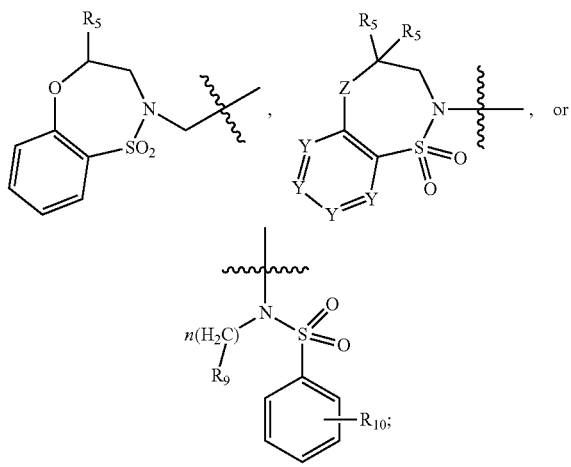

$R_7$ is hydrogen, aryl, heteroaryl, $C_{1-10}$heterocycloalkyl, —$C_{1-4}$alkyl or —$C_{3-7}$cycloalkyl;
X is CH;
Y is independently CH or N;
Z is O, $CH_2$ or $NR_5$;
wherein, when A is

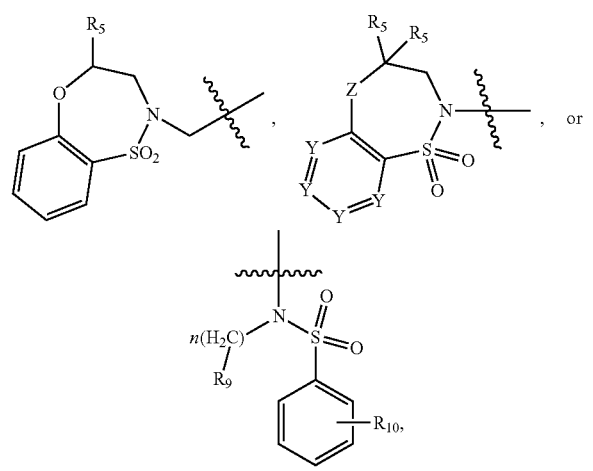

A is unsubstituted of substituted by one, two or three substituents selected from —$C_{1-4}$alkyl;
$R_9$ is -phenyl, which is unsubstituted or independently substituted by one or two substituents selected from halo, —C(O)OH, —$CF_3$, —$C_{1-4}$alkyl, —CN, —OMe, —C(O)NH$_2$ and —$OCF_3$;
$R_{10}$ is independently selected from hydrogen, halo, —C(O)OH, —$CF_3$, —$C_{1-4}$alkyl, —CN, —OMe, —C(O)NH$_2$, and —$OCF_3$;

m is 1, 2, 3 or 4; and
n is 0, 1, 2 or 3;
or a pharmaceutically acceptable salt thereof.

In another embodiment, the compound of Formula (I) is substituted as follows:
B is —$O(CH_2)$-triazolyl, unsubstituted or substituted by 1 or 2 substituents independently selected from $C_{1-6}$alkyl, wherein $C_{1-6}$alkyl is unsubstituted or further substituted by 1 or 2 substituents independently selected from $C_{1-4}$alkyl;
D is —C(O)OH;
$R_1$ is independently —$C_{1-3}$alkyl;
$R_2$ is —$C_{1-4}$alkyl;
$R_3$ is —$(CH_2)_m$;
A is

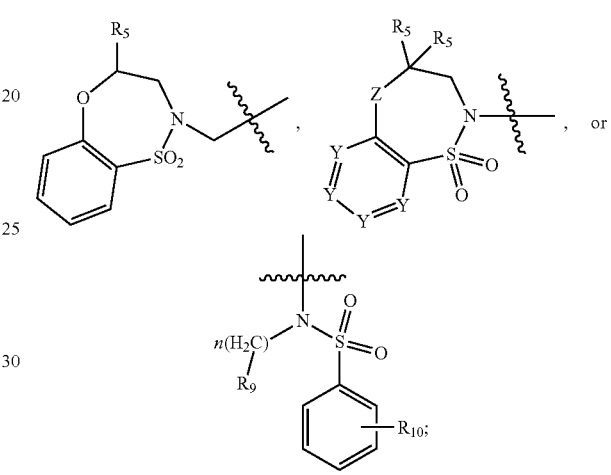

$R_5$ is hydrogen or $C_{1-5}$alkyl;
X is CH;
Y is independently CH or N;
Z is O, $CH_2$;
wherein, when A is

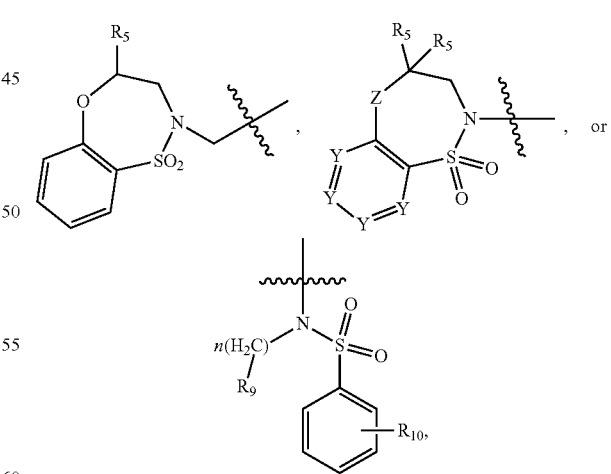

A is unsubstituted of substituted by one, two or three substituents selected from —$C_{1-4}$alkyl;
$R_9$ is -phenyl, which is unsubstituted or independently substituted by one or two substituents selected from halo, —C(O)OH, —$CF_3$, —CN, —OMe, —C(O)NH$_2$ and —$OCF_3$;

$R_{10}$ is independently selected from hydrogen, halo, —C(O)OH, —CF$_3$, —CN, —OMe, —C(O)NH$_2$, and —OCF$_3$; and m is 1 or 2;

or a pharmaceutically acceptable salt thereof.

In another embodiment, the compound of Formula (I) is substituted as follows:

B is —O(CH$_2$)-triazolyl, unsubstituted or substituted by 1 or 2 substituents independently selected from C$_{1-6}$alkyl, wherein C$_{1-6}$alkyl is unsubstituted or further substituted by 1 or 2 substituents independently selected from C$_{1-4}$alkyl;

D is —C(O)OH;

R$_1$ is independently —C$_{1-3}$alkyl;

R$_2$ is —C$_{1-4}$alkyl;

R$_3$ is —(CH$_2$)$_m$;

A is tetrahydrobenzoxazepinyl, tetrahydro-pyrido-oxazepinyl or tetrahydrobenzazepinyl, each of which is unsubstituted or substituted by 1, 2, or 3 substituents independently selected from —C$_{1-3}$alkyl, —C$_{3-6}$spirocycloalkyl, halo, CN, —O—C$_{1-3}$alkyl, —CH$_2$—O—CH$_3$, and OH;

X is CH; and m is 1 or 2;

or a pharmaceutically acceptable salt thereof.

In still yet another embodiment, the compound of Formula (I) is substituted as follows:

B is —O(CH$_2$)-triazolyl, unsubstituted or substituted by 1 or 2 substituents which are —C$_{1-6}$alkyl, D is —C(O)OH;

R$_1$ are each methyl;

R$_2$ is methyl;

R$_3$ is —(CH$_2$)$_m$;

A is tetrahydrobenzoxazepinyl, tetrahydro-pyrido-oxazepinyl or tetrahydrobenzazepinyl, each of which is unsubstituted or substituted by 1, 2, or 3 substituents independently selected from —C$_{1-3}$alkyl, —C$_{3-6}$spirocycloalkyl, halo, CN, —O—C$_{1-3}$alkyl, —CH$_2$—O—CH$_3$, and OH;

or A is

[chemical structures]

R$_5$ is independently hydrogen or C$_{1-5}$alkyl;

X is CH;

Y is independently CH or N;

Z is O or CH$_2$;

wherein, when A is

[chemical structures]

A is unsubstituted of substituted by one, two or three substituents selected from —C$_{1-4}$alkyl;

R$_9$ is -phenyl, which is unsubstituted or independently substituted by —C(O)OH;

R$_{10}$ is independently selected from hydrogen or —C(O)OH; and or a pharmaceutically acceptable salt thereof.

In yet a further embodiment, the compound of Formula (I) is substituted as follows:

B is —O(CH$_2$)-triazolyl, unsubstituted or substituted by 1 or 2 substituents which are —C$_{1-6}$alkyl, D is —C(O)OH;

R$_1$ are each methyl;

R$_2$ is methyl;

R$_3$ is —(CH$_2$)$_m$;

A is tetrahydrobenzoxazepinyl, tetrahydro-pyrido-oxazepinyl or tetrahydrobenzazepinyl, each of which is unsubstituted or substituted by 1, 2, or 3 substituents independently selected from —C$_{1-3}$ alkyl, —C$_{3-6}$ spirocycloalkyl, halo, CN, —O—C$_{1-3}$ alkyl, —CH$_2$—O—CH$_3$, and OH;

X is CH; and m is 1 or 2;

or a pharmaceutically acceptable salt thereof.

In yet a further embodiment, the compound of Formula (I) is substituted as follows:

B is —O(CH$_2$)-triazolyl, unsubstituted or substituted by 1 or 2 substituents which are C$_{1-6}$alkyl, D is —C(O)OH;

R$_1$ are each methyl;

R$_2$ is methyl;

R$_3$ is —(CH$_2$)$_m$;

A is

[chemical structures]

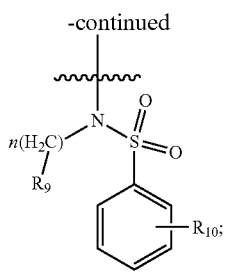

R₅ is independently hydrogen or $C_{1-5}$alkyl;
X is CH;
Y is independently CH or N;
Z is O or $CH_2$;
wherein, when A is

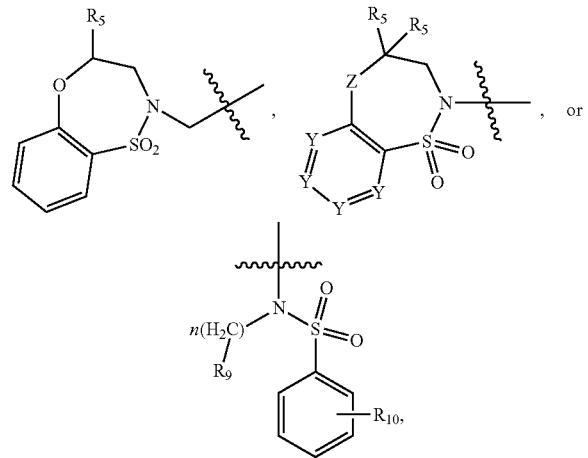

A is unsubstituted of substituted by one, two or three substituents selected from —$C_{1-4}$alkyl;
R₉ is -phenyl, which is unsubstituted or independently substituted by —C(O)OH;
R₁₀ is independently selected from hydrogen or —C(O)OH;
X is CH; and
m is 1 or 2;
or a pharmaceutically acceptable salt thereof.

It is to be understood that the present invention covers all combinations of the embodiments and particular groups described hereinabove.

Specific examples of compounds of the present invention include the following:

3-((1-(3-Bromobenzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoic acid;

3-((1-(3-(Azidomethyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)propanoic acid;

(R)-3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoic acid;

(S)-3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoic acid;

3-((1-Benzyl-1H-1,2,3-triazol-4-yl)methoxy)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid;

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-propyl-1H-1,2,3-triazol-4-yl)methoxy)propanoic acid;

3-(3-((4,4-Dimethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)propanoic acid;

3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoic acid;

3-((1-Ethyl-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-(3-((4,4-dimethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoic acid;

Rel-(S)-3-((1-isobutyl-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

Rel-(S)-3-((1-(2-(2-azidoethoxy)ethyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

Rel-(R)-3-((1-(2-(2-azidoethoxy)ethyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

Rel-(R)-3-((1-isobutyl-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-Cyclohexyl-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-((1-(Tert-butoxycarbonyl)piperidin-3-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-(4-(Azidomethyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-((1-(Tert-butoxycarbonyl)piperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((4-((2-Carboxy-1-(3-(((R)-4-ethyl-1,1-dioxido-3,4-dihydro-2H-benzo[b][1,4,5]oxathiazepin-2-yl)methyl)-4- methylphenyl)-2-methylpropoxy)methyl)-1H-1,2,3-triazol-1-yl)methyl)benzoic acid;

3'-((4-((2-Carboxy-1-(3-(((R)-4-ethyl-1,1-dioxido-3,4-dihydro-2H-benzo[b][1,4,5]oxathiazepin-2-yl)methyl)-4-methylphenyl)-2-methylpropoxy)methyl)-1H-1,2,3-triazol-1-yl)methyl)-[1,1'-biphenyl]-4-carboxylic acid;

3'-((4-((2-Carboxy-1-(3-(((R)-4-ethyl-1,1-dioxido-3,4-dihydro-2H-benzo[b][1,4,5]oxathiazepin-2-yl)methyl)-4-methylphenyl)-2-methylpropoxy)methyl)-1H-1,2,3-triazol-1-yl)methyl)-[1,1'-biphenyl]-3-carboxylic acid;

3'-((4-((2-Carboxy-1-(3-(((R)-4-ethyl-1,1-dioxido-3,4-dihydro-2H-benzo[b][1,4,5]oxathiazepin-2-yl)methyl)-4-methylphenyl)-2-methylpropoxy)methyl)-1H-1,2,3-triazol-1-yl)methyl)-3-fluoro-[1,1'-biphenyl]-4-carboxylic acid;

3'-((4-((2-Carboxy-2-methyl-1-(4-methyl-3-(((R)-4-methyl-1,1-dioxido-3,4-dihydro-2H-benzo[b][1,4,5]oxathiazepin-2-yl)methyl)phenyl)propoxy)methyl)-1H-1,2,3-triazol-1-yl)methyl)-[1,1'-biphenyl]-4-carboxylic acid;

3'-((4-((2-Carboxy-2-methyl-1-(4-methyl-3-(((R)-4-methyl-1,1-dioxido-3,4-dihydro-2H-benzo[b][1,4,5]oxathiazepin-2-yl)methyl)phenyl)propoxy)methyl)-1H-1,2,3-triazol-1-yl)methyl)-[1,1'-biphenyl]-3-carboxylic acid;

3-(3-(((R)-4-ethyl-1,1-dioxido-3,4-dihydro-2H-benzo[b][1,4,5]oxathiazepin-2-yl)methyl)-4-methylphenyl)-3-((1-(3-((4-(hydroxymethyl)-1H-1,2,3-triazol-1-yl)methyl)-5-methylbenzyl)-1H-1,2,3-triazol-4-yl)methoxy)-2,2-dimethylpropanoic acid;

3-(3-(((R)-4-ethyl-1,1-dioxido-3,4-dihydro-2H-benzo[b][1,4,5]oxathiazepin-2-yl)methyl)-4-methylphenyl)-3-((1-(3-((4-(hydroxymethyl)-1H-1,2,3-triazol-1-yl)methyl)benzyl)-1H-1,2,3-triazol-4-yl)methoxy)-2,2-dimethylpropanoic acid;

3-((1-(3-((4-(Hydromethyl)-1H-1,2,3-triazol-1-yl)methyl)-5-methyl benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-((1-(Cyclohexanecarbonyl)piperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-((1-Benzoylpiperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-((1-Acetylpiperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-((1-propionylpiperidin-4-yl)methyl)-1H-1,2,3-triazol-4-yl)methoxy)propanoic acid;

3-((1-((1-Butyrylpiperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-((1-(tetrahydro-2H-pyran-4-carbonyl)piperidin-4-yl)methyl)-1H-1,2,3-triazol-4-yl)methoxy)propanoic acid;

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(((1-(methylsulfonyl)piperidin-4-yl)methyl)-1H-1,2,3-triazol-4-yl)methoxy)propanoic acid;

3-((1-(3-((4-Isopropyl-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-(3-((4-Ethyl-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-(3-((4-(Hydromethyl)-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-(3-((4-(2-Hydroxyethyl)-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-(3-((4-(2-Hydroxypropan-2-yl)-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-(3-((4-(4-Hydroxybutyl)-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

1-(3-((4-((2-Carboxy-2-methyl-1-(4-methyl-3-(((R)-4-methyl-1,1-dioxido-3,4-dihydro-2H-benzo[b][1,4,5]oxathiazepin-2-yl)methyl)phenyl)propoxy)methyl)-1H-1,2,3-triazol-1-yl)methyl)benzyl)-1H-1,2,3-triazole-4-carboxylic acid;

3-((1-(3-((4-(Carboxymethyl)-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1-(3-((4-(2-Carboxyethyl)-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-((1-propylpiperidin-4-yl)methyl)-1H-1,2,3-triazol-4-yl)methoxy)propanoic acid;

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(piperidin-4-ylmethyl)-1H-1,2,3-triazol-4-yl)methoxy)propanoic acid, formic acid salt;

3-(3-((N-(cycloheptylmethyl)acetamido)methyl)-4-methylphenyl)-3-((1-ethyl-1H-1,2,3-triazol-4-yl)methoxy)-2,2-dimethylpropanoic acid;

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-((1'-methyl-[1,4'-bipiperidin]-4-yl)methyl)-1H-1,2,3-triazol-4-yl)methoxy)propanoic acid, formic acid salt;

3-((1-(3-Oxa-6-azaspiro[5.5]undecan-6-ium-9-ylmethyl)-1H-1,2,3-triazol-4-yl)methoxy)-2,2-dimethyl-3-(4- methyl-3-(((S)-4-methyl-1,1-dioxido-3,4-dihydro-2H-benzo[b][1,4,5]oxathiazepin-2-yl)methyl)phenyl)propanoate;

4-(3-((4-((3-Methoxy-2,2-dimethyl-1-(4-methyl-3-(((R)-4-methyl-1,1-dioxido-3,4-dihydro-2H-benzo[b][1,4,5]oxathiazepin-2-yl)methyl)phenyl)-3-oxopropoxy)methyl)-1H-1,2,3-triazol-1-yl)methyl)phenyl)picolinic acid;

6-(3-((4-((3-Methoxy-2,2-dimethyl-1-(4-methyl-3-(((R)-4-methyl-1,1-dioxido-3,4-dihydro-2H-benzo[b][1,4,5]oxathiazepin-2-yl)methyl)phenyl)-3-oxopropoxy)methyl)-1H-1,2,3-triazol-1-yl)methyl)phenyl)picolinic acid;

6-(3-((4-((3-Methoxy-2,2-dimethyl-1-(4-methyl-3-(((R)-4-methyl-1,1-dioxido-3,4-dihydro-2H-benzo[b][1,4,5]oxathiazepin-2-yl)methyl)phenyl)-3-oxopropoxy)methyl)-1H-1,2,3-triazol-1-yl)methyl)phenyl)picolinic acid;

3-(3-(((R)-4-Ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-difluoropropanoic acid;

(3R)-((1-ethyl-1H-1,2,3-triazol-4-yl)methoxy)-2,2-dimethyl-3-(4-methyl-3-(((S)-4-methyl-1,1-dioxido-4,5-dihydropyrido[4,3-f][1,2]thiazepin-2(3H)-yl)methyl)phenyl)propanoic acid;

(3R)-((1-ethyl-1H-1,2,3-triazol-4-yl)methoxy)-2,2-dimethyl-3-(4-methyl-3-(((S)-4-methyl-1,1-dioxido-4,5-dihydro pyrido[2,3-f][1,2]thiazepin-2 (3H)-yl)methyl)phenyl)propanoic acid;

(3S)-((1-ethyl-1H-1,2,3-triazol-4-yl)methoxy)-2,2-dimethyl-3-(4-methyl-3-(((R)-4-methyl-1,1-dioxido-4,5-dihydropyrido[4,3-f][1,2]thiazepin-2(3H)-yl)methyl)phenyl)propanoic acid;

(3S)-((1-ethyl-1H-1,2,3-triazol-4-yl)methoxy)-2,2-dimethyl-3-(4-methyl-3-(((R)-4-methyl-1,1-dioxido-4,5-dihydro pyrido[2,3-f][1,2]thiazepin-2 (3H)-yl)methyl)phenyl)propanoic acid;

(3S)-((1-ethyl-1H-1,2,3-triazol-4-yl)methoxy)-2,2-dimethyl-3-(4-methyl-3-(((R)-4-methyl-1,1-dioxido-4,5-dihydrobenzo[f][1,2]thiazepin-2(3H)-yl)methyl)phenyl)propanoic acid;

(3R)-((1-ethyl-1H-1,2,3-triazol-4-yl)methoxy)-2,2-dimethyl-3-(4-methyl-3-(((R)-4-methyl-1,1-dioxido-4,5-dihydropyrido[4,3-f][1,2]thiazepin-2(3H)-yl)methyl)phenyl)propanoic acid;

R)-2,2-dimethyl-3-(4-methyl-3-(((R)-4-methyl-1,1-dioxido-4,5-dihydropyrido[4,3-f][1,2]thiazepin-2 (3H)-yl)methyl)phenyl)-3-((1-propyl-1H-1,2,3-triazol-4-yl)methoxy)propanoic acid;

(3R)-((1-ethyl-1H-1,2,3-triazol-4-yl)methoxy)-2,2-dimethyl-3-(4-methyl-3-(((R)-4-methyl-1,1-dioxido-4,5-dihydropyrido[2,3-f][1,2]thiazepin-2(3H)-yl)methyl)phenyl)propanoic acid;

(3S)-((1-ethyl-1H-1,2,3-triazol-4-yl)methoxy)-2,2-dimethyl-3-(4-methyl-3-(((R)-4-ethyl-1,1-dioxido-4,5-dihydrobenzo[f][1,2]thiazepin-2(3H)-yl)methyl)phenyl)propanoic acid;

(3R)-((1-ethyl-1H-1,2,3-triazol-4-yl)methoxy)-2,2-dimethyl-3-(4-methyl-3-(((R)-4-methyl-1,1-dioxido-4,5-dihydrobenzo[f][1,2]thiazepin-2(3H)-yl)methyl)phenyl)propanoic acid;

(3S)-((1-(2-(2-methoxyethoxy)ethyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

(3S)-((1-ethyl-1H-1,2,3-triazol-4-yl)methoxy)-2,2-dimethyl-3-(4-methyl-3-(((S)-4-methyl-1,1-dioxido-4,5-dihydropyrido[2,3-f][1,2]thiazepin-2(3H)-yl)methyl)phenyl)propanoic acid;

(3S)-((1-ethyl-1H-1,2,3-triazol-4-yl)methoxy)-2,2-dimethyl-3-(4-methyl-3-(((R)-4-methyl-1,1-dioxido-4,5-dihydropyrido[4,3-f][1,2]thiazepin-2(3H)-yl)methyl)phenyl)propanoic acid;

3-(3-(((3-Bromo-N-(pyridin-2-ylmethyl)phenyl)sulfonamido)methyl)-4-methylphenyl)-3-((1-ethyl-1H-1,2,3-triazol-4-yl)methoxy)-2,2-dimethylpropanoic acid;

3S)-((1-ethyl-1H-1,2,3-triazol-4-yl)methoxy)-2,2-dimethyl-3-(4-methyl-3-(((S)-4-methyl-1,1-dioxido-4,5-dihydrobenzo[f][1,2]thiazepin-2(3H)-yl)methyl)phenyl)propanoic acid;

(3R)-(((R)-8-fluoro-4-methyl-1,1-dioxido-4,5-dihydrobenzo[f][1,2]thiazepin-2 (3H)-yl)methyl)-4-methylphenyl)-2,2-dimethyl-3-((1-propyl-1H-1,2,3-triazol-4-yl)methoxy)propanoic acid;

(3R)-((1-ethyl-1H-1,2,3-triazol-4-yl)methoxy)-2,2-dimethyl-3-(4-methyl-3-(((R)-4-ethyl-1,1-dioxido-4,5-dihydrobenzo[f][1,2]thiazepin-2(3H)-yl)methyl)phenyl)propanoic acid (R)-3-(3-((4,4-dimethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)propanoic acid;

(R)-2,2-dimethyl-3-(4-methyl-3-(((R)-4-methyl-1,1-dioxido-8-(trifluoromethyl)-4,5-dihydrobenzo[f][1,2]thiazepin-2(3H)-yl)methyl)phenyl)-3-((1-propyl-1H-1,2,3-triazol-4-yl)methoxy)propanoic acid;

(R)-3-((1-(2-(2-methoxyethoxy)ethyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

(3S)-((1-ethyl-1H-1,2,3-triazol-4-yl)methoxy)-2,2-dimethyl-3-(4-methyl-3-(((S)-4-ethyl-1,1-dioxido-4,5-dihydrobenzo[f][1,2]thiazepin-2(3H)-yl)methyl)phenyl)propanoic acid;

(R)-3-(3-(((R)-4-ethyl-1,1-dioxido-3,4-dihydro-2H-pyrido[3,2-b][1,4,5]oxathiazepin-2-yl)methyl)-4-methylphenyl)-3-((1-ethyl-1H-1,2,3-triazol-4-yl)methoxy)-2,2-dimethylpropanoic acid;

(R)-2,2-dimethyl-3-(4-methyl-3-(((S)-4-methyl-1,1-dioxido-4,5-dihydropyrido[4,3-f][1,2]thiazepin-2(3H)-yl)methyl)phenyl)-3-((1-propyl-1H-1,2,3-triazol-4-yl)methoxy)propanoic acid;

(3R)-((1-ethyl-1H-1,2,3-triazol-4-yl)methoxy)-2,2-dimethyl-3-(4-methyl-3-(((S)-4-methyl-1,1-dioxido-4,5-dihydrobenzo[f][1,2]thiazepin-2(3H)-yl)methyl)phenyl)propanoic acid;

(3R)-((1-ethyl-1H-1,2,3-triazol-4-yl)methoxy)-2,2-dimethyl-3-(4-methyl-3-(((S)-4-ethyl-1,1-dioxido-4,5-dihydrobenzo[f][1,2]thiazepin-2(3H)-yl)methyl)phenyl)propanoic acid;

(R)-2,2-dimethyl-3-(4-methyl-3-(((S)-4-methyl-1,1-dioxido-8-(trifluoromethyl)-4,5-dihydrobenzo[f][1,2]thiazepin-2(3H)-yl)methyl)phenyl)-3-((1-propyl-1H-1,2,3-triazol-4-yl)methoxy)propanoic acid;

(R)-3-(3-(((S)-8-fluoro-4-methyl-1,1-dioxido-4,5-dihydrobenzo[f][1,2]thiazepin-2(3H)-yl)methyl)-4-methylphenyl)-2,2-dimethyl-3-((1-propyl-1H-1,2,3-triazol-4-yl)methoxy)propanoic acid;

(R)-2,2-dimethyl-3-(4-methyl-3-(((S)-4-methyl-1,1-dioxido-4,5-dihydrobenzo[f][1,2]thiazepin-2(3H)-yl)methyl)phenyl)-3-((1-propyl-1H-1,2,3-triazol-4-yl)methoxy)propanoic acid;

(R)-2,2-dimethyl-3-(4-methyl-3-(((S)-4-methyl-1,1-dioxido-4,5-dihydropyrido[2,3-f][1,2]thiazepin-2(3H)-yl)methyl)phenyl)-3-((1-propyl-1H-1,2,3-triazol-4-yl)methoxy)propanoic acid;

(R)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)propanoic acid;

(R)-3-((N-(5-(2-carboxy-1-((1-ethyl-1H-1,2,3-triazol-4-yl)methoxy)-2-methylpropyl)-2-methylbenzyl)phenylsulfonamido)methyl)benzoic acid;

(R)-3-(N-(5-(2-carboxy-2-methyl-1-((1-propyl-1-1,2,3-triazol-4-yl)methoxy)propyl)-2-methylbenzyl)-N-(3-carboxybenzyl)sulfamoyl)benzoic acid;

(R)-3-(N-(5-(2-carboxy-1-((1-(2-methoxyethyl)-1H-1,2,3-triazol-4-yl)methoxy)-2-methylpropyl)-2-methylbenzyl)-N-(pyridin-2-ylmethyl)sulfamoyl)benzoic acid;

(R)-3-(N-benzyl-N-(5-(2-carboxy-1-((1-(2-methoxyethyl)-1H-1,2,3-triazol-4-yl)methoxy)-2-methylpropyl)-2-methylbenzyl)sulfamoyl)benzoic acid;

3-(N-benzyl-N-(5-(2-carboxy-1-((1-ethyl-1H-1,2,3-triazol-4-yl)methoxy)-2-methylpropyl)-2-methylbenzyl)sulfamoyl)benzoic acid;

3-(3-(((N-cyclohexyl-3-methoxyphenyl)sulfonamido)methyl)-4-methylphenyl)-3-((1-ethyl-1H-1,2,3-triazol-4-yl)methoxy)-2,2-dimethylpropanoic acid;

3-(3-(((N-cyclohexyl-4-methoxyphenyl)sulfonamido)methyl)-4-methylphenyl)-3-((1-ethyl-1H-1,2,3-triazol-4-yl)methoxy)-2,2-dimethylpropanoic acid;

3-(3-((N-cyclohexylphenylsulfonamido)methyl)-4-methylphenyl)-3-((1-ethyl-1H-1,2,3-triazol-4-yl)methoxy)-2,2-dimethylpropanoic acid;

3-(3-((N-benzylphenylsulfonamido)methyl)-4-methylphenyl)-3-((1-ethyl-1H-1,2,3-triazol-4-yl)methoxy)-2,2-dimethylpropanoic acid;

3-((1-(((1-Carbamoylpiperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

3-((1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid;

Rel-(R)-2,2-dimethyl-3-(4-methyl-3-(((S)-4-methyl-1,1-dioxido-4,5-dihydropyrido[4,3-f][1,2]thiazepin-2(3H)-yl)methyl)phenyl)-3-((1-(oxetan-3-yl)-1H-1,2,3-triazol-4-yl)methoxy)propanoic acid;

Rel-(S)-2,2-dimethyl-3-(4-methyl-3-(((S)-4-methyl-1,1-dioxido-4,5-dihydropyrido[4,3-f][1,2]thiazepin-2(3H)-yl)methyl)phenyl)-3-((1-(oxetan-3-yl)-1H-1,2,3-triazol-4-yl)methoxy)propanoic acid;

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(oxetan-3-yl)-1H-1,2,3-triazol-4-yl)methoxy)propanoic acid;

3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-((1-(oxetan-3-yl)-1H-1,2,3-triazol-4-yl)methoxy)propanoic acid;

3-(3-(((R)-4-ethyl-1,1-dioxido-3,4-dihydro-2H-benzo[b][1,4,5]oxathiazepin-2-yl)methyl)-4-methylphenyl)-3-((1-(2-methoxyethyl)-1H-1,2,3-triazol-4-yl)methoxy)-2,2-dimethylpropanoic acid;

3-(3-(((R)-4-ethyl-1,1-dioxido-3,4-dihydro-2H-benzo[b][1,4,5]oxathiazepin-2-yl)methyl)-4-methylphenyl)-3-((1-(2-(2-methoxyethoxy)ethyl)-1H-1,2,3-triazol-4-yl)methoxy)-2,2-dimethylpropanoic acid;

(R)-3-(3-(((R)-2-Ethyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)methoxy)propanoic acid hydrochloride;

(R)-3-(3-(((R)-2-isopropyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)methoxy)propanoic acid hydrochloride;

(R)-3-(3-(((R)-2-Ethyl-7-methyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)methoxy)propanoic acid trifluoroacetate;

(S)-methyl 3-(3-(((R)-2-ethyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)methoxy)propanoic acid, trifluoroacetate;

(S)-3-(3-(((R)-2-isopropyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)methoxy)propanoic acid, trifluoroacetate;

(R)-3-((1-Ethyl-1H-1,2,3-triazol-4-yl)methoxy)-3-(3-(((R)-2-ethyl-2,3-dihydropyrido[2,3-f][1,4]oxazepin-4(5H)-yl)methyl)-4-methylphenyl)-2,2-dimethylpropanoic acid, trifluoroacetate;

(S)-methyl 3-((1-ethyl-1H-1,2,3-triazol-4-yl)methoxy)-3-(3-(((R)-2-ethyl-2,3-dihydropyrido[2,3-f][1,4]oxazepin-4(5H)-yl)methyl)-4-methylphenyl)-2,2-dimethylpropanoic acid, trifluoroacetate;

(R)-methyl 3-((1-ethyl-1H-1,2,3-triazol-4-yl)methoxy)-3-(3-(((S)-6-ethyl-6,7-dihydro-5H-pyrido[2,3-c]azepin-8(9H)-yl)methyl)-4-methylphenyl)-2,2-dimethylpropanoic acid, trifluoroacetate;

(S)-methyl 3-((1-ethyl-1H-1,2,3-triazol-4-yl)methoxy)-3-(3-(((S)-6-ethyl-6,7-dihydro-5H-pyrido[2,3-c]azepin-8(9H)-yl)methyl)-4-methylphenyl)-2,2-dimethylpropanoic acid, trifluoroacetate;

(R)-methyl 3-((1-ethyl-1H-1,2,3-triazol-4-yl)methoxy)-3-(3-(((R)-2-ethyl-2,3-dihydrobenzo[f][1,4]oxazepin-4(5H)-yl)methyl)-4-methylphenyl)-2,2-dimethylpropanoic acid, trifluoroacetate;

(S)-methyl 3-((1-ethyl-1H-1,2,3-triazol-4-yl)methoxy)-3-(3-(((R)-2-ethyl-2,3-dihydrobenzo[f][1,4]oxazepin-4(5H)-yl)methyl)-4-methylphenyl)-2,2-dimethylpropanoic acid, trifluoroacetate;

(R)-3-(3-(((S)-4-Ethyl-1,1-dioxido-4,5-dihydrobenzo[f][1,2]thiazepin-2(3H)-yl)methyl)-4-methylphenyl)-2,2-dimethyl-3-((1-methyl-1H-1,2,3-triazol-4-yl)methoxy)propanoic acid;

(R)-3-(3-(((R)-4-Ethyl-1,1-dioxido-3,4-dihydro-2H-benzo[b][1,4,5]oxathiazepin-2-yl)methyl)-4-methylphenyl)-2,2-dimethyl-3-((1-methyl-1H-1,2,3-triazol-4-yl)methoxy)propanoic acid; and (R)-3-(3-(((R)-4-Ethyl-1,1-dioxido-3,4-dihydro-2H-pyrido[3,2-b][1,4,5]oxathiazepin-2-yl)methyl)-4-methylphenyl)-2,2-dimethyl-3-((1-methyl-1H-1,2,3-triazol-4-yl)methoxy)propanoic acid;

or a pharmaceutically acceptable salt thereof.

Additional compounds which fall within the scope of this invention are:

(R,rel-(3S,3'S))-3,3'-(((1,1'-(1,4-phenylenebis(methylene))bis(1H-1,2,3-triazole-4,1-diyl))bis(methylene))bis(oxy))bis(2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid);

(R)-3,3'-(((1,1'-(1,3-phenylenebis(methylene))bis(1H-1,2,3-triazole-4,1-diyl))bis(methylene))bis(oxy))bis(3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid);

(R)-3,3'-(((1,1'-(1,4-phenylenebis(methylene))bis(1H-1,2,3-triazole-4,1-diyl))bis(methylene))bis(oxy))bis(2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid);

(R,rel-(3R,3'R))-3,3'-(((1,1'-(1,4-phenylenebis(methylene))bis(1H-1,2,3-triazole-4,1-diyl))bis(methylene))bis(oxy))bis(2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid);

(R,rel-3S,rel-3'S)-3,3'-(((1,1'-(oxybis(ethane-2,1-diyl))bis(1H-1,2,3-triazole-4,1-diyl))bis(methylene))bis(oxy))bis(2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid); and (R,rel-3R,rel-3'R)-3,3'-(((1,1'-(oxybis(ethane-2,1-diyl))bis(1H-1,2,3-triazole-4,1-diyl))bis(methylene))bis(oxy))bis(2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid);

or a pharmaceutically acceptable salt thereof.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general Formula (I) and pharmaceutically acceptable derivatives and salts thereof may be accomplished as outlined below in Schemes 1-14. In the following description, the groups are as defined above for compounds of Formula (I) unless otherwise indicated. Abbreviations are as defined in the Examples section. Starting materials are commercially available or are made from commercially available starting materials using methods known to those skilled in the art.

Scheme 1

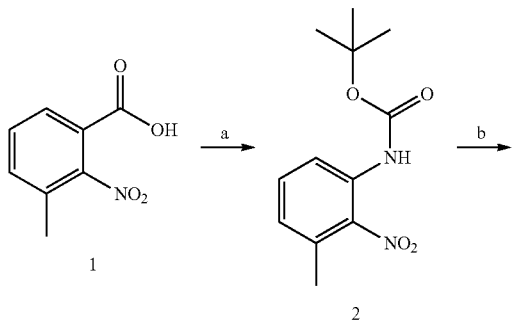

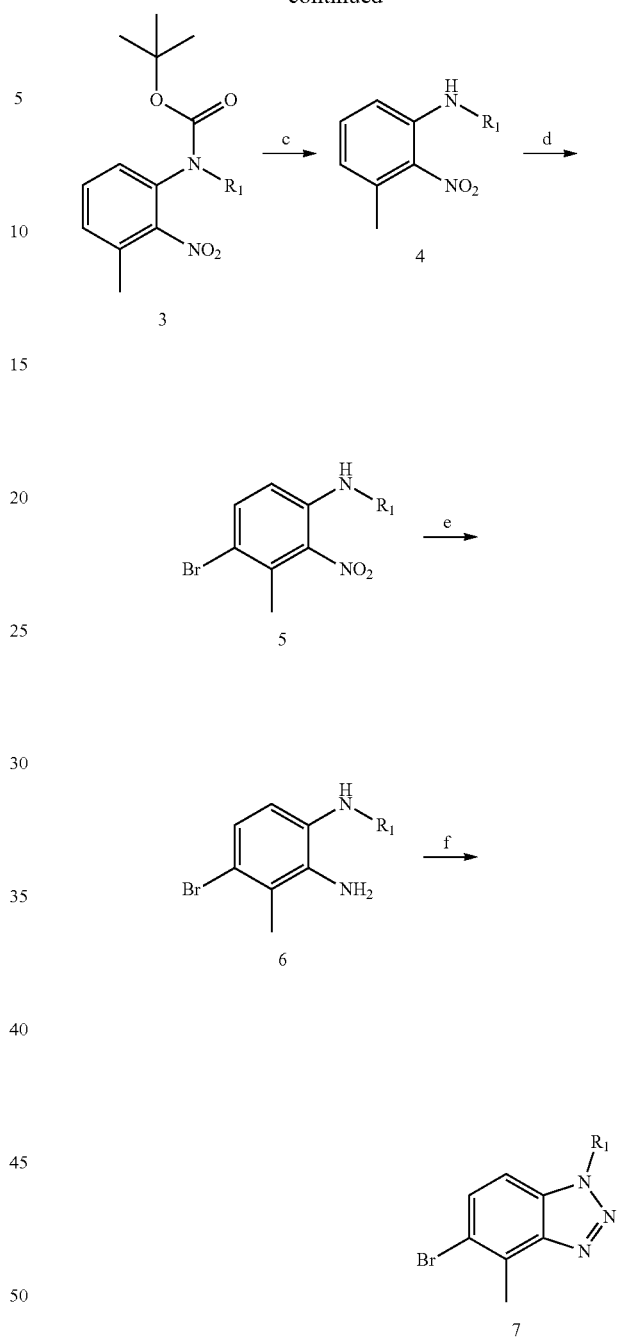

Conditions: a) DPPA, TEA, t-BuOH; b) NaH, R$_1$I, DMF; c) TFA, DCM; d) NBS, DMF; e) SnCl$_2$·2H$_2$O, EtOH; f) NaNO$_2$, H$_2$SO$_4$ Scheme 1 shows a general scheme for the preparation of triazole 7. In scheme 1, R$_1$ is C$_{1-3}$alkyl or —(CH$_2$)$_2$—O(CH$_2$)$_2$—OR$_4$. Starting with commercially available 3-methyl-2-nitrobenzoic acid, a Curtius rearrangement with DPPA provides intermediate 2. A skilled artisan will appreciate that compound 2 could be prepared from the appropriate aniline compound. Alkylation of the carbamate with an alkyl iodide provides intermediate 3. Deprotection of the amine with TFA and bromination with NBS provides intermediate 5. Reduction of the nitro to the aniline and diazotization and cyclization provides the required triazole 7.

Scheme 2

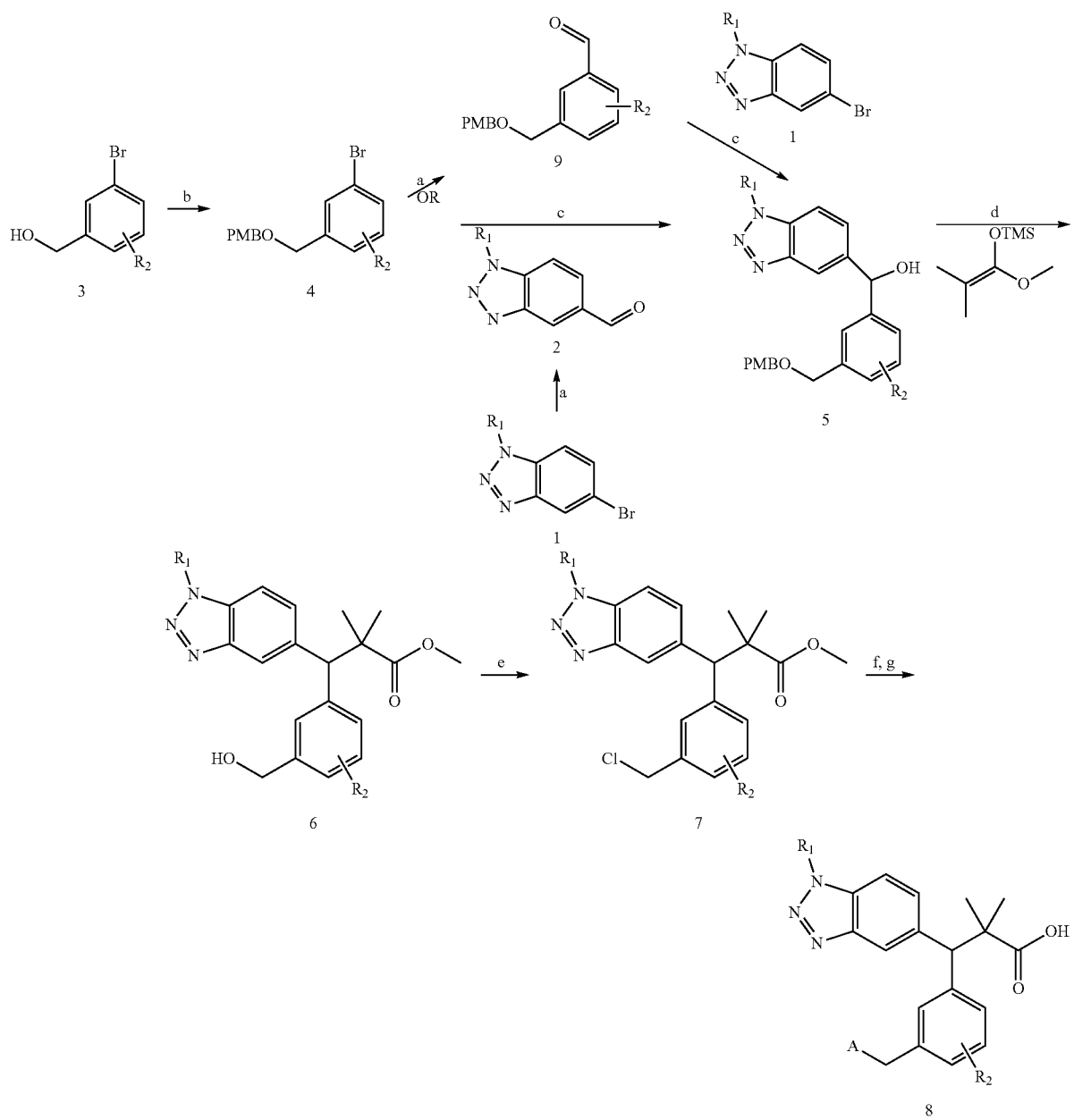

Conditions: a) n-BuLi, DMF, THF b) NaH, PMBCl, DMF c) t-BuLi or n-BuLi, THF d) TiCl$_4$, DCM (or) (i) DBU, Cl$_3$CCN, CH$_3$CN; ii) Tf$_2$NH, iii) DDQ, DCM/H$_2$O e) SO$_2$Cl, DCM f) R$_{13}$H, DIPEA, CH$_3$CN; (or) R$_{13}$H, NaH, DMF g) LiOH, MeOH, THF.

Scheme 2 represents a general scheme for the preparation of compounds according to Formula (I). In Scheme 2, R$_2$ and A are as defined previously. Triazole 1 is either commercially available or may be synthesized from readily available materials. Reaction conditions are as described above in the scheme; however, the skilled artisan will appreciate that certain modifications in the reaction conditions and/or reagents used are possible.

Treatment of triazole 1 with n-butyl lithium and DMF in presence of a suitable solvent produces the desired aldehyde product 2. The coupling partner for aldehyde 2 is obtained by first protecting the benzylic alcohol 3 as its para-methoxybenzylether. It will be appreciated that alternative protecting groups are possible. Coupling of the aldehyde 2 and bromide 4 can be accomplished via treatment of the bromide first with t-butyl lithium or n-butyl lithium followed by addition of the aldehyde. However, the skilled artisan will appreciate that other aldehydes, such as substituted phenyl aldehyde may also be applied. Intermediate alcohol 6, arises from treatment of alcohol 5 with the appropriate silylketene acetal in the presence of a Lewis acid or via one-pot brønsted base/brønsted acid system, followed by deprotection with DDQ. Benzylic alcohol 6 can be transformed to the requisite chloride 7 using thionyl chloride. Completion of the synthesis can be accomplished by displacement of chloride, following by hydrolysis of the ester to produce 8

It will be also be appreciated by the skilled artisan that intermediate 5 may be prepared by coupling bromide 1 with aldehyde 9.

Scheme 3

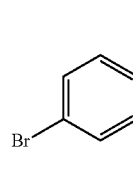
1

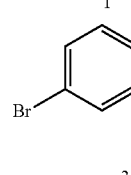
2

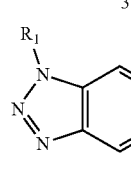
3

4

5

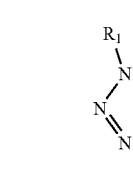
6

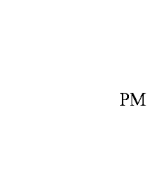
7

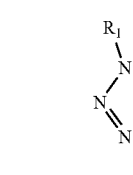
8

-continued

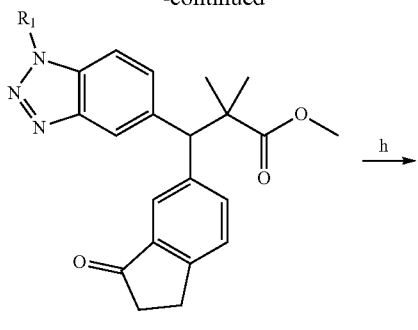
9

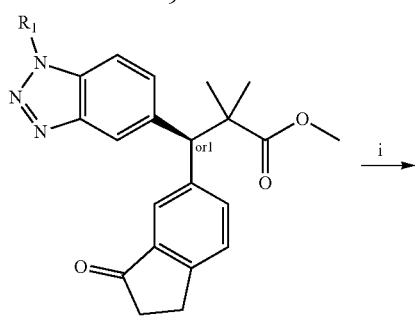
10

11

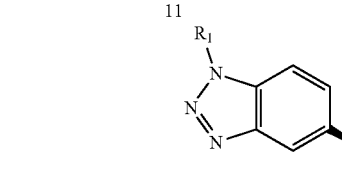
12

Conditions: a) NaBH$_4$, MeOH, THF; b) PMBCl, NaH; c) n-BuLi, DMF; d) t-BuLi, 4, THF; e) (i) Cl$_3$CCN, DBU, acetonitrile; (ii) Tf$_2$NH, Me$_2$C=C(OR$^2$)OTMS, acetonitrile; f) DDQ; g) Dess-Martin periodinane, DCM; h) Chiral SFC; (i) NaBH$_4$, MeOH; j) (i) SOCl$_2$, DCM; (ii) A, K$_2$CO$_3$, NaI, acetonitrile; k (iii) NaOH, MeOH/H$_2$O Scheme 3 represents a general scheme for the preparation of compounds according to Formula (I). In Scheme 2, R$_2$ and A are as defined previously. 6-Bromo-2,3-dihydro-1H-inden-1-one 1 is commercially available. Triazole 5 is either commercially available or may be synthesized from readily available materials. Reaction conditions are as described above in the scheme; however, the skilled artisan will appreciate that certain modifications in the reaction conditions and/or reagents used are possible.

Starting with commercially available indanone 1, reduction with NaBH₄ produces desired alcohol intermediate 2. Intermediate 2 hydroxyl group may be protected as the PMB ether by treating with NaH and PMBCl to give intermediate 3. It will be appreciated by the skilled artisan that the protecting group may vary and is not limited to PMB. Further transformation of intermediate 3 to the requisite aldehyde by treatment with butyl lithium and DMF yields desired intermediate 4. Coupling of 4 and 5 is accomplished by treatment of 5 with t-butyl lithium and intermediate 4 to form alcohol 6. Alcohol 6 was coverted to 7 by first treating with Cl₃CCN and DBU followed by the requisite, commercially available silyl ketene acetal in the presence of Tf₂NH. The deprotection of intermediate 7 with DDQ formed intermediate 8. Oxidation of 8 with Dess-Martin periodinane to give alcohol 9, and then resolved by Chiral SFC to give single enantiomerically pure isomer 10. Intermediate 10 was reduced with NaBH4 to alcohol 11. The intermediate 11 was first treated with SOCl₂ followed by lactam A and K₂CO₃, NaI before hydrolysis with NaOH to form racemic acid, which then followed by chiral SFC to give the desired acid as single isomer 12.

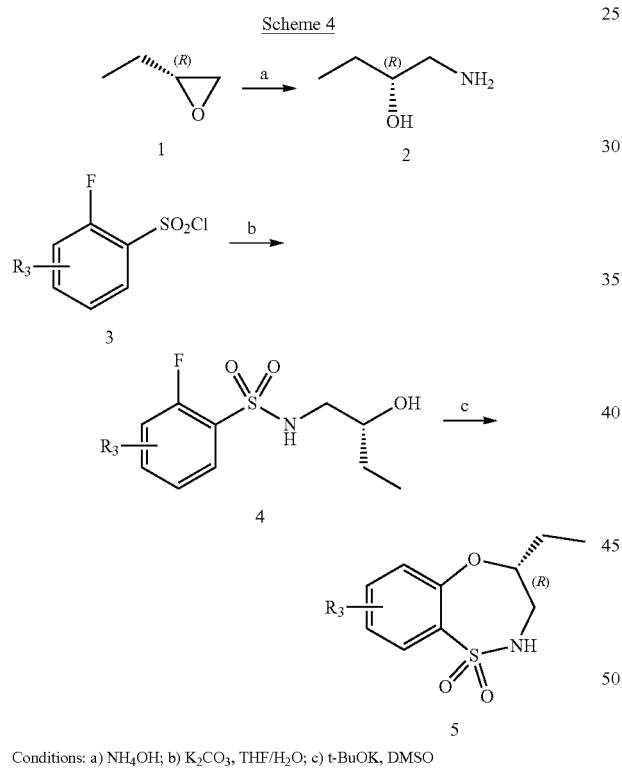

Conditions: a) NH₄OH; b) K₂CO₃, THF/H₂O; c) t-BuOK, DMSO

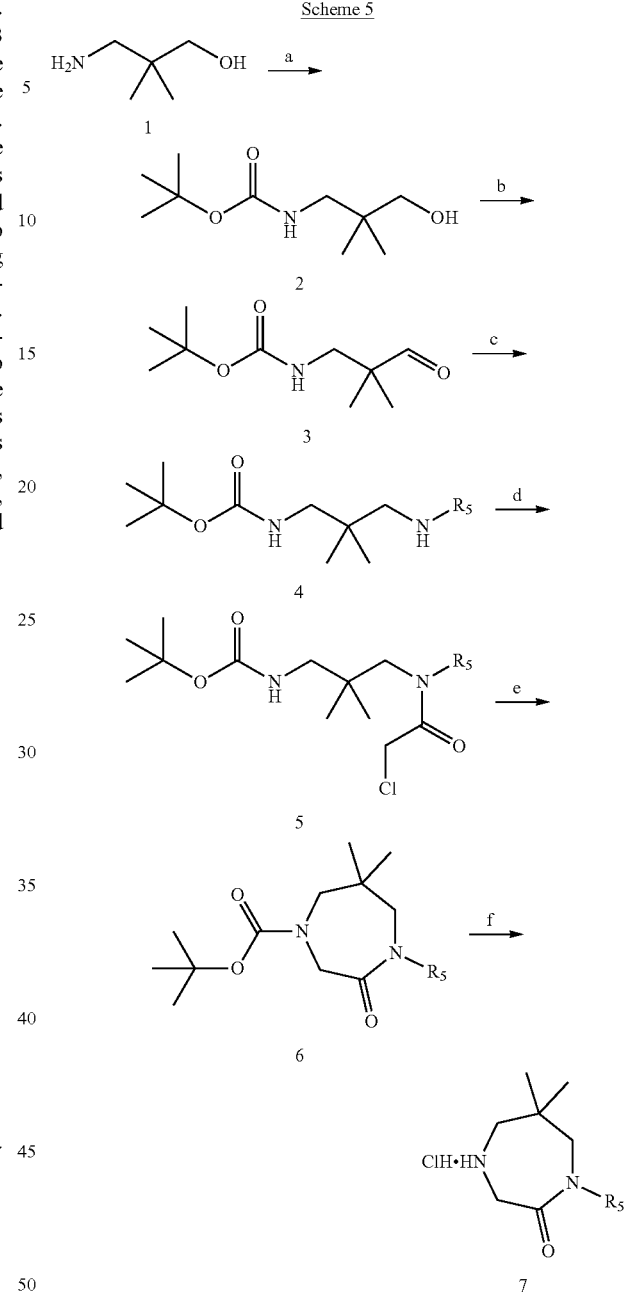

Conditions: a) (Boc)₂O, DCM b) TEMPO, KBr, NaHCO₃, NaOCl, DCM C) amine, NaCNBH₃, ACOH, MeOH d) Et₃N, 2-chloroacetyl chloride, DCM e) NaH, DMF f) HCl, dioxane, DCM Scheme 4 represents a general scheme for the preparation of sulfonamide 5. In this, (R)-2-ethyloxirane and substituted 2-fluorobenzene-1-sulfonyl chloride depicted as starting material are commercially available. Reaction conditions are as described above in the scheme; however, the skilled artisan will appreciate that certain modifications in the reaction conditions and/or reagents used are possible. Epoxide ring opening of (R)-2-ethyloxirane yields a single enantiomerically pure 2. Sulfonamide formation under basic condition with appropriate amino alcohol to give intermediate 4, followed by displacement of fluoride 3 with potassium tert-butoxide provides the required intermediate 5.

Scheme 5 represents a general scheme for the preparation of compounds according to Formula (I). 3-Amino-2,2-dimethylpropan-1-ol 1 is commercially available. Reaction conditions are as described above in the scheme; however, the skilled artisan will appreciate that certain modifications in the reaction conditions and/or reagents used are possible.

Protection of amine 1 as its Boc carbamate followed by oxidation of the alcohol to the aldehyde with TEMPO gives intermediate 3. Reductive amination with an appropriate amine yields compound 4. Compound 4 was reacted with 2-chloroacetyl chloride in the presence of triethylamine to give compound 5. Cyclization was successful with NaH to give lactam 6. Removing the Boc group with HCl gives lactam 7 as the hydrochloride salt.

Scheme 6

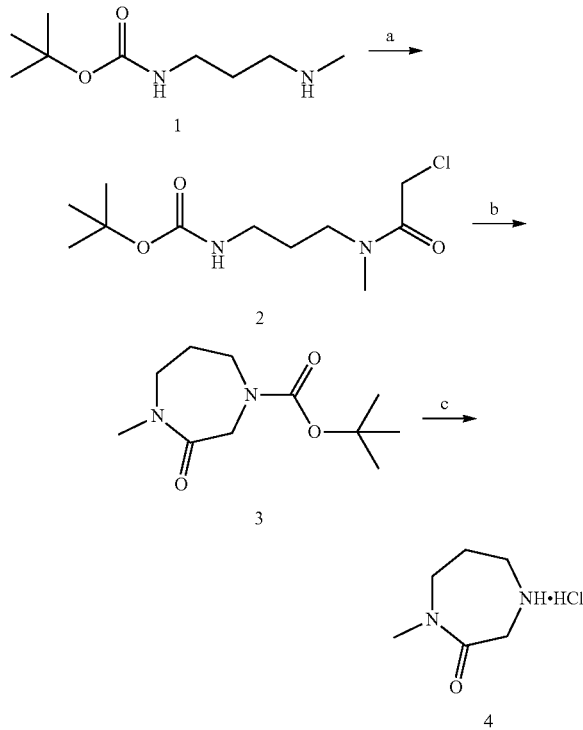

Conditions: a) Et₃N, 2-chloroacetyl chloride, THF b) NaH, DMF c) HCl, dioxane, DCM Scheme 6 represents a general scheme for the preparation of compounds 1-methyl-1,4-diazepan-2-one hydrochloride. tert-Butyl (3-(methylamino)propyl)carbamate 1 is commercially available. Reaction conditions are as described above in the scheme; however, the skilled artisan will appreciate that certain modifications in the reaction conditions and/or reagents used are possible. Alkylation of commercially available starting material 1 with 2-chloroacetyl chloride in the presence of triethylamine produces compound 2. Cyclization using NaH as base gives lactam 3. Deprotection the Boc group with HCl furnishes lactam 4 as the hydrochloride salt.

Scheme 7

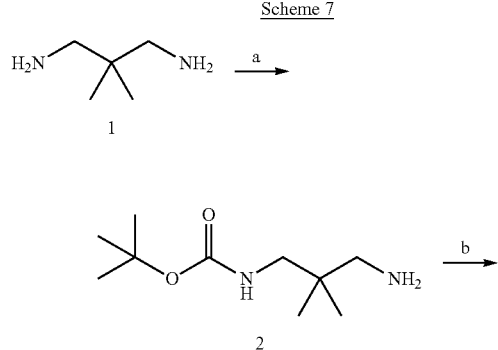

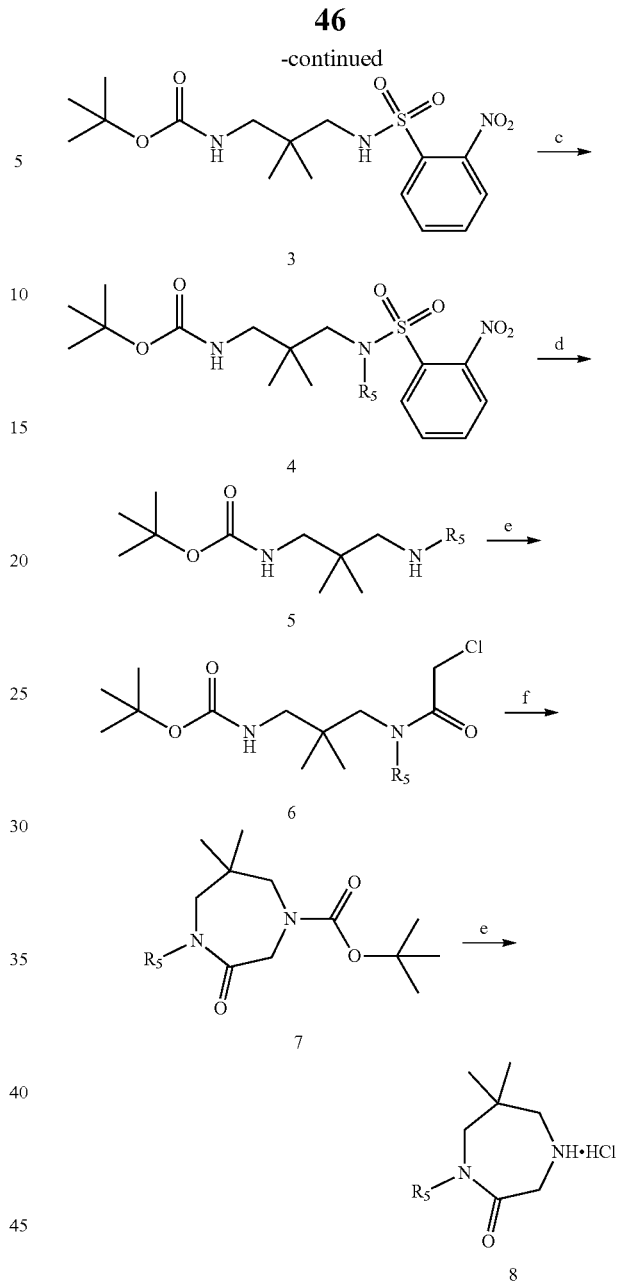

Conditions: a) (Boc)₂O, DCM; b) K₂CO₃, 2-nitrobenzene-1-sulfonyl chloride, DCM; c) R₅I, K₂CO₃, DMF, 90° C.; d) PhSH, K₂CO₃, DMF; e) Et₃N, 2-chloroacetyl chloride, DCM; f) NaH, DMF; g) HCl, dioxane, DCM Scheme 7 represents a general scheme for the preparation of compounds according to Formula (I). 2,2-Dimethylpropane-1,3-diamine 1 is commercially available. Reaction conditions are as described above in the scheme; however, the skilled artisan will appreciate that certain modifications in the reaction conditions and/or reagents used are possible. Protection of mono-amine 1 as its Boc carbamate followed by sulfonamide formation with 2-nitrobenzene-1-sulfonyl chloride under basic conditions provides compound 3. Treatment of compound 3 with an appropriate available alkyl iodide at high temperature provides compound 4, followed by deprotection to give amine 5. Compound 5 was reacted with 2-chloroacetyl chloride in the presence of triethylamine to furnish compound 6. Cyclization was successful with NaH to give lactam 7 which can be subsequently deprotected HCl to give lactam 8 as the hydrochloride salt.

Scheme 8

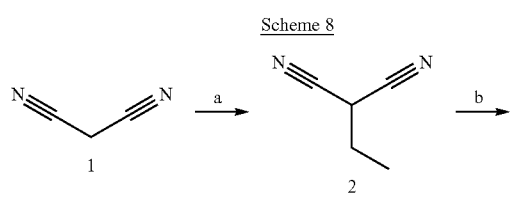

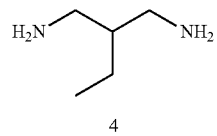

Conditions: a) iodoethane, tetrabutylammonium bromide, K₂CO₃; b) Raney-Ni, Boc anhydride, MeOH; c) HCl, dioxane, DCM

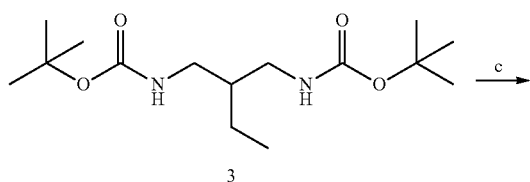

Scheme 8 represents a general scheme for the preparation of 6-Ethyl-1-methyl-1,4-diazepan-2-one hydrochloride. Malononitrile 1 is commercially available. Reaction conditions are as described above in the scheme; however, the skilled artisan will appreciate that certain modifications in the reaction conditions and/or reagents used are possible. Treatment of malononitrile with iodoethane under basic conditions gives compound 2. Hydrogenation followed by Boc protection to aid in purification produces compound 3. Removal of the Boc groups with HCl provides diamine 4 as hydrochloride salt. Following the same sequence as Scheme 8 above the lactam 6-ethyl-1-methyl-1,4-diazepan-2-one hydrochloride can be produced.

Scheme 9

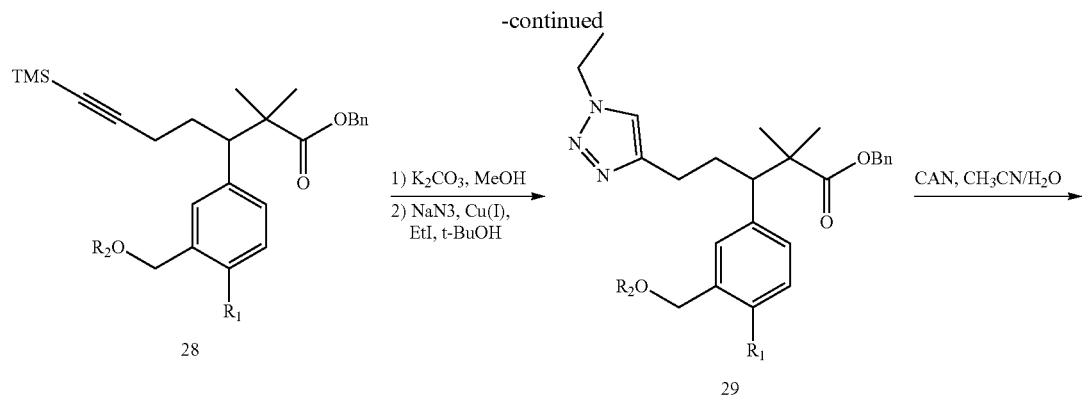

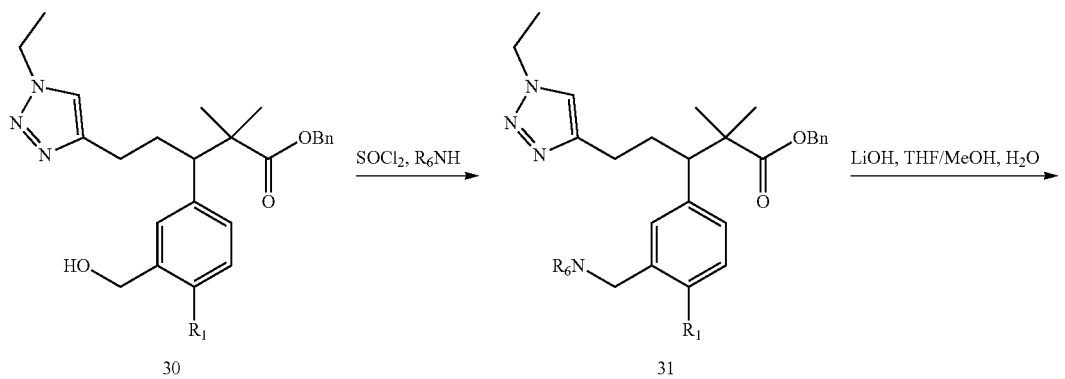

Scheme 9 represents a general scheme for the preparation of compounds according to Formula (I). $R_1$ $R_2$, and $R_6$ are as previously defined. The commercially available carboxylic acid 33 is reduced with a suitable reducing agent like $BH_3.Me_2S$ to provide the intermediate 22. Intermediate 23 is prepared by alkylation of 22 using a strong base and a suitable protecting group as defined for $R_2$. Intermediate 26 is prepared by the oxidation of the aceylenic alcohol with Dess-Martin periodinane in DCM. One skilled in the art could also envisage using other suitable alcohol oxidation methods to perform this conversion. A metal halogen exchange reaction is then performed on 23, after which, aldehyde 26 is added to provide the secondary benzylic alcohol 24. Conversion of the benzylic alcohol 26 to bromide 27 is achieved using triphenylphosphine and a bromide source such as carbontetrabromide. The reaction of 27 with enolates such as that derived from iso-butyates affords the sterically hindered esters 28. The use of an additive such as 1,3-dimethyl-3,4,5,6-tetrahydro-2(1H)-pyrimidinone (DMPU) may improve the effectiveness of this reaction. The dialkylated ester 28 containing the TMS protected acetylene can be de-silylated with aqueous potassium carbonate and subjected to a click reaction using sodium azide and ethyl iodide with a copper catalyst to afford the triazoles such as 29. The protected benzyl alcohol can be deprotected with ceric ammonium nitrate to provide 30. One skilled in the art could also envisage using other suitable oxidative or acidic methods to perform this reaction. The benzylic chloride, 31, is prepared by the activation of the benzylic alcohol using a chlorinating reagent like thionyl chloride. The subsequent displacement of the chloride with a suitable electrophile such as a secondary amine or a sulfonamide affords 32.

Scheme 10

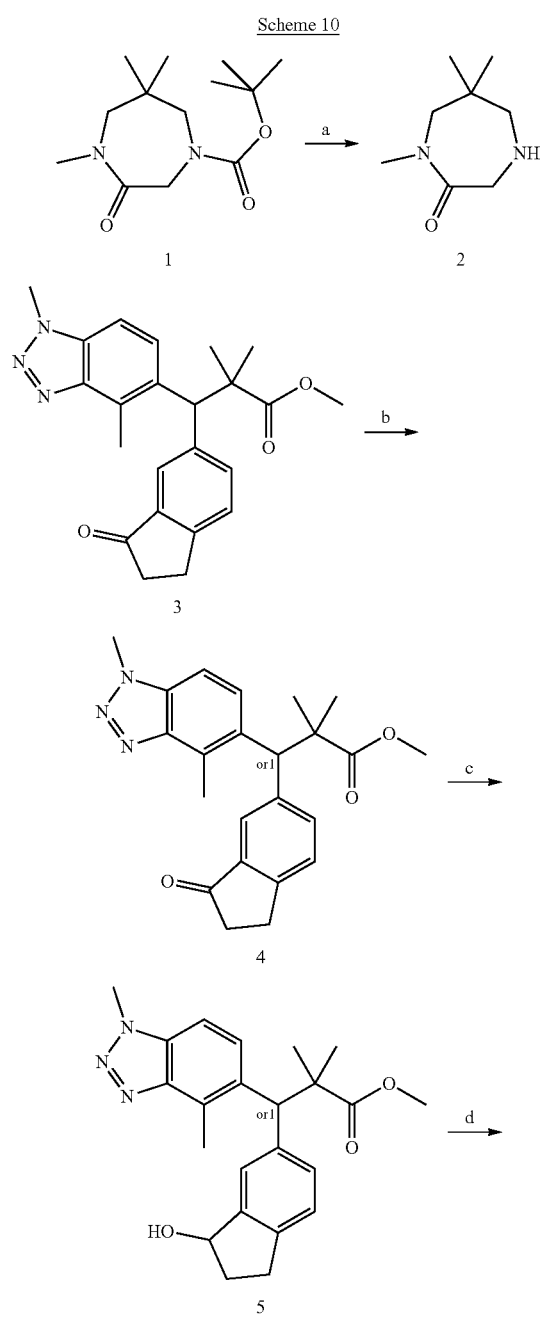

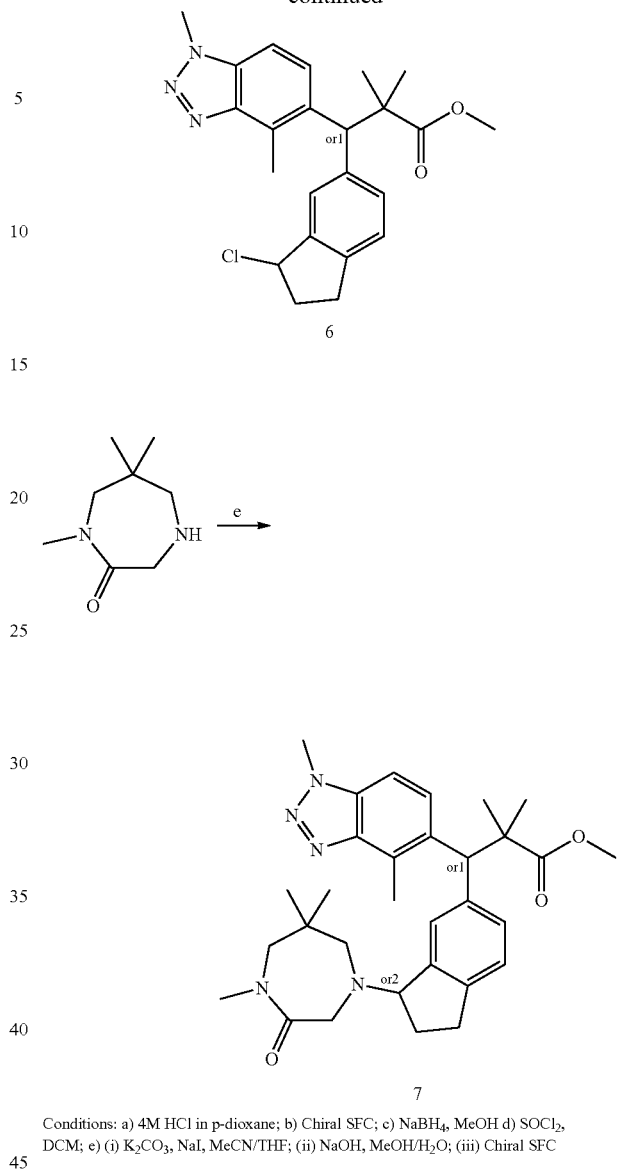

Conditions: a) 4M HCl in p-dioxane; b) Chiral SFC; c) NaBH₄, MeOH d) SOCl₂, DCM; e) (i) K₂CO₃, NaI, MeCN/THF; (ii) NaOH, MeOH/H₂O; (iii) Chiral SFC Scheme 10 represents a general scheme for the preparation of compounds according to Formula I. Starting material 1 and 3 are synthesized according to scheme 6 and scheme 3 respectively. Reaction conditions are as described above in the scheme; however, the skilled artisan will appreciate that certain modifications in the reaction conditions and/or reagents used are possible. Treatment of Boc protected lactam amine 1 with 4 M HCl in p-dioxane gave the corresponding amine HCl salt 2. The racemic bisaryl indanone 3 was chirally separated with chiral SFC gave both enantiomers 4. Each enantiomer 4 was treated with NaBH₄ to give hydroxyindane 5 which was further treated with SOCl₂ to give corresponding chloride 6. This bisaryl indane chloride 6 reacted with the above lactam amine 2 and K₂CO₃, NaI in MeCN/THF gave corresponding lactam amine substituted bisaryl indane ester. Further hydrolysis of the ester with NaOH in MeOH/H₂O followed by chiral SFC separation gave desired product 7.

Scheme 11

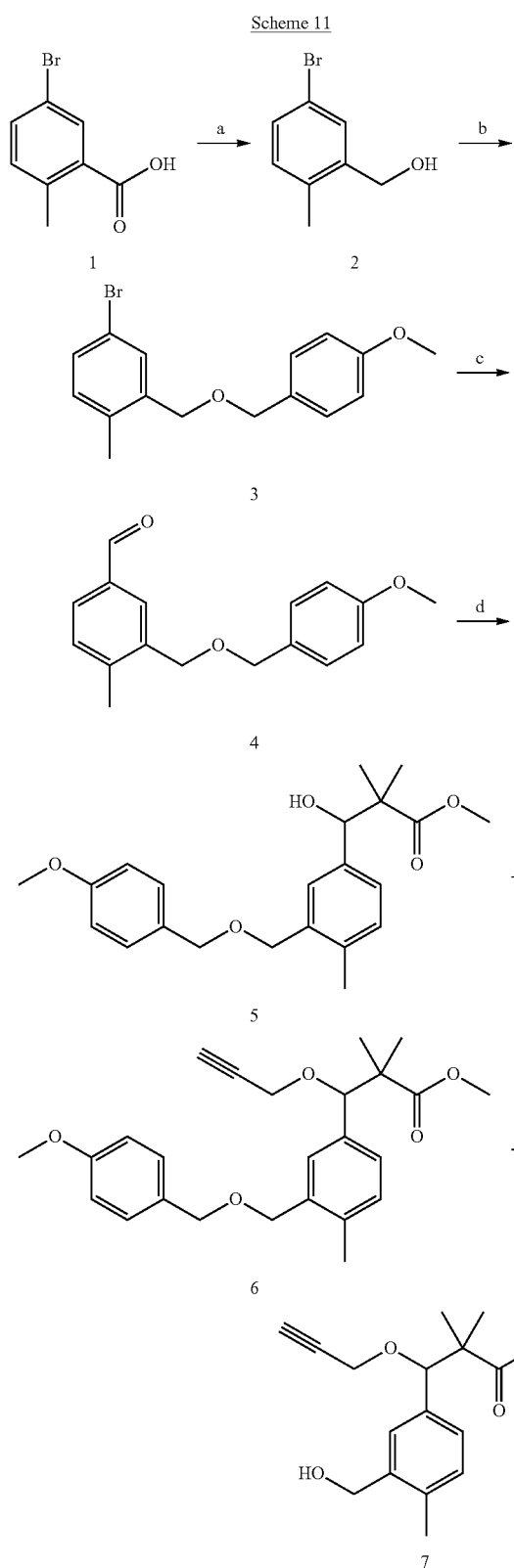

Conditions: a) BH₃—Me₂S, THF; b) NaH, DMF, PMB—Cl; c) nBuLi, THF, DMF; d) (i) 1-methylimidazole, ((1-methoxy-2-methylprop-1-en-1-yl)oxy)trimethylsilane, LiCl, DMF, (ii) NaOH, KHF₂, H₂O, HCl; e) 3-bromoprop-1-yne, NaH, DMF; f) DDQ, DCM/H₂O Scheme 11 represents a general scheme for the preparation of compounds according to Formula I. Reaction conditions are as described above in the scheme; however, the skilled artisan will appreciate that certain modifications in the reaction conditions and/or reagents used are possible. Carboxylic acid 1 can be reduced to the benzyl alcohol in THF using a solution of borane-methyl sulfide complex to provide 2. Alkylation of the alcohol using a strong base and a suitable protecting group provides intermediate 3. Formylation of the bromide using n-butyl lithium and DMF affords 4. Intermediate 5, arises from treatment of aldehyde 4 with the appropriate silylketene acetal in the presence of lithium chloride. Intermediate 6 can be prepared by treatment of the alcohol with an strong base, like sodium hydride, followed by addition of 3-bromoprop-1-yne. Deprotection of the benzyl alcohol can be achieved using an oxidative reagent such as DDQ to provide 7.

Scheme 12

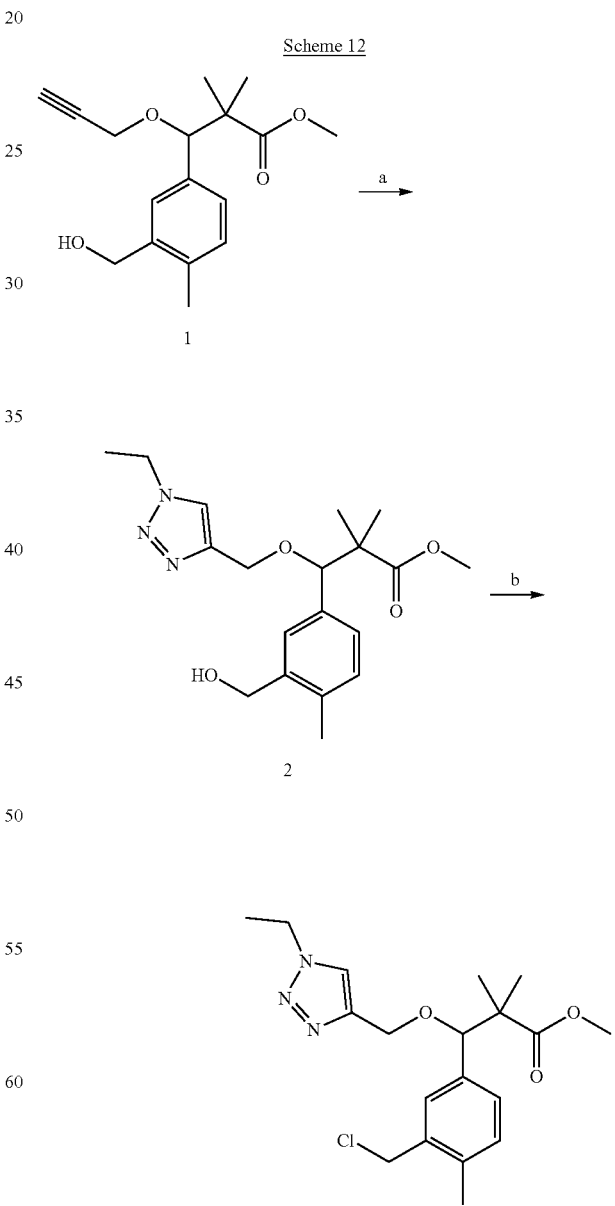

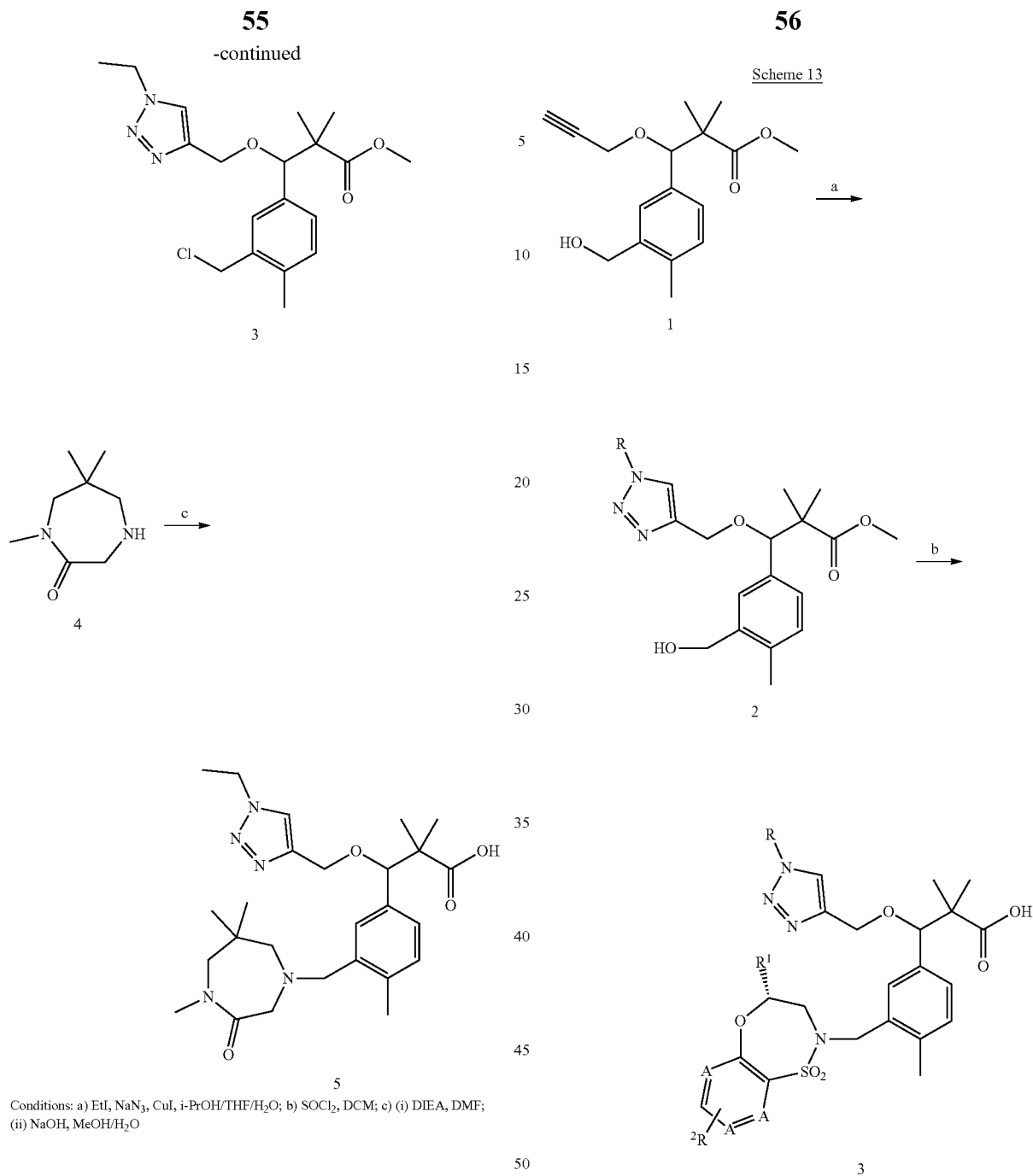

Conditions: a) EtI, NaN₃, CuI, i-PrOH/THF/H₂O; b) SOCl₂, DCM; c) (i) DIEA, DMF; (ii) NaOH, MeOH/H₂O Scheme 12 represents a general scheme for the preparation of compounds according to Formula I. In Scheme 13, $R_2$, $R_6$ and A are as defined previously. Starting material 1 and 4 are synthesized according to scheme and scheme 6 respectively. Reaction conditions are as described above in the scheme; however, the skilled artisan will appreciate that certain modifications in the reaction conditions and/or reagents used are possible. Application of click chemistry on starting material ether linked alkyne 1 with EtI, NaN₃, CuI, DIEA in i-PrOH/THF/H₂O gave the corresponding ether linked triazole 2. This ether linked triazole benzyl alcohol 2 was treated with SOCl₂ to give corresponding benzyl chloride 3. The benzyl chloride 3 reacted with the lactam amine 4 and DIEA in DMF gave corresponding lactam amine substituted ether linked bisaryl ester. Further hydrolysis of this ester with NaOH in MeOH/H₂O gave desired product 5.

Conditions: a) RI or RBr, NaN₃, CuI, DIEA, i-PrOH/THF/H₂O; b) (i) cyclic sulfonamide, PS-PPh₃, DIAD, THF; (ii) NaOH, MeOH/H₂O Scheme 13 represents a general scheme for the preparation of compounds according to Formula (I). Reaction conditions are as described above in the scheme; however, the skilled artisan will appreciate that certain modifications in the reaction conditions and/or reagents used are possible.

Ether linked alkyne intermediate 1 was treated with the appropriate alkyl iodide or alkyl bromide, NaN₃, CuI, DIEA in i-PrOH/(THF/)H₂O to give triazole intermediate 2. Intermediate 2 was then treated with the appropriate cyclic sulfonamide under Mitsunobu reaction conditions followed by hydrolysis with NaOH in MeOH/H₂O to give desired product 3.

Scheme 14

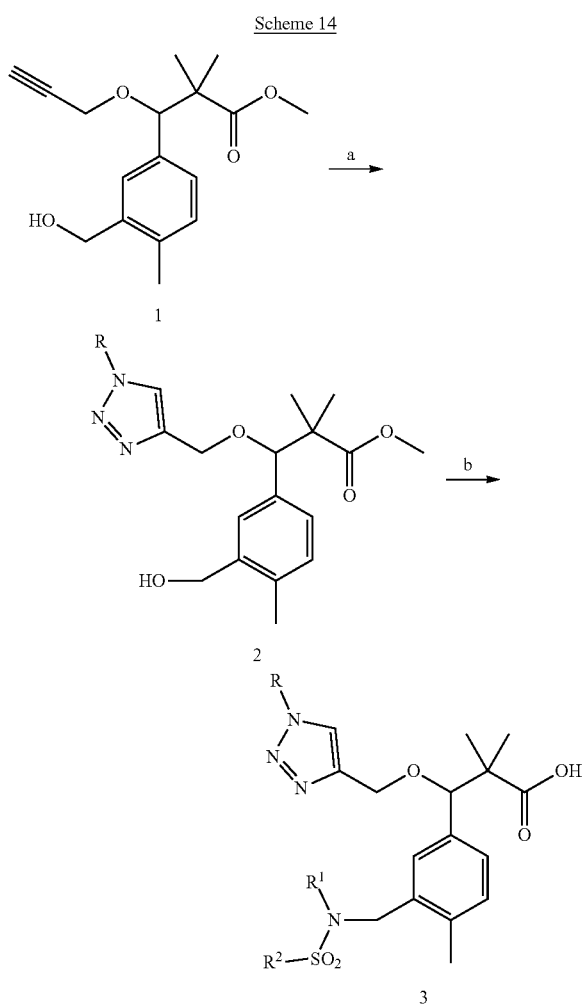

Conditions: a) RI or RBr, NaN₃, CuI, DIEA, i-PrOH/THF/H₂O; b) (i) SOCl₂, DCM; (ii) R¹NH₂, DIEA, MeCN/THF; (iii) R²SO₂Cl, DIEA, MeCN; (iv) NaOH, MeOH/H₂O Scheme 14 represents a general scheme for the preparation of compounds according to Formula (I). Reaction conditions are as described above in the scheme; however, the skilled artisan will appreciate that certain modifications in the reaction conditions and/or reagents used are possible.

Ether linked alkyne intermediate 1 was treated with the appropriate alkyl iodide or alkyl bromide, NaN$_3$, CuI, DIEA in i-PrOH/THF/H$_2$O to give triazole intermediate 2. Intermediate 2 was then treated with SOCl$_2$ in DCM to convert benzyl alcohol into benzyl chloride. The substitution of benzyl chloride with amine RNH$_2$ together with DIEA in MeCN followed by reaction with R²SO$_2$Cl and DIEA then followed by hydrolysis with NaOH in MeOH/H$_2$O gives the desired product 3.

Biological Activity

As stated above, the compounds according to Formula I are NRF2 activators, and are useful in the treatment or prevention of human diseases that exhibit oxidative stress components such as respiratory and non-respiratory disorders, including COPD, asthma, ALI, ARDS, fibrosis, chronic and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Nonalcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

The biological activity of the compounds according to Formula I can be determined using any suitable assay for determining the activity of a candidate compound as a Nrf2 activator, as well as tissue and in vivo models.

The biological activity of the compounds of Formula (I) are demonstrated by the following tests.

BEAS-2B NQO1 MTT Assay

NAD(P)H:quinone oxidoreductase 1 (NQO1), also called DT diaphorase, is a homodimeric FAD-containing enzyme that catalyzes obligatory NAD(P)H-dependent two-electron reductions of quinones and protects cells against the toxic and neoplastic effects of free radicals and reactive oxygen species arising from one-electron reductions. The transcription of NQO1 is finely regulated by NRF2, and thus NQO1 activity is a good marker for NRF2 activation. On day one, frozen BEAS-2B cells (ATCC) were thawed in a water bath, counted, and re-suspended at a concentration of 250,000 cells/mL. Fifty microliters of cells were plated in 384 well black clear-bottomed plates. Plates were incubated at 37° C., 5% CO$_2$ overnight. On day two, plates were centrifuged and 50 nL of compound or controls were added to the cells. Plates were then incubated at 37° C., 5% CO$_2$ for 48 hours. On day four, medium was aspirated from the plate and crude cell lysates were made by adding 13 uL of 1× Cell Signaling Technologies lysis buffer with 1 Complete, Mini, EDTA-free Protease Inhibitor Tablet (Roche) for each 10 mL of lysis buffer. After lysis plates were incubated for 20 minutes at room temperature. Two microliters of lysate were removed for use in Cell Titer Glo assay (Promega) and MTT cocktail was prepared (Prochaska et. al. 1998) for measurement of NQO1 activity. Fifty microliters of MTT cocktail was added to each well, plate was centrifuged, and analyzed on an Envision plate reader (Perkin Elmer) using Absorbance 570 nm label for 30 minutes. Product formation was measured kinetically and the pEC$_{50}$ of NQO1 specific activity induction was calculated by plotting the change in absorbance (Delta OD/min) versus the log of compound concentration followed by 3-parameter fitting.

pEC$_{50}$ is the negative log of the EC$_{50}$.

All examples described herein possessed NQO1 specific enzyme activity in BEAS-2B cells with EC$_{50}$s between >10 μM-<1 nM unless otherwise noted (see table below). EC$_{50}$s<1 nM (+++++), EC$_{50}$s 1 nM-10 nM (++++), EC$_{50}$s 10 nM-100 nM (+++), EC$_{50}$s 100 nM-1 uM (++), EC$_{50}$s 1 uM-10 uM (+); EC$_{50}$s>10 uM (−), or were not determined (ND).

| Ex # | EC$_{50}$ |
| --- | --- |
| *1 | +++++ |
| 2 | ++ |
| *3 | +++++ |
| *4 | +++++ |
| 5 | +++++ |
| 6 | ++++ |
| 7 | +++++ |
| *8 | ++++ |
| 9 | ++++ |
| *10 | +++++ |
| 11 | ++++ |
| 12 | ++++ |
| 13 | ++++ |
| 14 | ++++ |
| 15 | +++ |
| 16 | +++ |
| 17 | ++++ |
| 18 | ++++ |
| 19 | ++++ |
| 20 | ++++ |
| 21 | ++ |
| 22 | ++++ |
| 23 | +++ |
| 24 | +++ |
| 25 | +++ |
| 26 | +++ |
| 27 | ++++ |
| 28 | +++ |
| 29 | +++ |
| 30 | ++++ |
| 31 | +++ |
| 32 | +++ |
| 33 | +++ |
| 34 | +++ |
| 35 | ++ |
| 36 | +++ |
| 37 | ++++ |
| 38 | +++ |
| 39 | +++ |
| 40 | ++ |
| *41 | +++ |
| 42 | +++ |
| 43 | ++ |
| 44 | ++ |
| 45 | ++ |
| 46 | +++ |
| 47 | +++ |
| 48 | +++ |
| 49 | ++ |
| 50 | +++ |
| 51 | + |
| 52 | ++ |
| 53 | ++ |
| 54 | ++ |
| 55 | ++ |
| 56 | + |
| 57 | ++ |
| 58 | ++ |
| 59 | + |
| 60 | ++ |
| 61 | +++++ |
| 62 | +++++ |
| 63 | + |
| 64 | ++ |
| 65 | ++ |
| 66 | ++ |
| 67 | ++ |
| 68 | +++ |
| 69 | +++ |
| 70 | +++ |
| 71 | +++ |
| 72 | +++ |
| 73 | +++ |
| 74 | +++ |
| 75 | ++++ |
| 76 | ++++ |
| 77 | ++++ |
| 78 | ++++ |
| 79 | ++++ |
| 80 | ++++ |
| 81 | ++++ |
| 82 | ++++ |
| 83 | +++++ |
| 84 | +++++ |
| 85 | +++++ |
| 86 | +++++ |
| 87 | +++++ |
| 88 | +++++ |
| 89 | +++++ |
| 90 | +++++ |
| 91 | + |
| 92 | + |
| 93 | ++ |
| 94 | ++ |
| 95 | ++ |
| 96 | ++ |
| 97 | ++ |
| 98 | +++ |
| 99 | +++ |
| 100 | ++ |
| 101 | +++ |
| 102 | +++ |
| 103 | ++++ |
| 104 | +++ |
| 105 | ++++ |
| 106 | +++++ |
| 107 | +++++ |
| 108 | +++ |
| 109 | +++ |
| 110 | ++++ |
| 111 | ++ |
| 112 | +++ |
| 113 | +++ |
| 114 | ++ |
| 115 | ++++ |
| 116 | +++ |
| 117 | +++ |
| 118 | + |
| 119 | +++++ |
| 120 | +++++ |
| 121 | ++++ |

*in some determinations EC$_{50}$ values were <170 pM

Methods of Use

The compounds of the invention are NRF2 activators, and are useful in the treatment or prevention of respiratory and non-respiratory disorders, including COPD, asthma, ALI, ARDS, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

Accordingly, in another aspect the invention is directed to methods of treating such conditions.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, optic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per day. Preferred dosages are 1-500 mg once daily, more preferred is 1-100 mg per person per day. IV dosages range form 0.1-000 mg/day, preferred is 0.1-500 mg/day, and more preferred is 0.1-100 mg/day. Inhaled daily dosages range from 10 ug-10 mg/day, with preferred 10 ug-2 mg/day, and more preferred 50 uug-500 ug/day.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company) *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In another aspect, the invention is directed to a dosage form adapted for administration to a patient parenterally including subcutaneous, intramuscular, intravenous or intradermal. Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder compositions for use in accordance with the present invention are administered via inhalation devices. As an example, such devices can encompass capsules and cartridges of for example gelatin, or blisters of, for example, laminated aluminum foil. In various embodiments, each capsule, cartridge or blister may contain doses of composition according to the teachings presented herein. Examples of inhalation devices can include those intended for unit dose or multi-dose delivery of composition, including all of the devices set forth herein. As an example, in the case of multi-dose delivery, the formulation can be pre-metered (e.g., as in Diskus®, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g., as in Turbuhaler, see EP 69715, or in the devices described in U.S. Pat. No. 6,321,747). An example of a unit-dose device is Rotahaler (see GB 2064336). In one embodiment, the Diskus® inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additive taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder composition may also be presented in an inhalation device which permits separate containment of two different components of the composition. Thus, for example, these components are administrable simultaneously but are stored separately, e.g., in separate pharmaceutical compositions, for example as described in WO 03/061743 A1 WO 2007/012871 A1 and/or WO2007/068896, as well as U.S. Pat. Nos. 8,113,199, 8,161,968, 8,511,304, 8,534,281, 8,746,242 and 9,333,310.

In one embodiment an inhalation device permitting separate containment of components is an inhaler device having two peelable blister strips, each strip containing pre-metered doses in blister pockets arranged along its length, e.g., multiple containers within each blister strip, e.g., as found in ELLIPTA®. Said device has an internal indexing mechanism which, each time the device is actuated, peels opens a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUGHALER™ of Innovata. In addition, various structures of inhalation devices provide for the sequential or separate delivery of the pharmaceutical composition(s) from the device, in addition to simultaneous delivery.

Aerosols may be formed by suspending or dissolving a compound of the invention in a liquefied propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g., ethanol, isopropyl alcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compounds of Formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

Suitably, for the treatment of asthma, compounds or pharmaceutical formulations of the invention may be administered together with an anti-inflammatory agent such as, for example, a corticosteroid, or a pharmaceutical formulation thereof. For example, a compound of the invention may be formulated together with an anti-inflammatory agent, such as a corticosteroid, in a single formulation, such as a dry powder formulation for inhalation. Alternatively, a pharmaceutical formulation comprising a compound of the invention may be administered in conjunction with a pharmaceutical formulation comprising an anti-inflammatory agent, such as a corticosteroid, either simultaneously or sequentially. In one embodiment, a pharmaceutical formulation comprising a compound of the invention and a pharmaceutical formulation comprising an anti-inflammatory agent, such as a corticosteroid, may each be held in device suitable for the simultaneous administration of both formulations via inhalation.

Suitable corticosteroids for administration together with a compound of the invention include, but are not limited to, fluticasone furoate, fluticasone propionate, beclomethasone diproprionate, budesonide, ciclesonide, mometasone furoate, triamcinolone, flunisolide and prednisilone. In one embodiment of the invention a corticosteroids for administration together with a compound of the invention via inhalation includes fluticasone furoate, fluticasone propionate, beclomethasone diproprionate, budesonide, ciclesonide, mometasone furoate, and, flunisolide.

Suitably, for the treatment of COPD, compounds or pharmaceutical formulations of the invention may be administered together with one or more bronchodilators, or pharmaceutical formulations thereof. For example, a compound of the invention may be formulated together with one or more bronchodilators in a single formulation, such as a dry powder formulation for inhalation. Alternatively, a pharmaceutical formulation comprising a compound of the invention may be administered in conjunction with a pharmaceutical formulation comprising one or more bronchodilators, either simultaneously or sequentially. In a further alternative, a formulation comprising a compound of the invention and a bronchodilator may be administered in conjunction with a pharmaceutical formulation comprising a further bronchodilator. In one embodiment, a pharmaceutical formulation comprising a compound of the invention and a pharmaceutical formulation comprising one or more bronchodilators may each be held in device suitable for the simultaneous administration of both formulations via inhalation. In a further embodiment, a pharmaceutical formulation comprising a compound of the invention together with a bronchodilator and a pharmaceutical formulation comprising a further bronchodilator may each be held in one or more devices suitable for the simultaneous administration of both formulations via inhalation.

Suitable bronchodilators for administration together with a compound of the invention include, but are not limited to, $\beta_2$-adrenoreceptor agonists and anticholinergic agents. Examples of $\beta_2$-adrenoreceptor agonists, include, for example, vilanterol, salmeterol, salbutamol, formoterol, salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt of salbutamol or the fumarate salt of formoterol. Suitable anticholinergic agents include umeclidinium (for example, as the bromide), ipratropium (for example, as the bromide), oxitropium (for example, as the bromide) and tiotropium (for example, as the bromide). In one embodiment of the invention, a compound of the invention may be administered together with a $\beta_2$-adrenoreceptor agonist, such as vilanterol, and an anticholinergic agent, such as, umeclidinium.

The compounds may also be used in combination with agents for aiding transplantation including Cyclosporines, Tacrolimus, Mycophenolate mofetil, Prednisone, Azathioprine, Sirolimus, Daclizumab, Basiliximab and OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics and insulin.

The compounds may be used in combination with antihypertensives such as diuretics, ACE inhibitors, ARBS, calcium channel blockers, and beta blockers.

One embodiment of the invention encompasses combinations comprising one or two other therapeutic agents. It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of the invention together with another therapeutically active agent.

EXAMPLES

The following examples illustrate the invention. These examples are not intended to limit the scope of the present invention, but rather to provide guidance to the skilled artisan to prepare and use the compounds, compositions, and methods of the present invention.

While particular embodiments of the present invention are described, the skilled artisan will appreciate that various changes and modifications can be made without departing from the spirit and scope of the invention.

All temperatures are given in degrees Celsius, all solvents are highest available purity and all reactions run under anhydrous conditions in an argon (Ar) or nitrogen ($N_2$) atmosphere where necessary.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. The CombiFlash® system used for purification in this application was purchased from Isco, Inc. CombiFlash® purification was carried out using prepacked silica gel columns, a detector with UV wavelength at 254 nm and a variety of solvents or solvent combinations.

Preparative HPLC was performed using a Gilson Preparative System with variable wavelength UV detection or an Agilent Mass Directed AutoPrep (MDAP) system with both mass and variable wavelength UV detection or Waters Preparative System with UV/PDA detection or an Shimadzu PREP LC 20AP. A variety of reverse phase columns, e.g., Luna 5m C18(2) 100A, SunFire C18, XBridge C18, Atlantics T3 were used in the purification with the choice of column support dependent upon the conditions used in the purification. The compounds are eluted using a gradient of $CH_3CN$ and water. Neutral conditions used an $CH_3CN$ and water gradient with no additional modifier, acidic conditions used an acid modifier, 0.1% TFA (added to both the $CH_3CN$ and water) or 0.1% formic acid and basic conditions used a basic modifier, 0.1% $NH_4OH$ (added to the water) or 10 mM ammonium bicarbonate.

Analytical HPLC was run using an Agilent system, Shimadzu/Sciex LCMS with variable wavelength UV detection using reverse phase chromatography with a $CH_3CN$ and water gradient with a 0.02 or 0.1% TFA modifier (added to each solvent). LC-MS was determined using either a PE Sciex Single Quadrupole 150EX LC-MS, or Waters ZQ Single Quadrupole LC-MS or Agilent 1200 series SL (dectectors: Agilent 6140 single quadrupole and Agilent 1200 MWD SL) instruments. The compound is analyzed using a reverse phase column, e.g., Thermo Hypersil Gold C18, eluted using a gradient of $CH_3CN$ and water with a low percentage of an acid modifier such as 0.02% TFA or 0.1% formic acid or a base modifier such as 5 mM ammonium bicarbonate (adjusted to pH 10 with aqueous ammonia). When specified "acid method" refers to 0.1% formic acid in water and $CH_3CN$ gradient (1.8 min. 0.9 mL/min flow) with a Waters Acquity UPLC HSS C18; 1.8µ; 2.1×50 mm at 50° C.; "basic method" refers to 95:5 $H_2O+0.1\%$ $NH_4OH$:$CH_3CN$ (pH=9.4) and water gradient (1.8 min. 0.9 mL/min flow) with a Waters Acquity UPLC BEH C18; 1.7µ; 2.1×50 mm at 50° C. and "overnight basic method" refers to 95:5 $H_2O+0.1\%$ $NH_4OH$:$CH_3CN$ (pH=9.4) and water gradient (16 min. 0.8 mL/min flow) with a Waters Acquity UPLC BEH C18; 1.7µ; 2.1×50 mm at 50° C.

Preparative Chiral SFC was performed using a Thar/Waters Preparative SFC System with single wavelength UV detection system or PDA detector. A variety of chiral SFC columns, e.g. Chiralpak IA, IC, AY, AD. OD, OJ, C2 were used in the purification. The compounds are eluted using supercritical fluid $CO_2$ and co-solvents, such as MeOH, EtOH, IPA, and combination of these solvent in different ratio based on the compound selectivity. Modifiers (0.1% of TFA, $NH_4OH$, DEA) would be used as needed.

Analytical Chiral SFC was run using a Thar/Waters SFC system with variable wavelength UV detection or PDA detector. A variety of chiral SFC columns, e.g. Chiralpak IA, IB, IC, ID, AY, AD, AS, CCL4 were used in the purification. The compounds are eluted using supercritical fluid $CO_2$ and co-solvents, such as MeOH, EtOH, IPA, and combination of these solvent in different ratio based on the compound selectivity. Modifiers (0.1% of TFA, $NH_4OH$, DEA) would be used as needed.

Celite® is a filter aid composed of acid-washed diatomaceous silica, and is a registered trademark of Manville Corp., Denver, Colo. Isolute® is a functionalized silica gel based sorbent, and is a registered trademark of Biotage AB Corp., Sweden.

Nuclear magnetic resonance spectra were recorded at 400 MHz using a Bruker AVANCE 400 or Brucker DPX400 or Varian MR400 400 MHz spectrometer. $CDCl_3$ is deuteriochloroform, DMSO-$D_6$ is hexadeuteriodimethylsulfoxide, and MeOD is tetradeuteriomethanol, $CD_2Cl_2$ is deuteriodichloromethane. Chemical shifts are reported in parts per million (δ) downfield from the internal standard tetramethylsilane (TMS) or calibrated to the residual proton signal in the NMR solvent (e.g., $CHCl_3$ in $CDCl_3$). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

Heating of reaction mixtures with microwave irradiations was carried out on a Biotage Initiator® or CEM microwave reactor, typically employing the high absorbance setting.

Cartridges or columns containing polymer based functional groups (acid, base, metal chelators, etc) can be used as part of compound workup. The "amine" columns or cartridges are used to neutralize or basify acidic reaction mixtures or products. These include $NH_2$ Aminopropyl SPE-ed SPE Cartridges available from Applied Separations and diethylamino SPE cartridges available from United Chemical Technologies, Inc.

Table of Abbreviations

[Rh(cod)Cl]$_2$ or [RhCl(cod)]$_2$: di-µ-chlorido-bis[$\eta^2,\eta^2$-(cycloocta-1,5-diene)rhodium
®T3P: 2,4,6-tripropyl-1,3,5,2,4,6-trioxatriphosphorinane 2,4,6-trioxide
∟ C: degree Celsius
AcOH: acetic acid
ADDP: (E)-diazene-1,2-diylbis(piperidin-1-ylmethanone)
aq = aqueous
BINAP: 2,2'-bis(diphenylphosphino)-1,1'-binaphthalene
CDI: Carbonyl dimidazole
$CH_2Cl_2$: dichloromethane
$CH_3CN$: acetonitrile
$CHCl_3$: chloroform
$Cs_2CO_3$: cesium carbonate
DBU: 1,8-diazabicyclo[5.4.0]undec-7-ene
DCE: dichloroethane
DCM: dichloromethane
DIPEA or DIEA: diisopropylethyl amine
DME: dimethyl ether
DMF: N,N-dimethylformamide
DMF—DMA or DMF-dimethyl acetal: N,N-dimethylformaide-dimethyl acetal
DMSO: dimethyl sulfoxide
EDC: 1-ethyl-3-(3-dimethylaminopropyl)carbodiimide
$Et_2O$: diethyl ether
$Et_3N$: triethylamine
EtOAc: ethyl acetate
EtOH: ethanol
g: gram(s)
h: hour(s)
HATU: O-(7-azabenzotriazol-1-yl)-N,N,N',N'-tetramethyluronium hexafluorophosphate
HBTU: N,N,N',N'-tetramethyl-O-(1H-benzotriazol-1-yl)uronium hexafluorophosphate
HCl: hydrochloric acid
HOAt: 1-hydroxy-7-azabenzotriazole
HPLC: high performance liquid chromatography
IPA: isopropyl alcohol
$K_2CO_3$: potassium carbonate
KOAc: potassium acetate
LAH: lithium aluminum hydride
LC: liquid chromatography
LC-MS: liquid chromatography-mass spectroscopy
$LiBH_4$: lithium borohydride
LiHMDS: lithium hexamethyldisilazane
LiOH: lithium hydroxide
M: molar
MeCN: acetonitrile
MeI: methyl iodide
MeOH: methanol
mg: milligram(s)
$MgCl_2$: magnesium chloride
$MgSO_4$: magnesium sulfate
MHz: megahertz
min: minute(s)
mL: milliliter(s)
mmol: millimole(s)
MS: mass spectroscopy
$N_2$: nitrogen gas
$Na_2CO_3$: sodium carbonate
$Na_2SO_4$: sodium sulfate

Table of Abbreviations

NaBH$_3$CN or NaCNBH$_3$: sodium cyanoborohydride
NaCl: sodium chloride
NaH: sodium hydride
NaHCO$_3$: sodium bicarbonate
NaHMDS: sodium hexamethyldisilazane
NaHSO$_4$: sodium bisulfate
NaOAc: sodium acetate
NaOH: sodium hydroxide
NBS: N-bromosuccinimide
nBuLi: n-butyl lithium
NH$_4$Cl: ammonium chloride
NMR: nuclear magnetic resonance
P(tBu)$_3$: tri-t-butyl phosphine
Pd(PhP$_3$)$_4$: tetrakistriphenylphosphine palladium
Pd/C: pallidium on carbon
Pd$_2$(dba)$_3$: tris(dibenzylideneacetone)-dipalladium(0)
PdCl$_2$(dppf) or Pd(dppf)Cl$_2$: [1,1'-bis(diphenylphosphino)-ferrocene]dichloropalladium(II)
Petrol: petroleum ether
PS-PPh$_3$: polymer supported triphenylphosphine
PtO$_2$: platinum(IV) oxide
RT: room temperature
T3P: 2,4,6-tripropyl-1,3,5,2,4,6-trioxatriphosphorinane-2,4,6-trioxide solution
TEA: triethylamine
TFA: trifluoroacetic acid
TFFH: tetrafluoroformamidinium hexafluorophosphate
THF: tetrahydrofuran
triflic anhydride: trifluoromethanesulfonic anhydride
TsOH: p-toluenesulfonic acid
wt %: weight percent Intermediates Intermediate 1: 2-Fluoro-N-(2-hydroxy-2-methyl-propyl)benzenesulfonamide

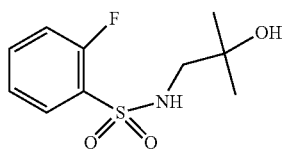 [SMILES: CC(C)(O)CNS(=O)(=O)c1ccccc1F]

To a solution of 2-fluorobenzene-1-sulfonyl chloride (15 g, 77 mmol) in tetrahydrofuran (THF) (300 mL) at 0° C. was added potassium carbonate (13.85 g, 100 mmol), water (110 mL) and 1-amino-2-methylpropan-2-ol (6.87 g, 77 mmol) and was stirred for 4 h at 25° C. The reaction mixture was quenched with ice cold water (200 mL) and extracted with ethyl acetate (2×200 mL), washed with brine (100 mL) then concentrated to provide the title compound as a white solid. (17 g, 67.9 mmol, 88% yield). LCMS m/z 248.2 (M+H)+, 1.678 min (ret.time).

Intermediate 2: 4,4-Dimethyl-3,4-dihydro-2Hbenzo[b][1,4,5]oxathiazepine 1,1-dioxide

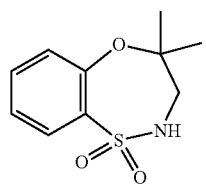

To a solution of 2-fluoro-N-(2-hydroxy-2-methylpropyl)benzenesulfonamide (10 g, 40.4 mmol) in dimethyl sulfoxide (DMSO) (100 mL) was added potassium tert-butoxide (13.61 g, 121 mmol) at 10° C. then heated to 90° C. for 4 hr in a sealed tube. The reaction mixture was cooled to ambient temperature and poured into ice water (100 mL), then extracted with ethyl acetate (2×200 mL) and concentrated to give the crude compound. The crude residue was purified by flash column chromatography using EtOAc:Hexane (4:6) as solvent, to provide the title compound. (5 g, 21.92 mmol, 54.2% yield). LCMS m/z 228 (M+H)+, 1.73 min (ret.time).

Intermediate 3: 2-Chloropyridine-3-sulfonyl chloride

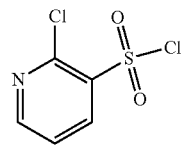 [SMILES: O=S(=O)(Cl)c1cccnc1Cl]

Step A: Thionyl chloride (159 mL, 2178 mmol) was added drop wise over 60 min to water (450 mL) at 0° C. The solution was allowed to stirred at ambient temperature for 17 h then copper(I) chloride (0.554 g, 5.60 mmol) was added to the mixture at −3° C. and the resulting yellow green solution was stirred for 1 hour at −3° C.

Step B: 37% HCl (503 mL, 6129 mmol) was added with vigorous stirring to 2-chloropyridin-3-amine (40 g, 311 mmol) at −5° C. and a solution of sodium nitrite (37.8 g, 548 mmol) in water (82 mL) was added drop wise over 45 min, the temperature of the reaction mixture was maintained at −5° C. and stirred for 10 min.

Step C: The mixture obtained from step B was added to the solution obtained from step A over 30 min at −3° C. The reaction mixture was maintained at 0° C. for 75 min with vigorous stirring. The solid was filtered and dried to give the title compound (20 g, 92 mmol, 29.5% yield) as brown color solid. LCMS m/z 212.02 (M+H)+, 2.058 min (ret. time)

Intermediate 4:
2-Chloro-N-(2-methylallyl)pyridine-3-sulfonamide

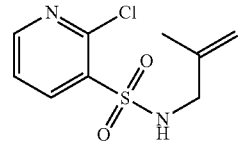

To a solution of 2-chloropyridine-3-sulfonyl chloride (20 g, 94 mmol) in dichloromethane (DCM) (200 mL) was added 2-methylprop-2-en-1-amine (7.38 g, 104 mmol) and TEA (26.3 mL, 189 mmol). It was stirred for 1 h at ambient temperature. The reaction mixture was quenched with water (100 mL) and extracted with DCM (3×80 mL). The combined organic layer was washed with brine solution (80 mL), dried over anhydrous Na$_2$SO$_4$, filtered and concentrated. The crude residue was purified by column chromatography eluting with 25% ethyl acetate in n-hexane. Desired fractions were concentrated to give the title compound (16 g, 63.5 mmol, 67.4% yield). LCMS m/z 246.97 (M+H)+, 1.800 min (ret. time)

Intermediate 5: 4-Methyl-2,3,4,5-tetrahydropyrido[2,3-f][1,2]thiazepine 1,1-dioxide

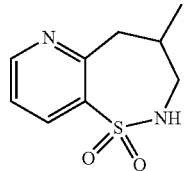

To a solution of 2-chloro-N-(2-methylallyl)pyridine-3-sulfonamide (15 g, 60.8 mmol) in toluene (150 mL) was added AIBN (1.997 g, 12.16 mmol) and heated to 75° C. then tri-n-butyltin hydride (48.7 mL, 182 mmol) was added and the reaction mixture was heated to 110° C. for 20 h. The reaction mixture was concentrated. The residue was diluted with ethyl acetate (200 mL), water was added and extracted. The organic layer was washed with brine solution (80 mL), dried over anhydrous $Na_2SO_4$, filtered and concentrated. The crude residue was purified by column chromatography eluting with 25% ethyl acetate in n-hexane. Desired fractions were concentrated to give the title compound (4.27 g, 19.80 mmol, 32.6% yield) LCMS m/z 213.07 $(M+H)^+$, 1.372 min (ret. time)

Intermediate 6: (S)-4-Methyl-2,3,4,5-tetrahydropyrido[2,3-f][1,2]thiazepine 1,1-dioxide and

Intermediate 7: (R)-4-methyl-2,3,4,5-tetrahydropyrido[2,3-f][1,2]thiazepine 1,1-dioxide

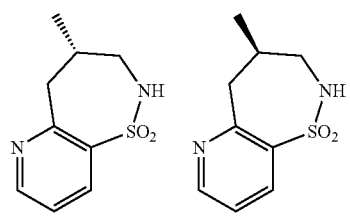

4-methyl-2,3,4,5-tetrahydropyrido[2,3-f][1,2]thiazepine 1,1-dioxide (4.27 g, 20.12 mmol) was resolved by Chiral SFC (Column: Chiralpak IC 20×150 mm, 5u; co-solvent: 20% IPA; flowrate: 50 g/min; Back pressure: 100Bar) to give (S)-4-methyl-2,3,4,5-tetrahydropyrido[2,3-f][1,2]thiazepine 1,1-dioxide (1.96 g, 9.23 mmol, 45.9% yield) LC-MS m/z 213.0 $(M+H)^+$, 0.43 min (ret. time) (chiral SFC ret. time: 2.95 min) and (R)-4-methyl-2,3,4,5-tetrahydropyrido[2,3-f][1,2]thiazepine 1,1-dioxide (1.96 g, 9.23 mmol, 45.9% yield) LC-MS m/z 213.0 $(M+H)^+$, 0.44 min (ret. time) (chiral SFC ret. time: 4.09 min)

Intermediate 8: 2-Bromo-N-(2-methylallyl)benzenesulfonamide

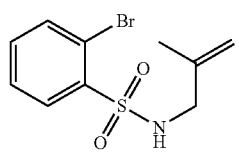

To a solution of 2-bromobenzene-1-sulfonyl chloride (25 g, 98 mmol) in dichloromethane (DCM) (250 mL) at 0° C. was added TEA (13.64 mL, 98 mmol) and 2-methylprop-2-en-1-amine (6.96 g, 98 mmol) and stirred for 10 min. The reaction was then stirred at ambient temperature for 16 h. The reaction mixture was quenched with ice cold water and extracted with DCM (2×200 mL). The combined organic layer was washed with ice cold water (2×100 mL), washed with brine solution (100 mL), and dried over anhydrous $Na_2SO_4$, filtered and concentrated to give the title compound (20 g, 68.3 mmol, 69.8% yield). LC-MS m/z 289.81 $(M+H)^+$, 2.20 min (ret. time).

Intermediate 9: 4-Methyl-2,3,4,5-tetrahydrobenzo[f][1,2]thiazepine 1,1-dioxide

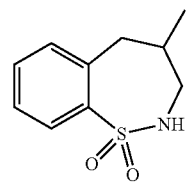

To a solution of 2-bromo-N-(2-methylallyl)benzenesulfonamide (16 g, 55.1 mmol) in toluene (160 mL) at ambient temperature was added AIBN (1.811 g, 11.03 mmol). The reaction mixture was heated to 75° C. and tri-n-butyltin hydride (29.4 mL, 110 mmol) was added. It was heated at 110° C. for 18 h. The reaction mixture was cooled to ambient temperature and diluted with ice water (500 mL) and extracted with EtOAc (2×300 mL). The combined organic layer was washed with chilled brine solution (200 mL) and dried over anhydrous $Na_2SO_4$, filtered and concentrated. The crude residue was purified by flash column chromatography eluting with 15% ethyl acetate in hexane. Desired fractions were concentrated to give the title compound (8.51 g, 39.9 mmol, 72.3% yield) as a white solid. LC-MS m/z 211.11 $(M+H)^+$, 1.826 min (ret. time).

Intermediate 10: (S)-4-Methyl-2,3,4,5-tetrahydrobenzo[f][1,2]thiazepine 1,1-dioxide and

Intermediate 11: (R)-4-methyl-2,3,4,5-tetrahydrobenzo[f][1,2]thiazepine 1,1-dioxide

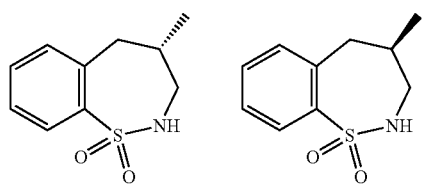

4-Methyl-2,3,4,5-tetrahydrobenzo[f][1,2]thiazepine 1,1-dioxide (4000 mg, 18.93 mmol) was resolved by Chiral SFC (Column: Chiralpak AY 20×250 mm, 5u; co-solvent: 20% EtOH; Flow rate: 50 mg/min; Back pressure: 100Bar) to give (S)-4-methyl-2,3,4,5-tetrahydrobenzo[f][1,2]thiazepine 1,1-dioxide (2.2996 g, 10.88 mmol, 57.5% yield) (chiral SFC ret. time: 1.85 min) LC-MS m/z 211.9 $(M+H)^+$, 0.72 min (ret. time) and (R)-4-methyl-2,3,4,5-tetrahydrobenzo[f][1,2]thiazepine 1,1-dioxide (2.2195 g, 10.50 mmol, 55.5% yield) (chiral SFC ret. time: 2.5 min) LC-MS m/z 211.9 (M+H)⁺, 0.72 min (ret. time).

Intermediate 12: 2-Bromo-5-fluoro-N-(2-methylallyl)benzenesulfonamide

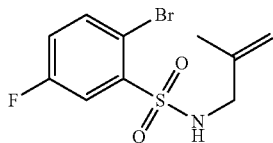

To a solution of 2,5-dibromobenzene-1-sulfonyl chloride (25 g, 74.8 mmol) in dichloromethane (250 mL) 2-methylprop-2-en-1-amine (5.32 g, 74.8 mmol) and TEA (10.42 mL, 74.8 mmol) was added at 0° C. and stirred for 10 min. The reaction was then stirred at ambient temperature for 16 h. The reaction mixture was quenched with ice cold water (50 mL) and extracted with DCM (2×100 mL). The combined organic layers were washed with ice cold water (2×50 mL), washed with brine (50 mL), dried over anhydrous Na$_2$SO$_4$ and concentrated under reduced pressure to afford the title compound (20 g, 44.3 mmol, 59.3% yield), LCMS m/z 308 (M+H)⁺, 2.23 min (ret. time).

Intermediate 13: 8-Fluoro-4-methyl-2,3,4,5-tetrahydrobenzo[f][1,2]thiazepine 1,1-dioxide

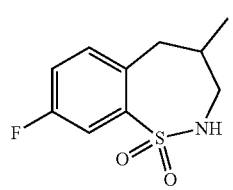

To a solution of 2-bromo-5-fluoro-N-(2-methylallyl)benzenesulfonamide (6.5 g, 20.04 mmol) in toluene (50 mL) was added AIBN (0.617 g, 3.75 mmol) at ambient temperature. The reaction mixture was heated to 75° C. and tri-n-butyltin hydride (7.52 mL, 28.2 mmol) was added and stirred at 110° C. for 18 h. The reaction mixture was quenched with ice cold water (40 mL) and extracted with ethyl acetate (2×50 mL). The combined organic layers were washed with ice cold water (2×50 mL), brine (50 mL) and dried over anhydrous Na$_2$SO$_4$. The solvent was concentrated and the residue was purified by flash chromatography eluting with 12% EtOAc/petroleum ether to provide the title compound. (1.5 g, 33% yield) LC/MS m/z=228 (M+H)⁺, 1.97 min (ret time).

Intermediate 14: (S)-8-Fluoro-4-methyl-2,3,4,5-tetrahydrobenzo[f][1,2]thiazepine 1,1-dioxide and Intermediate 15: (R)-8-fluoro-4-methyl-2,3,4,5-tetrahydrobenzo[f][1,2]thiazepine 1,1-dioxide N60122-20-A2

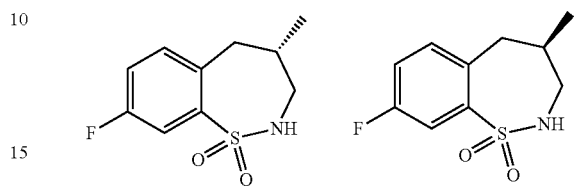

8-fluoro-4-methyl-2,3,4,5-tetrahydrobenzo[f][1,2]thiazepine 1,1-dioxide (14 g, 59.8 mmol) was purified with chiral SFC (Column: Lux Amylose-2(250×30)mm, 5µ; Co-Solvent: 10% EtOH; Total flow rate: 100 g/min; Pressure: 100 Bar, 90% CO2) to give (S)-8-fluoro-4-methyl-2,3,4,5-tetrahydrobenzo[f][1,2]thiazepine 1,1-dioxide (5.7 g, 40% yield). LC-MS m/z 228 (M+H)⁺, 2.42 min (ret. time), and (R)-8-fluoro-4-methyl-2,3,4,5-tetrahydrobenzo[f][1,2]thiazepine 1,1-dioxide (5.2 g, 36% yield). LCMS m/z 228 (M+H)⁺, 2.42 min (ret. time).

Intermediate 16: (S)-4-methyl-8-(trifluoromethyl)-2,3,4,5-tetrahydrobenzo[f][1,2]thiazepine 1,1-dioxide

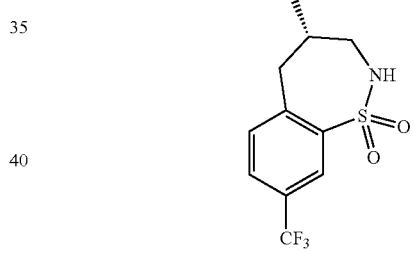

(S)-4-Methyl-8-(trifluoromethyl)-2,3,4,5-tetrahydrobenzo[f][1,2]thiazepine 1,1-dioxide of the invention was made using compounds described in WO 2017/060854 on page 137, published Apr. 13, 2017, and incorporated herein by reference.

Intermediate 17: (R)-4-methyl-8-(trifluoromethyl)-2,3,4,5-tetrahydrobenzo[f][1,2]thiazepine 1,1-dioxide

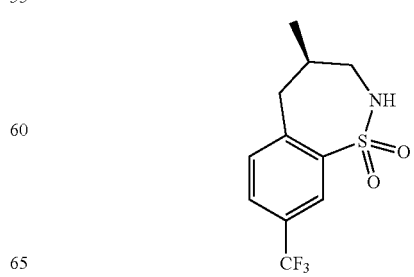

Similar procedure to (S)-4-Methyl-8-(trifluoromethyl)-2,3,4,5-tetrahydrobenzo[f][1,2]thiazepine 1,1-dioxide of the invention was made using compounds described in WO 2017/060854 on page 137, published Apr. 13, 2017, and incorporated herein by reference.

Intermediate 18: (S)-4-ethyl-2,3,4,5-tetrahydrobenzo[f][1,2]thiazepine 1,1-dioxide

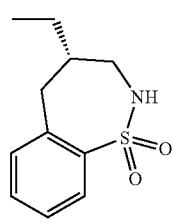

(S)-4-Ethyl-2,3,4,5-tetrahydrobenzo[f][1,2]thiazepine 1,1-dioxide of the invention was made using compounds described in WO 2017/060854 on page 135, published Apr. 13, 2017, and incorporated herein by reference.

Intermediate 19: (R)-4-ethyl-2,3,4,5-tetrahydrobenzo[f][1,2]thiazepine 1,1-dioxide

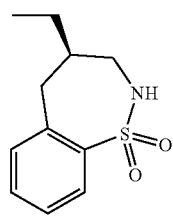

Similar procedure to (S)-4-Ethyl-2,3,4,5-tetrahydrobenzo[f][1,2]thiazepine 1,1-dioxide of the invention was made using compounds described in WO 2017/060854 on page 135, published Apr. 13, 2017, and incorporated herein by reference.

Intermediate 20: 4-Chloropyridine-3-sulfonyl chloride

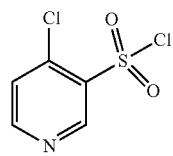 [SMILES: O=S(=O)(Cl)c1cnccc1Cl]

To a suspension of 4-hydroxypyridine-3-sulfonic acid (25 g, 143 mmol) was added $PCl_5$ (104 g, 500 mmol) and $POCl_3$ (26.6 ml, 285 mmol) at 0° C. and stirred at 120° C. for 1 h. The reaction mixture was cool to ambient temperature, the reaction mass was concentrated. The residue was diluted with EtOAc and poured in to ice. Solid $NaHCO_3$ was added and the aqueous phase was extracted with EtOAc. The organic layer was dried over anhydrous $Na_2SO_4$ and filtered to afford the title compound (25 g, 98 mmol, 68.6% yield). LCMS m/z 212 (M+H)$^+$, 1.93 min (ret. time).

Intermediate 21: 4-Chloro-N-(2-methylallyl)pyridine-3-sulfonamide N53574-21-A1

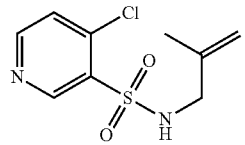

To a solution of 4-chloropyridine-3-sulfonyl chloride (25 g, 98 mmol) in dichloromethane (DCM) (200 mL) at 0° C. was added 2-methylprop-2-en-1-amine (7.66 g, 108 mmol) and TEA (27.3 mL, 196 mmol). The reaction mixture was stirred at ambient temperature for 16h. The reaction mixture was quenched with cold water, extracted with DCM (2×). The combined organic layers were washed with brine, dried over anhydrous $Na_2SO_4$ and filtered. The filtrate was evaporated under reduced pressure to afford the title compound which was used without further purification for the next step. (21 g, 85 mmol, 87% yield). LCMS m/z 246 (M+H)$^+$, 2.11 min (ret. time).

Intermediate 22: 4-Methyl-2,3,4,5-tetrahydropyrido[4,3-f][1,2]thiazepine 1,1-dioxide N53574-28-A1

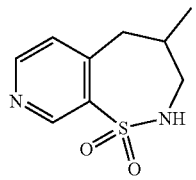

To a solution of 4-chloro-N-(2-methylallyl)pyridine-3-sulfonamide (10 g, 35.7 mmol) in benzene (90 mL) was added AIBN (1.757 g, 10.70 mmol) and heated at 70° C. Tributylstannane (11.42 g, 39.2 mmol) was added at this temperature. The reaction was stirred at 85° C. for 16 h. The reaction mixture was concentrated to get the crude compound of 4-methyl-2,3,4,5-tetrahydropyrido[4,3-f][1,2]thiazepine 1,1-dioxide (10 g, 3.77 mmol, 10.57% yield). LCMS m/z 213 (M+H)$^+$, 1.77 min (ret. time). This batch of compound was combined with other batches prepared by the same method and purified by column chromatography by using EtOAc:Petroleum ether (1:1) to afford the title compound (2.7 g), LCMS m/z 213 (M+H)$^+$, 1.79 min (ret. time).

Intermediate 23: (R)-4-Methyl-2,3,4,5-tetrahydropyrido[4,3-f][1,2]thiazepine 1,1-dioxide and Intermediate 24: (S)-4-methyl-2,3,4,5-tetrahydropyrido[4,3-f][1,2]thiazepine 1,1-dioxide

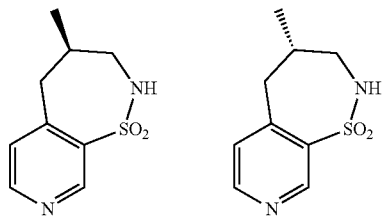

4-methyl-2,3,4,5-tetrahydropyrido[4,3-f][1,2]thiazepine 1,1-dioxide (2.39 g, 11.28 mmol) was purified with chiral SFC (Column: Chiralpak IC, 20×250 mm, 5u; Co-Solvent: 30% EtOH; Total flow rate: 50 g/min; Pressure: 100 Bar) to give (R)-4-methyl-2,3,4,5-tetrahydropyrido[4,3-f][1,2]thiazepine 1,1-dioxide (1.10 g, 45% yield). LC-MS m/z 213 (M+H)+, 0.49 min (ret. time), and (S)-4-methyl-2,3,4,5-tetrahydropyrido[4,3-f][1,2]thiazepine 1,1-dioxide (1.07 g, 45% yield). LCMS m/z 213 (M+H)+, 0.49 min (ret. time).

Intermediate 25: (R)-1-Azidobutan-2-ol

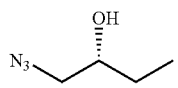

To a round bottom flask equipped with a reflux condenser was added (R)-2-ethyloxirane (26.0 g, 361 mmol), sodium azide (28.1 g, 433 mmol) and ammonium chloride (23.15 g, 433 mmol) followed by a solution of ethanol (200 mL) and water (200 mL). The reaction mixture was heated at 100° C. for 24 hr. The reaction mixture was cooled, the ethanol removed under reduced pressure and the residual aqueous layer extracted with diethyl ether (3×250 mL). The organic extracts were combined, washed with brine, dried over sodium sulfate, filtered and the solvent evaporated under reduced pressure to afford an oil. The oil was purified by silica gel chromatography (0-10% MeOH/DCM) to afford (R)-1-azidobutan-2-ol (19.8 g, 172 mmol, 47.7% yield). $^1$H NMR (CHCl$_3$-d) δ: 3.64-3.76 (m, 1H), 3.35-3.46 (m, 1H), 3.20-3.34 (m, 1H), 2.19 (s, 1H), 1.47-1.60 (m, 2H), 0.90-1.06 (m, 3H)

Intermediate 26: (R)-1-Aminobutan-2-ol

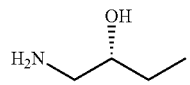

To a solution of (R)-1-azidobutan-2-ol (19.80 g, 172 mmol) in ethanol (250 mL) was added 10% palladium on carbon (1.830 g, 17.20 mmol) and the suspension was placed under a hydrogen atmosphere for 72 hr. Additional 10% palladium on carbon (1.830 g, 17.20 mmol) was added at 24 and 48 hr time points. The reaction mixture was filtered through celite and then evaporated under reduced pressure to afford a light yellow oil (R)-1-aminobutan-2-ol (13.5 g, 151 mmol, 88% yield). $^1$H NMR (CHCl$_3$-d) δ: 3.43 (m, 1H), 2.77 (m, 1H), 2.64 (br. s., 3H), 2.52 (m, 1H), 1.36-1.48 (m, 2H), 0.87-0.96 (m, 3H).

Intermediate 27: (R)-3-fluoro-N-(2-hydroxybutyl)pyridine-2-sulfonamide

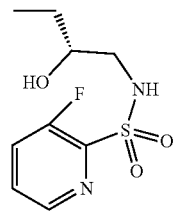 [SMILES: CC[C@@H](O)CNS(=O)(=O)c1ncccc1F]

To the mixture of isopropyl magnesium chloride (17.05 mL, 34.1 mmol) in tetrahydrofuran (15 mL) was added BuLi (21.31 mL, 34.1 mmol) dropwise under nitrogen atmosphere at ambient temperature and stirred for 15 min. The solution was cooled to −10° C. and 2-bromo-3-fluoropyridine (5 g, 28.4 mmol) in tetrahydrofuran (15 mL) was added dropwise over 5 min and stirred for 45 min. The mixture was then added to a solution of sulfuryl chloride (6.93 mL, 85 mmol) in toluene (15.00 mL) at −10° C. and stirred for 20 min. Then temperature was raised to 10° C. and a mixture of (R)-1-aminobutan-2-ol (380 mg, 4.26 mmol) and DIEA (0.744 mL, 4.26 mmol) in tetrahydrofuran (1.500 mL) was added and stirred at ambient temperature for 18 hr. The reaction mixture was quenched with saturated NH$_4$Cl solution (15 mL) and extracted with ethyl acetate (3×10 mL). The combined organic layer was washed with brine (15 mL) and dried over anhydrous Na$_2$SO$_4$, filtered, concentrated under reduced pressure to give the title compound (2.5 g, 7.61 mmol, 26.8% yield). LCMS m/z 248.89 (M+Na)+, 1.33 min (ret. time).

Intermediate 28: (R)-4-ethyl-3,4-dihydro-2H-pyrido[3,2-b][1,4,5]oxathiazepine 1,1-dioxide

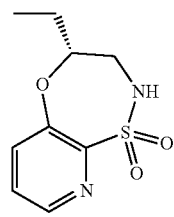

To the mixture of (R)-3-fluoro-N-(2-hydroxybutyl)pyridine-2-sulfonamide (2.5 g, 8.06 mmol) in DMSO (15 mL) was added potassium tert-butoxide (1.810 g, 16.13 mmol) at 0° C. The reaction mixture was stirred at 100° C. for 16h after which was added 1N HCl to pH 6-7 and the mixture extracted with ethyl acetate (3×30 mL). The combined organic layer was washed with brine (30 mL), dried over Na$_2$SO$_4$, filtered and concentrated under reduced pressure, purified with flash silica gel column chromatography to give

Intermediate 29: Methyl (R)-3-hydroxy-3-(3-(((4-methoxybenzyl)oxy)methyl)-4-methylphenyl)-2,2-dimethylpropanoate

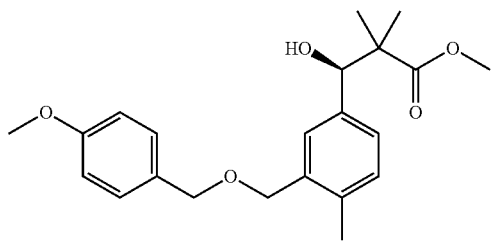

Methyl 3-hydroxy-3-(3-(((4-methoxybenzyl)oxy)methyl)-4-methylphenyl)-2,2-dimethylpropanoate (5.9 g, 15.84 mmol) was purified with chiral SFC (Column: AY, 20×250 mm, 5u; Co-Solvent: 30% EtOH; Total flow rate: 50 g/min; Pressure: 100 Bar) to give the title compound (3.7614 g, 10.10 mmol, 63.8% yield). LC-MS m/z 395.2 (M+Na)⁺, 1.17 min (ret. time).

Intermediate 30: Methyl (R)-3-(3-(((4-methoxybenzyl)oxy)methyl)-4-methylphenyl)-2,2-dimethyl-3-(prop-2-yn-1-yloxy)propanoate

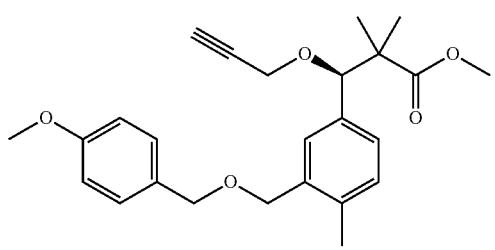

To a mixture of methyl (R)-3-hydroxy-3-(3-(((4-methoxybenzyl)oxy)methyl)-4-methylphenyl)-2,2-dimethylpropanoate (2.6 g, 6.98 mmol) in N,N-dimethylformamide (30 mL) was added 3-bromoprop-1-yne (80% in toluene) (1.128 mL, 10.47 mmol) followed by NaH (0.251 g, 10.47 mmol). The resulting reaction mixture was stirred at ambient temperature for 30 min after which was added a solution of sodium bicarbonate (0.586 g, 6.98 mmol) in water (40 mL) and extracted with EtOAc (2×40 mL). The combined organic layer was washed with LiCl (30 mL, 5%) then brine (30 mL), dried over MgSO₄, filtered, evaporated down under vacuum, purified via flash chromatography over silica gel to get the title compound (2.2200 g, 5.41 mmol, 77% yield). LC-MS m/z 433.3 (M+Na)⁺, 1.38 min (ret. time).

the title compound (750 mg, 3.26 mmol, 40.4% yield). LCMS m/z 229.06 (M+Na)⁺, 1.50 min (ret. time).

Intermediate 31: Methyl (R)-3-(3-(hydroxymethyl)-4-methylphenyl)-2,2-dimethyl-3-(prop-2-yn-1-yloxy)propanoate

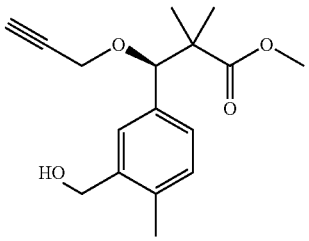 [SMILES: C#CCO[C@H](c1ccc(C)c(CO)c1)C(C)(C)C(=O)OC]

To a mixture of methyl (R)-3-(3-(((4-methoxybenzyl)oxy)methyl)-4-methylphenyl)-2,2-dimethyl-3-(prop-2-yn-1-yloxy)propanoate (2.22 g, 5.41 mmol) in acetonitrile (25 mL) and water (5 mL) was added ceric ammonium nitrate (5.93 g, 10.82 mmol). The resulting reaction mixture was stirred at ambient temperature for 20 min then was evaporated down under vacuum, extracted with DCM (2×30 mL), purified via flash chromatography over silica gel to give the title compound (1.1404 g, 3.93 mmol, 72.6% yield). LC-MS m/z 313.1 (M+Na)⁺, 0.94 min (ret. time).

Intermediate 32: Methyl (R)-3-(3-(hydroxymethyl)-4-methylphenyl)-2,2-dimethyl-3-((1-propyl-1H-1,2,3-triazol-4-yl)methoxy)propanoate

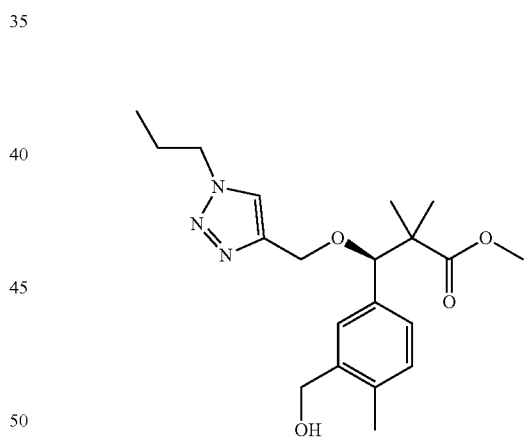

To a mixture of methyl (R)-3-(3-(hydromethyl)-4-methylphenyl)-2,2-dimethyl-3-(prop-2-yn-1-yloxy)propanoate (1.12 g, 3.86 mmol) in isopropanol (6 mL), tetrahydrofuran (8 mL) and water (4 mL) was added sodium azide (0.627 g, 9.64 mmol), DIEA (0.135 mL, 0.771 mmol), iodopropane (0.863 mL, 8.87 mmol) and copper(I) iodide (0.110 g, 0.579 mmol). The resulting reaction mixture was heated with microwave at 80° C. for 60 min then was evaporated down under vacuum, purified via flash chromatography over silica gel using ethyl acetate and hexanes as eluent to afford the title compound (825.6 mg, 2.199 mmol, 57.0% yield). LC-MS m/z 376.2 (M+H)⁺, 0.89 min (ret. time).

Intermediate 33: Methyl 3-((1-ethyl-1H-1,2,3-triazol-4-yl)methoxy)-3-(3-(hydroxymethyl)-4-methylphenyl)-2,2-dimethylpropanoate Intermediate 34: Methyl (R)-3-((1-ethyl-1H-1,2,3-triazol-4-yl)methoxy)-3-(3-(hydroxymethyl)-4-methylphenyl)-2,2-dimethylpropanoate

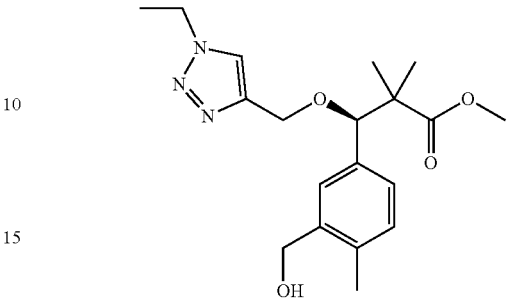

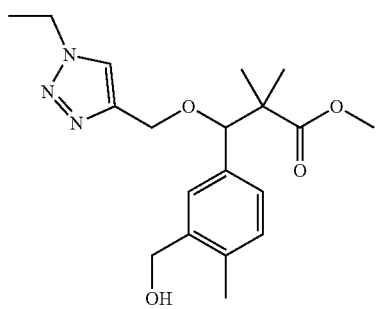 [SMILES: CCn1cc(COC(c2ccc(C)c(CO)c2)C(C)(C)C(=O)OC)nn1]

To a mixture of methyl 3-(3-(hydroxymethyl)-4-methylphenyl)-2,2-dimethyl-3-(prop-2-yn-1-yloxy)propanoate (1.12 g, 3.86 mmol) in isopropanol (10 mL), tetrahydrofuran (4 mL) and water (4 mL) was added NaN$_3$ (0.627 g, 9.64 mmol), DIEA (0.135 mL, 0.771 mmol), iodoethane (0.717 mL, 8.87 mmol) and copper(I) iodide (0.110 g, 0.579 mmol). The resulting reaction mixture was heated with microwave at 70° C. for 60 min then was evaporated down under vacuum, purified by purified via flash chromatography over silica gel then further purified with chiral SFC (Instrument: Thar 80; Column: Chiralpak AY 20×250 mm, 5u; Co-solvent: 20% EtOH; Flow rate: 50 g/min; Back pressure: 100Bar; UV wavelength: 220 nm; Temperature: 30° C.; Injection vol: 2.5 ml) to give the title chiral compound (0.4838 g, 1.339 mmol, 34.7% yield). LC-MS m/z 362.1 (M+H)$^+$, 0.82 min (ret. time).

To a mixture of methyl 3-(3-(hydroxymethyl)-4-methylphenyl)-2,2-dimethyl-3-(prop-2-yn-1-yloxy)propanoate (1.0 g, 3.44 mmol) in isopropanol (10 mL), tetrahydrofuran (4 mL) and water (4 mL) was added NaN$_3$ (0.560 g, 8.61 mmol), DIEA (0.120 mL, 0.689 mmol), iodoethane (0.640 mL, 7.92 mmol) and copper(I) iodide (0.098 g, 0.517 mmol). The resulting reaction mixture was heated with microwave at 70° C. for 60 min then was evaporated down under vacuum, purified via flash chromatography over silica gel using ethyl acetate and hexanes as eluent to give the title compound (1.3326 g, 3.69 mmol, 107% yield). LC-MS m/z 362.1 (M+H)$^+$, 0.83 min (ret. time).

The compounds in Table A were prepared by a method similar to the one described for the preparation of methyl (R)-3-((1-ethyl-1H-1,2,3-triazol-4-yl)methoxy)-3-(3-(hydromethyl)-4-methylphenyl)-2,2-dimethylpropanoate. As is appreciated by those skilled in the art, these analogous examples may involve variations in general reaction conditions.

TABLE A

| Structure/Intermediate # | Name | LCMS [M + H]$^+$ | Retention Time (min) |
|---|---|---|---|
| Intermediate 35 | Methyl (S)-3-((1-ethyl-1H-1,2,3-triazol-4-yl)methoxy)-3-(3-(hydroxymethyl)-4-methylphenyl)-2,2-dimethylpropanoate | 362.1 | 0.82 |

TABLE A-continued

| Structure/Intermediate # | Name | LCMS [M + H]+ | Retention Time (min) |
|---|---|---|---|
| 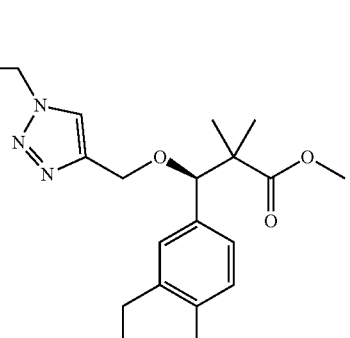<br>Intermediate 36 | Methyl (R)-3-(3-(hydroxymethyl)-4-methylphenyl)-3-((1-(2-(2-methoxyethoxy)ethyl)-1H-1,2,3-triazol-4-yl)methoxy)-2,2-dimethylpropanoate | 436.3 | 0.82 |
| 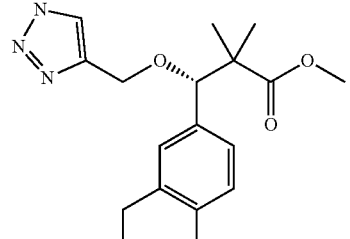<br>Intermediate 37 | Methyl (S)-3-(3-(hydroxymethyl)-4-methylphenyl)-3-((1-(2-(2-methoxyethoxy)ethyl)-1H-1,2,3-triazol-4-yl)methoxy)-2,2-dimethylpropanoate | 436.2 | 0.82 |

Intermediate 38: Methyl (R)-3-(3-(hydroxymethyl)-4-methylphenyl)-3-((1-(2-methoxyethyl)-1H-1,2,3-triazol-4-yl)methoxy)-2,2-dimethylpropanoate

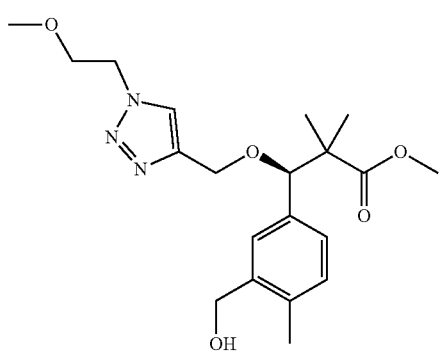

To a mixture of 1-bromo-2-methoxyethane (1.068 mL, 11.37 mmol) in N,N-dimethylformamide (6.00 mL) was added sodium azide (0.739 g, 11.37 mmol). The resulting reaction mixture was stirred at 80° C. for 20 h after which was added the mixture of methyl 3-(3-(hydroxymethyl)-4-methylphenyl)-2,2-dimethyl-3-(prop-2-yn-1-yloxy)propanoate (1.10 g, 3.79 mmol) in isopropanol (6 mL) and tetrahydrofuran (6 mL) then DIEA (0.132 mL, 0.758 mmol) and copper(I) iodide (0.108 g, 0.568 mmol). The resulting reaction mixture was heated with microwave at 80° C. for 30 min then a further 60 min. The reaction mixture was evaporated down under vacuum, purified via flash chromatography over silica gel then further purified with chiral SFC (Instrument: Thar 80; Column: Chiralpak IG 20×250 mm, 5u; Co-solvent: 20% EtOH; Flow rate: 50 g/min; Back pressure: 100Bar) to give the title compound (0.52 g, 1.328 mmol, 35.1% yield). LC-MS m/z 392.2 (M+H)+, 0.81 min (ret. time).

Intermediate 39: Methyl 3-((1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoate

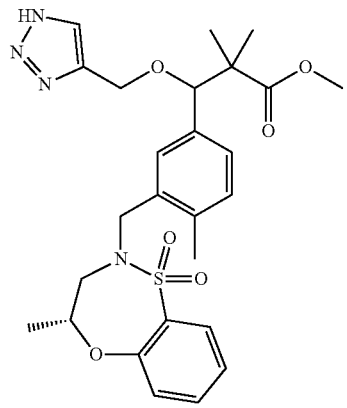 [SMILES: COC(=O)C(C)(C)C(OCc1c[nH]nn1)c1ccc(C)c(CN2C[C@@H](C)Oc3ccccc3S2(=O)=O)c1]

In two 20 mL microwave vials, each was added half amount of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate (2.86 g, 5.89 mmol) in isopropanol (20 mL), tetrahydrofuran (10 mL) and water (8.0 mL) then sodium azide (0.957 g, 14.72 mmol), DIEA (0.206 mL, 1.178 mmol), tert-butyl 4-(bromomethyl)piperidine-1-carboxylate (3.77 g, 13.55 mmol) and copper(I) iodide (0.168 g, 0.883 mmol). The resulting reaction mixture was each heated with microwave at 80° C. for 1 h then heated again with microwave at 80° C. for 30 min. The combined reaction mixture was evaporated down under vacuum, purified via flash chromatography over silica gel using ethyl acetate and hexanes as eluent to give the title compound (0.7197 g, 1.399 mmol, 23.12% yield). LC-MS m/z 529.3 (M+H)$^+$, 1.12 min (ret. time).

Intermediate 40: 3-Bromo-N-(pyridin-2-ylmethyl)benzenesulfonamide

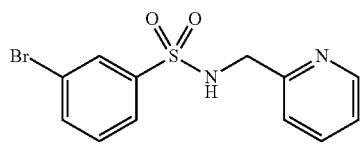 [SMILES: O=S(=O)(NCc1ccccn1)c1cccc(Br)c1]

To the mixture of 2-picolylamine (0.403 mL, 3.91 mmol) in tetrahydrofuran (15 mL) and water (5 mL) was added K$_2$CO$_3$ (0.541 g, 3.91 mmol) then 3-bromobenzenesulfonyl chloride (1.0 g, 3.91 mmol) in tetrahydrofuran (5 mL). The resulting reaction mixture was stirred at ambient temperature for 23 h then was extracted with EtOAc (2×20 mL). The combined organic layer was dried over MgSO$_4$, filtered, evaporated down under vacuum to give the title compound (1.3206 g, 4.04 mmol, 103% yield). LC-MS m/z 326.8 (M+H)$^+$, 0.60 min (ret. time).

Intermediate 41: Rel-(R)-methyl 2,2-dimethyl-3-(4-methyl-3-(((S)-4-methyl-1,1-dioxido-4,5-dihydropyrido[4,3-f][1,2]thiazepin-2(3H)-yl)methyl)phenyl)-3-(prop-2-yn-1-yloxy)propanoate

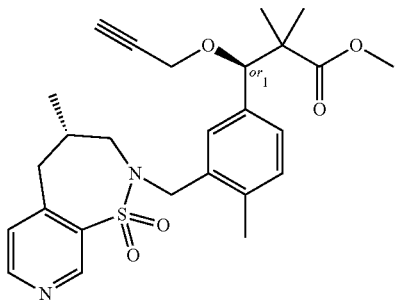 [SMILES: C#CCO[C@H](c1ccc(C)c(CN2C[C@@H](C)Cc3ccncc3S2(=O)=O)c1)C(C)(C)C(=O)OC]

To the mixture of methyl 3-(3-(hydroxymethyl)-4-methylphenyl)-2,2-dimethyl-3-(prop-2-yn-1-yloxy)propanoate (800 mg, 2.76 mmol) in dichloromethane (4 mL) was added SOCl$_2$ (0.603 mL, 8.27 mmol). The resulting reaction mixture was stirred at ambient temperature for 18 h before being evaporated down under vacuum to give intermediate.

To the mixture of (S)-4-methyl-2,3,4,5-tetrahydropyrido[4,3-f][1,2]thiazepine 1,1-dioxide (702 mg, 3.31 mmol) in N,N-dimethylformamide (10 mL) was added NaH (93 mg, 3.86 mmol). The resulting reaction mixture was stirred at ambient temperature for 5 min after which was added the solution of the above intermediate in N,N-dimethylformamide (5 mL). The resulting reaction mixture was stirred at ambient temperature for 2.5 h after which was added more NaH (13.22 mg, 0.551 mmol). The resulting reaction mixture was stirred at ambient temperature for 2.5 h after which was added more NaH (13.22 mg, 0.551 mmol). The resulting reaction mixture was stirred at ambient temperature for 17 h then quenched with HCl (1.0 N) (1.102 mL, 1.102 mmol), diluted with EtOAc (150 mL), washed with H$_2$O (2×50 mL), brine (50 mL), dried over MgSO$_4$, filtered, evaporated down under vacuum, purified via flash chromatography over silica gel using ethyl acetate and hexanes as eluent then further purified with chiral SFC (Instrument: Thar 80Column: Chiralpak OJ 20×250 mm, 5u; Co-solvent: 20% EtOH; Flow rate: 50 g/min; Back pressure: 100Bar) to give the title compound (555.4 mg, 1.146 mmol, 41.6% yield). LC-MS m/z 485.3 (M+H)$^+$, 1.21 min (ret. time).

The compounds in Table B were prepared by a method similar to the one described for the preparation of rel-(R)-methyl 2,2-dimethyl-3-(4-methyl-3-(((S)-4-methyl-1,1-dioxido-4,5-dihydropyrido[4,3-f][1,2]thiazepin-2(3H)-yl)methyl)phenyl)-3-(prop-2-yn-1-yloxy)propanoate.

As is appreciated by those skilled in the art, these analogous examples may involve variations in general reaction conditions.

TABLE B

| Structure/Intermediate # | Name | LCMS [M + H]+ | Retention Time (min) |
|---|---|---|---|
| 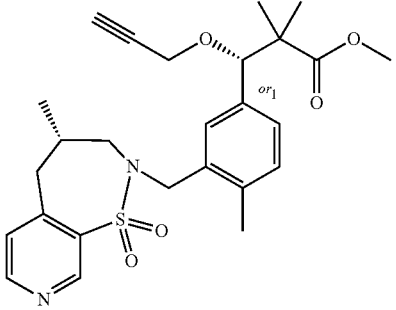<br>Intermediate 42 | Rel-(S)-methyl 2,2-dimethyl-3-(4-methyl-3-(((S)-4-methyl-1,1-dioxido-4,5-dihydropyrido-[4,3-f][1,2]thiazepin-2(3H)-yl)methyl)phenyl)-3-(prop-2-yn-1-yloxy)propanoate | 485.3 | 1.21 |

Example 1

3-((1-(3-Bromobenzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

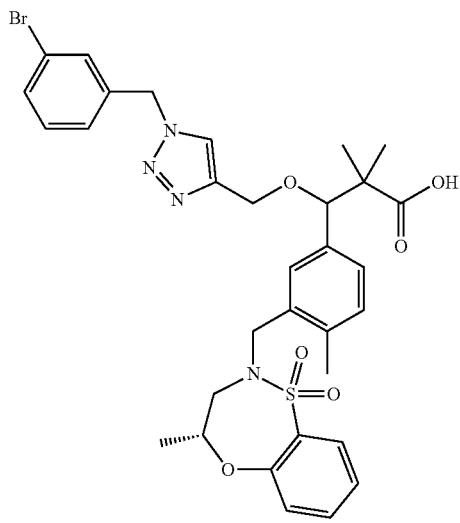 [SMILES: Cc1ccc(C(OCc2cn(Cc3cccc(Br)c3)nn2)C(C)(C)C(=O)O)cc1CN1C[C@@H](C)Oc2ccccc2S1(=O)=O]

(5-Bromo-2-methylphenyl)methanol

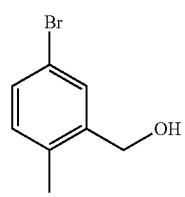

To a solution of 5-bromo-2-methylbenzoic acid (70 g, 326 mmol) in tetrahydrofuran (THF) (700 mL) stirred under nitrogen at 0° C. was added a toluene solution of borane-methyl sulfide complex (244 mL, 488 mmol) drop wise during 15 min. The reaction mixture was stirred for 16 h. The reaction was cooled to 0° C. and quenched with methanol (500 mL) drop wise. The reaction mixture was stirred at ambient temperature for 3 h and then concentrated. The crude residue was diluted with ethyl acetate (1 L) and washed with 1N HCl (500 mL), brine solution (500 mL) and dried over $Na_2SO_4$, filtered and concentrated to give the title compound (49 g, 244 mmol, 74.9% yield). $^1$H NMR (400 MHz, DMSO) δ=7.52 (d, J=2.6 Hz, 1H), 7.31 (dd, J=8.0, 2.2 Hz, 1H), 7.12-7.03 (m, 1H), 5.22 (td, J=5.5, 1.8 Hz, 1H), 4.48 (dd, J=5.1, 1.8 Hz, 2H), 2.17 (s, 3H).

4-Bromo-2-(((4-methoxybenzyl)oxy)methyl)-1-methylbenzene

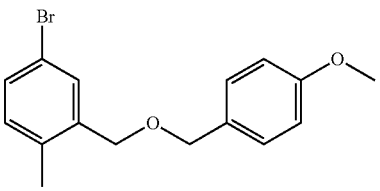 [SMILES: COc1ccc(COCc2cc(Br)ccc2C)cc1]

To a stirred solution of (5-bromo-2-methylphenyl)methanol (100 g, 497 mmol) in dry DMF (800 mL) was added NaH (21.88 g, 547 mmol). After the reaction mixture was stirred for 30 minutes, 1-(chloromethyl)-4-methoxybenzene (82 g, 522 mmol) was added at 0° C. and the reaction mixture was stirred for another 2 h at ambient temperature. The reaction was then diluted with $Et_2O$ (200 mL) and water (200 mL). The organic phase was washed with brine (300 mL) and dried with $Na_2SO_4$ and concentrated under reduced pressure. The residue was purified via silica gel column to yield 4-bromo-2-(((4-methoxybenzyl)oxy)methyl)-1-methylbenzene (140 g, 436 mmol, 88% yield) as a clear oil. $^1$H NMR (400 MHz, CHLOROFORM-d) δ ppm 2.27 (s, 3H) 3.84 (s, 3H) 4.49 (s, 2H), 4.54 (s, 2H), 6.92 (d, J=8.8, 2H), 6.94 (d, J=8.4, 1H), 7.31-7.35 (m, 3H), 7.54 (d, J=2, 1H).

3-(4-Methoxybenzyl)oxy)methyl)-4-methylbenzaldehyde

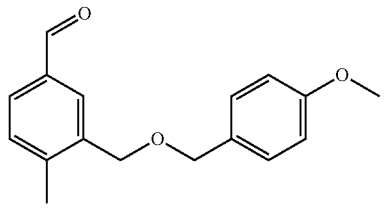 [SMILES: COc1ccc(COCc2cc(C=O)ccc2C)cc1]

To a stirred solution of 4-bromo-2-(((4-methoxybenzyl)oxy)methyl)-1-methylbenzene (80 g, 249 mmol) in THF (800 mL) at −78° C. under $N_2$, 2.5 M n-BuLi in hexane (120 mL, 299 mmol) was carefully added. The reaction mixture was stirred at −78° C. for 65 min, and then DMF (38.6 mL, 498 mmol) was added. The reaction mixture was stirred at −78° C. to 25° C. for another 30 min. The mixture was quenched with saturated $NH_4Cl$ (300 mL), and extracted with EtOAc (2×500 mL). The organic layer was washed with water (300 mL) and brine (2×100 mL), dried ($Na_2SO_4$) and concentrated. The residue was washed with petroleum ether:EtOAc=10/1 (2000 mL) to give the title compound (50 g, 185 mmol, 74.3% yield) as a solid. LC-MS m/z 288.1 $(M+H_2O)^+$, 2.04 min (ret. time).

Methyl 3-hydroxy-3-(3-(((4-methoxybenzyl)oxy)methyl)-4-methylphenyl)-2,2-dimethylpropanoate

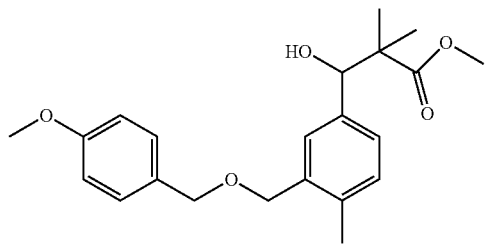

A mixture of 3-(((4-methoxybenzyl)oxy)methyl)-4-methylbenzaldehyde (4 g, 14.80 mmol), 1-methylimidazole (0.118 mL, 1.480 mmol), ((1-methoxy-2-methylprop-1-en-1-yl)oxy)trimethylsilane (5.16 g, 29.6 mmol) and lithium chloride (0.125 g, 2.96 mmol) in N,N-dimethylformamide (DMF) (15 mL) was stirred at ambient temperature for 17 h. NaOH (14.80 mL, 14.80 mmol) was added and the reaction mixture was stirred for 2 h. Water (20 mL) and potassium hydrogen fluoride (1.734 g, 22.20 mmol) were added and stirred for 2 h, followed by adding of 1N HCl (14.80 mL, 14.80 mmol). It was stirred for 16 h. The reaction mixture was diluted with ice water (10 mL) and extracted with EtOAc (2×20 mL). The combined organic layer was washed with brine solution (20 mL), dried over $Na_2SO_4$, filtered and concentrated. The crude residue was purified with flash column chromatography eluting with EtOAc:Hexane (2:8). Desired fractions were concentrated to give the title compound (2 g, 5.37 mmol, 36.3% yield) as yellow liquid. LCMS m/z 390.23 $(M+18)^+$, 4.07 min (ret. time)

Methyl 3-(3-(((4-methoxybenzyl)oxy)methyl)-4-methylphenyl)-2,2-dimethyl-3-(prop-2-yn-1-yloxy)propanoate

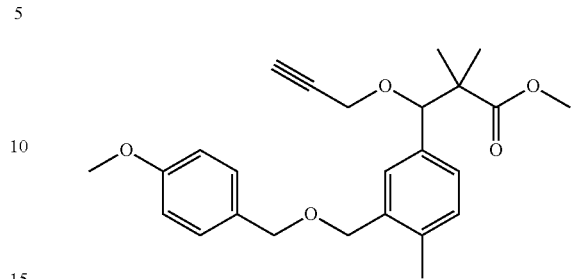

To a solution of methyl 3-hydroxy-3-(3-(((4-methoxybenzyl)oxy)methyl)-4-methylphenyl)-2,2-dimethylpropanoate (24 g, 64.4 mmol) and 3-bromoprop-1-yne in toluene (14.37 g, 97 mmol) in N,N-dimethylformamide (DMF) (250 mL) at 0° C. was added NaH (2.320 g, 97 mmol) under nitrogen. It was stirred for 30 min. The reaction mixture was quenched with saturated $NaHCO_3$ solution and extracted with EtOAc. The organic layer was concentrated under vacuum to afford the title compound (26 g, 55.2 mmol, 86% yield) as liquid. LCMS m/z 428.17 $(M+18)^+$, 2.92 min (ret. time)

Methyl 3-(3-(hydroxymethyl)-4-methylphenyl)-2,2-dimethyl-3-(prop-2-yn-1-yloxy)propanoate

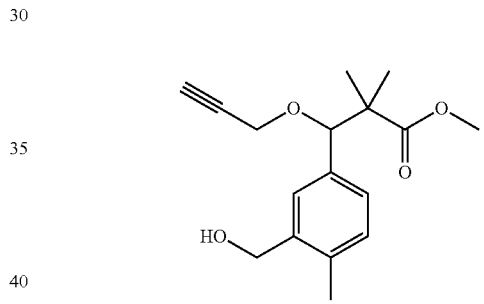

To a solution of methyl 3-(3-(((4-methoxybenzyl)oxy)methyl)-4-methylphenyl)-2,2-dimethyl-3-(prop-2-yn-1-yloxy)propanoate (13 g, 31.7 mmol) in dichloromethane (DCM) (40 mL) and water (10 mL) at 0° C. was added DDQ (10.78 g, 47.5 mmol). It was stirred at ambient temperature for 30 min. It was quenched with ice water, extracted with DCM twice. The organic layer was dried under anhydrous $Na_2SO_4$, filtered and concentrated. The crude residue was purified on flash column chromatography eluting with EtOAc:hexane (12:88). Desired fractions were concentrated under to give the title compound (8 g, 13.63 mmol, 43.0% yield) as color less liquid. LC MS m/z 291.20 $(M+H)^+$, 2.20 min (ret. time)

(R)-2-Fluoro-N-(2-hydroxypropyl)benzenesulfonamide

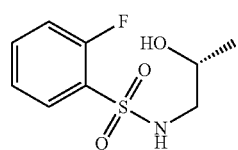

To a suspension of 2-fluorobenzene-1-sulfonyl chloride (28 g, 144 mmol) in tetrahydrofuran (THF) (250 mL) and water (75 mL) at 0° C. was added (R)-1-aminopropan-2-ol (10.81 g, 144 mmol) and $K_2CO_3$ (19.88 g, 144 mmol). The reaction mixture was stirred at ambient temperature for 16 h. The reaction mixture was quenched with ice water, extracted with EtOAc twice. The combined organic layer was washed with ice water twice, brine solution. The organic layer was dried under anhydrous $Na_2SO_4$, filtered and concentrated to give the title compound (31 g, 129 mmol, 89% yield) as liquid. LCMS m/z 233.88 (M+H)$^+$, 1.46 min (ret. time)

(R)-4-Methyl-3,4-dihydro-2H-benzo[b][1,4,5]oxathiazepine 1,1-dioxide

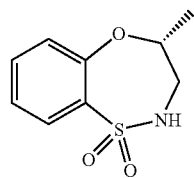

To a solution of (R)-2-fluoro-N-(2-hydroxypropyl)benzenesulfonamide (31 g, 133 mmol) in dimethyl sulfoxide (DMSO) (200 mL) at 0° C. was added KO$_t$Bu (29.8 g, 266 mmol). The reaction mixture was stirred at 80° C. for 6 h. The reaction mixture was neutralized with 1N HCl, extracted with EtOAc twice. The combined organic layer was washed with ice water twice, brine solution, dried under anhydrous $Na_2SO_4$, filtered and concentrated. The crude product was triturated with diethyl ether to afford the title compound (15.7 g, 73.3 mmol, 55.1% yield) as white solid. LCMS m/z 214.09 (M+H)$^+$, 1.59 min (ret. time)

Methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate

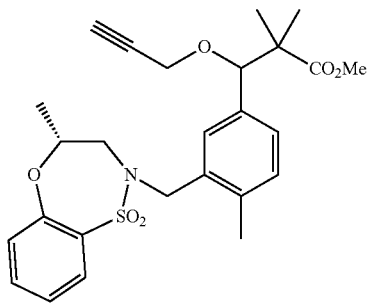 [SMILES: C#CCOC(c1ccc(C)c(CN2C[C@@H](C)Oc3ccccc3S2(=O)=O)c1)C(C)(C)C(=O)OC]

To the mixture of methyl 3-(3-(hydroxymethyl)-4-methylphenyl)-2,2-dimethyl-3-(prop-2-yn-1-yloxy)propanoate (3.59 g, 12.36 mmol) in tetrahydrofuran (175 mL) was added (R)-4-methyl-3,4-dihydro-2H-benzo[b][1,4,5]oxathiazepine 1,1-dioxide (3.96 g, 18.55 mmol), PS—PPh$_3$ (11.59 g, 18.55 mmol) and DIAD (3.61 mL, 18.55 mmol). The resulting reaction mixture was stirred at ambient temperature for 21 h. The reaction mixture was filtered, evaporated down under vacuum, purified via flash chromatography to give the title compound (5.7762 g, 11.90 mmol, 96% yield). LCMS m/z 508.2 (M+Na)$^+$, 1.32 min (ret. time).

Methyl 3-((1-(3-bromobenzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoate

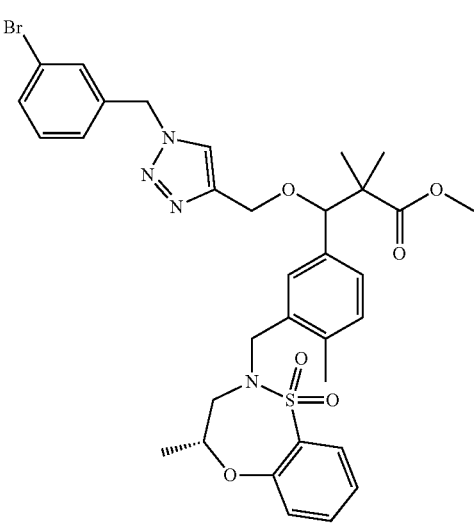 [SMILES: COC(=O)C(C)(C)C(OCc1cn(Cc2cccc(Br)c2)nn1)c1ccc(C)c(CN2C[C@@H](C)Oc3ccccc3S2(=O)=O)c1]

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate (0.971 g, 2.0 mmol) in isopropanol (9 mL), tetrahydrofuran (3 mL) and water (4 mL) was added sodium azide (0.325 g, 5.00 mmol), DIEA (0.070 mL, 0.400 mmol), 1-bromo-3-(bromomethyl)benzene (1.150 g, 4.60 mmol) and copper(I) iodide (0.057 g, 0.300 mmol). The resulting reaction mixture was heated with microwave at 80° C. for 30 min. The reaction mixture was evaporated down under vacuum, purified via flash chromatography to give the title compound (1.2115 g, 1.737 mmol, 87% yield). LCMS m/z 697.2 (M+H)$^+$, 1.39 min (ret. time).

3-((1-(3-Bromobenzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

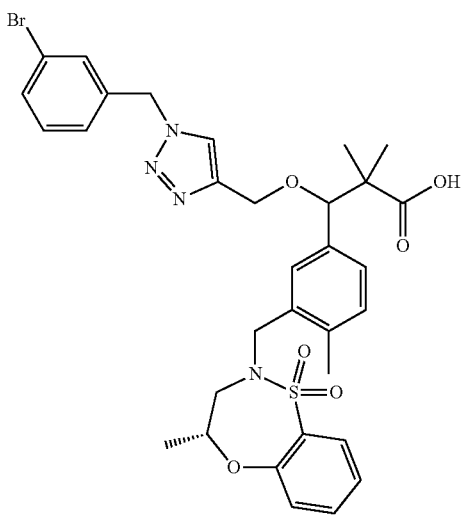 [SMILES: Cc1ccc(C(OCc2cn(Cc3cccc(Br)c3)nn2)C(C)(C)C(=O)O)cc1CN1C[C@@H](C)Oc2ccccc2S1(=O)=O]

To the mixture of methyl 3-((1-(3-bromobenzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoate (50 mg, 0.072 mmol) in methanol (1.0 mL) was added NaOH (3.0 N) (0.119 mL, 0.358 mmol). The resulting reaction mixture was heated with microwave at 120° C. for 1 h. To the reaction mixture was added HCl (3.0 N) (0.119 mL, 0.358 mmol) then was evaporated down under vacuum, purified by reverse phase HPLC (formic acid modifier) to give the title compound (31.9 mg, 0.047 mmol, 65.1% yield). LC/MS: m/z 683.1 (M+H)$^+$, 1.27 min (ret. time).

Example 2

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoic Acid

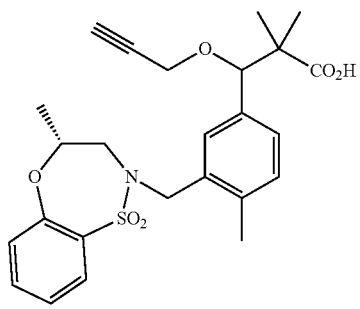 [SMILES: C#CCOC(c1ccc(C)c(CN2C[C@@H](C)Oc3ccccc3S2(=O)=O)c1)C(C)(C)C(=O)O]

To the mixture of methyl 3-(3-(hydroxymethyl)-4-methylphenyl)-2,2-dimethyl-3-(prop-2-yn-1-yloxy)propanoate (50 mg, 0.172 mmol) in tetrahydrofuran (2 mL) was added (R)-4-methyl-3,4-dihydro-2H-benzo[b][1,4,5]oxathiazepine 1,1-dioxide (55.1 mg, 0.258 mmol), PS—PPh3 (215 mg, 0.344 mmol) and DIAD (0.067 mL, 0.344 mmol). The resulting reaction mixture was stirred at ambient temperature for 66 h. The reaction mixture was filtered, evaporated down under vacuum. This residue was dissolved in methanol (2.000 mL) then was added NaOH (3.0 N) (0.459 mL, 1.378 mmol). The resulting reaction mixture was heated with microwave at 100° C. for 30 min twice and heated with microwave again at 120° C. for 30 min. To the reaction mixture was added HCl (3.0 N) (0.459 mL, 1.378 mmol), evaporated down under vacuum, purified by reverse phase HPLC (formic acid modifier) to give the title compound (25.6 mg, 0.054 mmol, 31.5% yield). LC/MS: m/z 472.2 (M+H)$^+$, 1.17 min (ret. time).

Example 3

3-((1-(3-(Azidomethyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

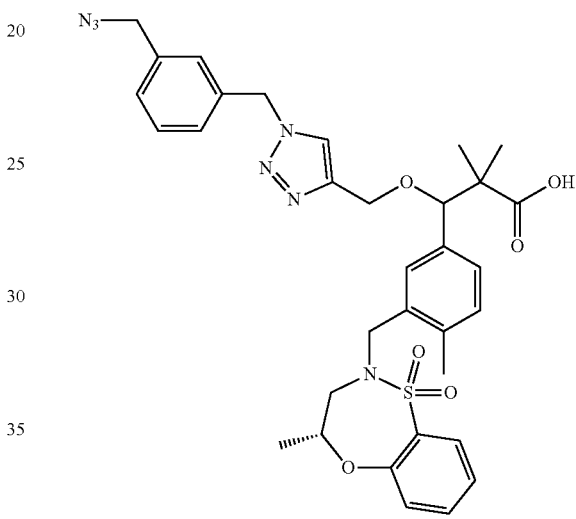

Methyl 3-((1-(3-(azidomethyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoate

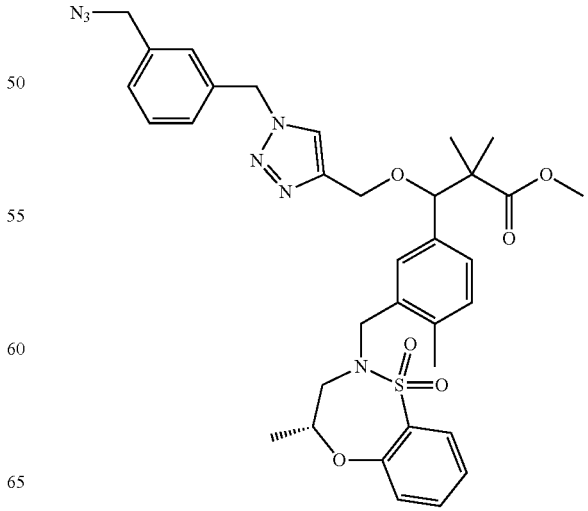

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate (971 mg, 2.0 mmol) in isopropanol (12 mL) and water (4 mL) was added sodium azide (650 mg, 10.00 mmol), DIEA (0.070 mL, 0.400 mmol), 1,3-bis(bromomethyl)benzene (1214 mg, 4.60 mmol) and copper(I) iodide (57.1 mg, 0.300 mmol). The resulting reaction mixture was heated with microwave at 80° C. for 30 min. The reaction mixture was evaporated down under vacuum, purified via flash chromatography to give the title compound (691.1 mg, 1.026 mmol, 51.3% yield). LC/MS: m/z 674.3 (M+H)+, 1.36 min (ret. time).

3-((1-(3-(Azidomethyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

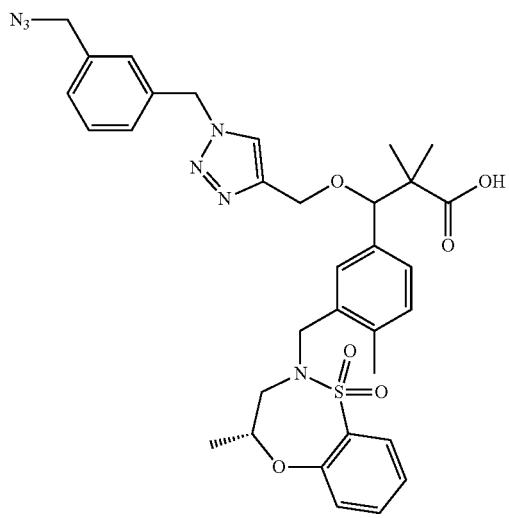 [SMILES: Cc1ccc(C(OCc2cn(Cc3cccc(CN=[N+]=[N-])c3)nn2)C(C)(C)C(=O)O)cc1CN1C[C@@H](C)Oc2ccccc2S1(=O)=O]

To the mixture of methyl 3-((1-(3-(azidomethyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoate (50 mg, 0.074 mmol) in methanol (1.0 mL) was added NaOH (3.0 N) (0.124 mL, 0.371 mmol). The resulting reaction mixture was heated with microwave at 120° C. for 1 h. To the reaction mixture was added HCl (3.0 N) (0.124 mL, 0.371 mmol) then was evaporated down under vacuum, purified by reverse phase HPLC (formic acid modifier) to give the title compound (30.6 mg, 0.046 mmol, 62.5% yield). LC/MS: m/z 660.1 (M+H)+, 1.23 min (ret. time).

Example 4

3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)propanoic Acid

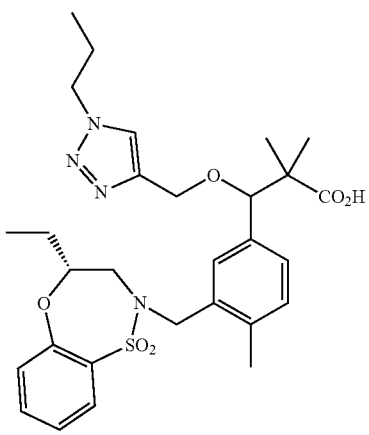 [SMILES: CCCn1cc(COC(c2ccc(C)c(CN3C[C@@H](CC)Oc4ccccc4S3(=O)=O)c2)C(C)(C)C(=O)O)nn1]

(R)-2-Fluoro-N-(2-hydroxybutyl)benzenesulfonamide

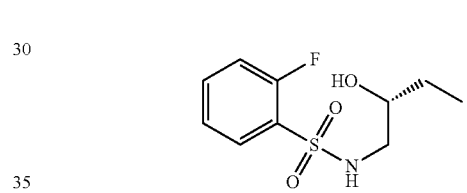

To a solution of (R)-1-aminobutan-2-ol (14.66 g, 164 mmol) in tetrahydrofuran (THF) (200 mL) and water (60 mL) at ambient temperature was added K₂CO₃ (14.20 g, 103 mmol) and 2-fluorobenzene-1-sulfonyl chloride (20 g, 103 mmol). It was stirred for 16 h. The reaction mixture was diluted with water (100 mL) and extracted with EtOAc (2×100 mL). The combined organic layer was washed with brine solution (200 mL) and dried over anhydrous Na₂SO₄, filtered and concentrated to give the title compound (14 g, 53.8 mmol, 52.3% yield) as a gummy liquid. LC-MS m/z 494.83 (2M−H)+, 1.660 min (ret. time).

(R)-4-Ethyl-3,4-dihydro-2H-benzo[b][1,4,5]oxathiazepine 1,1-dioxide

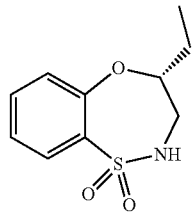

To a solution of (R)-2-fluoro-N-(2-hydroxybutyl)benzenesulfonamide (14 g, 56.6 mmol) in dimethyl sulfoxide (DMSO) (140 mL) at 0° C. was added potassium tert-butoxide (6.35 g, 56.6 mmol). It was then heated at 80° C. for 4 h. The reaction mixture was cooled and neutralized with 1N HCl, diluted with ice water (500 mL) and extracted with EtOAc (2×400 mL). The combined organic layer was washed with chilled brine solution (200 mL) and dried over anhydrous Na$_2$SO$_4$, filtered and concentrated. The crude residue was purified on flash column chromatography eluting with 50% EtOAc in hexane. Desired fractions were concentrated to give the title compound (11.12 g, 48.9 mmol, 86% yield) as a white solid. LC-MS m/z 228.05 (M+H)$^+$, 1.84 min (ret. time).

Methyl 3-(3-(hydroxymethyl)-4-methylphenyl)-2,2-dimethyl-3-(0-propyl-1H-1,2,3-triazol-4-yl)methoxy)propanoate

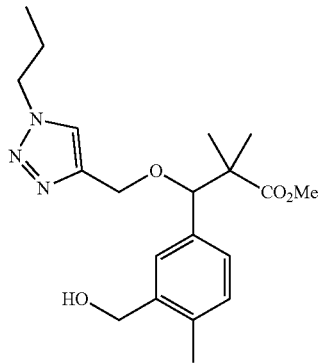 [SMILES: CCCn1cc(COC(c2ccc(C)c(CO)c2)C(C)(C)C(=O)OC)nn1]

To the mixture of methyl 3-(3-(hydroxymethyl)-4-methylphenyl)-2,2-dimethyl-3-(prop-2-yn-1-yloxy)propanoate (0.43 g, 1.481 mmol) in isopropanol (6.0 mL) and water (2.0 mL) was added sodium azide (0.241 g, 3.70 mmol), DIEA (0.052 mL, 0.296 mmol), copper(I) iodide (0.042 g, 0.222 mmol) and iodopropane (0.331 mL, 3.41 mmol). The resulting reaction mixture was heated with microwave at 70° C. for 1 h. The reaction mixture was evaporated down under vacuum, extracted with DCM (3×7 mL), dried over Na$_2$SO$_4$, filtered, evaporated down under vacuum, purified via flash chromatography to give the title compound (296.1 mg, 0.789 mmol, 53.3% yield). LC/MS: m/z 376.2 (M+H)$^+$, 0.93 min (ret. time).

3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-(0-propyl-1H-1,2,3-triazol-4-yl)methoxy)propanoic Acid

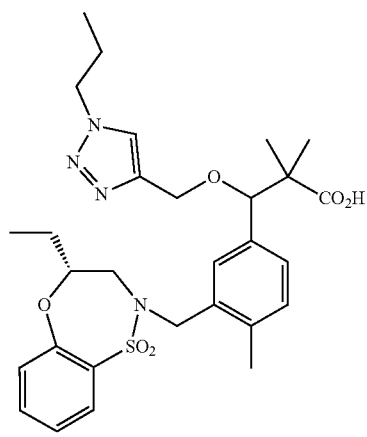 [SMILES: CCCn1cc(COC(c2ccc(C)c(CN3C[C@@H](CC)Oc4ccccc4S3(=O)=O)c2)C(C)(C)C(=O)O)nn1]

To the mixture of methyl 3-(3-(hydroxymethyl)-4-methylphenyl)-2,2-dimethyl-3-((1-propyl-1H-1,2,3-triazol-4-yl)methoxy)propanoate (55 mg, 0.146 mmol) in tetrahydrofuran (2 mL) was added (R)-4-ethyl-3,4-dihydro-2H-benzo[b][1,4,5]oxathiazepine 1,1-dioxide (49.9 mg, 0.220 mmol), PS—PPh$_3$ (183 mg, 0.293 mmol) and DIAD (0.057 mL, 0.293 mmol). The resulting reaction mixture was stirred at ambient temperature for 21 h. The reaction mixture was filtered, evaporated down under vacuum. The residue was redissolved in methanol (2.000 mL) then was added NaOH (3.0 N) (0.391 mL, 1.172 mmol). The resulting reaction mixture was heated with microwave at 100° C. for 30 min then heated again with microwave at 120° C. for 30 min. To the reaction mixture was added HCl (3.0 N) (0.391 mL, 1.172 mmol) then evaporated down under vacuum, purified by reverse phase HPLC (formic acid modifier) to give the title compound (17.5 mg, 0.031 mmol, 20.93% yield). LC/MS: m/z 571.3 (M+H)+, 1.19 min (ret. time).

Example 5

(R)-3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoic Acid

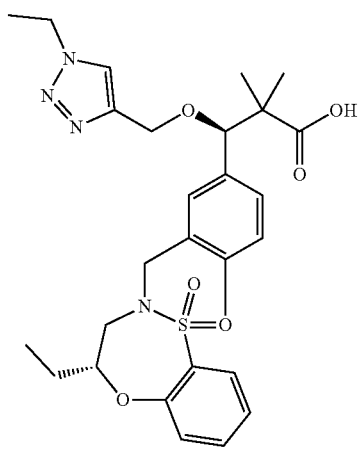

Methyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-(prop-2-yn-1-yloxy)propanoate

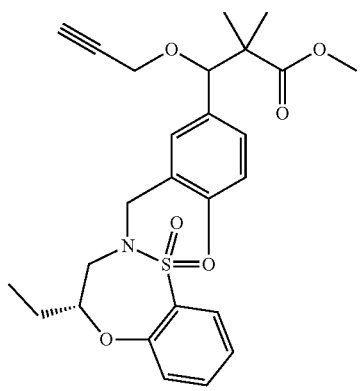

To the mixture of methyl 3-(3-(hydroxymethyl)-4-methylphenyl)-2,2-dimethyl-3-(prop-2-yn-1-yloxy)propanoate (3 g, 10.33 mmol) in dichloromethane (30 mL) was added SOCl₂ (3.77 mL, 51.7 mmol). The resulting reaction mixture was stirred at ambient temperature for 17.5 h then was evaporated down under vacuum. The residue was dissolved in N,N-dimethylformamide (20 mL) to give intermediate solution. To (R)-4-ethyl-3,4-dihydro-2H-benzo[b][1,4,5]oxathiazepine 1,1-dioxide (2.82 g, 12.40 mmol) in N,N-dimethylformamide (40 mL) was added NaH (0.298 g, 12.40 mmol). The resulting reaction mixture was stirred at ambient temperature for 5 min then was added into the above intermediate solution. The resulting reaction mixture was stirred at ambient temperature for 4 h then was added more NaH (0.050 g, 2.066 mmol). The resulting reaction mixture was stirred at ambient temperature for 22 h. The reaction was quenched with HCl (1.0 N) (2.066 mL, 2.066 mmol), diluted with EtOAc (300 mL), washed with H₂O (2×100 mL), brine (50 mL), dried over MgSO₄, filtered, evaporated down under vacuum, purified by flash chromatography to give the title compound (4.0916 g, 8.19 mmol, 79% yield). LC/MS: m/z 522.1 (M+Na)⁺, 1.36 min (ret. time).

Methyl 3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoate

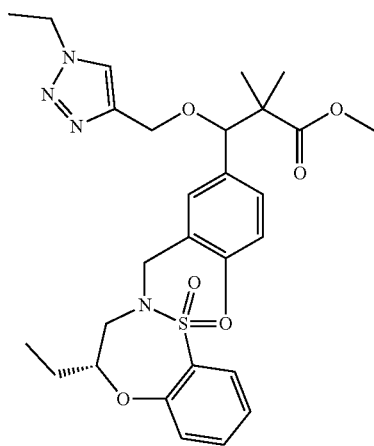

To the mixture of methyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-(prop-2-yn-1-yloxy)propanoate (2.72 g, 5.44 mmol) in isopropanol (18 mL), tetrahydrofuran (12 mL) and water (8 mL) was added sodium azide (0.885 g, 13.61 mmol), DIEA (0.190 mL, 1.089 mmol), ethyl iodide (1.012 mL, 12.52 mmol) and copper(I) iodide (0.156 g, 0.817 mmol). The resulting reaction mixture was heated with microwave at 80° C. for 30 min. The reaction mixture was evaporated down under vacuum, purified by flash chromatography to give the title compound (2.5336 g, 4.44 mmol, 82% yield). LC/MS: m/z 571.2 (M+H)⁺, 1.26 min (ret. time).

(R)-methyl 3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoate

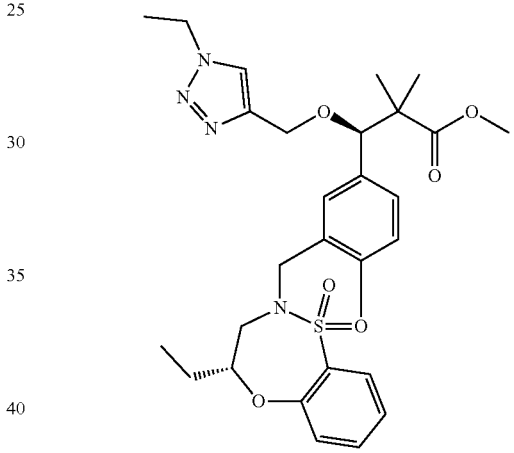

Methyl 3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoate (2.53 g, 4.43 mmol) was separated by chiral SFC (Column: Chiralpak IA 20×250 mm, 5u; Co-solvent: 20% MeOH; Flowrate: 50 g/min; Back pressure: 100Bar) to give the title compound (1.0058 g, 1.762 mmol, 39.8% yield). LC/MS: m/z 571.3 (M+H)⁺, 1.26 min (ret. time).

The compounds in Table 1 were prepared by a method similar to the one described for the preparation of (R)-methyl 3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoate. As is appreciated by those skilled in the art, these analogous examples may involve variations in general reaction conditions.

TABLE 1

| Structure | Name | LCMS [M + H]+ | Retention Time (min) |
|---|---|---|---|
| 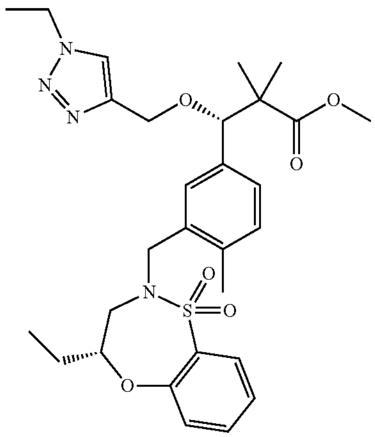 [SMILES: CC[C@@H]1CN(Cc2cc([C@H](OCc3cn(CC)nn3)C(C)(C)C(=O)OC)ccc2C)S(=O)(=O)c2ccccc2O1] | (S)-methyl 3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoate | 571.3 | 1.25 |

(R)-3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoic Acid

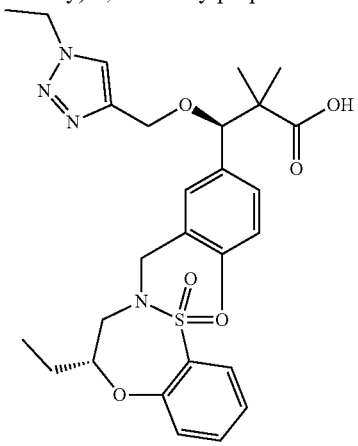

To the mixture of (R)-methyl 3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoate (1.00 g, 1.752 mmol) in methanol (10 mL) was added NaOH (3.0 N) (2.92 mL, 8.76 mmol). The resulting reaction mixture was heated with microwave at 120° C. for 30 min. To the reaction mixture was added HCl (3.0 N) (2.92 mL, 8.76 mmol), evaporated down under vacuum, extracted with EtOAc (3×20 mL). The combined organic layer was dried over $Na_2SO_4$, filtered, evaporated under vacuum to give the title compound (843.9 mg, 1.516 mmol, 87% yield). LC/MS: m/z 557.3 (M+H)+, 1.15 min (ret. time).

The compounds in Table 2 were prepared by a method similar to the one described for the preparation of (3R)-3-(3-{[(4R)-4-ethyl-1,1-dioxo-3,4-dihydro-2H-5,1$\lambda^6$,2-benzoxathiazepin-2-yl]methyl}-4-methylphenyl)-3-[(1-ethyl-1H-1,2,3-triazol-4-yl)methoxy]-2,2-dimethylpropanoic acid. As is appreciated by those skilled in the art, these analogous examples may involve variations in general reaction conditions.

TABLE 2

| Ex # | Structure | Name | LCMS [M + H]+ | Retention Time (min) |
|---|---|---|---|---|
| Ex. 6 | 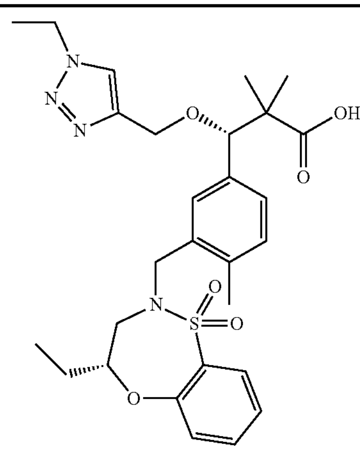 | (S)-3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoic acid | 557.3 | 1.14 |

Example 7

3-((1-Benzyl-1H-1,2,3-triazol-4-yl)methoxy)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic Acid

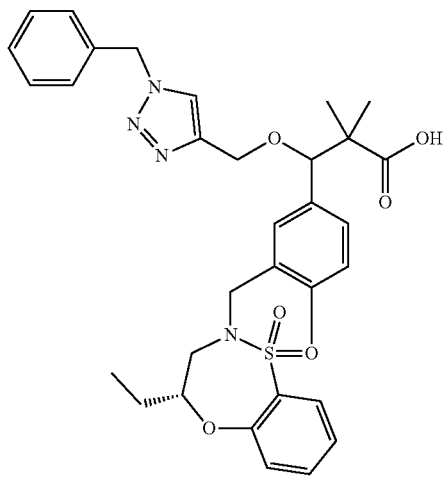

Methyl 3-((1-(3-bromobenzyl)-1H-1,2,3-triazol-4-yl)methoxy)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoate

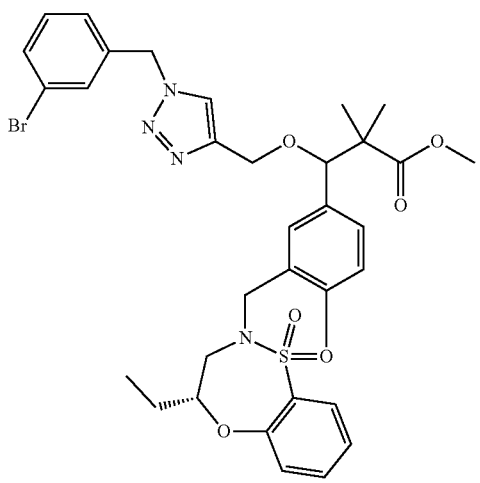

To the mixture of methyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-(prop-2-yn-1-yloxy)propanoate (1.09 g, 2.182 mmol) in isopropanol (9 mL), tetrahydrofuran (3 mL) and water (4 mL) was added sodium azide (0.355 g, 5.45 mmol), DIEA (0.076 mL, 0.436 mmol), 1-bromo-3-(bromomethyl)benzene (1.254 g, 5.02 mmol) and copper(I) iodide (0.062 g, 0.327 mmol). The resulting reaction mixture was heated with microwave at 80° C. for 30 min. The reaction mixture was evaporated down under vacuum, purified via flash chromatography to give the title compound (1.4913 g, 2.096 mmol, 96% yield). LC/MS: m/z 711.2 (M+H)$^+$, 1.44 min (ret. time).

3-(0-Benzyl-1H-1,2,3-triazol-4-yl)methoxy)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic Acid

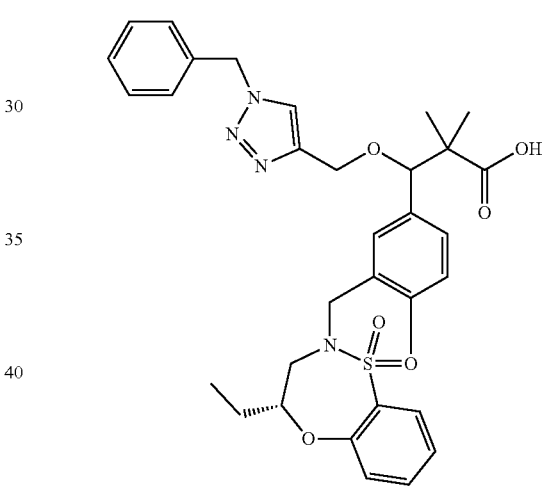

The mixture of methyl 3-((1-(3-bromobenzyl)-1H-1,2,3-triazol-4-yl)methoxy)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoate (70 mg, 0.098 mmol) in methanol (10 mL) was hydrogenated on H-Cube apparatus at 1 bar Hz, 1 mL/min, on 10% Pd/C cartridge, at 20° C.; 1 run. The reaction mixture was evaporated down under vacuum, redissolved in methanol (2 mL) then was added NaOH (6 N) (0.082 mL, 0.492 mmol). The resulting reaction mixture was heated with microwave at 120° C. for 30 min. To the reaction mixture was added HCl (6 N) (0.082 mL, 0.492 mmol), evaporated down under vacuum, purified by reverse phase HPLC (formic acid modifier) to give the title compound (14.5 mg, 0.023 mmol, 23.83% yield). LC/MS: m/z 619.3 (M+H)$^+$, 1.25 min (ret. time).

Example 8

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-propyl-1H-1,2,3-triazol-4-yl)methoxy)propanoic Acid

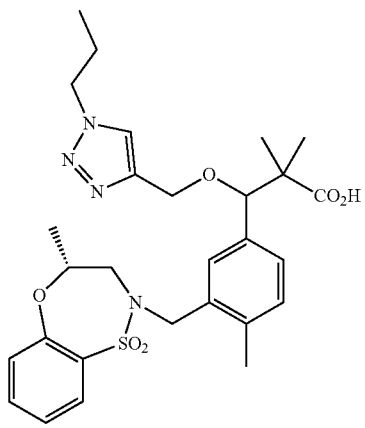 [SMILES: CCCn1cc(COC(c2ccc(C)c(CN3C[C@@H](C)Oc4ccccc4S3(=O)=O)c2)C(C)(C)C(=O)O)nn1]

To the mixture of methyl 3-(3-(hydroxymethyl)-4-methylphenyl)-2,2-dimethyl-3-((1-propyl-1H-1,2,3-triazol-4-yl)methoxy)propanoate (55 mg, 0.146 mmol) in tetrahydrofuran (2 mL) was added (R)-4-methyl-3,4-dihydro-2H-benzo[b][1,4,5]oxathiazepine 1,1-dioxide (46.9 mg, 0.220 mmol), PS—PPh3 (183 mg, 0.293 mmol) and DIAD (0.057 mL, 0.293 mmol). The resulting reaction mixture was stirred at ambient temperature for 21 h. The reaction mixture was filtered, evaporated down under vacuum. This residue was redissolved in methanol (2.000 mL) then was added NaOH (3.0 N) (0.391 mL, 1.172 mmol). The resulting reaction mixture was heated with microwave at 100° C. for 30 min then heated again with microwave at 120° C. for 30 min. To the reaction mixture was added HCl (3.0 N) (0.391 mL, 1.172 mmol), evaporated under vacuum, purified by reverse phase HPLC (formic acid modifier) to give the title compound (40.5 mg, 0.073 mmol, 49.7% yield). LC/MS: m/z 557.3 (M+H)+, 1.13 min (ret. time).

The compounds in Table 3 were prepared by a method similar to the one described for the preparation of 2,2-Dimethyl-3-(4-methyl-3-{[(4R)-4-methyl-1,1-dioxo-3,4-dihydro-2H-5,1$\lambda^6$,2-benzoxathiazepin-2-yl]methyl}phenyl)-3-[(1-propyl-1H-1,2,3-triazol-4-yl)methoxy]propanoic acid. As is appreciated by those skilled in the art, these analogous examples may involve variations in general reaction conditions.

TABLE 3

| Ex # | Structure | Name | LCMS [M + H]+ | Retention Time (min) |
|---|---|---|---|---|
| Ex. 9 | 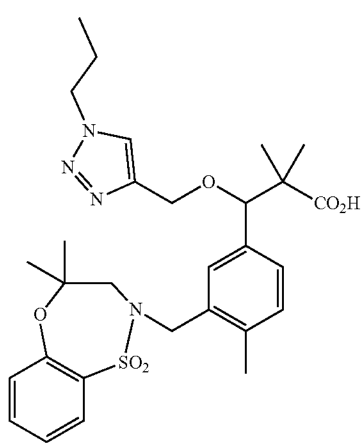 [SMILES: CCCn1cc(COC(c2ccc(C)c(CN3CC(C)(C)Oc4ccccc4S3(=O)=O)c2)C(C)(C)C(=O)O)nn1] | 3-(3-((4,4-Dimethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)-propanoic acid G | 571.4 | 1.17 |

Example 10

3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoic Acid

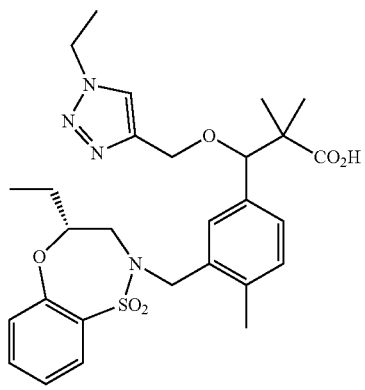 [SMILES: CC[C@@H]1CN(Cc2cc(C(OCc3cn(CC)nn3)C(C)(C)C(=O)O)ccc2C)S(=O)(=O)c2ccccc2O1]

To the mixture of methyl 3-((1-ethyl-1H-1,2,3-triazol-4-yl)methoxy)-3-(3-(hydroxymethyl)-4-methylphenyl)-2,2-dimethylpropanoate (55 mg, 0.152 mmol) in tetrahydrofuran (2 mL) was added (R)-4-ethyl-3,4-dihydro-2H-benzo[b][1,4,5]oxathiazepine 1,1-dioxide (51.9 mg, 0.228 mmol), PS—PPh$_3$ (190 mg, 0.304 mmol) and DIAD (0.059 mL, 0.304 mmol). The resulting reaction mixture was stirred at ambient temperature for 18 h. The reaction mixture was filtered, evaporated down under vacuum. This residue was redissolved in methanol (2.000 mL) then was added NaOH (3.0 N) (0.406 mL, 1.217 mmol). The resulting reaction mixture was heated with microwave at 130° C. for 1 h then heated again with microwave at 130° C. for 1 h. To the reaction mixture was added HCl (3.0 N) (0.406 mL, 1.217 mmol) (60-6), evaporated down under vacuum, purified by reverse phase HPLC (formic acid modifier) to give the title compound (30.1 mg, 0.054 mmol, 35.5% yield). LC/MS: m/z 557.3 (M+H)+, 1.13 min (ret. time).

The compounds in Table 4 were prepared by a method similar to the one described for the preparation of 3-(3-{[(4R)-4-ethyl-1,1-dioxo-3,4-dihydro-2H-5,1$\lambda^6$,2-benzoxathiazepin-2-yl]methyl}-4-methylphenyl)-3-[(1-ethyl-1H-1,2,3-triazol-4-yl)methoxy]-2,2-dimethylpropanoic acid. As is appreciated by those skilled in the art, these analogous examples may involve variations in general reaction conditions.

TABLE 4

| Ex # | Structure | Name | LCMS [M + H]$^+$ | Retention Time (min) |
|---|---|---|---|---|
| Ex 11 | 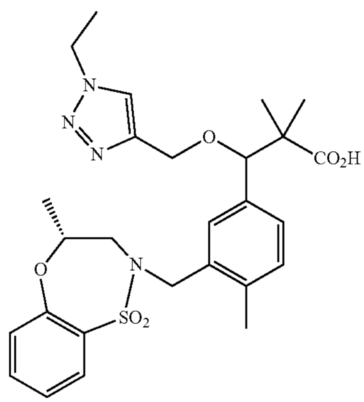 [SMILES: CCn1cc(COC(c2ccc(C)c(CN3C[C@@H](C)Oc4ccccc4S3(=O)=O)c2)C(C)(C)C(=O)O)nn1] | 3-((1-Ethyl-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 543.4 | 1.09 |
| Ex 12 | 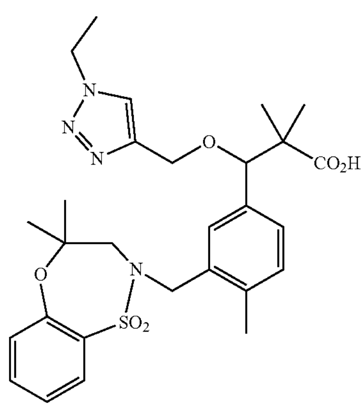 [SMILES: CCn1cc(COC(c2ccc(C)c(CN3CC(C)(C)Oc4ccccc4S3(=O)=O)c2)C(C)(C)C(=O)O)nn1] | 3-(3-((4,4-dimethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-dimethylpropanoic acid | 557.3 | 1.12 |

Example 13

Rel-(S)-3-((1-isobutyl-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

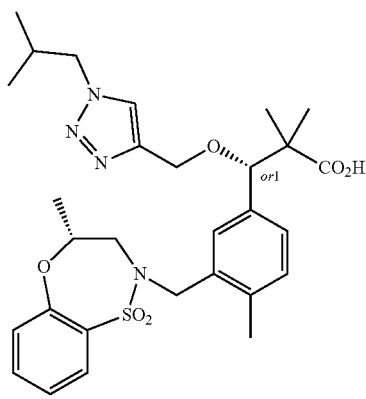 [SMILES: Cc1ccc([C@H](OCc2cn(CC(C)C)nn2)C(C)(C)C(=O)O)cc1CN1C[C@@H](C)Oc2ccccc2S1(=O)=O]

Rel-(S)-methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate

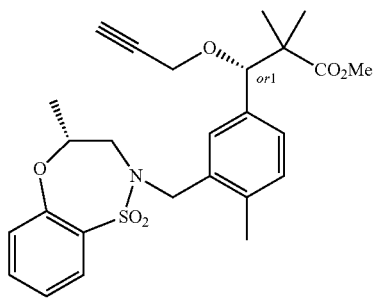 [SMILES: C#CCO[C@@H](c1ccc(C)c(CN2C[C@@H](C)Oc3ccccc3S2(=O)=O)c1)C(C)(C)C(=O)OC]

To the mixture of methyl 3-(3-(hydroxymethyl)-4-methylphenyl)-2,2-dimethyl-3-(prop-2-yn-1-yloxy)propanoate (0.95 g, 3.27 mmol) in tetrahydrofuran (40 mL) was added (R)-4-methyl-3,4-dihydro-2H-benzo[b][1,4,5]oxathiazepine 1,1-dioxide (1.047 g, 4.91 mmol), PS—PPh$_3$ (3.07 g, 4.91 mmol) and DIAD (0.954 mL, 4.91 mmol). The resulting reaction mixture was stirred at ambient temperature for 30 min. The reaction mixture was filtered, evaporated down under vacuum, purified via flash chromatography then separated by chiral SFC (Column: Chiralpak AY 20×250 mm, 5u; Co-solvent: 25% IPA; Flowrate: 50 g/min; Back pressure: 100Bar) to give the title compound (352.0 mg, 0.725 mmol, 22.16% yield). LC/MS: m/z 508.2 (M+Na)$^+$, 1.32 min (ret. time).

The compounds in the following Table 5 were prepared by a method similar to the one described for the preparation of rel-(S)-methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate. As is appreciated by those skilled in the art, these analogous examples may involve variations in general reaction conditions.

TABLE 5

| Product Name | Product Structure | (M + Na)$^+$ | Ret. Time (min) |
| --- | --- | --- | --- |
| Rel-(R)-methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate | | 508.2 | 1.30 |

Rel-(S)-3-((1-isobutyl-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

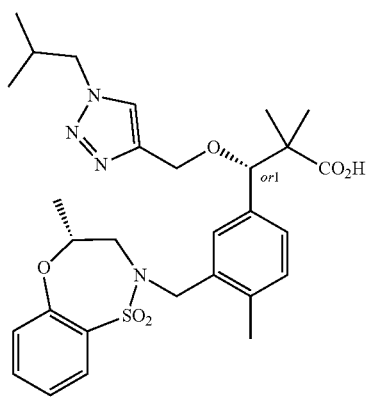 [SMILES: Cc1ccc([C@H](OCc2cn(CC(C)C)nn2)C(C)(C)C(=O)O)cc1CN1C[C@@H](C)Oc2ccccc2S1(=O)=O]

To the mixture of rel-(S)-methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate (48.6 mg, 0.10 mmol) in isopropanol (1.0 mL) and water (0.3 mL) was added sodium azide (16.25 mg, 0.250 mmol), DIEA (3.49 μl, 0.020 mmol), i-butanol (0.026 mL, 0.230 mmol) and copper(I) iodide (2.86 mg, 0.015 mmol). The resulting reaction mixture was stirred at 70° C. for 2 h. The reaction mixture was evaporated down under vacuum. This residue was dissolved in methanol (1.0 mL) then was added NaOH (3.0 N) (0.233 mL, 0.700 mmol). The resulting reaction mixture was heated with microwave at 100° C. for 30 min. To the reaction mixture was added HCl (3.0 N) (0.233 mL, 0.700 mmol), evaporated down under vacuum, purified by reverse phase HPLC (formic acid modifier) to give the title compound (12.7 mg, 0.022 mmol, 22.25% yield). LC/MS: m/z 571.4 (M+H)$^+$, 1.18 min (ret. time).

The compounds in Table 6 were prepared by a method similar to the one described for the preparation of rel-(3S)-2,2-dimethyl-3-(4-methyl-3-{[(4R)-4-methyl-1,1-dioxo-3,4-dihydro-2H-5,1λ$^6$,2-benzoxathiazepin-2-yl]methyl}phenyl)-3-{[1-(2-methylpropyl)-1H-1,2,3-triazol-4-yl]methoxy}propanoic acid. As is appreciated by those skilled in the art, these analogous examples may involve variations in general reaction conditions.

TABLE 6

| Ex # | Structure | Name | LCMS [M + H]$^+$ | Retention Time (min) |
|---|---|---|---|---|
| Ex 14 | 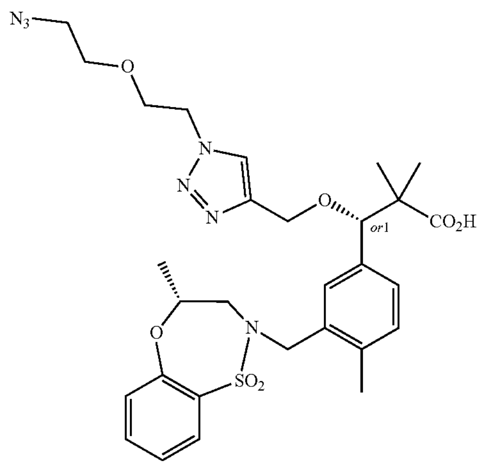 [SMILES: Cc1ccc([C@H](OCc2cn(CCOCCN=[N+]=[N-])nn2)C(C)(C)C(=O)O)cc1CN1C[C@@H](C)Oc2ccccc2S1(=O)=O] | Rel-(S)-3-((1-(2-(2-azidoethoxy)ethyl)-1H-1,2,3-triazol-4-yl)methoxy)-2,2-dimethyl-3-(4-methyl-3-(((R)-4-methyl-1,1-dioxido-3,4-dihydro-2H-benzo[b]-[1,4,5]oxathiazepin-2-yl)methyl)phenyl)propanoic acid | 628.2 | 1.13 |
| Ex 15 | 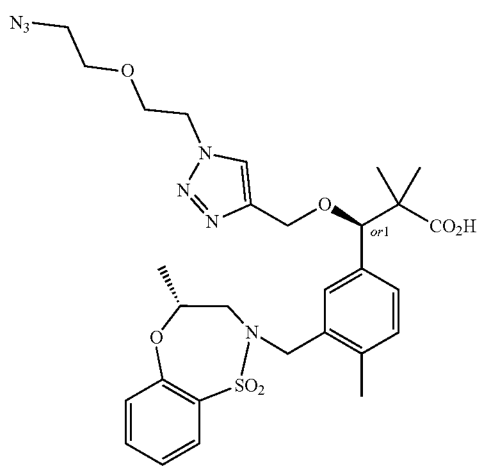 [SMILES: Cc1ccc([C@@H](OCc2cn(CCOCCN=[N+]=[N-])nn2)C(C)(C)C(=O)O)cc1CN1C[C@@H](C)Oc2ccccc2S1(=O)=O] | Rel-(R)-3-((1-(2-(2-azidoethoxy)ethyl)-1H-1,2,3-triazol-4-yl)methoxy)-2,2-dimethyl-3-(4-methyl-3-(((R)-4-methyl-1,1-dioxido-3,4-dihydro-2H-benzo[b]-[1,4,5]oxathiazepin-2-yl)methyl)phenyl)propanoic acid | 628.2 | 1.13 |

| Ex # | Structure | Name | LCMS [M + H]+ | Retention Time (min) |
|---|---|---|---|---|
| Ex 16 | 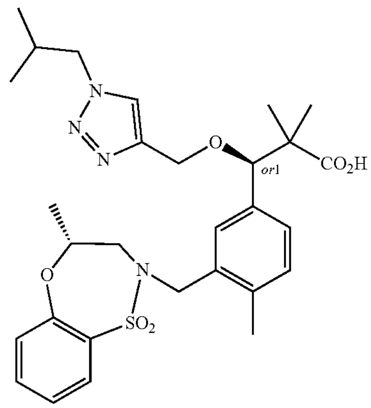 [SMILES: Cc1ccc([C@@H](OCc2cn(CC(C)C)nn2)C(C)(C)C(=O)O)cc1CN1C[C@@H](C)Oc2ccccc2S1(=O)=O] | Rel-(R)-3-((1-isobutyl-1H-1,2,3-triazol-4-yl)methoxy)-2,2-dimethyl-3-(4-methyl-3-(((R)-4-methyl-1,1-dioxido-3,4-dihydro-2H-benzo[b]-[1,4,5]oxathiazepin-2-yl)methyl)phenyl) propanoic acid | 571.4 | 1.18 |

Example 17

3-((1-Cyclohexyl-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

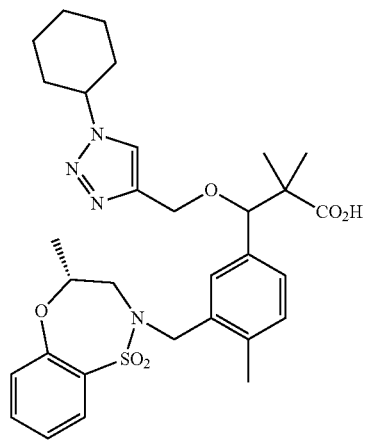 [SMILES: Cc1ccc(C(OCc2cn(C3CCCCC3)nn2)C(C)(C)C(=O)O)cc1CN1C[C@@H](C)Oc2ccccc2S1(=O)=O]

To the mixture of iodocyclohexane (0.048 mL, 0.371 mmol) in N,N-dimethylformamide (0.500 mL) was added sodium azide (24.10 mg, 0.371 mmol). The resulting reaction mixture was stirred at 80° C. for 23 h. The reaction mixture was cooled down to ambient temperature before was added isopropanol (0.5 mL), methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate (60 mg, 0.124 mmol), DIEA (4.32 µl, 0.025 mmol), water (0.3 mL) and copper(I) iodide (3.53 mg, 0.019 mmol). The resulting reaction mixture was heated with microwave at 80° C. for 10 min. The reaction mixture was evaporated down under vacuum, redissolved in methanol (1.0 mL) then was added NaOH (6.0 N) (0.165 mL, 0.988 mmol). The resulting reaction mixture was heated with microwave at 120° C. for 30 min. To the reaction mixture was added more NaOH (6.0 N) (0.062 mL, 0.371 mmol). The resulting reaction mixture was heated with microwave at 120° C. for 1 h. To the reaction mixture was added HCl (6.0 N) (0.227 mL, 1.359 mmol), evaporated down under vacuum, purified by reverse phase HPLC (formic acid modifier) to give the title compound (26.4 mg, 0.044 mmol, 35.8% yield). LC/MS: m/z 597.3 (M+H)+, 1.23 min (ret. time).

Example 18

3-((1-((1-(Tert-butoxycarbonyl)piperidin-3-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

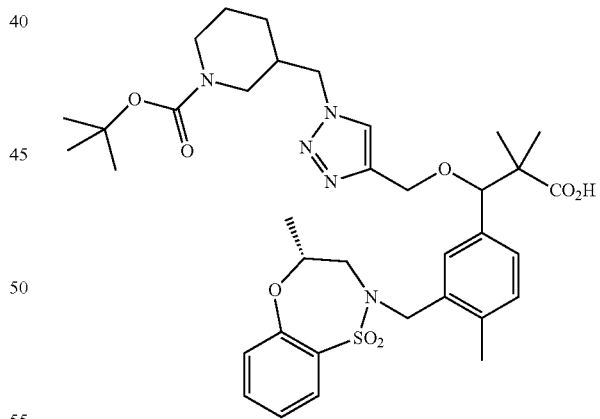

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate (48.6 mg, 0.10 mmol) in isopropanol (1.0 mL), tetrahydrofuran (0.3 mL) and water (0.3 mL) was added sodium azide (16.25 mg, 0.250 mmol), DIEA (3.49 µl, 0.020 mmol), tert-butyl 3-(bromomethyl)piperidine-1-carboxylate (64.0 mg, 0.230 mmol) and copper(I) iodide (2.86 mg, 0.015 mmol). The resulting reaction mixture was heated with microwave at 80° C. for 1 h, heated again with microwave at 80° C. for 30 min. The reaction mixture was evaporated down under vacuum. The residue was dissolved in methanol (1.0 mL) then was added NaOH (6.0 N) (0.167 mL, 1.000 mmol). The resulting reaction mixture was heated with microwave at 120° C. for 30 min. To the reaction mixture was HCl (6.0 N) (0.167 mL, 1.000 mmol), evaporated down under vacuum, purified by reverse phase HPLC (formic acid modifier) to give the title compound (13.7 mg, 0.019 mmol, 19.25% yield). LC/MS: m/z 712.4 (M+H)$^+$, 1.26 min (ret. time).

The compounds in Table 7 were prepared by a method similar to the one described for the preparation of 3-{[1-({1-[(tert-butoxy)carbonyl]piperidin-3-yl}methyl)-1H-1,2,3-triazol-4-yl]methoxy}-2,2-dimethyl-3-(4-methyl-3-{[(4R)-4-methyl-1,1-dioxo-3,4-dihydro-2H-5,1$\lambda^6$,2-benzoxathiazepin-2-yl]methyl}phenyl)propanoic acid. As is appreciated by those skilled in the art, these analogous examples may involve variations in general reaction conditions.

TABLE 7

| Ex # | Structure | Name | LCMS [M + H]$^+$ | Retention Time (min) |
|---|---|---|---|---|
| Ex 19 | 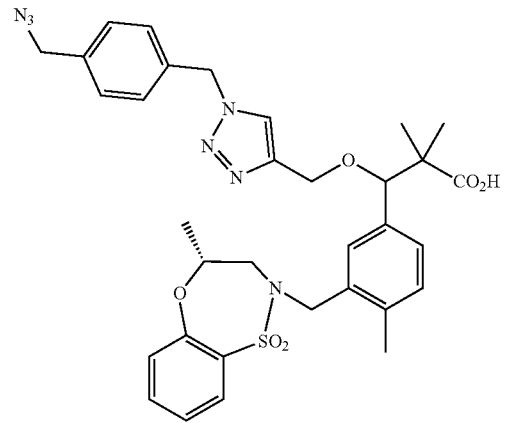 [SMILES: Cc1ccc(C(OCc2cn(Cc3ccc(CN=[N+]=[N-])cc3)nn2)C(C)(C)C(=O)O)cc1CN1C[C@@H](C)Oc2ccccc2S1(=O)=O] | 3-((1-(4-(Azidomethyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 660.3 | 1.24 |
| Ex 20 | 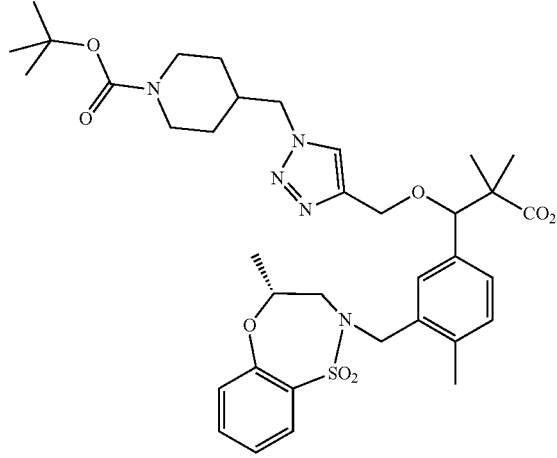 | 3-((1-((1-(Tert-butoxycarbonyl)piperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 712.3 | 1.28 |
| Ex 21 | 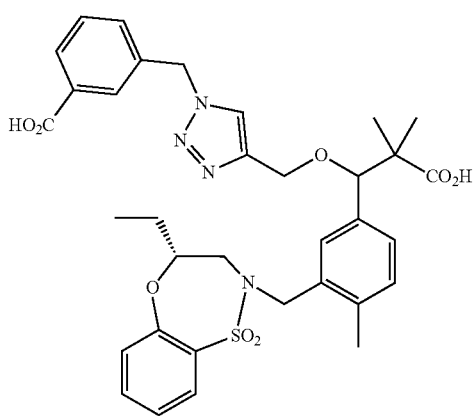 [SMILES: CC[C@@H]1CN(Cc2cc(C(OCc3cn(Cc4cccc(C(=O)O)c4)nn3)C(C)(C)C(=O)O)ccc2C)S(=O)(=O)c2ccccc2O1] | 3-((4-((2-Carboxy-1-(3-(((R)-4-ethyl-1,1-dioxido-3,4-dihydro-2H-benzo[b][1,4,5]oxathiazepin-2-yl)methyl)-4-methylphenyl)-2-methylpropoxy)methyl)-1H-1,2,3-triazol-1-yl)methyl)benzoic acid | 663.0 | 1.12 |

Example 22

3'-((4-((2-Carboxy-1-(3-(((R)-4-ethyl-1,1-dioxido-3,4-dihydro-2H-benzo[b][1,4,5]oxathiazepin-2-yl)methyl)-4-methylphenyl)-2-methylpropoxy)methyl)-1H-1,2,3-triazol-1-yl)methyl)-[1,1'-biphenyl]-4-carboxylic Acid

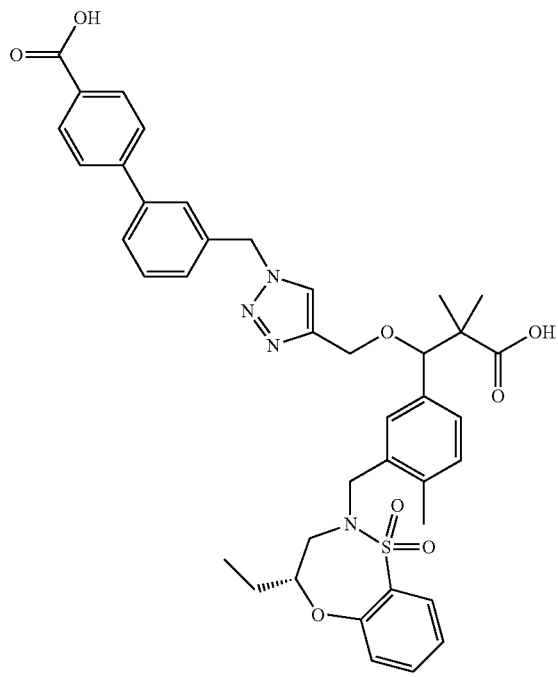 [SMILES: CC[C@@H]1CN(Cc2cc(C(OCc3cn(Cc4cccc(-c5ccc(C(=O)O)cc5)c4)nn3)C(C)(C)C(=O)O)ccc2C)S(=O)(=O)c2ccccc2O1]

To the mixture of methyl 3-((1-(3-bromobenzyl)-1H-1,2,3-triazol-4-yl)methoxy)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoate (50 mg, 0.070 mmol) in 1,4-dioxane (1.5 mL) and water (0.5 mL) was added 4-boronobenzoic acid (17.49 mg, 0.105 mmol), $K_2CO_3$ (48.6 mg, 0.351 mmol) and $Pd(Ph_3P)_4$ (4.06 mg, 3.51 μmol). The resulting reaction mixture was heated with microwave at 130° C. for 30 min. The reaction mixture was evaporated down under vacuum then was added methanol (1.5 mL) and NaOH (3.0 N) (0.187 mL, 0.562 mmol). The resulting reaction mixture was heated with microwave at 120° C. for 30 min. To the reaction mixture was added HCl (3.0 N) (0.187 mL, 0.562 mmol), evaporated down under vacuum, purified by reverse phase HPLC (formic acid modifier) to give the title compound (35.1 mg, 0.048 mmol, 67.6% yield). LC/MS: m/z 739.5 $(M+H)^+$, 1.22 min (ret. time).

The compounds in Table 8 were prepared by a method similar to the one described for the preparation of 4-{3-[(4-{[2-carboxy-1-(3-{[(4R)-4-ethyl-1,1-dioxo-3,4-dihydro-2H-5,1λ$^6$,2-benzoxathiazepin-2-yl]methyl}-4-methylphenyl)-2,2-dimethylethoxy]methyl}-1H-1,2,3-triazol-1-yl)methyl]phenyl}benzoic acid. As is appreciated by those skilled in the art, these analogous examples may involve variations in general reaction conditions.

TABLE 8

| Ex # | Structure | Name | LCMS [M + H]$^+$ | Retention Time (min) |
|---|---|---|---|---|
| Ex 23 | 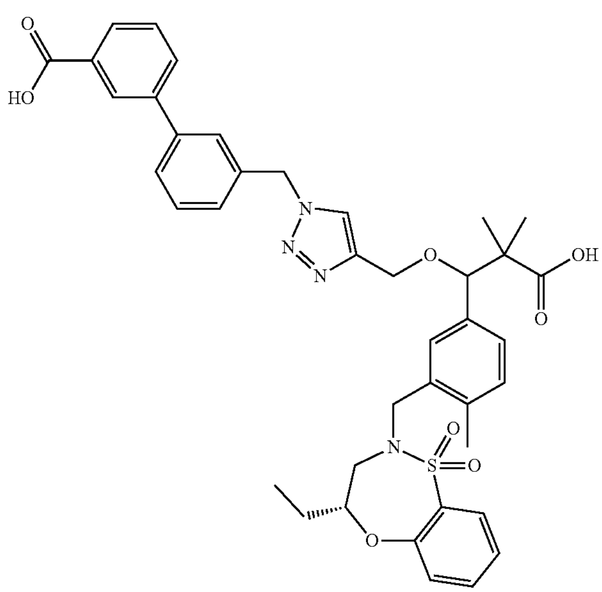 [SMILES: CC[C@@H]1CN(Cc2cc(C(OCc3cn(Cc4cccc(-c5cccc(C(=O)O)c5)c4)nn3)C(C)(C)C(=O)O)ccc2C)S(=O)(=O)c2ccccc2O1] | 3'-((4-((2-Carboxy-1-(3-(((R)-4-ethyl-1,1-dioxido-3,4-dihydro-2H-benzo[b][1,4,5]oxathiazepin-2-yl)methyl)-4-methylphenyl)-2-methylpropoxy)methyl)-1H-1,2,3-triazol-1-yl)methyl)-[1,1'-biphenyl]-3-carboxylic acid | 739.5 | 1.24 |

TABLE 8-continued

| Ex # | Structure | Name | LCMS [M + H]+ | Retention Time (min) |
|---|---|---|---|---|
| Ex 24 | 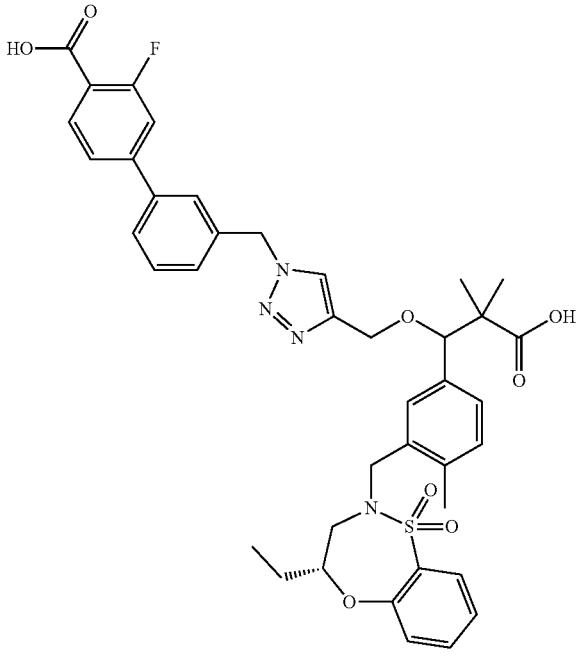 [SMILES: CC[C@@H]1CN(Cc2cc(C(OCc3cn(Cc4cccc(-c5ccc(C(=O)O)c(F)c5)c4)nn3)C(C)(C)C(=O)O)ccc2C)S(=O)(=O)c2ccccc2O1] | 3'-((4-((2-Carboxy-1-(3-(((R)-4-ethyl-1,1-dioxido-3,4-dihydro-2H-benzo[b][1,4,5]oxathiazepin-2-yl)methyl)-4-methylphenyl)-2-methylpropoxy)methyl)-1H-1,2,3-triazol-1-yl)methyl)-3-fluoro-[1,1'-biphenyl]-4-carboxylic acid | 757.4 | 1.22 |
| Ex 25 | 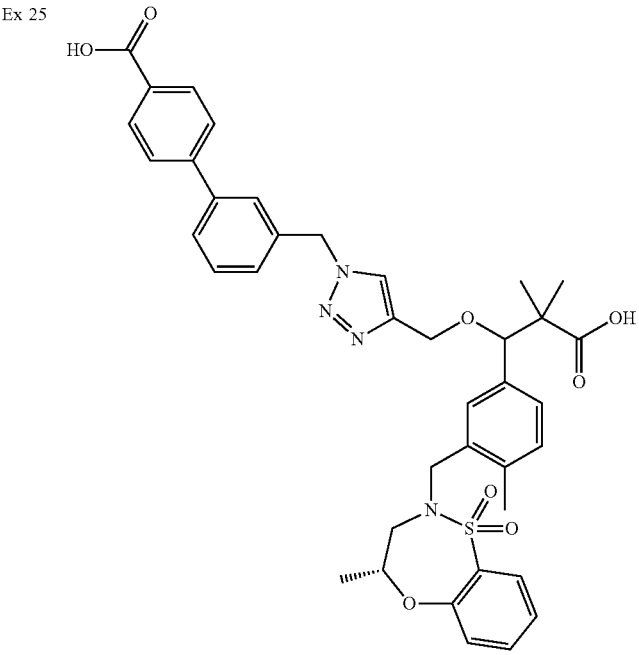 | 3'-((4-((2-Carboxy-2-methyl-1-(4-methyl-3-(((R)-4-methyl-1,1-dioxido-3,4-dihydro-2H-benzo[b][1,4,5]oxathiazepin-2-yl)methyl)phenyl)propoxy)methyl)-1H-1,2,3-triazol-1-yl)methyl)-[1,1'-biphenyl]-4-carboxylic acid | 725.3 | 1.17 |

TABLE 8-continued

| Ex # | Structure | Name | LCMS [M + H]+ | Retention Time (min) |
|---|---|---|---|---|
| Ex 26 | 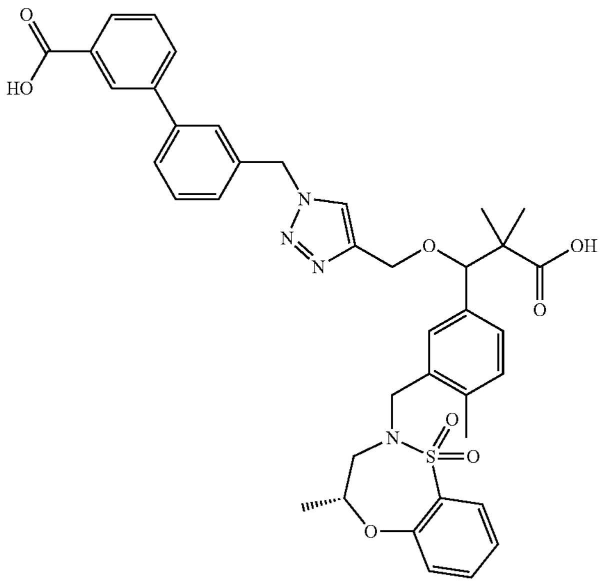 [SMILES: Cc1ccc(C(OCc2cn(Cc3cccc(-c4cccc(C(=O)O)c4)c3)nn2)C(C)(C)C(=O)O)cc1CN1C[C@@H](C)Oc2ccccc2S1(=O)=O] | 3'-((4-((2-Carboxy-2-methyl-1-(4-methyl-3-(((R)-4-methyl-1,1-dioxido-3,4-dihydro-2H-benzo[b][1,4,5]oxathiazepin-2-yl)methyl)phenyl)propoxy)methyl)-1H-1,2,3-triazol-1-yl)methyl)-[1,1'-biphenyl]-3-carboxylic acid | 725.3 | 1.19 |

Example 27

3-(3-(((R)-4-ethyl-1,1-dioxido-3,4-dihydro-2H-benzo[b][1,4,5]oxathiazepin-2-yl)methyl)-4-methylphenyl)-3-((1-(3-((4-(hydroxymethyl)-1H-1,2,3-triazol-1-yl)methyl)-5-methylbenzyl)-1H-1,2,3-triazol-4-yl)methoxy)-2,2-dimethylpropanoic Acid (1-(3-(Azidomethyl)-5-methylbenzyl)-1H-1,2,3-triazol-4-yl)methanol

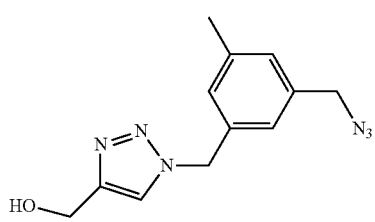

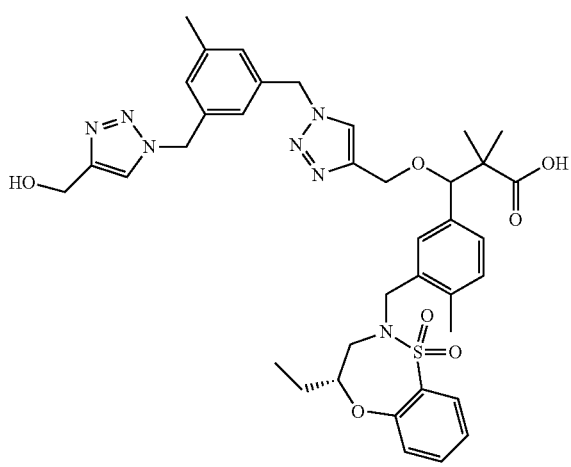 [SMILES: CC[C@@H]1CN(Cc2cc(C(OCc3cn(Cc4cc(C)cc(Cn5cc(CO)nn5)c4)nn3)C(C)(C)C(=O)O)ccc2C)S(=O)(=O)c2ccccc2O1]

To the mixture of prop-2-yn-1-ol (0.116 mL, 2 mmol) in isopropanol (15 mL) and water (5 mL) was added sodium azide (650 mg, 10.00 mmol), DIEA (0.070 mL, 0.400 mmol), 1,3-bis(bromomethyl)-5-methylbenzene (1279 mg, 4.60 mmol) and copper(I) iodide (57.1 mg, 0.300 mmol). The resulting reaction mixture was heated with microwave at 70° C. for 60 min. The reaction mixture was evaporated down under vacuum, purified via flash chromatography to give the title compound (297.9 mg, 1.153 mmol, 57.7% yield). LC/MS: m/z 259.0 (M+H)+, 0.72 min (ret. time).

The compounds in Table 9 were prepared by a method similar to the one described for the preparation of (1-(3-(Azidomethyl)-5-methylbenzyl)-1H-1,2,3-triazol-4-yl) methanol. As is appreciated by those skilled in the art, these analogous examples may involve variations in general reaction conditions.

TABLE 9

| Structure | Name | LCMS [M + H]+ | Retention Time (min) |
|---|---|---|---|
| 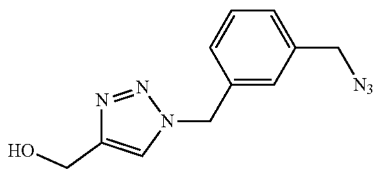 [SMILES: [N-]=[N+]=NCc1cccc(Cn2cc(CO)nn2)c1] | (1-(3-(azidomethyl) benzyl)-1H-1,2,3-triazol-4-yl)methanol | 244.9 | 0.61 |

3-(3-(((R)-4-ethyl-1,1-dioxido-3,4-dihydro-2H-benzo[b][1,4,5]oxathiazepin-2-yl)methyl)-4-methylphenyl)-3-((1-(3-((4-(hydroxymethyl)-1H-1,2,3-triazol-1-yl)methyl)-5-methylbenzyl)-1H-1,2,3-triazol-4-yl)methoxy)-2,2-dimethylpropanoic Acid

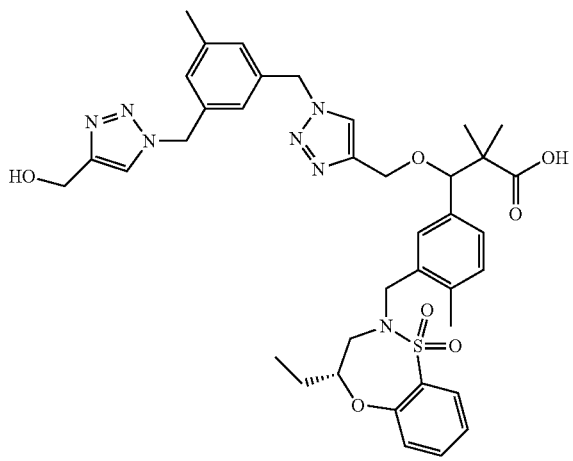 [SMILES: CC[C@@H]1CN(Cc2cc(C(OCc3cn(Cc4cc(C)cc(Cn5cc(CO)nn5)c4)nn3)C(C)(C)C(=O)O)ccc2C)S(=O)(=O)c2ccccc2O1]

To the mixture of methyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-(prop-2-yn-1-yloxy)propanoate (85 mg, 0.170 mmol) in isopropanol (1.5 mL) and tetrahydrofuran (0.7 mL) was added (1-(3-(azidomethyl)-5-methylbenzyl)-1H-1,2,3-triazol-4-yl)methanol (43.9 mg, 0.170 mmol), DIEA (8.91 μl, 0.051 mmol) and copper(I) iodide (6.48 mg, 0.034 mmol). The resulting reaction mixture was heated with microwave at 80° C. for 30 min. The reaction mixture was evaporated down under vacuum then was added methanol (2 mL), tetrahydrofuran (0.7 mL) and NaOH (3.0 N) (0.454 mL, 1.361 mmol). The resulting reaction mixture was heated with microwave at 120° C. for 60 min. To the reaction mixture was added HCl (3.0 N) (0.454 mL, 1.361 mmol), evaporated down under vacuum, purified by reverse phase HPLC (formic acid modifier) to give the title compound (91.3 mg, 0.123 mmol, 72.1 yield). LC/MS: m/z 744.3 (M+H)+, 1.13 min (ret. time).

The compounds in Table 10 were prepared by a method similar to the one described for the preparation of 3-(3-{[(4R)-4-ethyl-1,1-dioxo-3,4-dihydro-2H-5,1λ⁶,2-benzoxathiazepin-2-yl]methyl}-4-methylphenyl)-3-({1-[(3-{[4-(hydroxymethyl)-1H-1,2,3-triazol-1-yl]methyl}-5-methylphenyl)methyl]-1H-1,2,3-triazol-4-yl}methoxy)-2,2-dimethylpropanoic acid. As is appreciated by those skilled in the art, these analogous examples may involve variations in general reaction conditions.

TABLE 10

| Ex # | Structure | Name | LCMS [M + H]+ | Retention Time (min) |
|---|---|---|---|---|
| Ex 28 | 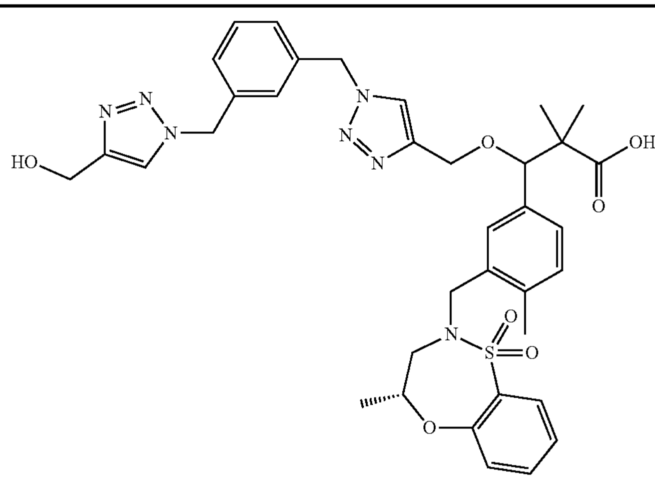 | 3-(3-(((R)-4-ethyl-1,1-dioxido-3,4-dihydro-2H-benzo[b][1,4,5]oxathiazepin-2-yl)methyl)-4-methylphenyl)-3-((1-(3-((4-(hydroxymethyl)-1H-1,2,3-triazol-1-yl)methyl)benzyl)-1H-1,2,3-triazol-4-yl)methoxy)-2,2-dimethyl-propanoic acid | 730.3 | 1.10 |

TABLE 10-continued

| Ex # | Structure | Name | LCMS [M + H]+ | Retention Time (min) |
|---|---|---|---|---|
| Ex 29 | 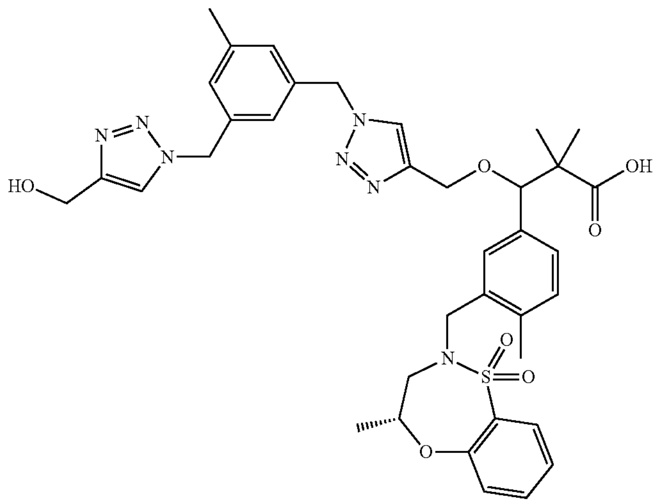 [SMILES: Cc1cc(Cn2cc(CO)nn2)cc(Cn2cc(COC(c3ccc(C)c(CN4C[C@@H](C)Oc5ccccc5S4(=O)=O)c3)C(C)(C)C(=O)O)nn2)c1] | 3-((1-(3-((4-(Hydroxy-methyl)-1H-1,2,3-triazol-1-yl)methyl)-5-methylbenzyl)-1H-1,2,3-triazol-4-yl)methoxy)-2,2-dimethyl-3-(4-methyl-3-(((R)-4-methyl-1,1-dioxido-3,4-dihydro-2H-benzo[b]-[1,4,5]oxathiazepin-2-yl)methyl)phenyl)propanoic acid | 730.3 | 1.08 |

Example 30

3-((1-((1-(Cyclohexanecarbonyl)piperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

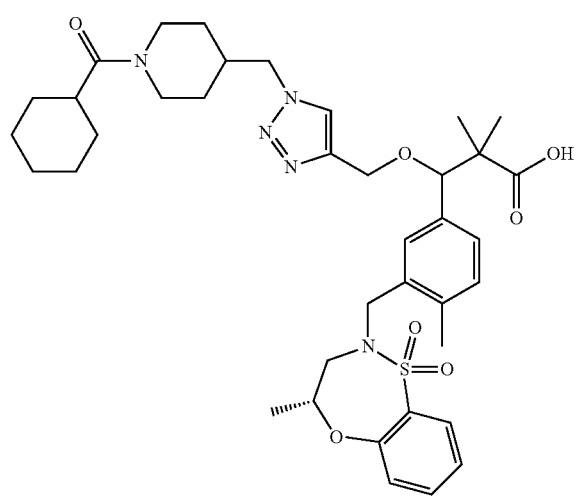 [SMILES: Cc1ccc(C(OCc2cn(CC3CCN(C(=O)C4CCCCC4)CC3)nn2)C(C)(C)C(=O)O)cc1CN1C[C@@H](C)Oc2ccccc2S1(=O)=O]

tert-Butyl 4-((44(3-methoxy-2,2-dimethyl-1-(4-methyl-3-(((R)-4-methyl-1,1-dioxido-3,4-dihydro-2H-benzo[b][1,4,5]oxathiazepin-2-yl)methyl)phenyl)-3-oxopropoxy)methyl)-1H-1,2,3-triazol-1-yl)methyl)piperidine-1-carboxylate

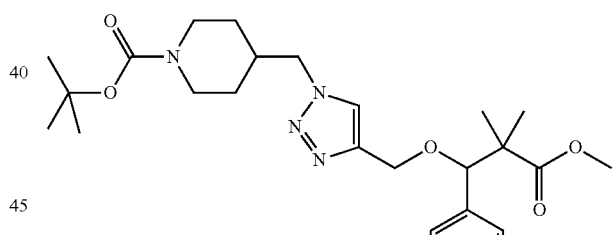

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate (2.86 g, 5.89 mmol) in isopropanol (20 mL), tetrahydrofuran (10 mL) and water (8.0 mL) was added sodium azide (0.957 g, 14.72 mmol), DIEA (0.206 mL, 1.178 mmol), tert-butyl 4-(bromomethyl)piperidine-1-car boxylate (3.77 g, 13.55 mmol) and copper(I) iodide (0.168 g, 0.883 mmol). The resulting reaction mixture was each heated with microwave at 80° C. for 1 h then heated again with microwave at 80° C. for 30 min. The reaction mixture was evaporated down under vacuum, purified via flash chromatography to give the title compound (1.5552 g, 2.142 mmol, 36.4% yield). LC/MS: m/z 726.5 (M+H)+, 1.36 min (ret. time).

Methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(piperidin-4-ylmethyl)-1H-1,2,3-triazol-4-yl)methoxy)propanoate, Hydrochloride, 1,4-DIOXANE (SOLVATE

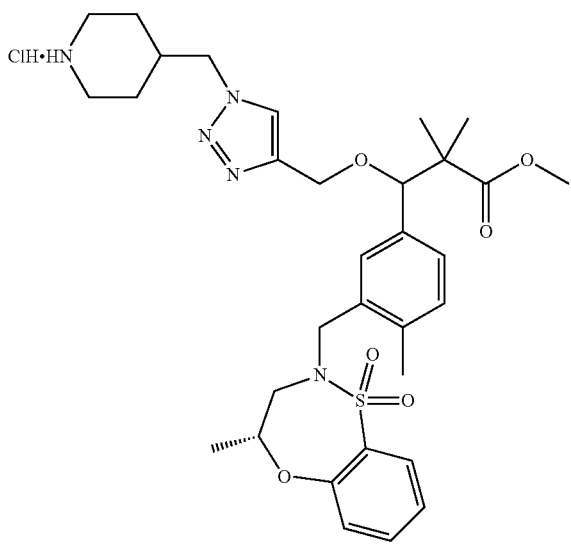

To tert-butyl 4-((4-((3-methoxy-2,2-dimethyl-1-(4-methyl-3-(((R)-4-methyl-1,1-dioxido-3,4-dihydro-2H-benzo[b][1,4,5]oxathiazepin-2-yl)methyl)phenyl)-3-oxopropoxy)methyl)-1H-1,2,3-triazol-1-yl)methyl)piperidine-1-carboxylate (1.5 g, 2.066 mmol) was added HCl (4.0 M in p-dioxane) (2.58 ml, 10.33 mmol). The resulting reaction mixture was stirred at ambient temperature for 2 h. The reaction mixture was evaporated down under vacuum to give the title compound (1.4198 g, 1.892 mmol, 92% yield). LC/MS: m/z 626.3 (M+H)+, 1.00 min (ret. time).

3-((1-((1-(Cyclohexanecarbonyl)piperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

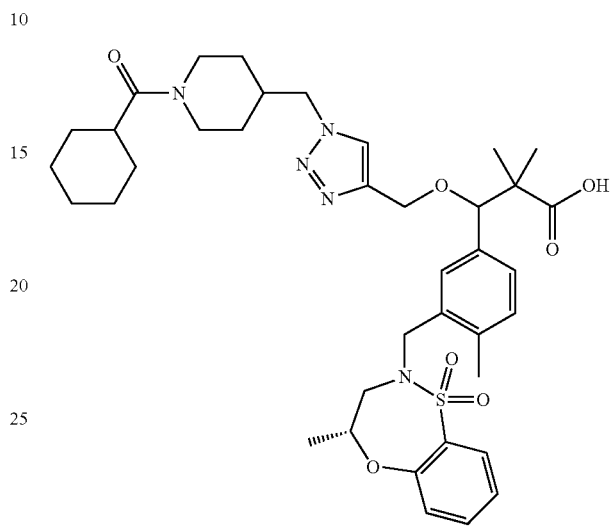

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(piperidin-4-ylmethyl)-1H-1,2,3-triazol-4-yl)methoxy)propanoate, hydrochloride (60 mg, 0.091 mmol) in dichloromethane (1.000 mL) was added DIEA (0.040 mL, 0.227 mmol) and cyclohexanecarbonyl chloride (0.015 mL, 0.109 mmol). The resulting reaction mixture was stirred at ambient temperature for 20 min. The reaction mixture was evaporated down under vacuum. The residue was dissolved in methanol (1.0 mL) then was added NaOH (6.0 N) (0.121 mL, 0.725 mmol). The resulting reaction mixture was heated with microwave at 100° C. for 30 min. To the reaction mixture was added HCl (6.0 N) (0.121 mL, 0.725 mmol), evaporated down under vacuum, purified by reverse phase HPLC (neutral), purified by reverse phase HPLC (formic acid modifier) to give the title compound (35.4 mg, 0.049 mmol, 54.1% yield). LC/MS: m/z 722.5 (M+H)+, 1.22 min (ret. time).

The compounds in Table 11 were prepared by a method similar to the one described for the preparation of 3-({1-[(1-cyclohexanecarbonylpiperidin-4-yl)methyl]-1H-1,2,3-triazol-4-yl}methoxy)-2,2-dimethyl-3-(4-methyl-3-{[(4R)-4-methyl-1,1-dioxo-3,4-dihydro-2H-5,1λ6,2-benzoxathiazepin-2-yl]methyl}phenyl)propanoic acid. As is appreciated by those skilled in the art, these analogous examples may involve variations in general reaction conditions.

TABLE 11

| Ex # | Structure | Name | LCMS [M + H]+ | Retention Time (min) |
|---|---|---|---|---|
| Ex 31 | 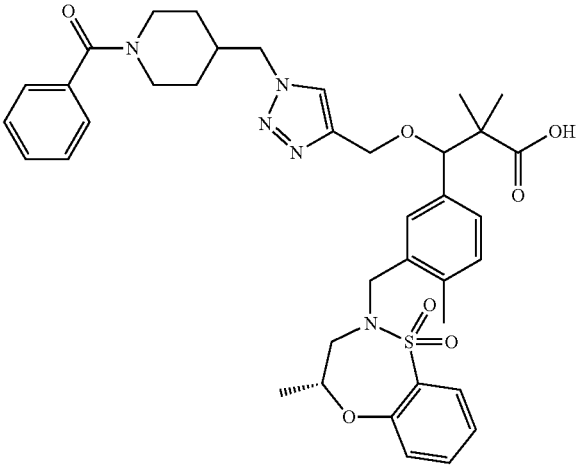 [SMILES: Cc1ccc(C(OCc2cn(CC3CCN(C(=O)c4ccccc4)CC3)nn2)C(C)(C)C(=O)O)cc1CN1C[C@@H](C)Oc2ccccc2S1(=O)=O] | 3-((1-((1-Benzoylpiperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 716.3 | 1.15 |
| Ex 32 | 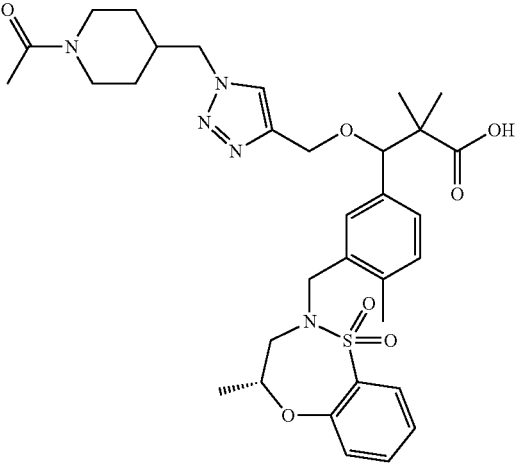 [SMILES: CC(=O)N1CCC(Cn2cc(COC(c3ccc(C)c(CN4C[C@@H](C)Oc5ccccc5S4(=O)=O)c3)C(C)(C)C(=O)O)nn2)CC1] | 3-((1-((1-Acetylpiperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 654.4 | 1.01 |
| Ex 33 | 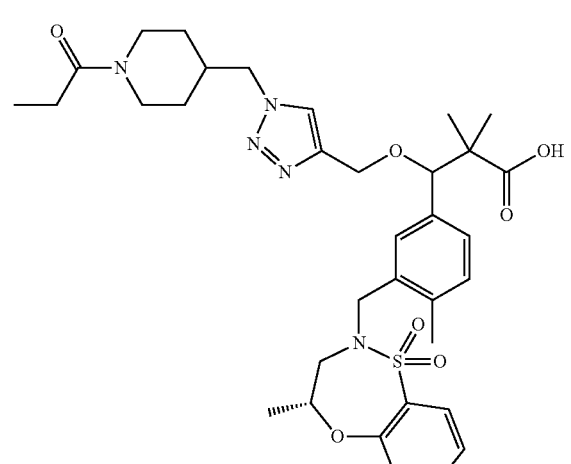 | 2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-((1-propionylpiperidin-4-yl)methyl)-1H-1,2,3-triazol-4-yl)methoxy)propanoic acid | 668.4 | 1.06 |

TABLE 11-continued

| Ex # | Structure | Name | LCMS [M + H]+ | Retention Time (min) |
|---|---|---|---|---|
| Ex 34 | 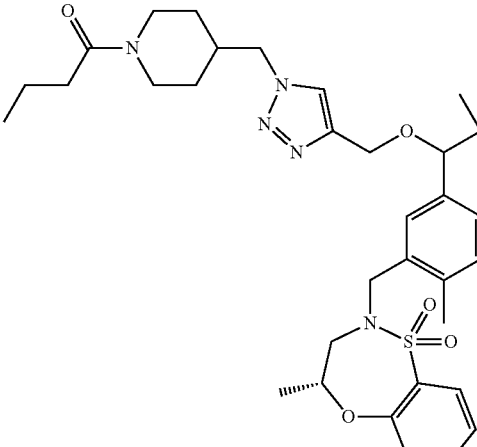 | 3-((1-((1-Butyrylpiperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 682. | 1.10 |
| Ex 35 | 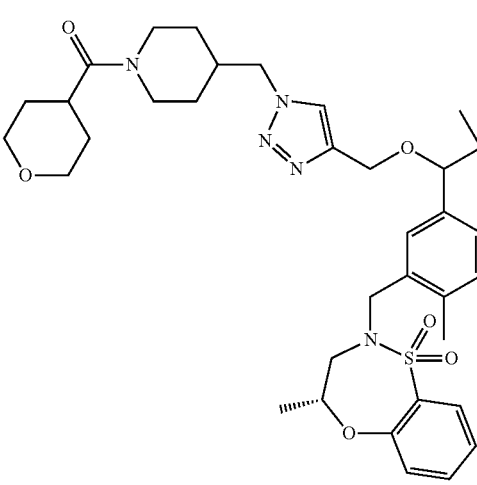 | 2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-((1-(tetrahydro-2H-pyran-4-carbonyl)piperidin-4-yl)methyl)-1H-1,2,3-triazol-4-yl)methoxy)propanoic acid | 4724.5 | 1.04 |
| Ex 36 | 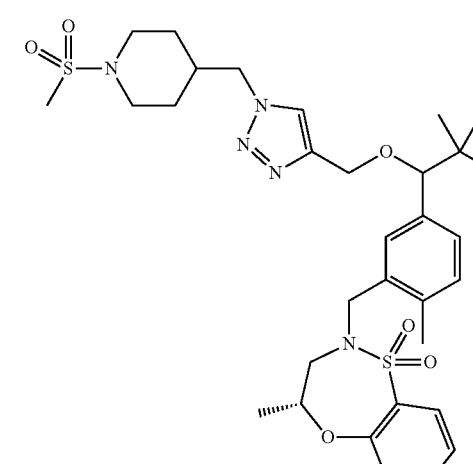 | 2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-((1-(methylsulfonyl)piperidin-4-yl)methyl)-1H-1,2,3-triazol-4-yl)methoxy)propanoic acid | 690.3 | 1.08 |

Example 37

3-((1-(3-((4-Isopropyl-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

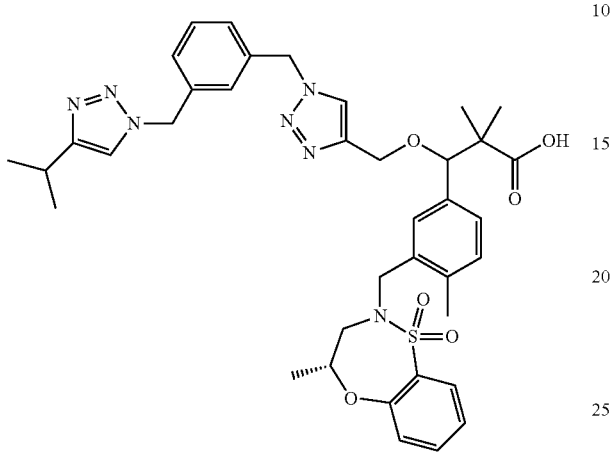

Methyl 3-((1-(3-(azidomethyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoate

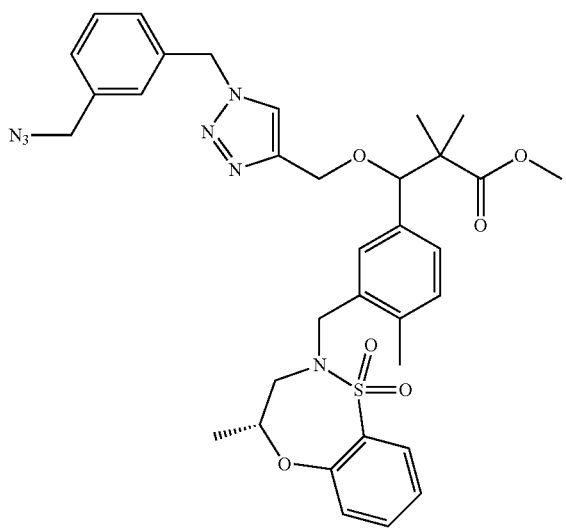 [SMILES: COC(=O)C(C)(C)C(OCc1cn(Cc2cccc(CN=[N+]=[N-])c2)nn1)c1ccc(C)c(CN2C[C@@H](C)Oc3ccccc3S2(=O)=O)c1]

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate (971 mg, 2.0 mmol) in isopropanol (12 mL) and water (4 mL) was added sodium azide (650 mg, 10.00 mmol), DIEA (0.070 mL, 0.400 mmol), 1,3-bis(bromomethyl)benzene (1214 mg, 4.60 mmol) and copper(I) iodide (57.1 mg, 0.300 mmol). The resulting reaction mixture was heated with microwave at 80° C. for 30 min. The reaction mixture was evaporated down under vacuum, purified by flash chromatography to give the title compound (691.1 mg, 1.026 mmol, 51.3% yield). LC/MS: m/z 674.3 (M+H)⁺, 1.36 min (ret. time).

3-((1-(3-((4-isopropyl-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

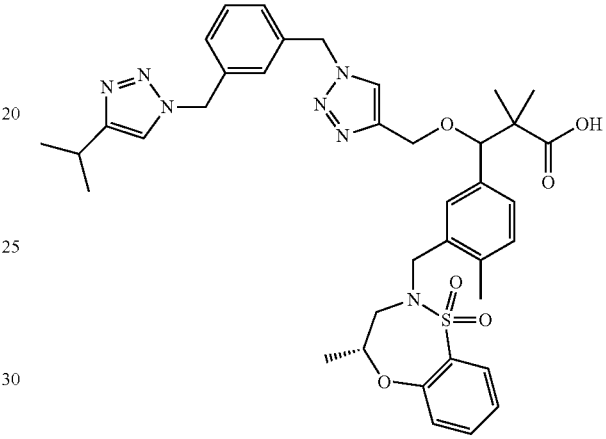

To the mixture of methyl 3-((1-(3-(azidomethyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoate (50 mg, 0.074 mmol) in isopropanol (1.0 mL) and tetrahydrofuran (0.5 mL) was added 3-methylbut-1-yne (0.023 mL, 0.223 mmol), DIEA (3.89 µl, 0.022 mmol) and copper(I) iodide (2.83 mg, 0.015 mmol). The resulting reaction mixture was heated with microwave at 80° C. for 30 min (48-1). The reaction mixture was evaporated down under vacuum then was added methanol (1.5 mL) and NaOH (3.0 N) (0.198 mL, 0.594 mmol). The resulting reaction mixture was heated with microwave at 120° C. for 60 min. To the reaction mixture was added HCl (3.0 N) (0.198 mL, 0.594 mmol), evaporated down under vacuum, purified by reverse phase HPLC (neutral), purified by reverse phase HPLC (formic acid modifier) to give the title compound (28.0 mg, 0.038 mmol, 51.8% yield). LC/MS: m/z 728.5 (M+H)⁺, 1.22 min (ret. time).

The compounds in Table 12 were prepared by a method similar to the one described for the preparation of 2,2-dimethyl-3-(4-methyl-3-{[(4R)-4-methyl-1,1-dioxo-3,4-dihydro-2H-5,1λ⁶,2-benzoxathiazepin-2-yl]methyl}phenyl)-3-({1-[(3-{[4-(propan-2-yl)-1H-1,2,3-triazol-1-yl]methyl}phenyl)methyl]-1H-1,2,3-triazol-4-yl}methoxy)propanoic acid. As is appreciated by those skilled in the art, these analogous examples may involve variations in general reaction conditions.

TABLE 12

| Ex # | Structure | Name | LCMS [M + H]+ | Retention Time (min) |
|---|---|---|---|---|
| Ex 38 | 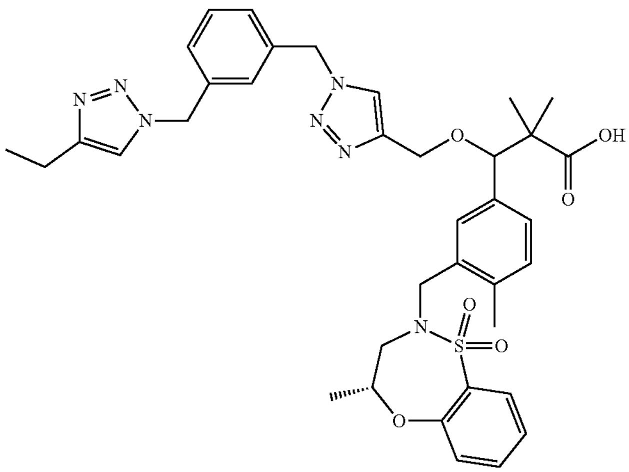 [SMILES: CCc1cn(Cc2cccc(Cn3cc(COC(c4ccc(C)c(CN5C[C@@H](C)Oc6ccccc6S5(=O)=O)c4)C(C)(C)C(=O)O)nn3)c2)nn1] | 3-((1-(3-((4-Ethyl-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 714.4 | 1.17 |
| Ex 39 | 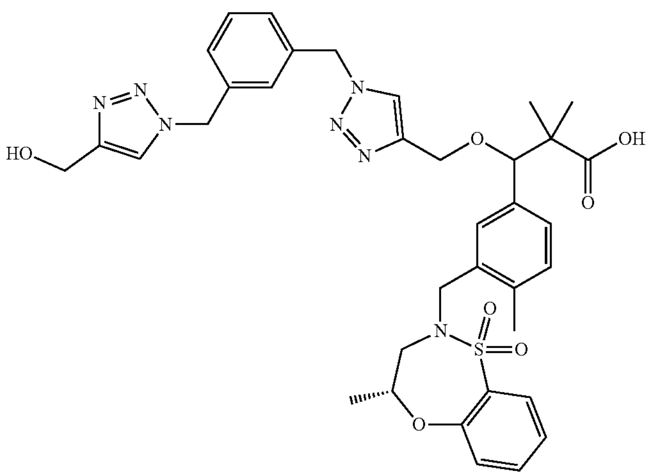 [SMILES: Cc1ccc(C(OCc2cn(Cc3cccc(Cn4cc(CO)nn4)c3)nn2)C(C)(C)C(=O)O)cc1CN1C[C@@H](C)Oc2ccccc2S1(=O)=O] | 3-((1-(3-((4-(Hydroxymethyl)-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 716.1 | 1.06 |
| Ex 40 | 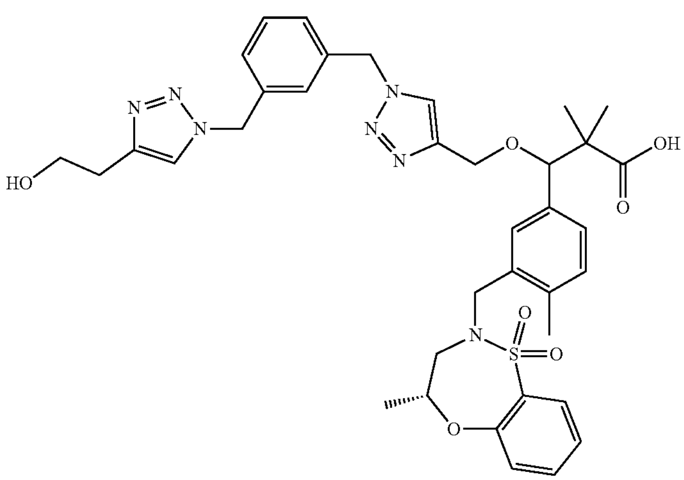 [SMILES: Cc1ccc(C(OCc2cn(Cc3cccc(Cn4cc(CCO)nn4)c3)nn2)C(C)(C)C(=O)O)cc1CN1C[C@@H](C)Oc2ccccc2S1(=O)=O] | 3-((1-(3-((4-(2-Hydroxyethyl)-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 730.5 | 1.06 |

TABLE 12-continued

| Ex # | Structure | Name | LCMS [M + H]+ | Retention Time (min) |
|---|---|---|---|---|
| Ex 41 | 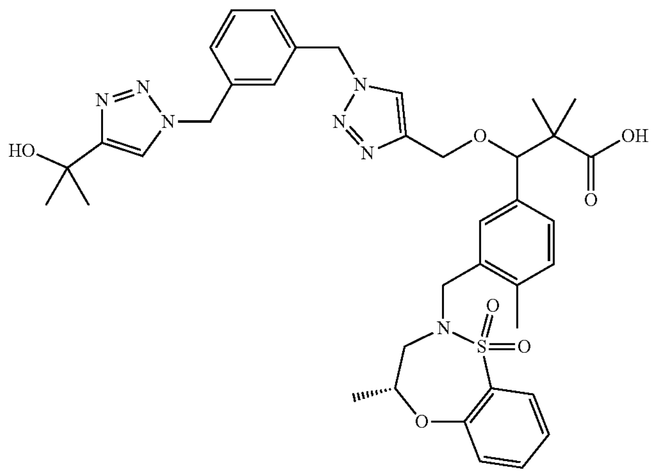 [SMILES: Cc1ccc(C(OCc2cn(Cc3cccc(Cn4cc(C(C)(C)O)nn4)c3)nn2)C(C)(C)C(=O)O)cc1CN1C[C@@H](C)Oc2ccccc2S1(=O)=O] | 3-((1-(3-((4-(2-Hydroxypropan-2-yl)-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 744.5 | 1.10 |
| Ex 42 | 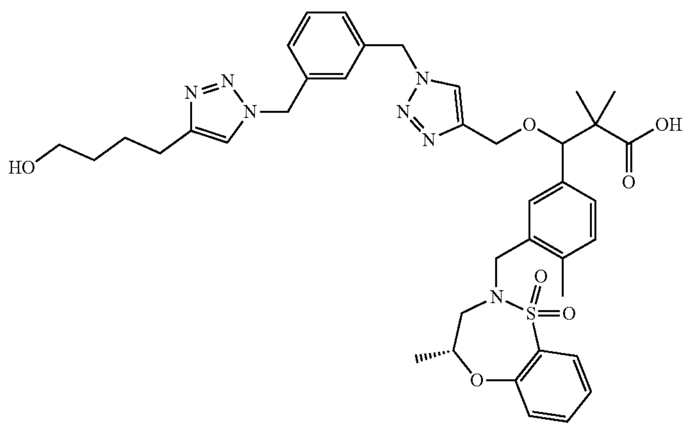 [SMILES: Cc1ccc(C(OCc2cn(Cc3cccc(Cn4cc(CCCCO)nn4)c3)nn2)C(C)(C)C(=O)O)cc1CN1C[C@@H](C)Oc2ccccc2S1(=O)=O] | 3-((1-(3-((4-(4-Hydroxybutyl)-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 758.4 | 1.07 |
| Ex 43 | 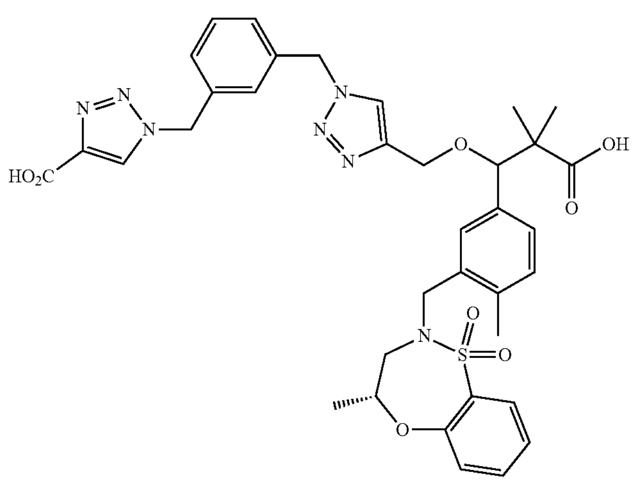 [SMILES: Cc1ccc(C(OCc2cn(Cc3cccc(Cn4cc(C(=O)O)nn4)c3)nn2)C(C)(C)C(=O)O)cc1CN1C[C@@H](C)Oc2ccccc2S1(=O)=O] | 1-(3-((4-((2-Carboxy-2-methyl-1-(4-methyl-3-(((R)-4-methyl-1,1-dioxido-3,4-dihydro-2H-benzo[b][1,4,5]oxathiazepin-2-yl)methyl)phenyl)propoxy)methyl)-1H-1,2,3-triazol-1-yl)methyl)benzyl)-1H-1,2,3-triazole-4-carboxylic acid | 730.4 | 1.06 |

TABLE 12-continued

| Ex # | Structure | Name | LCMS [M + H]+ | Retention Time (min) |
|---|---|---|---|---|
| Ex 44 | 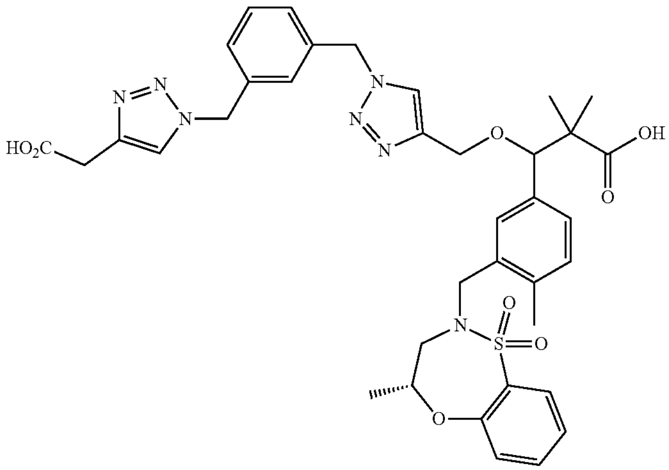 [SMILES: Cc1ccc(C(OCc2cn(Cc3cccc(Cn4cc(CC(=O)O)nn4)c3)nn2)C(C)(C)C(=O)O)cc1CN1C[C@@H](C)Oc2ccccc2S1(=O)=O] | 3-((1-(3-((4-(Carboxymethyl)-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 744.4 | 1.06 |
| Ex 45 | 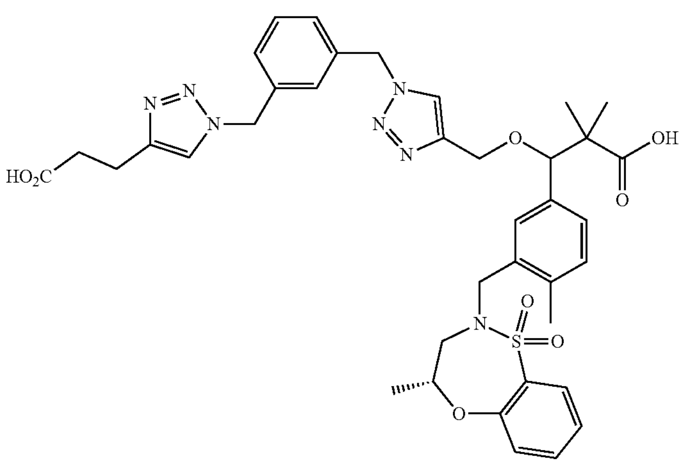 [SMILES: Cc1ccc(C(OCc2cn(Cc3cccc(Cn4cc(CCC(=O)O)nn4)c3)nn2)C(C)(C)C(=O)O)cc1CN1C[C@@H](C)Oc2ccccc2S1(=O)=O] | 3-((1-(3-((4-(2-Carboxyethyl)-1H-1,2,3-triazol-1-yl)methyl)benzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 758.5 | 1.07 |

Example 46

(R,rel-(3S,3'S))-3,3'-(((1,1'-(1,4-phenylenebis(methylene))bis(1H-1,2,3-triazole-4,1-diyl))bis(methylene))bis(oxy))bis(2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

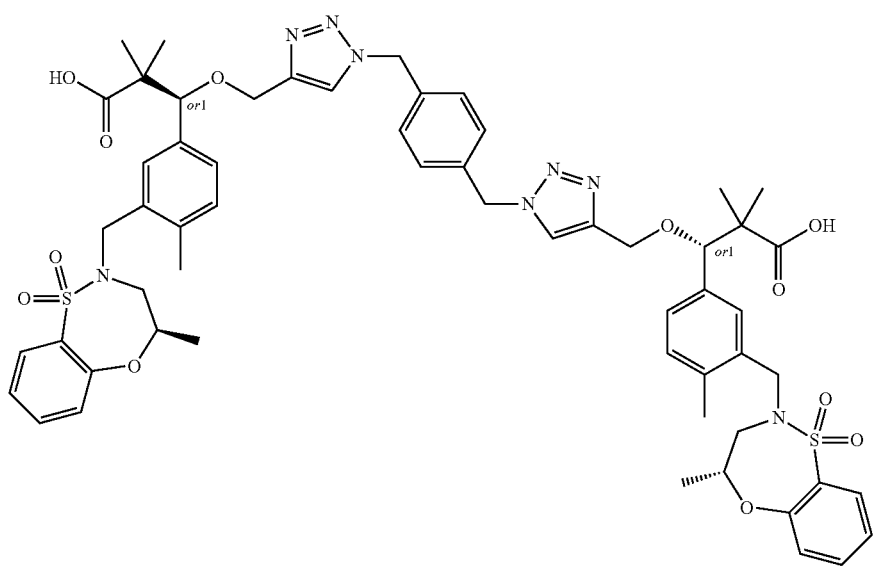 [SMILES: Cc1ccc([C@H](OCc2cn(Cc3ccc(Cn4cc(CO[C@@H](c5ccc(C)c(CN6C[C@@H](C)Oc7ccccc7S6(=O)=O)c5)C(C)(C)C(=O)O)nn4)cc3)nn2)C(C)(C)C(=O)O)cc1CN1C[C@@H](C)Oc2ccccc2S1(=O)=O]

To the mixture of rel-(S)-methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate (214 mg, 0.441 mmol) in isopropanol (4.0 mL) and water (1.2 mL) was added sodium azide (43.0 mg, 0.661 mmol), DIEA (0.015 mL, 0.088 mmol), copper(I) iodide (12.59 mg, 0.066 mmol) and 1,4-bis(bromomethyl)benzene (52.3 mg, 0.198 mmol). The resulting reaction mixture was stirred at 80° C. for 18 h. The reaction mixture was evaporated down under vacuum, extracted with DCM (3×5 mL), dried over Na$_2$SO$_4$, filtered, evaporated down under vacuum. The residue was dissolved in methanol (4.00 mL) and tetrahydrofuran (THF) (4.00 mL) then was added NaOH (3.0 N) (0.734 mL, 2.203 mmol). The resulting reaction mixture was heated with microwave at 100° C. for 30 min. The reaction mixture was acidified with HCl (3.0 N) (0.734 mL, 2.203 mmol), evaporated down under vacuum, purified by reverse phase HPLC (formic acid modifier) to give the title compound (69.8 mg, 0.062 mmol, 28.0% yield). LC/MS: m/z 1131.6 (M+H)$^+$, 1.36 min (ret. time).

The compounds in Table 13 were prepared by a method similar to the one described for the preparation of (3S)-3-{[1-({4-[(4-{[(1S)-2-carboxy-2,2-dimethyl-1-(4-methyl-3-{[(4R)-4-methyl-1,1-dioxido-3,4-dihydro-2H-5,1λ$^6$,2-benzoxathiazepin-2-yl]methyl}phenyl)ethoxy]methyl}-1H-1,2,3-triazol-1-yl)methyl]phenyl}methyl)-1H-1,2,3-triazol-4-yl]methoxy}-2,2-dimethyl-3-(4-methyl-3-{[(4R)-4-methyl-1,1-dioxo-3,4-dihydro-2H-5,1λ$^6$,2-benzoxathiazepin-2-yl]methyl}phenyl)propanoic acid. As is appreciated by those skilled in the art, these analogous examples may involve variations in general reaction conditions.

TABLE 13

| Ex # | Structure | Name | LCMS [M + H]+ | Retention Time (min) |
|---|---|---|---|---|
| Ex 47 | 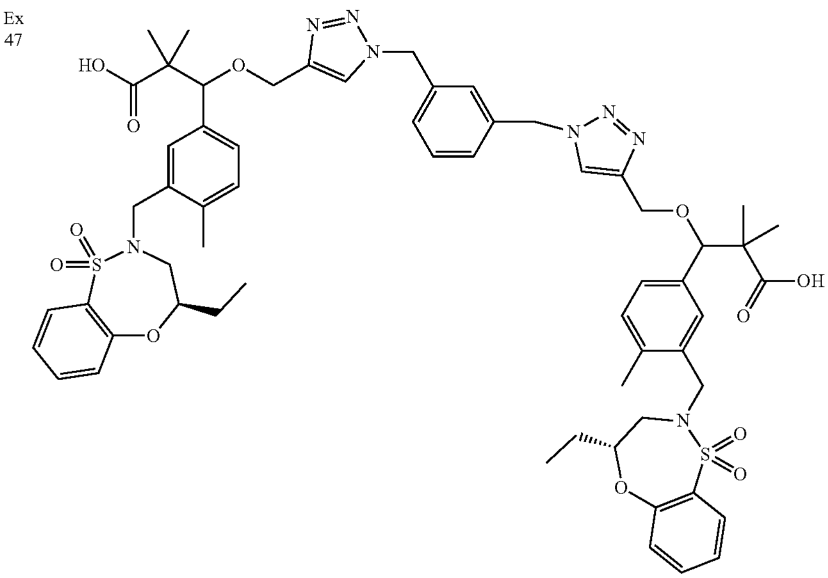 | (R)-3,3'-(((1,1'-(1,3-phenylenebis(methylene))bis(1H-1,2,3-triazole-4,1-diyl))bis(methylene))bis(oxy))bis(3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid) | 1159.6 | 1.44 |
| Ex 48 | 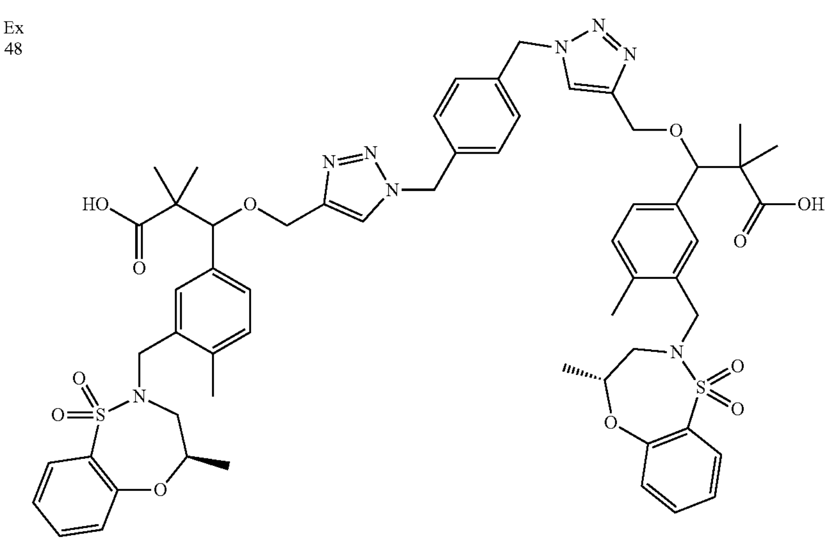 | (R)-3,3'-(((1,1'-(1,4-phenylenebis(methylene))bis(1H-1,2,3-triazole-4,1-diyl))bis(methylene))bis(oxy))bis(2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid) | 1131.6 | 1.36 |

TABLE 13-continued

| Ex # | Structure | Name | LCMS [M + H]+ | Retention Time (min) |
|---|---|---|---|---|
| Ex 49 | 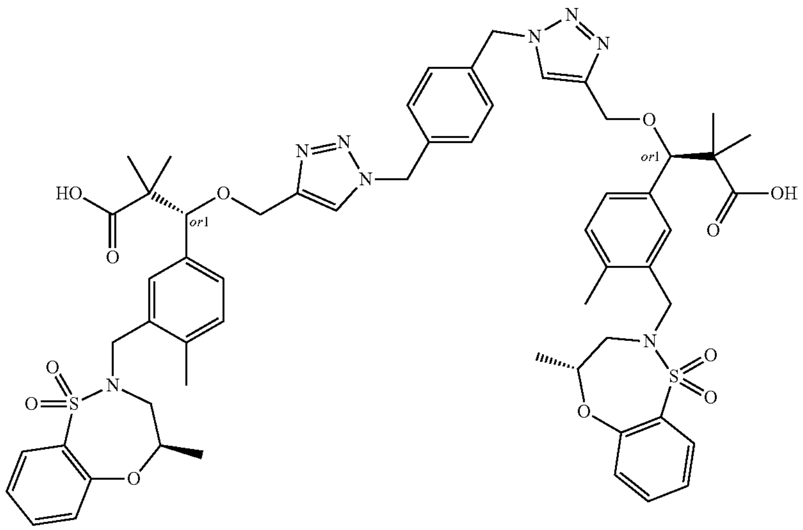 [SMILES: Cc1ccc([C@@H](OCc2cn(Cc3ccc(Cn4cc(CO[C@H](c5ccc(C)c(CN6C[C@@H](C)Oc7ccccc7S6(=O)=O)c5)C(C)(C)C(=O)O)nn4)cc3)nn2)C(C)(C)C(=O)O)cc1CN1C[C@@H](C)Oc2ccccc2S1(=O)=O] | (R,rel-(3R,3'R))-3,3'-(((1,1'-(1,4-phenylenebis(methylene))bis(1H-1,2,3-triazole-4,1-diyl))bis(methylene))bis(oxy))bis(2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid) | 1131.7 | 1.37 |
| Ex 50 | 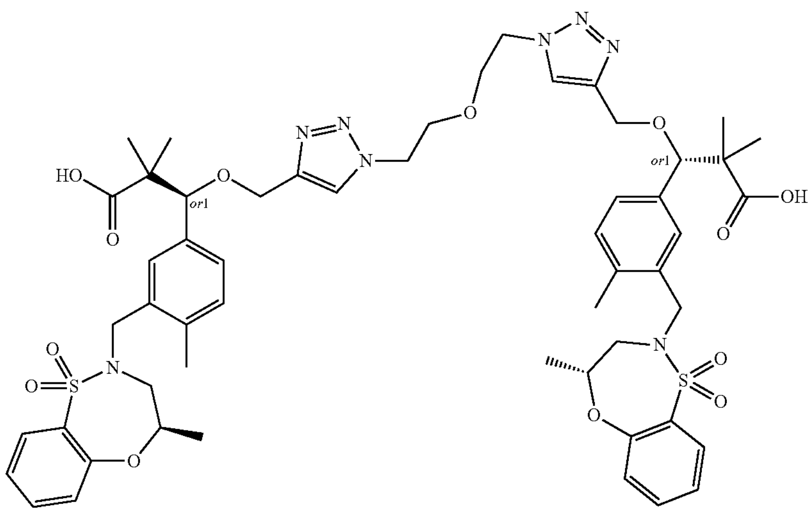 [SMILES: Cc1ccc([C@H](OCc2cn(CCOCCn3cc(CO[C@@H](c4ccc(C)c(CN5C[C@@H](C)Oc6ccccc6S5(=O)=O)c4)C(C)(C)C(=O)O)nn3)nn2)C(C)(C)C(=O)O)cc1CN1C[C@@H](C)Oc2ccccc2S1(=O)=O] | (R,rel-3S,rel-3'S)-3,3'-(((1,1'-(oxybis(ethane-2,1-diyl))bis(1H-1,2,3-triazole-4,1-diyl))bis(methylene))bis(oxy))bis(2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid) | 1099.7 | 1.33 |
| Ex 51 | 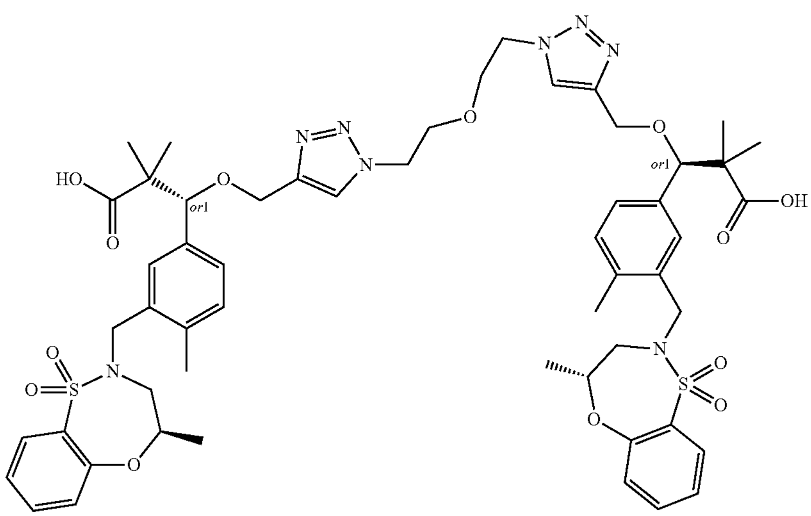 [SMILES: Cc1ccc([C@@H](OCc2cn(CCOCCn3cc(CO[C@H](c4ccc(C)c(CN5C[C@@H](C)Oc6ccccc6S5(=O)=O)c4)C(C)(C)C(=O)O)nn3)nn2)C(C)(C)C(=O)O)cc1CN1C[C@@H](C)Oc2ccccc2S1(=O)=O] | (R,rel-3R,rel-3'R)-3,3'-(((1,1'-(oxybis(ethane-2,1-diyl))bis(1H-1,2,3-triazole-4,1-diyl))bis(methylene))bis(oxy))bis(2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid) | 1099.8 | 1.33 |

Example 52

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-((1-propylpiperidin-4-yl)methyl)-1H-1,2,3-triazol-4-yl)methoxy)propanoic Acid

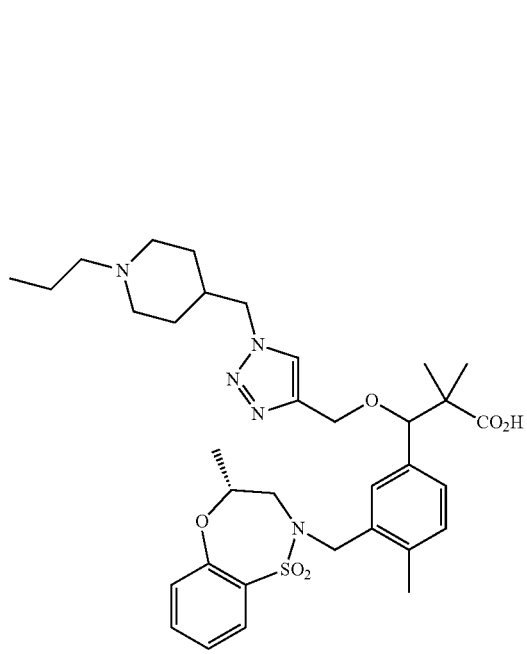 [SMILES: CCCN1CCC(Cn2cc(COC(c3ccc(C)c(CN4C[C@@H](C)Oc5ccccc5S4(=O)=O)c3)C(C)(C)C(=O)O)nn2)CC1]

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(piperidin-4-ylmethyl)-1H-1,2,3-triazol-4-yl)methoxy)propanoate, hydrochloride (60 mg, 0.091 mmol) in dichloromethane (1.000 mL) was added DIEA (0.040 mL, 0.227 mmol) and iodopropane (10.58 µl, 0.109 mmol). The resulting reaction mixture was heated with microwave at 100° C. for 60 min. To the reaction mixture was added more iodopropane (4.41 µl, 0.045 mmol) and DIEA (0.016 mL, 0.091 mmol). The resulting reaction mixture was heated with microwave at 100° C. for 30 min. The reaction mixture was evaporated under vacuum. The residue was dissolved in methanol (1.0 mL) then was added NaOH (6.0 N) (0.121 mL, 0.725 mmol). The resulting reaction mixture was heated with microwave at 100° C. for 30 min. To the reaction mixture was added HCl (6.0 N) (0.121 mL, 0.725 mmol), evaporated down under vacuum, purified by reverse phase HPLC (neutral) to give the title compound (33.5 mg, 0.051 mmol, 56.6% yield). LC/MS: m/z 654.4 (M+H)$^+$, 0.82 min (ret. time).

Example 53

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(piperidin-4-ylmethyl)-1H-1,2,3-triazol-4-yl)methoxy)propanoic Acid, Formic Acid Salt

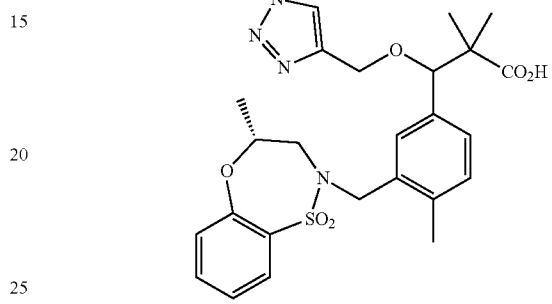

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(piperidin-4-ylmethyl)-1H-1,2,3-triazol-4-yl)methoxy)propanoate, hydrochloride (60 mg, 0.091 mmol) in methanol (1.0 mL) was added NaOH (6.0 N) (0.091 mL, 0.544 mmol). The resulting reaction mixture was heated with microwave at 120° C. for 30 min. To the reaction mixture was added HCl (6.0 N) (0.076 mL, 0.453 mmol), evaporated down under vacuum, purified by reverse phase HPLC (formic acid modifier) to give the title compound (32.1 mg, 0.049 mmol, 53.9% yield). LC/MS: m/z 612.3 (M+H)$^+$, 0.91 min (ret. time).

Example 54

3-(3-((N-(cycloheptylmethyl)acetamido)methyl)-4-methylphenyl)-3-((1-ethyl-1H-1,2,3-triazol-4-yl)methoxy)-2,2-dimethylpropanoic Acid

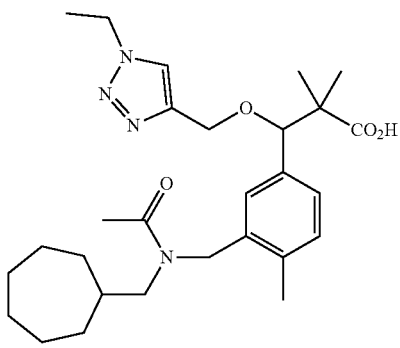 [SMILES: CCn1cc(COC(c2ccc(C)c(CN(CC3CCCCCC3)C(C)=O)c2)C(C)(C)C(=O)O)nn1]

To the mixture of methyl 3-((1-ethyl-1H-1,2,3-triazol-4-yl)methoxy)-3-(3-(hydroxymethyl)-4-methylphenyl)-2,2-dimethylpropanoate (60 mg, 0.166 mmol) in dichloromethane (0.5 mL) was added SOCl$_2$ (0.024 mL, 0.332 mmol).

The resulting reaction mixture was stirred at ambient temperature for 10 min then was evaporated down under vacuum. This residue was dissolved acetonitrile (3.0 mL) and tetrahydrofuran (1.0 mL) then was added cycloheptylmethanamine (0.048 mL, 0.332 mmol) and DIEA (0.116 mL, 0.664 mmol). The resulting reaction mixture was heated with microwave at 100° C. for 1 h. To the reaction mixture was added DIEA (0.058 mL, 0.332 mmol) and acetyl chloride (0.024 mL, 0.332 mmol). The resulting reaction mixture was stirred at ambient temperature for 30 min. The reaction mixture was evaporated down under vacuum, redissolved in methanol (2.0 mL) then was added NaOH (3.0 N) (0.443 mL, 1.328 mmol). The resulting reaction mixture was heated with microwave at 80° C. for 20 min once then heated with microwave at 100° C. for 20 min twice. The reaction mixture was acidified with HCl (3.0 N) (0.443 mL, 1.328 mmol), evaporated down under vacuum, purified by reverse phase HPLC (formic acid modifier) to give the title compound (33.6 mg, 0.067 mmol, 40.6% yield). LC/MS: m/z 499.4 (M+H)$^+$, 1.18 min (ret. time).

Example 55

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-((1'-methyl-[1,4'-bipiperidin]-4-yl)methyl)-1H-1,2,3-triazol-4-yl)methoxy)propanoic Acid, Formic Acid Salt

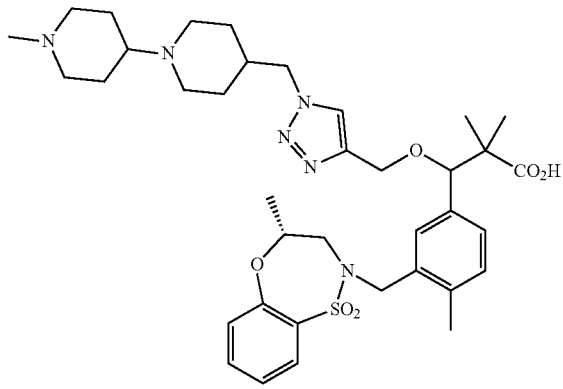 [SMILES: Cc1ccc(C(OCc2cn(CC3CCN(C4CCN(C)CC4)CC3)nn2)C(C)(C)C(=O)O)cc1CN1C[C@@H](C)Oc2ccccc2S1(=O)=O]

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(piperidin-4-yl-methyl)-1H-1,2,3-triazol-4-yl)methoxy)propanoate, hydrochloride (60 mg, 0.091 mmol) in dichloromethane (1.000 mL) was added 1-methylpiperidin-4-one (0.033 mL, 0.272 mmol) and sodium triacetoxyborohydride (57.6 mg, 0.272 mmol). The resulting reaction mixture was stirred at ambient temperature for 77 h. The reaction mixture was evaporated down under vacuum. The residue was dissolved in methanol (1.0 mL) then was added NaOH (6.0 N) (0.121 mL, 0.725 mmol). The resulting reaction mixture was heated with microwave at 120° C. for 30 min. To the reaction mixture was added more NaOH (6.0 N) (0.045 mL, 0.272 mmol) then was heated with microwave at 120° C. for 60 min. To the reaction mixture was added HCl (6.0 N) (0.166 mL, 0.997 mmol), evaporated down under vacuum, purified by reverse phase HPLC (formic acid modifier) to give the title compound (43.7 mg, 0.058 mmol, 63.9% yield). LC/MS: m/z 709.4 (M+H)$^+$, 0.66 min (ret. time).

Example 56

3-((1-(3-Oxa-6-azaspiro[5.5]undecan-6-ium-9-ylmethyl)-1H-1,2,3-triazol-4-yl)methoxy)-2,2-dimethyl-3-(4-methyl-3-(((S)-4-methyl-1,1-dioxido-3,4-dihydro-2H-benzo[b][1,4,5]oxathiazepin-2-yl)methyl)phenyl)propanoate

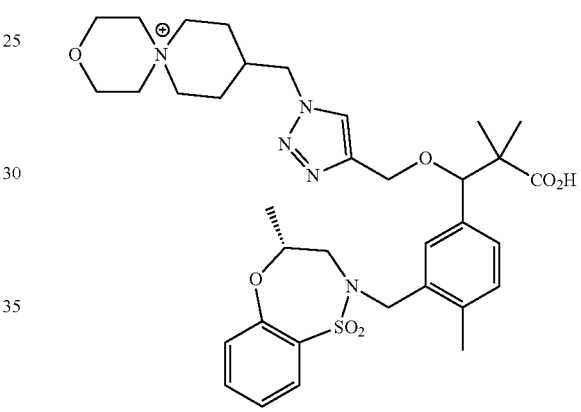

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(piperidin-4-yl-methyl)-1H-1,2,3-triazol-4-yl)methoxy)propanoate, hydrochloride (60 mg, 0.091 mmol) in acetonitrile (1.0 mL) was added DIEA (0.063 mL, 0.362 mmol) and 1-bromo-2-(2-bromoethoxy)ethane (9.46 mg, 0.041 mmol). The resulting reaction mixture was heated with microwave at 100° C. for 1 h. To the reaction mixture was added more 1-bromo-2-(2-bromoethoxy)ethane (9.46 mg, 0.041 mmol) and DIEA (0.063 mL, 0.362 mmol). The resulting reaction mixture was heated with microwave at 100° C. for 1 h (2×). The reaction mixture was evaporated down under vacuum. The residue was dissolved in methanol (1.0 mL) then was added NaOH (6.0 N) (0.121 mL, 0.725 mmol). The resulting reaction mixture was heated with microwave at 100° C. for 30 min twice. The reaction mixture was quenched with HCl (6.0 N) (0.121 mL, 0.725 mmol), evaporated under vacuum, purified by reverse phase HPLC (basic condition) to give the title compound (47.2 mg, 0.069 mmol, 76% yield). LC/MS*: m/z 682.3 (M+H)$^+$, 1.73 min (ret. time).

Example 57

4-(3-((4-((3-Methoxy-2,2-dimethyl-1-(4-methyl-3-(((R)-4-methyl-1,1-dioxido-3,4-dihydro-2H-benzo[b][1,4,5]oxathiazepin-2-yl)methyl)phenyl)-3-oxopropoxy)methyl)-1H-1,2,3-triazol-1-yl)methyl)phenyl)picolinic Acid

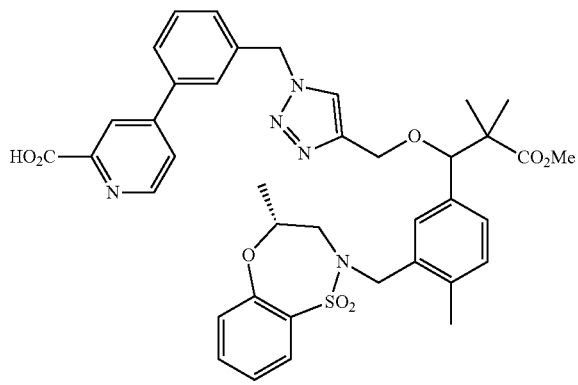 [SMILES: COC(=O)C(C)(C)C(OCc1cn(Cc2cccc(-c3ccnc(C(=O)O)c3)c2)nn1)c1ccc(C)c(CN2C[C@@H](C)Oc3ccccc3S2(=O)=O)c1]

Methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(3-(4,4,5,5-tetramethyl-1,3,2-dioxaborolan-2-yl)benzyl)-1H-1,2,3-triazol-4-yl)methoxy)propanoate

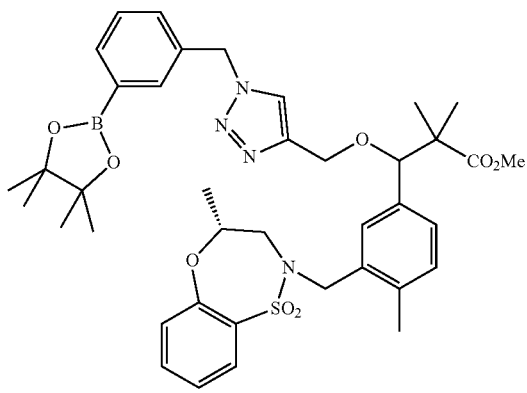 [SMILES: COC(=O)C(C)(C)C(OCc1cn(Cc2cccc(B3OC(C)(C)C(C)(C)O3)c2)nn1)c1ccc(C)c(CN2C[C@@H](C)Oc3ccccc3S2(=O)=O)c1]

To the mixture of methyl 3-((1-(3-bromobenzyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoate (0.86 g, 1.233 mmol) in N,N-dimethylformamide (10 mL) was added 4,4,4',4',5,5,5',5'-octamethyl-2,2'-bi(1,3,2-dioxaborolane) (0.470 g, 1.849 mmol), PdCl$_2$(dppf) (0.045 g, 0.062 mmol) and KOAc (0.242 g, 2.465 mmol). The resulting reaction mixture was heated with microwave at 100° C. for 60 min. The reaction mixture was evaporated down under vacuum, purified flash chromatograph to give the title compound (713.2 mg, 0.958 mmol, 78% yield). LC/MS: m/z 619.2 (M+H)$^+$, 1.32 min (ret. time).

4-(3-((4-((3-Methoxy-2,2-dimethyl-1-(4-methyl-3-(((R)-4-methyl-1,1-dioxido-3,4-dihydro-2H-benzo[b][1,4,5]oxathiazepin-2-yl)methyl)phenyl)-3-oxopropoxy)methyl)-1H-1,2,3-triazol-1-yl)methyl)phenyl)picolinic Acid

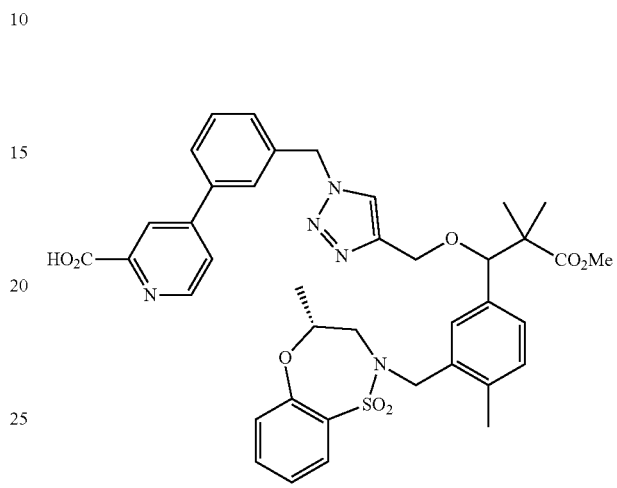

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(3-(4,4,5,5-tetramethyl-1,3,2-dioxaborolan-2-yl)benzyl)-1H-1,2,3-triazol-4-yl)methoxy)propanoate (50 mg, 0.067 mmol) in 1,4-dioxane (1.5 mL) and water (0.5 mL) was added methyl 4-bromopicolinate (17.41 mg, 0.081 mmol), K$_2$CO$_3$ (46.4 mg, 0.336 mmol) and Pd(Ph$_3$P)$_4$ (3.88 mg, 3.36 μmol). The resulting reaction mixture was heated with microwave at 130° C. for 30 min. The reaction mixture was evaporated down under vacuum. To the residue was added methanol (1.5 mL) and then NaOH (3.0 N) (0.179 mL, 0.537 mmol). The resulting reaction mixture was heated with microwave at 120° C. for 60 min. To the reaction mixture was added HCl (3.0 N) (0.179 mL, 0.537 mmol), evaporated down under vacuum, purified by reverse phase HPLC (formic acid modifier) to give the title compound (15.5 mg, 0.021 mmol, 31.2% yield). LC/MS: m/z 740.5 (M+H)$^+$, 1.11 min (ret. time).

The compounds in Table 14 were prepared by a method similar to the one described for the preparation of 4-{3-[(4-{[3-methoxy-2,2-dimethyl-1-(4-methyl-3-{[(4R)-4-methyl-1,1-dioxo-3,4-dihydro-2H-5,1λ$^6$,2-benzoxathiazepin-2-yl]methyl}phenyl)-3-oxopropoxy]methyl}-1H-1,2,3-triazol-1-yl)methyl]phenyl}pyridine-2-carboxylic acid. As is appreciated by those skilled in the art, these analogous examples may involve variations in general reaction conditions.

TABLE 14

| Ex # | Structure | Name | LCMS [M + H]+ | Retention Time (min) |
|------|-----------|------|---------------|----------------------|
| Ex 58 | 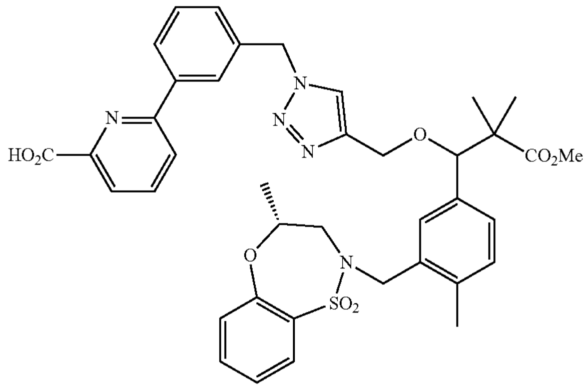 [SMILES: COC(=O)C(C)(C)C(OCc1cn(Cc2cccc(-c3cccc(C(=O)O)n3)c2)nn1)c1ccc(C)c(CN2C[C@@H](C)Oc3ccccc3S2(=O)=O)c1] | 6-(3-((4-((3-Methoxy-2,2-dimethyl-1-(4-methyl-3-(((R)-4-methyl-1,1-dioxido-3,4-dihydro-2H-benzo[b]-[1,4,5]oxathiazepin-2-yl)methyl)phenyl)-3-oxopropoxy)methyl)-1H-1,2,3-triazol-1-yl)methyl)-phenyl)picolinic acid | 740.4 | 1.25 |
| Ex 59 | 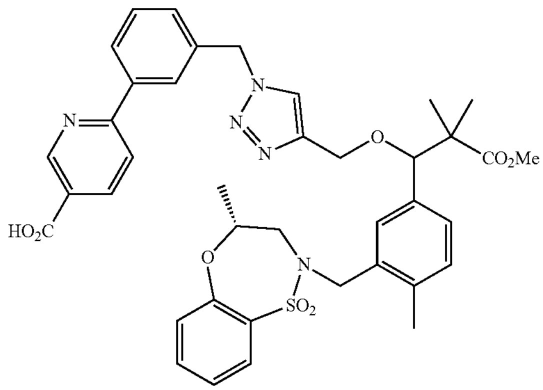 [SMILES: COC(=O)C(C)(C)C(OCc1cn(Cc2cccc(-c3ccc(C(=O)O)cn3)c2)nn1)c1ccc(C)c(CN2C[C@@H](C)Oc3ccccc3S2(=O)=O)c1] | 6-(3-((4-((3-Methoxy-2,2-dimethyl-1-(4-methyl-3-(((R)-4-methyl-1,1-dioxido-3,4-dihydro-2H-benzo[b][1,4,5]oxathiazepin-2-yl)methyl)phenyl)-3-oxopropoxy)methyl)-1H-1,2,3-triazol-1-yl)methyl)-phenyl)nicotinic acid | 740.5 | 1.22 |

Example 60

3-(3-(((R)-4-Ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-difluoropropanoic Acid

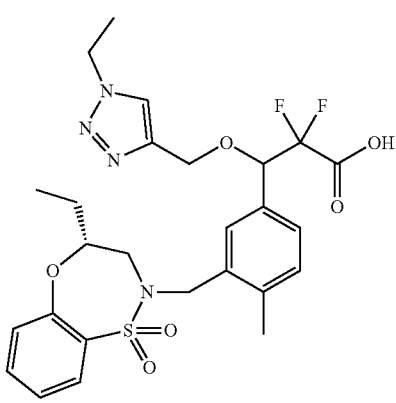 [SMILES: CC[C@@H]1CN(Cc2cc(C(OCc3cn(CC)nn3)C(F)(F)C(=O)O)ccc2C)S(=O)(=O)c2ccccc2O1]

(5-Bromo-2-methylphenyl)methanol

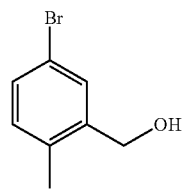

To a solution of 5-bromo-2-methylbenzoic acid (70 g, 326 mmol) in tetrahydrofuran (THF) (700 mL) stirred under nitrogen at 0° C. was added a toluene solution of borane-methyl sulfide complex (244 mL, 488 mmol) drop wise during 15 min. The reaction mixture was stirred for 16 h. The reaction was cooled to 0° C. and quenched with methanol (500 mL) drop wise. The reaction mixture was stirred at ambient temperature for 3 h and then concentrated. The crude residue was diluted with ethyl acetate (1 L) and washed with 1N HCl (500 mL), brine solution (500 mL) and dried over $Na_2SO_4$, filtered and concentrated to give the title compound (49 g, 244 mmol, 74.9% yield). $^1$H NMR (400 MHz, DMSO) δ=7.52 (d, J=2.6 Hz, 1H), 7.31 (dd, J=8.0, 2.2 Hz, 1H), 7.12-7.03 (m, 1H), 5.22 (td, J=5.5, 1.8 Hz, 1H), 4.48 (dd, J=5.1, 1.8 Hz, 2H), 2.17 (s, 3H).

4-Bromo-2-(((4-methoxybenzyl)oxy)methyl)-1-methylbenzene

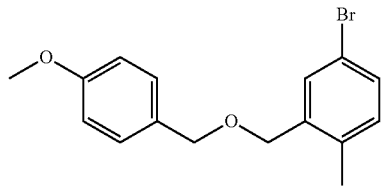 [SMILES: COc1ccc(COCc2cc(Br)ccc2C)cc1]

To a solution of (5-bromo-2-methylphenyl)methanol (20 g, 99 mmol) in N,N-dimethylformamide (DMF) (120 mL) at 0° C. under nitrogen, sodium hydride (4.77 g, 119 mmol) was added in two portions. The reaction mixture was stirred at 0° C. for 20 min. Then 1-(chloromethyl)-4-methoxybenzene (17.14 g, 109 mmol) was added and the reaction mixture was stirred at 0° C. to 25° C. for 1 h. The reaction mixture was quenched with water (200 mL) and extracted with ethyl acetate (3×200 mL). The organic layer was washed with water (2×200 mL) and brine (2×200 mL), dried over $Na_2SO_4$ and concentrated. The residue was purified by silica gel chromatography (petroleum ether/ethyl acetate=4:1) to give the title compound 4-bromo-2-(((4-methoxybenzyl)oxy)methyl)-1-methylbenzene (25 g, 70.0 mmol, 70.4% yield) as yellow oil. LC/MS m/z 321.7 (M+H)+, 1.90 min (ret. time).

3-(((4-Methoxybenzyl)oxy)methyl)-4-methylbenzaldehyde

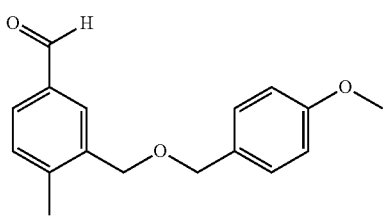 [SMILES: COc1ccc(COCc2cc(C=O)ccc2C)cc1]

To a solution of 4-bromo-2-(((4-methoxybenzyl)oxy)methyl)-1-methylbenzene (80 g, 249 mmol) in tetrahydrofuran (THF) (800 mL) at −78° C. under nitrogen, butyllithium (120 mL, 299 mmol) was carefully added. The reaction mixture was stirred at −78° C. for 65 min, and then DMF (38.6 mL, 498 mmol) was added. The reaction mixture was stirred at −78° C. to 25° C. for another 30 min. It was quenched with saturated $NH_4Cl$ (300 mL), and extracted with ethyl acetate (2×500 mL), the organic layer was washed with water (300 mL) and brine (2×100 mL), dried over $Na_2SO_4$, filtered and concentrated. The residue was washed with petroleum ether/ethyl acetate=10/1 (2000 mL) to obtain the title compound 3-(((4-methoxybenzyl)oxy)methyl)-4-methylbenzaldehyde (50 g, 185 mmol, 74.3% yield) as a solid. LC-MS m/z 288.1 (M+$H_2O$), 2.044 min (ret. time).

Ethyl 2,2-difluoro-3-hydroxy-3-(3-(((4-methoxybenzyl)oxy)methyl)-4-methylphenyl)propanoate

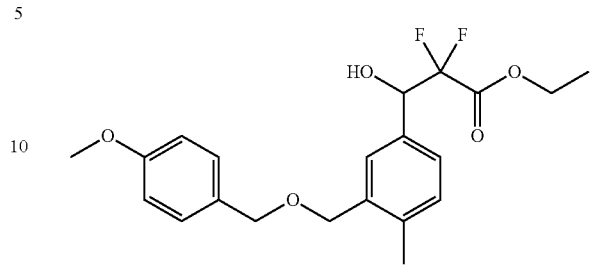

To a suspension of zinc dust (0.728 g, 11.14 mmol) in anhydrous THF (10 mL) was added ethyl 2-bromo-2,2-difluoroacetate (1.429 mL, 11.14 mmol) followed by chlorotrimethylsilane (0.095 mL, 0.743 mmol). The reaction mixture was stirred for 10 minutes until it cooled to 23° C. A solution of 3-(((4-methoxybenzyl)oxy)methyl)-4-methylbenzaldehyde (1.004 g, 3.71 mmol) in anhydrous THF (10 mL) was added dropwise to the reaction mixture. The reaction mixture was stirred for 90 minutes at 25° C. The reaction was quenched with saturated $NH_4Cl$ sol. (10 mL), filtered, diluted with EtOAc and $H_2O$, separated, and the aqueous layer was extracted three times with EtOAc. The combined organic portions were dried over $MgSO_4$, filtered, and concentrated yielding a light yellow oil. The crude mixture was purified via flash chromatography to afford the title compound as light yellow oil (1.6910 g, 110%). $^1$H NMR (DMSO-$d_6$) δ: 7.37 (s, 1H), 7.21-7.32 (m, 3H), 7.17 (d, J=7.8 Hz, 1H), 6.92 (d, J=8.5 Hz, 2H), 6.54 (d, J=5.5 Hz, 1H), 5.02 (dt, J=17.8, 6.8 Hz, 1H), 4.49 (s, 2H), 4.47 (s, 2H), 4.27 (q, J=7.1 Hz, 2H), 3.75 (s, 3H), 2.25 (s, 3H), 1.23 (t, J=7.0 Hz, 3H).

Ethyl 2,2-difluoro-3-(3-(((4-methoxybenzyl)oxy)methyl)-4-methylphenyl)-3-(prop-2-yn-1-yloxy)propanoate

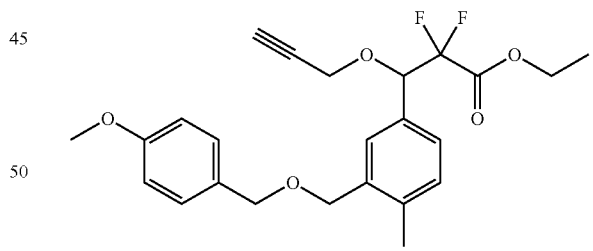

To a solution of ethyl 2,2-difluoro-3-hydroxy-3-(3-(((4-methoxybenzyl)oxy)methyl)-4-methylphenyl)propanoate (1.16910 g, 4.29 mmol) and propargyl bromide (0.554 mL, 5.14 mmol, 80% solution in toluene) in anhydrous THF (43 mL), NaH (0.141 g, 5.57 mmol, 95%) was added and the reaction mixture was stirred for 20 minutes at 23° C. The reaction was quenched with saturated $NH_4Cl$ solution (10 mL) and diluted with $H_2O$. The mixture was then separated and the aqueous later extracted with EtOAc three times. The combined organic extracts were concentrated and the residue was purified via flash chromatography to afford the title compound as an oil (502.7 mg, 25%). $^1$H NMR (DMSO-$d_6$) δ: 7.35 (s, 1H), 7.19-7.32 (m, 4H), 6.92 (d, J=8.5 Hz, 2H), 5.10 (dd, J=17.9, 7.4 Hz, 1H), 4.51 (s, 2H), 4.48 (s, 2H), 4.22-4.36 (m, 2H), 4.22-4.36 (m, 1H), 3.95 (dd, J=16.1, 2.0 Hz, 1H), 3.75 (s, 3H), 3.53-3.59 (m, 1H), 2.26 (s, 3H), 1.26 (t, J=7.0 Hz, 3H).

Ethyl 3-((1-ethyl-1H-1,2,3-triazol-4-yl)methoxy)-2,2-difluoro-3-(3-(((4-methoxybenzyl)oxy)methyl)-4-methylphenyl)propanoate

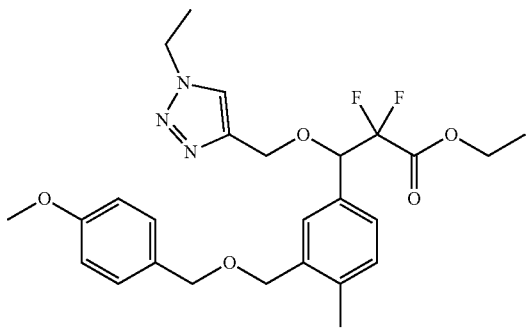 [SMILES: CCOC(=O)C(F)(F)C(OCc1cn(CC)nn1)c1ccc(C)c(COCc2ccc(OC)cc2)c1]

To a suspension of NaN₃ (32 mg, 0.486 mmol) in anhydrous acetonitrile (0.5 mL), iodoethane (0.04 mL, 0.486 mmol) was added and the reaction mixture was heated to reflux at 70° C. for 2 hours in a capped vial. The solution was subsequently cooled to 23° C. and added to a solution of CuI (1.762 mg, 9.25 µmol), DIPEA (3.22 µL, 0.018 mmol), acetic acid (1.058 µL, 0.018 mmol), and ethyl 2,2-difluoro-3-(3-(((4-methoxybenzyl)oxy)methyl)-4-methylphenyl)-3-(prop-2-yn-1-yloxy)propanoate (100 mg, 0.231 mmol) anhydrous acetonitrile (0.25 mL). The resulting reaction mixture was stirred at 23° C. for 2 hours. Additional DIPEA (6.44 µL, 0.037 mmol), acetic acid (2.12 µL, 0.037 mmol) in anhydrous acetonitrile (few drops) were added to the reaction mixture which was then stirred for another 30 minutes at 23° C. Additional CuI (1.762 mg, 9.25 µmol) was added and the reaction mixture was stirred for an additional 1 hour at 23° C. Additional CuI (3.52 mg, 0.018 mmol) was added and the reaction mixture was stirred for an additional 16 hours at 23° C. The solvent was subsequently removed under reduced pressure and the residue was suspended in DCM, filtered, and purified via flash chromatography to afford the title compound (55.7 mg, 45%). LC/MS: m/z 504.3 (M+H)⁺, 1.26 min (ret. time)

Ethyl 3-((1-ethyl-1H-1,2,3-triazol-4-yl)methoxy)-2,2-difluoro-3-(3-(hydroxymethyl)-4-methylphenyl)propanoate

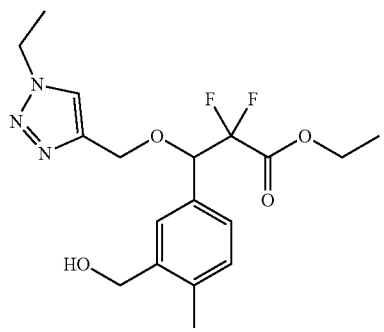 [SMILES: CCOC(=O)C(F)(F)C(OCc1cn(CC)nn1)c1ccc(C)c(CO)c1]

To a solution of ethyl 3-((1-ethyl-1H-1,2,3-triazol-4-yl)methoxy)-2,2-difluoro-3-(3-(((4-methoxybenzyl)oxy)methyl)-4-methylphenyl)propanoate (20 mg, 0.040 mmol) in acetonitrile (0.2 mL) was added a solution of ceric ammonium nitrate (87 mg, 0.159 mmol) in H₂O (0.2 mL) and the reaction mixture was stirred for 60 minutes at 23° C. The reaction mixture was diluted with EtOAc and H₂O, separated, and the aqueous layer was extracted with EtOAc three times. The combined organic extracts were saved. A second batch of the ethyl 3-((1-ethyl-1H-1,2,3-triazol-4-yl)methoxy)-2,2-difluoro-3-(3-(((4-methoxybenzyl)oxy)methyl)-4-methylphenyl)propanoate (23 mg, 0.046 mmol) in acetonitrile (0.2 mL) was prepared to which then a solution of ceric ammonium nitrate (100 mg, 0.183 mmol) in H₂O (0.2 mL) was added and the reaction mixture was stirred for 45 minutes at 23° C. The reaction mixture was diluted with EtOAc and H₂O, separated, and the aqueous layer was extracted with EtOAc four times. The organic extracts were combined with those from the first batch and concentrated under reduced pressure yielding the crude product mixture as a dark orange oil. The crude product was purified via flash chromatography to afford the title compound as a colorless oil (33.4 mg, 97%). LC/MS: m/z 384.2 (M+H)⁺, 0.89 min (ret. time)

Ethyl 3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-difluoropropanoate

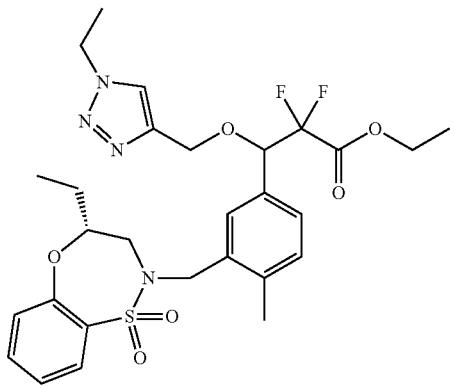 [SMILES: CCOC(=O)C(F)(F)C(OCc1cn(CC)nn1)c1ccc(C)c(CN2C[C@@H](CC)Oc3ccccc3S2(=O)=O)c1]

To a solution of ethyl 3-((1-ethyl-1H-1,2,3-triazol-4-yl)methoxy)-2,2-difluoro-3-(3-(hydroxymethyl)-4-methylphenyl)propanoate (29.7 mg, 0.077 mmol) and (R)-4-ethyl-3,4-dihydro-2H-benzo[b][1,4,5]oxathiazepine 1,1-dioxide (21.13 mg, 0.093 mmol) in anhydrous THF (1.5 mL), (E)-diazene-1,2-diylbis(piperidin-1-ylmethanone) (39.1 mg, 0.155 mmol) and tributylphosphine (0.04 mL, 0.155 mmol) were added and the reaction was stirred at 23° C. for 16 hours. The solvents were evaporated under reduced pressure and the remaining residue was suspended in DCM, filtered, and purified via flash chromatography to afford the title compound as a light yellow oil (48.5 mg, 100%). LC/MS: m/z 593.3 (M+H)⁺, 1.26 min (ret. time)

161

3-(3-(((R)-4-Ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-difluoropropanoic Acid

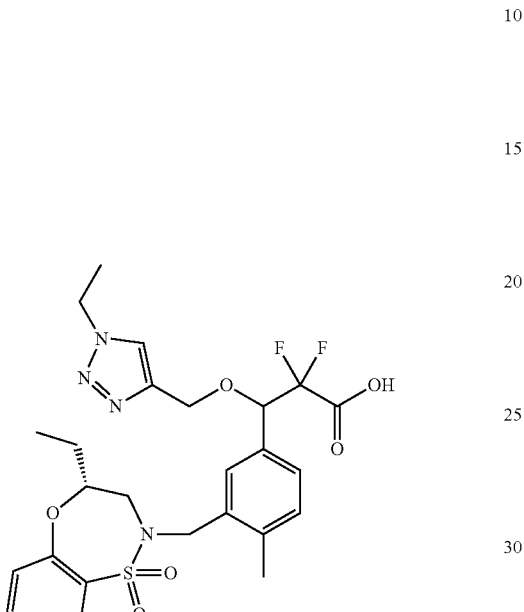

To a solution of ethyl 3-(3-(((R)-4-ethyl-1,1-dioxido-3,4-dihydro-2H-benzo[b][1,4,5]oxathiazepin-2-yl)methyl)-4-methylphenyl)-3-((1-ethyl-1H-1,2,3-triazol-4-yl)methoxy)-2,2-difluoropropanoate (48.5 mg, 0.082 mmol) in EtOH (0.1 mL) was added $H_2O$ (0.1 mL) followed by 2N NaOH (90 µl, 0.180 mmol) and the mixture was heated to 60° C. for 60 minutes. The solvents were evaporated under reduced pressure. A base extraction was attempted; however the desired compound was noted to remain in the organic layer. The solvents were once again removed under reduced pressure with heating. The resulting solid was redissolved in 3 N HCl (6 mL) solution and EtOAc (6 mL). The mixture was separated and the aqueous layer extracted three times with EtOAc. The combined organic extracts were dried over $MgSO_4$, filtered, and concentrated yielding a light yellow oil (35.8 mg) which was purified via reverse phase chromatography to afford the title compound (9.9 mg, 19%). LC/MS: m/z 565.1 (M+H)$^+$, 1.04 min (ret. time).

162

Example 61

(3R)-((1-ethyl-1H-1,2,3-triazol-4-yl)methoxy)-2,2-dimethyl-3-(4-methyl-3-(((S)-4-methyl-1,1-dioxido-4,5-dihydropyrido[4,3-f][1,2]thiazepin-2(3H)-yl)methyl)phenyl)propanoic Acid

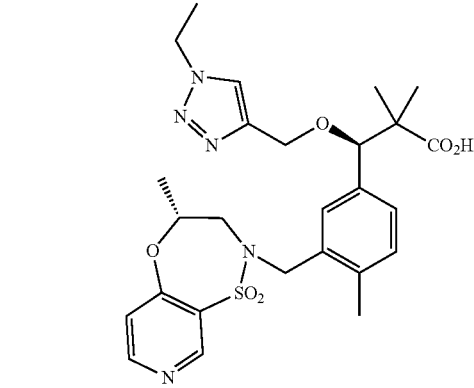 [SMILES: CCn1cc(CO[C@H](c2ccc(C)c(CN3C[C@@H](C)Oc4ccncc4S3(=O)=O)c2)C(C)(C)C(=O)O)nn1]

To the mixture of methyl (R)-3-((1-ethyl-1H-1,2,3-triazol-4-yl)methoxy)-3-(3-(hydroxymethyl)-4-methylphenyl)-2,2-dimethylpropanoate (54.2 mg, 0.15 mmol) in tetrahydrofuran (2 mL) was added (S)-4-methyl-2,3,4,5-tetrahydropyrido[4,3-f][1,2]thiazepine 1,1-dioxide (47.8 mg, 0.225 mmol), PS—PPh$_3$ (188 mg, 0.300 mmol) and DIAD (0.058 mL, 0.300 mmol). The resulting reaction mixture was stirred at ambient temperature for 2 h. The reaction mixture was then filtered, evaporated down under vacuum. The residue was dissolved in methanol (2.000 mL) after which was added NaOH (6.0 N) (0.200 mL, 1.200 mmol). The resulting reaction mixture was heated with microwave at 120° C. for 30 min. To the reaction mixture was added HCl (6.0 N) (0.200 mL, 1.200 mmol), evaporated down under vacuum, purified with reverse phase HPLC (formic acid modifier) to give the title product (34.2 mg, 0.063 mmol, 42.1% yield). LC/MS: m/z 542.4 (M+H)$^+$, 0.96 min (ret. time).

The compounds in Table 15 were prepared by a method similar to the one described for the preparation of (3R)-((1-ethyl-1H-1,2,3-triazol-4-yl)methoxy)-2,2-dimethyl-3-(4-methyl-3-(((S)-4-methyl-1,1-dioxido-4,5-dihydropyrido[4,3-f][1,2]thiazepin-2(3H)-yl)methyl)phenyl)propanoic acid. As is appreciated by those skilled in the art, these analogous examples may involve variations in general reaction conditions.

TABLE 15

| Ex # | Structure | Name | LCMS [M + H]+ | Retention Time (min) |
| --- | --- | --- | --- | --- |
| Ex 62 | 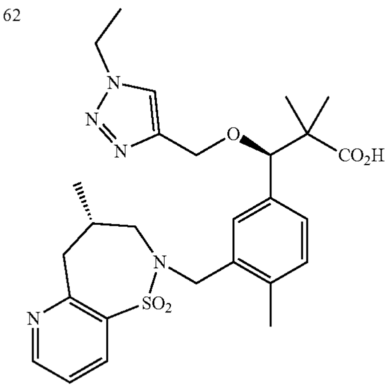 | (3R)-((1-ethyl-1H-1,2,3-triazol-4-yl)methoxy)-2,2-dimethyl-3-(4-methyl-3-(((S)-4-methyl-1,1-dioxido-4,5-dihydropyrido[2,3-f][1,2]thiazepin-2(3H)-yl)methyl)phenyl)propanoic acid | 542.4 | 0.98 |
| Ex 63 | 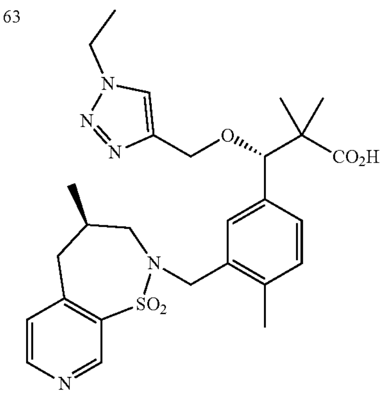 | (3S)-((1-ethyl-1H-1,2,3-triazol-4-yl)methoxy)-2,2-dimethyl-3-(4-methyl-3-(((R)-4-methyl-1,1-dioxido-4,5-dihydropyrido[4,3-f][1,2]thiazepin-2(3H)-yl)methyl)phenyl)propanoic acid | 542.3 | 0.96 |
| Ex 64 | 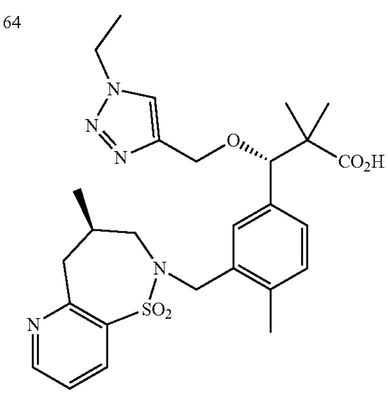 | (3S)-((1-ethyl-1H-1,2,3-triazol-4-yl)methoxy)-2,2-dimethyl-3-(4-methyl-3-(((R)-4-methyl-1,1-dioxido-4,5-dihydropyrido[2,3-f][1,2]thiazepin-2(3H)-yl)methyl)phenyl)propanoic acid | 542.4 | 0.99 |
| Ex 65 | 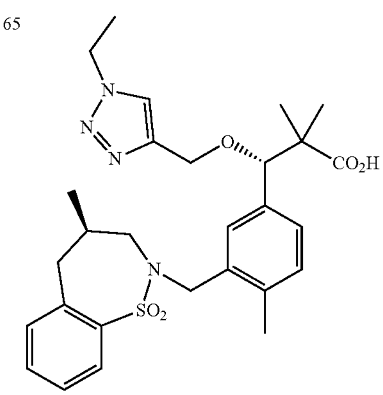 | (3S)-((1-ethyl-1H-1,2,3-triazol-4-yl)methoxy)-2,2-dimethyl-3-(4-methyl-3-(((R)-4-methyl-1,1-dioxido-4,5-dihydrobenzo[f][1,2]thiazepin-2(3H)-yl)methyl)phenyl)propanoic acid | 541.4 | 1.15 |

TABLE 15-continued

| Ex # | Structure | Name | LCMS [M + H]+ | Retention Time (min) |
|---|---|---|---|---|
| Ex 66 | 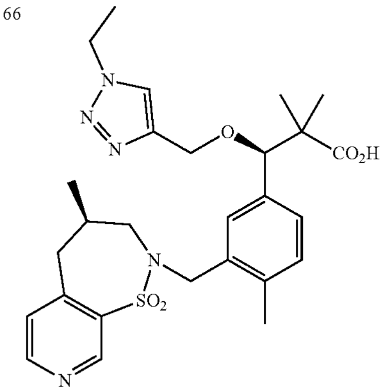 | (3R)-((1-ethyl-1H-1,2,3-triazol-4-yl)methoxy)-2,2-dimethyl-3-(4-methyl-3-(((R)-4-methyl-1,1-dioxido-4,5-dihydropyrido[4,3-f][1,2]thiazepin-2(3H)-yl)methyl)phenyl)propanoic acid | 542.4 | 0.95 |
| Ex 67 | 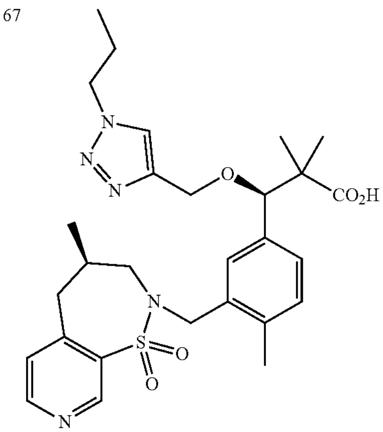 | (R)-2,2-dimethyl-3-(4-methyl-3-(((R)-4-methyl-1,1-dioxido-4,5-dihydropyrido[4,3-f][1,2]thiazepin-2(3H)-yl)methyl)phenyl)-3-((1-propyl-1H-1,2,3-triazol-4-yl)methoxy)propanoic acid | 556.4 | 1.01 |
| Ex 68 | 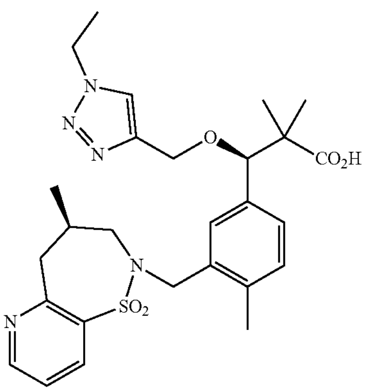 [SMILES: CCn1cc(CO[C@H](c2ccc(C)c(CN3C[C@H](C)Cc4ncccc4S3(=O)=O)c2)C(C)(C)C(=O)O)nn1] | (3R)-((1-ethyl-1H-1,2,3-triazol-4-yl)methoxy)-2,2-dimethyl-3-(4-methyl-3-(((R)-4-methyl-1,1-dioxido-4,5-dihydropyrido[2,3-f][1,2]thiazepin-2(3H)-yl)methyl)phenyl)propanoic acid | 542.4 | 0.99 |
| Ex 69 | 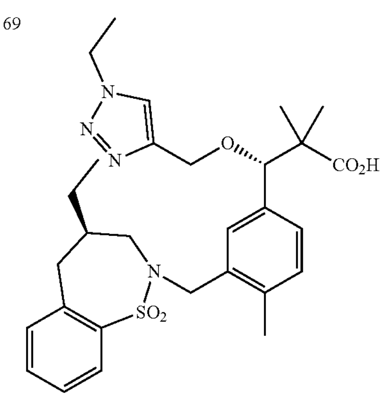 | (3S)-((1-ethyl-1H-1,2,3-triazol-4-yl)methoxy)-2,2-dimethyl-3-(4-methyl-3-(((R)-4-ethyl-1,1-dioxido-4,5-dihydrobenzo[f][1,2]thiazepin-2(3H)-yl)methyl)phenyl)propanoic acid | 555.4 | 1.22 |

TABLE 15-continued

| Ex # | Structure | Name | LCMS [M + H]+ | Retention Time (min) |
|---|---|---|---|---|
| Ex 70 | 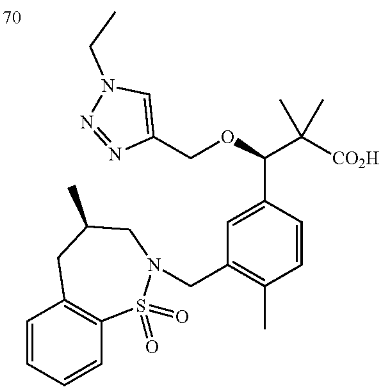 | (3R)-((1-ethyl-1H-1,2,3-triazol-4-yl)methoxy)-2,2-dimethyl-3-(4-methyl-3-(((R)-4-methyl-1,1-dioxido-4,5-dihydrobenzo[f][1,2]thiazepin-2(3H)-yl)methyl)phenyl)propanoic acid | 541.4 | 1.16 |
| Ex 71 | 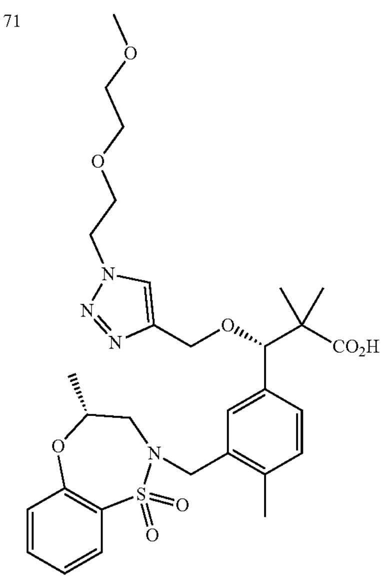 | (3S)-((1-(2-(2-methoxyethoxy)ethyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 617.4 | 1.06 |
| Ex 72 | 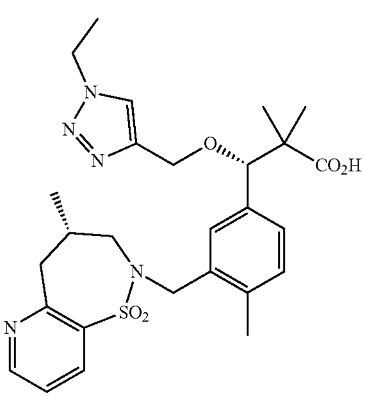 [SMILES: CCn1cc(CO[C@@H](c2ccc(C)c(CN3C[C@@H](C)Cc4ncccc4S3(=O)=O)c2)C(C)(C)C(=O)O)nn1] | (3S)-((1-ethyl-1H-1,2,3-triazol-4-yl)methoxy)-2,2-dimethyl-3-(4-methyl-3-(((S)-4-methyl-1,1-dioxido-4,5-dihydropyrido[2,3-f][1,2]thiazepin-2(3H)-yl)methyl)phenyl)propanoic acid | 542.4 | 0.99 |

TABLE 15-continued

| Ex # | Structure | Name | LCMS [M + H]+ | Retention Time (min) |
|---|---|---|---|---|
| Ex 73 | 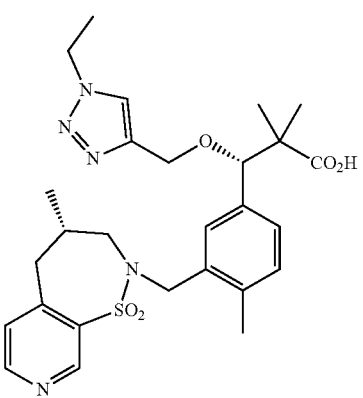 [SMILES: CCn1cc(CO[C@@H](c2ccc(C)c(CN3C[C@@H](C)Cc4ccncc4S3(=O)=O)c2)C(C)(C)C(=O)O)nn1] | (3S)-((1-ethyl-1H-1,2,3-triazol-4-yl)methoxy)-2,2-dimethyl-3-(4-methyl-3-(((R)-4-methyl-1,1-dioxido-4,5-dihydropyrido[4,3-f][1,2]thiazepin-2(3H)-yl)methyl)phenyl)propanoic acid | 542.4 | 0.96 |
| Ex 74 | 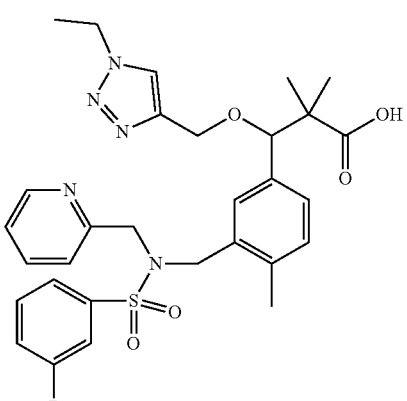 | 3-(3-(((3-Bromo-N-(pyridin-2-ylmethyl)phenyl)sulfonamido)methyl)-4-methylphenyl)-3-((1-ethyl-1H-1,2,3-triazol-4-yl)methoxy)-2,2-dimethylpropanoic acid | 658.2 | 1.09 |
| Ex 75 | 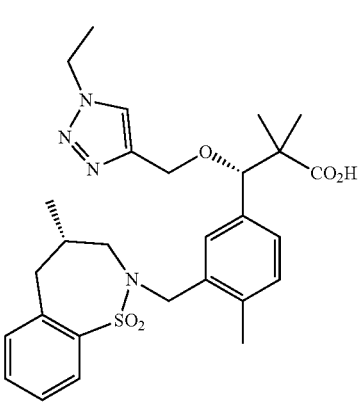 [SMILES: CCn1cc(CO[C@@H](c2ccc(C)c(CN3C[C@@H](C)Cc4ccccc4S3(=O)=O)c2)C(C)(C)C(=O)O)nn1] | (3S)-((1-ethyl-1H-1,2,3-triazol-4-yl)methoxy)-2,2-dimethyl-3-(4-methyl-3-(((S)-4-methyl-1,1-dioxido-4,5-dihydrobenzo[f][1,2]thiazepin-2(3H)-yl)methyl)phenyl)propanoic acid | 541.4 | 1.15 |

TABLE 15-continued

| Ex # | Structure | Name | LCMS [M + H]+ | Retention Time (min) |
|---|---|---|---|---|
| Ex 76 | 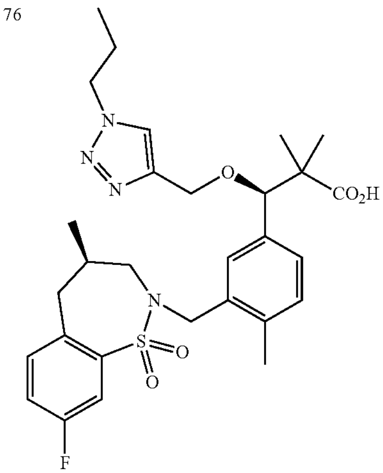 | (3R)-(3-(((R)-8-fluoro-4-methyl-1,1-dioxido-4,5-dihydrobenzo[f][1,2]thiazepin-2(3H)-yl)methyl)-4-methylphenyl)-2,2-dimethyl-3-((1-propyl-1H-1,2,3-triazol-4-yl)methoxy)propanoic acid | 573.4 | 1.24 |
| Ex 77 | 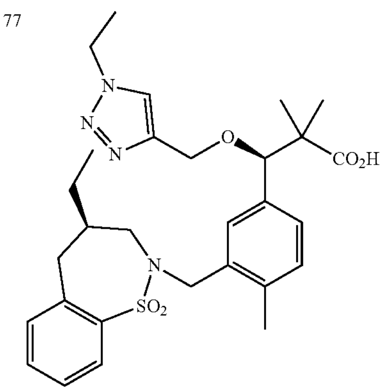 | (3R)-((1-ethyl-1H-1,2,3-triazol-4-yl)methoxy)-2,2-dimethyl-3-(4-methyl-3-(((R)-4-ethyl-1,1-dioxido-4,5-dihydrobenzo[f][1,2]thiazepin-2(3H)-yl)methyl)phenyl)propanoic acid | 555.4 | 1.21 |
| Ex 78 | 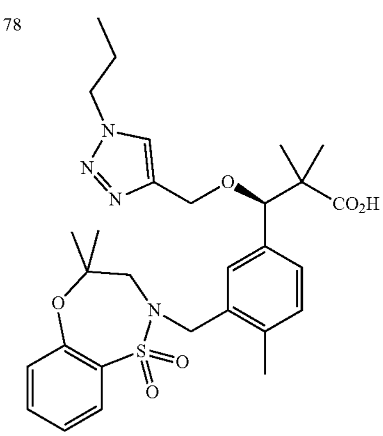 | (R)-3-(3-((4,4-dimethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)propanoic acid | 571.4 | 1.15 |

TABLE 15-continued

| Ex # | Structure | Name | LCMS [M + H]+ | Retention Time (min) |
|---|---|---|---|---|
| Ex 79 | 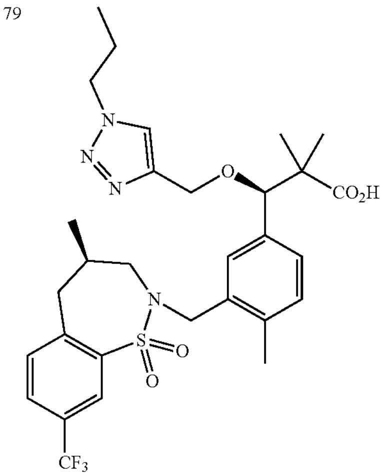 | (R)-2,2-dimethyl-3-(4-methyl-3-(((R)-4-methyl-1,1-dioxido-8-(trifluoromethyl)-4,5-dihydrobenzo[f][1,2]thiazepin-2(3H)-yl)methyl)phenyl)-3-((1-propyl-1H-1,2,3-triazol-4-yl)methoxy)propanoic acid | 623.5 | 1.32 |
| Ex 80 | 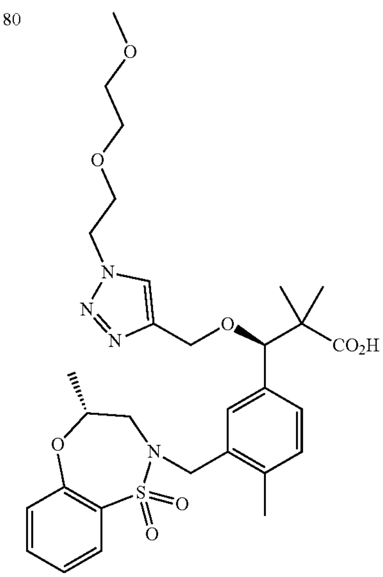 | (R)-3-((1-(2-(2-methoxyethoxy)ethyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic acid | 617.3 | 1.06 |
| Ex 81 | 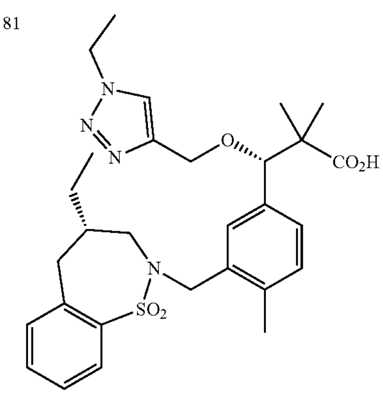 | (3S)-((1-ethyl-1H-1,2,3-triazol-4-yl)methoxy)-2,2-dimethyl-3-(4-methyl-3-(((S)-4-ethyl-1,1-dioxido-4,5-dihydrobenzo[f][1,2]thiazepin-2(3H)-yl)methyl)phenyl)propanoic acid | 555.4 | 1.20 |

TABLE 15-continued

| Ex # | Structure | Name | LCMS [M + H]⁺ | Retention Time (min) |
|---|---|---|---|---|
| Ex 82 | 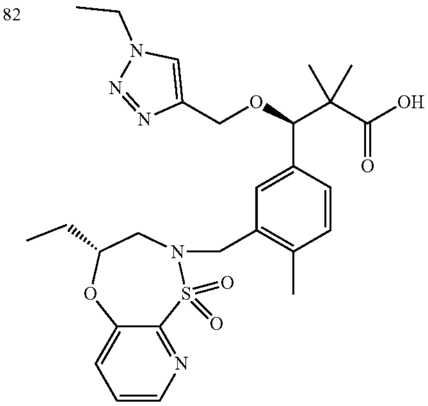 | (R)-3-(3-(((R)-4-ethyl-1,1-dioxido-3,4-dihydro-2H-pyrido[3,2-b][1,4,5]oxathiazepin-2-yl)methyl)-4-methylphenyl)-3-((1-ethyl-1H-1,2,3-triazol-4-yl)methoxy)-2,2-dimethylpropanoic acid | 558.4 | 0.99 |
| Ex 83 | 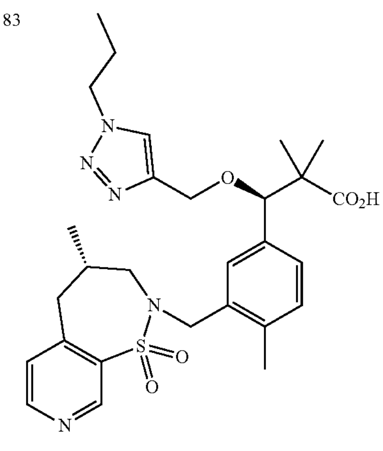 | (R)-2,2-dimethyl-3-(4-methyl-3-(((S)-4-methyl-1,1-dioxido-4,5-dihydropyrido[4,3-f][1,2]thiazepin-2(3H)-yl)methyl)phenyl)-3-((1-propyl-1H-1,2,3-triazol-4-yl)methoxy)propanoic acid | 556.4 | 1.01 |
| Ex 84 | 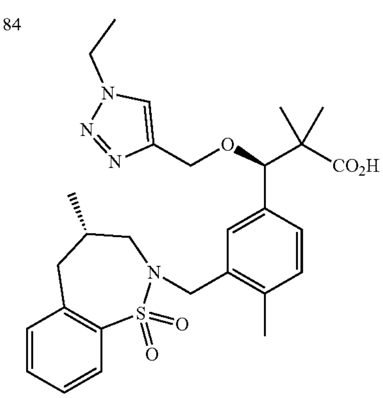 | (3R)-((1-ethyl-1H-1,2,3-triazol-4-yl)methoxy)-2,2-dimethyl-3-(4-methyl-3-(((S)-4-methyl-1,1-dioxido-4,5-dihydrobenzo[f][1,2]thiazepin-2(3H)-yl)methyl)phenyl)propanoic acid | 541.4 | 1.15 |

TABLE 15-continued

| Ex # | Structure | Name | LCMS [M + H]+ | Retention Time (min) |
|---|---|---|---|---|
| Ex 85 | 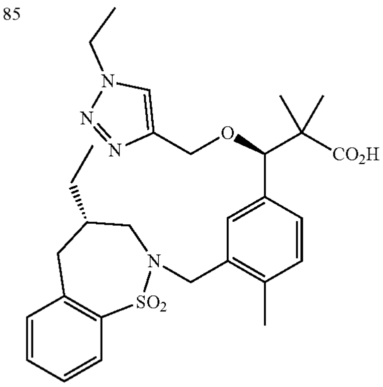 | (3R)-((1-ethyl-1H-1,2,3-triazol-4-yl)methoxy)-2,2-dimethyl-3-(4-methyl-3-(((S)-4-ethyl-1,1-dioxido-4,5-dihydrobenzo[f][1,2]thiazepin-2(3H)-yl)methyl)phenyl)propanoic acid | 555.4 | 1.21 |
| Ex 86 | 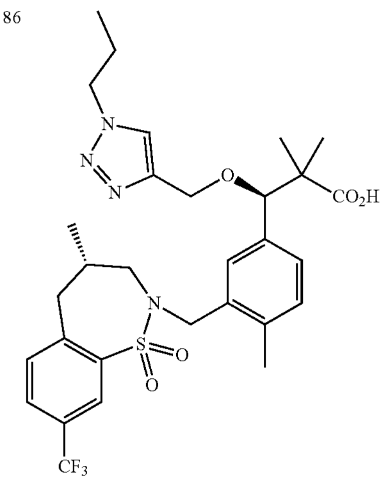 | (R)-2,2-dimethyl-3-(4-methyl-3-(((S)-4-methyl-1,1-dioxido-8-(trifluoromethyl)-4,5-dihydrobenzo[f][1,2]thiazepin-2(3H)-yl)methyl)phenyl)-3-((1-propyl-1H-1,2,3-triazol-4-yl)methoxy)propanoic acid | 623.5 | 1.32 |
| Ex 87 | 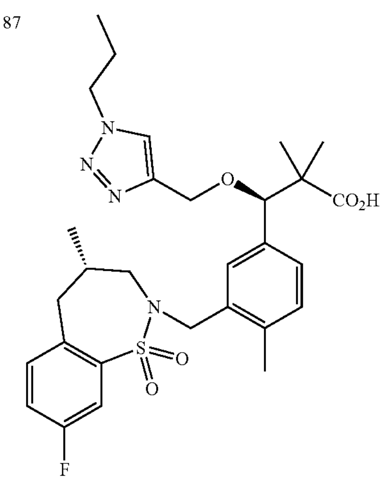 | (R)-3-(3-(((S)-8-fluoro-4-methyl-1,1-dioxido-4,5-dihydrobenzo[f][1,2]thiazepin-2(3H)-yl)methyl)-4-methylphenyl)-2,2-dimethyl-3-((1-propyl-1H-1,2,3-triazol-4-yl)methoxy)propanoic acid | 573.4 | 1.23 |

TABLE 15-continued

| Ex # | Structure | Name | LCMS [M + H]+ | Retention Time (min) |
|---|---|---|---|---|
| Ex 88 | 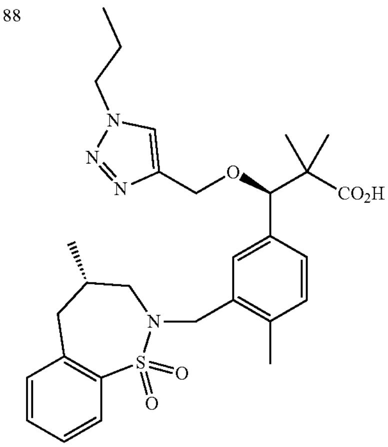 | (R)-2,2-dimethyl-3-(4-methyl-3-(((S)-4-methyl-1,1-dioxido-4,5-dihydrobenzo[f][1,2]thiazepin-2(3H)-yl)methyl)phenyl)-3-((1-propyl-1H-1,2,3-triazol-4-yl)methoxy)propanoic acid | 555.2 | 1.18 |
| Ex 89 | 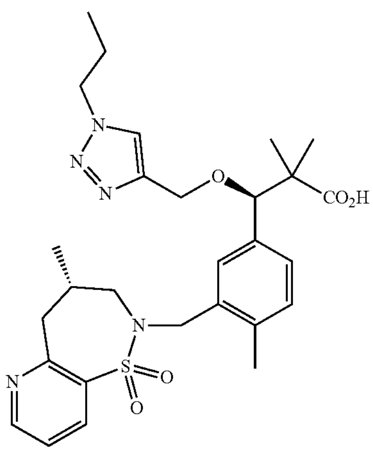 [SMILES: CCCn1cc(CO[C@H](c2ccc(C)c(CN3C[C@@H](C)Cc4ncccc4S3(=O)=O)c2)C(C)(C)C(=O)O)nn1] | (R)-2,2-dimethyl-3-(4-methyl-3-(((S)-4-methyl-1,1-dioxido-4,5-dihydropyrido[2,3-f][1,2]thiazepin-2(3H)-yl)methyl)phenyl)-3-((1-propyl-1H-1,2,3-triazol-4-yl)methoxy)propanoic acid | 556.2 | 1.02 |
| Ex 90 | 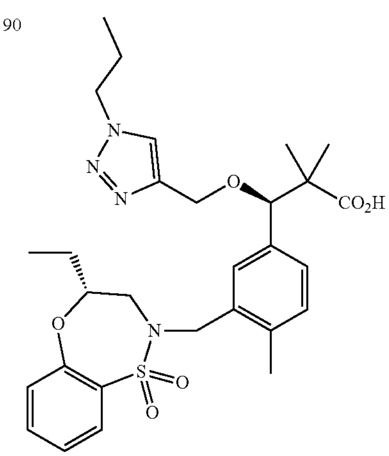 | (R)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)propanoic acid | 571.2 | 1.16 |

Example 91

(R)-3-((N-(5-(2-carboxy-1-((1-ethyl-1H-1,2,3-triazol-4-yl)methoxy)-2-methylpropyl)-2-methylbenzyl)phenylsulfonamido)methyl)benzoic Acid

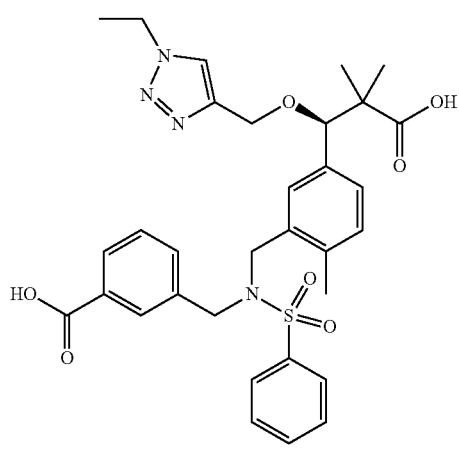 [SMILES: CCn1cc(CO[C@H](c2ccc(C)c(CN(Cc3cccc(C(=O)O)c3)S(=O)(=O)c3ccccc3)c2)C(C)(C)C(=O)O)nn1]

Tert-butyl (R)-3-((N-(5-(1-((1-ethyl-1H-1,2,3-triazol-4-yl)methoxy)-3-methoxy-2,2-dimethyl-3-oxopropyl)-2-methylbenzyl)phenylsulfonamido)methyl)benzoate

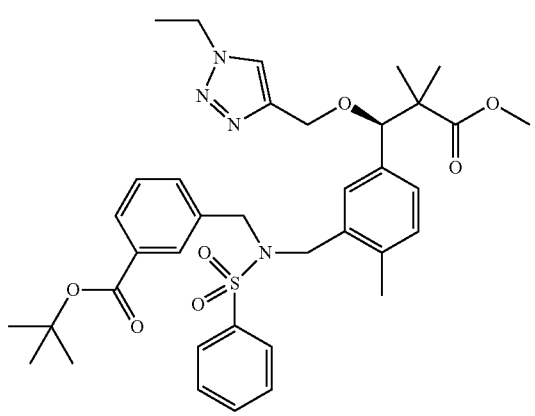 [SMILES: CCn1cc(CO[C@H](c2ccc(C)c(CN(Cc3cccc(C(=O)OC(C)(C)C)c3)S(=O)(=O)c3ccccc3)c2)C(C)(C)C(=O)OC)nn1]

To the mixture of methyl (R)-3-((1-ethyl-1H-1,2,3-triazol-4-yl)methoxy)-3-(3-(hydroxymethyl)-4-methylphenyl)-2,2-dimethylpropanoate (100 mg, 0.277 mmol in dichloromethane (1 mL) was added SOCl$_2$ (0.101 mL, 1.383 mmol). The resulting reaction mixture was stirred at ambient temperature for 30 min then was evaporated down under vacuum. The residue was dissolved in acetonitrile (4 mL) after which was added tert-butyl 3-(aminomethyl)benzoate (86 mg, 0.415 mmol) and DIEA (0.193 mL, 1.107 mmol). The resulting reaction mixture was heated with microwave at 100° C. for 1 h after which was added benzenesulfonyl chloride (0.054 mL, 0.415 mmol). The resulting reaction mixture was stirred at ambient temperature for 1 h before was quenched with water (0.2 mL), evaporated down under vacuum, purified via flash chromatography over silica gel to give the title compound (95.7 mg, 0.139 mmol, 50.1% yield). LC/MS: m/z 691.4 (M+H)$^+$, 1.47 min (ret. time).

(R)-3-((N-(5-(2-carboxy-1-((1-ethyl-1H-1,2,3-triazol-4-yl)methoxy)-2-methylpropyl)-2-methylbenzyl)phenylsulfonamido)methyl)benzoic Acid

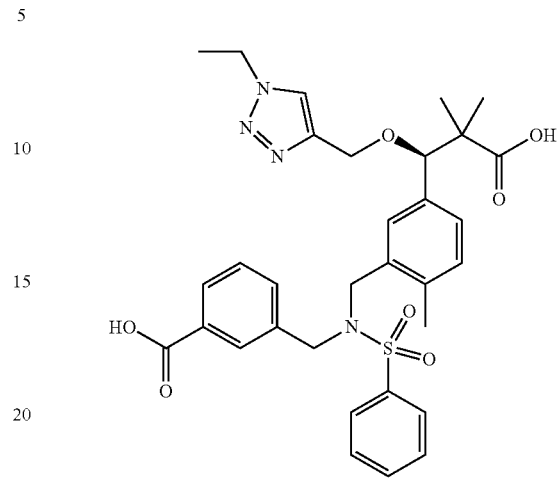

To tert-butyl (R)-3-((N-(5-(1-((1-ethyl-1H-1,2,3-triazol-4-yl)methoxy)-3-methoxy-2,2-dimethyl-3-oxopropyl)-2-methylbenzyl)phenylsulfonamido)methyl)benzoate (95 mg, 0.138 mmol) was added HCl (4.0 M in p-dioxane) (0.344 mL, 1.375 mmol). The resulting reaction mixture was stirred at ambient temperature for 2 h then was evaporated down under vacuum. The residue was dissolved in methanol (2 mL) after which was added NaOH (6.0 N) (0.183 mL, 1.100 mmol). The resulting reaction mixture was heated with microwave at 120° C. for 1 h after which was added with HCl (6.0 N) (0.183 mL, 1.100 mmol), evaporated down under vacuum, extracted with DCM (3×5 mL), dried over MgSO$_4$, filtered, evaporated down under vacuum to give the title product (70.6 mg, 0.114 mmol, 83% yield). LC/MS: m/z 621.3 (M+H)$^+$, 1.05 min (ret. time).

Example 92

(R)-3-(N-(5-(2-carboxy-2-methyl-1-((1-propyl-1H-1,2,3-triazol-4-yl)methoxy)propyl)-2-methylbenzyl)-N-(3-carboxybenzyl)sulfamoyl)benzoic Acid

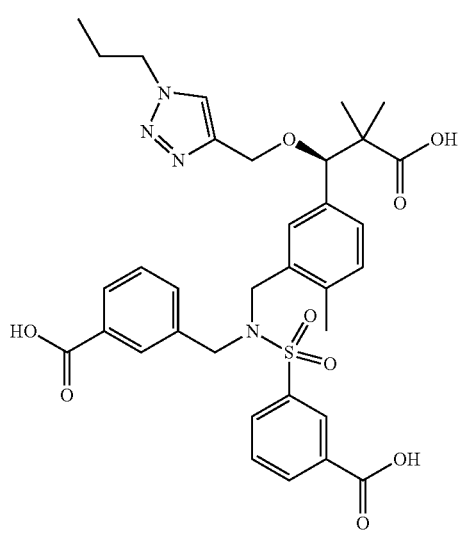 [SMILES: CCCn1cc(CO[C@H](c2ccc(C)c(CN(Cc3cccc(C(=O)O)c3)S(=O)(=O)c3cccc(C(=O)O)c3)c2)C(C)(C)C(=O)O)nn1]

Methyl (R)-3-(3-(chloromethyl)-4-methylphenyl)-2,2-dimethyl-3-((1-propyl-1H-1,2,3-triazol-4-yl)methoxy)propanoate

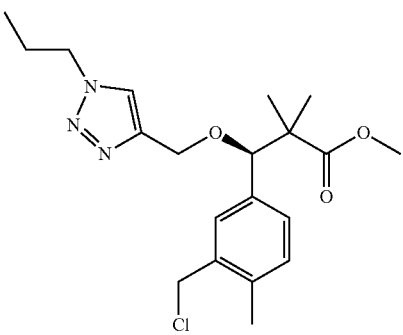 [SMILES: CCCn1cc(CO[C@H](c2ccc(C)c(CCl)c2)C(C)(C)C(=O)OC)nn1]

To the mixture of methyl (R)-3-(3-(hydromethyl)-4-methylphenyl)-2,2-dimethyl-3-((1-propyl-1H-1,2,3-triazol-4-yl)methoxy)propanoate (160 mg, 0.426 mmol) in dichloromethane (1.0 mL) was added thionyl chloride (0.155 mL, 2.131 mmol). The resulting reaction mixture was stirred at ambient temperature for 2 h then was evaporated down under vacuum to give the title compound (185.4 mg, 0.471 mmol, 110% yield). LC/MS: m/z 394.2 (M+H)$^+$, 1.17 min (ret. time).

Tert-butyl (R)-3-(((N-(5-(3-methoxy-2,2-dimethyl-3-oxo-1-((1-propyl-1H-1,2,3-triazol-4-yl)methoxy)propyl)-2-methylbenzyl)-3-(methoxycarbonyl)phenyl)sulfonamido)methyl)benzoate

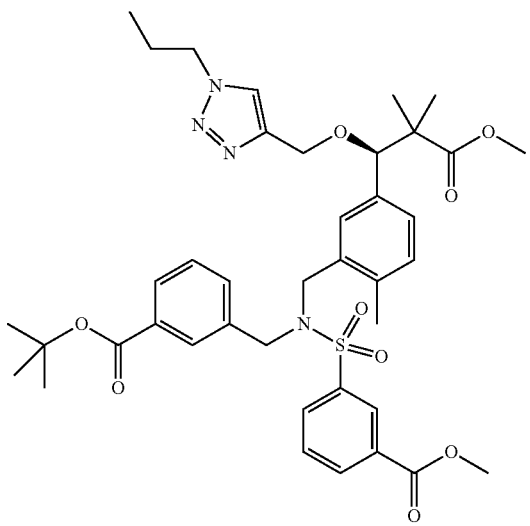 [SMILES: CCCn1cc(CO[C@H](c2ccc(C)c(CN(Cc3cccc(C(=O)OC(C)(C)C)c3)S(=O)(=O)c3cccc(C(=O)OC)c3)c2)C(C)(C)C(=O)OC)nn1]

To the mixture of methyl (R)-3-(3-(chloromethyl)-4-methylphenyl)-2,2-dimethyl-3-((1-propyl-1H-1,2,3-triazol-4-yl)methoxy)propanoate (90 mg, 0.228 mmol) in acetonitrile (3 mL) was added tert-butyl 3-(aminomethyl)benzoate (71.0 mg, 0.343 mmol) and DIEA (0.160 mL, 0.914 mmol). The resulting reaction mixture was heated with microwave at 100° C. for 1 h after which was added methyl 3-(chlorosulfonyl)benzoate (80 mg, 0.343 mmol). The resulting reaction mixture was stirred at ambient temperature for 23 h then was evaporated down under vacuum, purified via flash chromatography over silica gel to give the title compound (103.6 mg, 0.136 mmol, 59.4% yield). LC/MS: m/z 763.5 (M+H)$^+$, 1.48 min (ret. time).

(R)-3-(N-(5-(2-carboxy-2-methyl-1-((1-propyl-1H-1,2,3-triazol-4-yl)methoxy)propyl)-2-methylbenzyl)-N-(3-carboxybenzyl)sulfamoyl)benzoic Acid

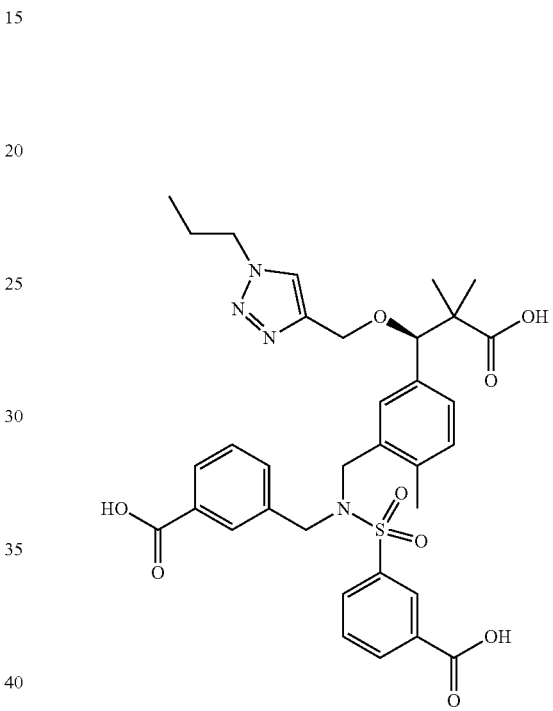

To tert-butyl (R)-3-(((N-(5-(3-methoxy-2,2-dimethyl-3-oxo-1-((1-propyl-1H-1,2,3-triazol-4-yl)methoxy)propyl)-2-methylbenzyl)-3-(methoxycarbonyl)phenyl)sulfonamido)methyl)benzoate (103 mg, 0.135 mmol) was added HCl (4.0 M in p-dioxane) (0.338 mL, 1.350 mmol). The resulting reaction mixture was stirred at ambient temperature for 3 h then was evaporated down under vacuum. The residue was dissolved in methanol (2 mL) after which was added NaOH (6.0 N) (0.180 mL, 1.080 mmol). The resulting reaction mixture was heated with microwave at 120° C. for 1 h then was quenched with HCl (6.0 N) (0.180 mL, 1.080 mmol), evaporated down under vacuum, extracted with DCM (3×5 mL), dried over MgSO$_4$, filtered, evaporated down under vacuum to give the title compound (96.5 mg, 0.142 mmol, 105% yield). LC/MS: m/z 679.4 (M+H)$^+$, 1.00 min (ret. time).

Example 93

(R)-3-(N-(5-(2-carboxy-1-((1-(2-methoxyethyl)-1H-1,2,3-triazol-4-yl)methoxy)-2-methylpropyl)-2-methylbenzyl)-N-(pyridin-2-ylmethyl)sulfamoyl) benzoic Acid

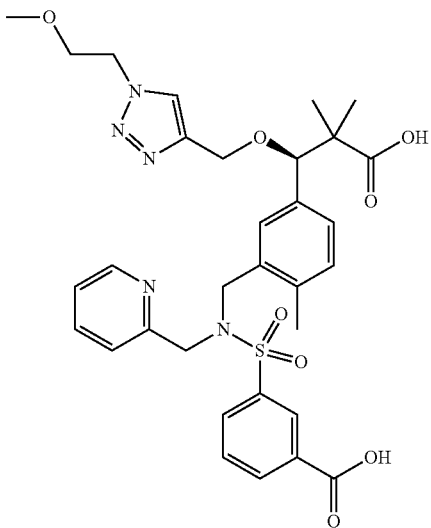 [SMILES: COCCn1cc(CO[C@H](c2ccc(C)c(CN(Cc3ccccn3)S(=O)(=O)c3cccc(C(=O)O)c3)c2)C(C)(C)C(=O)O)nn1]

To the mixture of methyl (R)-3-(3-(hydromethyl)-4-methylphenyl)-3-((1-(2-methoxyethyl)-1H-1,2,3-triazol-4-yl)methoxy)-2,2-dimethylpropanoate (50 mg, 0.128 mmol) in dichloromethane (0.5 mL) was added $SOCl_2$ (0.047 mL, 0.639 mmol). The resulting reaction mixture was stirred at ambient temperature for 30 min then was evaporated down under vacuum. The residue was dissolved in acetonitrile (2 mL) after which was added pyridin-2-ylmethanamine (0.020 mL, 0.192 mmol) and DIEA (0.089 mL, 0.511 mmol). The resulting reaction mixture was heated with microwave at 100° C. for 1 h after which methyl 3-(chlorosulfonyl) benzoate (45.0 mg, 0.192 mmol) was added. The resulting reaction mixture was stirred at ambient temperature for 30 min after which was added more DIEA (0.089 mL, 0.511 mmol). The resulting reaction mixture was stirred at ambient temperature for 1 h then was evaporated down under vacuum. The residue was dissolved in methanol (1 mL) and was added NaOH (6.0 N) (0.170 mL, 1.022 mmol). The resulting reaction mixture was heated with microwave at 120° C. for 1 h then was quenched with HCl (6.0 N) (0.170 mL, 1.022 mmol), evaporated down under vacuum, purified with reverse phase HPLC (formic acid modifier) to give the title compound (23.7 mg, 0.036 mmol, 28.5% yield). LC/MS: m/z 652.4 $(M+H)^+$, 0.83 min (ret. time).

The compounds in Table 16 were prepared by a method similar to the one described for the preparation of (R)-3-(N-(5-(2-carboxy-14(1-(2-methoxyethyl)-1H-1,2,3-triazol-4-yl)methoxy)-2-methylpropyl)-2-methylbenzyl)-N-(pyridin-2-ylmethyl)sulfamoyl)benzoic acid. As is appreciated by those skilled in the art, these analogous examples may involve variations in general reaction conditions.

TABLE 16

| Ex # | Structure | Name | LCMS $[M + H]^+$ | Retention Time (min) |
|---|---|---|---|---|
| Example 94 | 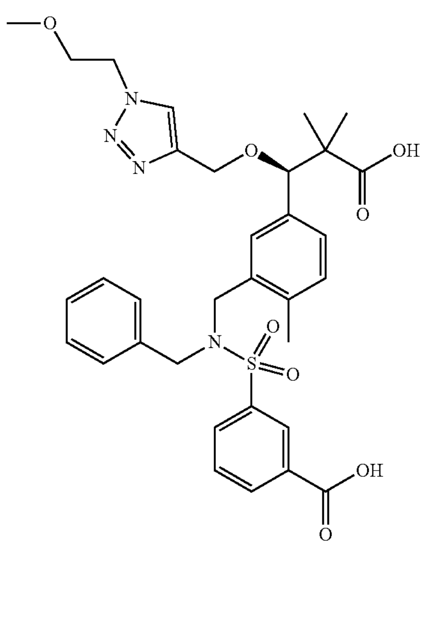 [SMILES: COCCn1cc(CO[C@H](c2ccc(C)c(CN(Cc3ccccc3)S(=O)(=O)c3cccc(C(=O)O)c3)c2)C(C)(C)C(=O)O)nn1] | (R)-3-(N-benzyl-N-(5-(2-carboxy-1-((1-(2-methoxyethyl)-1H-1,2,3-triazol-4-yl)methoxy)-2-methylpropyl)-2-methylbenzyl)sulfamoyl) benzoic acid | 651.4 | 1.08 |

TABLE 16-continued

| Ex # | Structure | Name | LCMS [M + H]+ | Retention Time (min) |
|---|---|---|---|---|
| Example 95 | 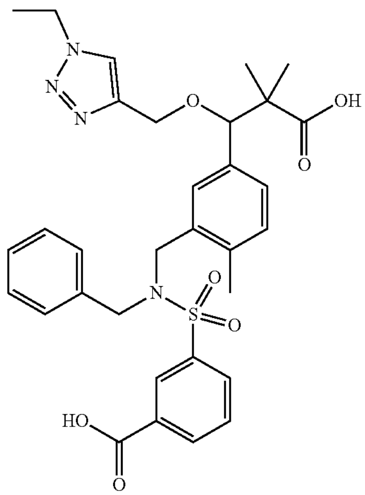 [SMILES: CCn1cc(COC(c2ccc(C)c(CN(Cc3ccccc3)S(=O)(=O)c3cccc(C(=O)O)c3)c2)C(C)(C)C(=O)O)nn1] | 3-(N-benzyl-N-(5-(2-carboxy-1-((1-ethyl-1H-1,2,3-triazol-4-yl)methoxy)-2-methylpropyl)-2-methylbenzyl)sulfamoyl)benzoic acid | 621.5 | 1.11 |
| Example 96 | 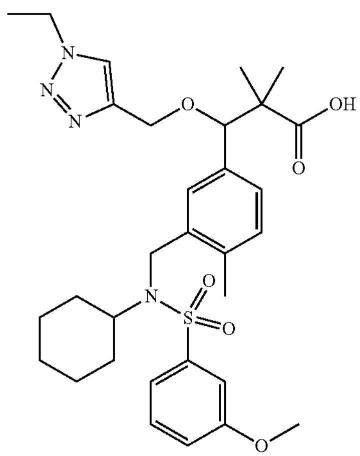 [SMILES: CCn1cc(COC(c2ccc(C)c(CN(C3CCCCC3)S(=O)(=O)c3cccc(OC)c3)c2)C(C)(C)C(=O)O)nn1] | 3-(3-(((N-cyclohexyl-3-methoxyphenyl)sulfonamido)methyl)-4-methylphenyl)-3-((1-ethyl-1H-1,2,3-triazol-4-yl)methoxy)-2,2-dimethylpropanoic acid | 599.3 | 1.28 |
| Example 97 | 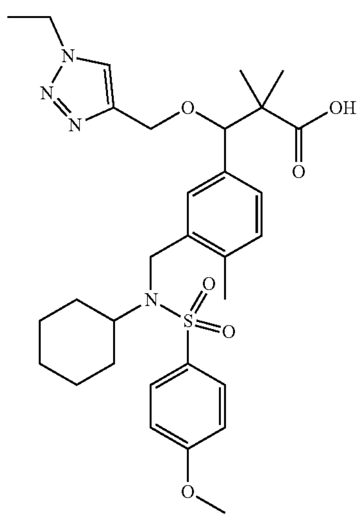 [SMILES: CCn1cc(COC(c2ccc(C)c(CN(C3CCCCC3)S(=O)(=O)c3ccc(OC)cc3)c2)C(C)(C)C(=O)O)nn1] | 3-(3-(((N-cyclohexyl-4-methoxyphenyl)sulfonamido)methyl)-4-methylphenyl)-3-((1-ethyl-1H-1,2,3-triazol-4-yl)methoxy)-2,2-dimethylpropanoic acid | 599.3 | 1.26 |

TABLE 16-continued
| Ex # | Structure | Name | LCMS [M + H]+ | Retention Time (min) |
|---|---|---|---|---|
| Example 98 | 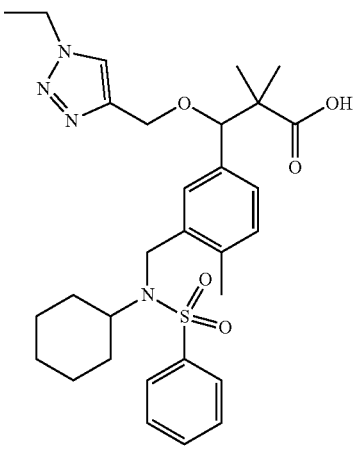 [SMILES: CCn1cc(COC(c2ccc(C)c(CN(C3CCCCC3)S(=O)(=O)c3ccccc3)c2)C(C)(C)C(=O)O)nn1] | 3-(3-((N-cyclohexylphenylsulfonamido)methyl)-4-methylphenyl)-3-((1-ethyl-1H-1,2,3-triazol-4-yl)methoxy)-2,2-dimethylpropanoic acid | 569.3 | 1.26 |
| Example 99 | 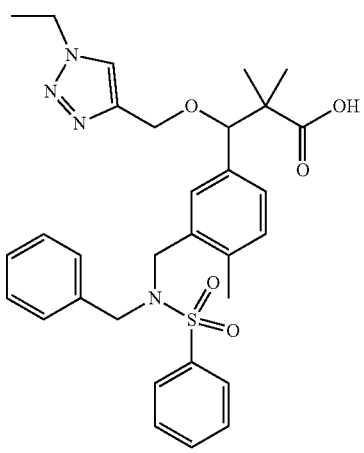 [SMILES: CCn1cc(COC(c2ccc(C)c(CN(Cc3ccccc3)S(=O)(=O)c3ccccc3)c2)C(C)(C)C(=O)O)nn1] | 3-(3-((N-benzylphenylsulfonamido)methyl)-4-methylphenyl)-3-((1-ethyl-1H-1,2,3-triazol-4-yl)methoxy)-2,2-dimethylpropanoic acid | 577.2 | 1.21 |

Example 100

3-((1-((1-Carbamoylpiperidin-4-yl)methyl)-1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

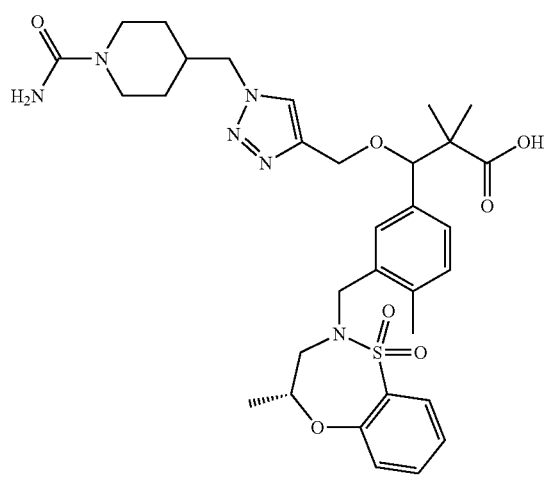 [SMILES: Cc1ccc(C(OCc2cn(CC3CCN(C(N)=O)CC3)nn2)C(C)(C)C(=O)O)cc1CN1C[C@@H](C)Oc2ccccc2S1(=O)=O]

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(piperidin-4-ylmethyl)-1H-1,2,3-triazol-4-yl)methoxy)propanoate, hydrochloride (60 mg, 0.091 mmol) in dichloromethane (1.000 mL) was added DIEA (0.040 mL, 0.227 mmol) and AcCl (9.66 µl, 0.136 mmol). The resulting reaction mixture was stirred at ambient temperature for 20 min then was evaporated down under vacuum. The residue was dissolved in methanol (1.0 mL) after which was added NaOH (6.0 N) (0.121 mL, 0.725 mmol). The resulting reaction mixture was heated with microwave at 120° C. for 30 min twice after which was added HCl (6.0 N) (0.121 mL, 0.725 mmol) and dimethyl sulfoxide (1.000 mL), and evaporated down under vacuum. To the resulting dimethyl sulfoxide solution was added DIEA (0.040 mL, 0.227 mmol) and TMS-NCO (0.025 mL, 0.181 mmol). The resulting reaction mixture was stirred at ambient temperature for 69 h then was quenched with HCl (6.0 N) (0.015 mL, 0.091 mmol), purified by reverse phase HPLC (formic acid modifier) to give the title (8.7 mg, 0.013 mmol, 14.67% yield). LC/MS: m/z 655.4 (M+H)$^+$, 0.97 min (ret. time).

Example 101

3-((1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoic Acid

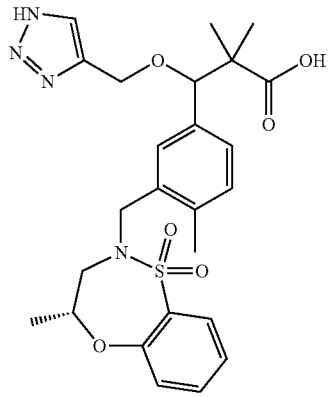 [SMILES: Cc1ccc(C(OCc2c[nH]nn2)C(C)(C)C(=O)O)cc1CN1C[C@@H](C)Oc2ccccc2S1(=O)=O]

To the mixture of methyl 3-((1H-1,2,3-triazol-4-yl)methoxy)-2,2-dimethyl-3-(4-methyl-3-(((R)-4-methyl-1,1-dioxido-3,4-dihydro-2H-benzo[b][1,4,5]oxathiazepin-2-yl)methyl)phenyl)propanoate (60 mg, 0.114 mmol) in methanol (1.0 mL) was added NaOH (6.0 N) (0.095 mL, 0.568 mmol). The resulting reaction mixture was heated with microwave at 120° C. for 30 min after which was added HCl (6.0 N) (0.095 mL, 0.568 mmol), evaporated down under vacuum, purified by reverse phase HPLC (formic acid modifier) to give the title compound (24.9 mg, 0.048 mmol, 42.6% yield). LC/MS: m/z 515.3 (M+H)$^+$, 1.03 min (ret. time).

Example 102

Rel-(R)-2,2-dimethyl-3-(4-methyl-3-(((S)-4-methyl-1,1-dioxido-4,5-dihydropyrido[4,3-f][1,2]thiazepin-2(3H)-yl)methyl)phenyl)-3-((1-(oxetan-3-yl)-1H-1,2,3-triazol-4-yl)methoxy)propanoic Acid

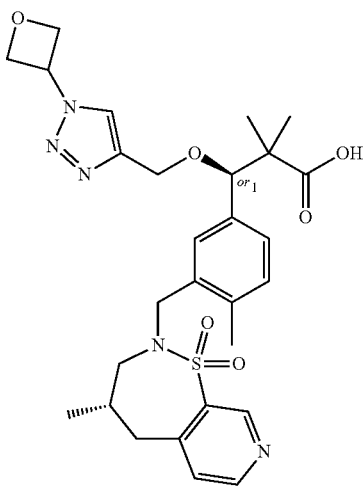 [SMILES: Cc1ccc([C@@H](OCc2cn(C3COC3)nn2)C(C)(C)C(=O)O)cc1CN1C[C@@H](C)Cc2ccncc2S1(=O)=O]

To the mixture of rel-(R)-methyl 2,2-dimethyl-3-(4-methyl-3-(((S)-4-methyl-1,1-dioxido-4,5-dihydropyrido[4,3-f][1,2]thiazepin-2(3H)-yl)methyl)phenyl)-3-(prop-2-yn-1-yloxy)propanoate (50 mg, 0.103 mmol) in isopropanol (0.5 mL) and tetrahydrofuran (0.5 mL) was added DIEA (3.60 µl, 0.021 mmol), 3-azidooxetane (0.5 M in MTBE) (0.619 mL, 0.310 mmol) and copper(I) iodide (2.95 mg, 0.015 mmol). The resulting reaction mixture was heated with microwave at 70° C. for 30 min then was evaporated down under vacuum. To the residue was added methanol (1.5 mL) and then NaOH (6 N) (0.172 mL, 1.032 mmol). The resulting reaction mixture was heated with microwave at 80° C. for 30 min after which was added a solution of HCl (6 N) (0.172 mL, 1.032 mmol) in methanol (1.5 mL), evaporated down under vacuum (80-4) and purified with reverse phase HPLC (with 0.1% formic acid) to give the title compound (43.4 mg, 0.076 mmol, 73.8% yield). LC/MS: m/z 570.4 (M+H)⁺, 0.94 min (ret. time).

The compounds in Table 17 were prepared by a method similar to the one described for the preparation of rel-(R)-2,2-dimethyl-3-(4-methyl-3-(((S)-4-methyl-1,1-dioxido-4,5-dihydropyrido[4,3-f][1,2]thiazepin-2(3H)-yl)methyl)phenyl)-3-((1-(oxetan-3-yl)-1H-1,2,3-triazol-4-yl)methoxy)propanoic acid. As is appreciated by those skilled in the art, these analogous examples may involve variations in general reaction conditions.

TABLE 17

| Ex # | Structure | Name | LCMS [M + H]⁺ | Retention Time (min) |
|---|---|---|---|---|
| Example 103 | 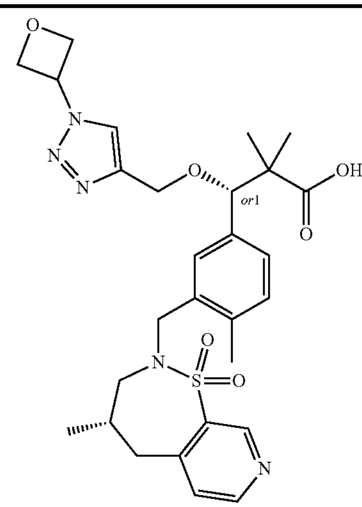 | Rel-(S)-2,2-dimethyl-3-(4-methyl-3-(((S)-4-methyl-1,1-dioxido-4,5-dihydropyrido[4,3-f][1,2]thiazepin-2(3H)-yl)methyl)phenyl)-3-((1-(oxetan-3-yl)-1H-1,2,3-triazol-4-yl)methoxy)propanoic acid | 570.3 | 0.94 |

Example 104

2,2-Dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(oxetan-3-yl)-1H-1,2,3-triazol-4-yl)methoxy)propanoic Acid

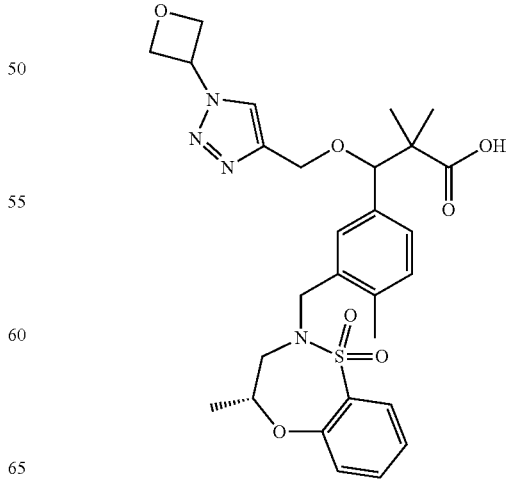

To the mixture of methyl 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-(prop-2-yn-1-yloxy)propanoate (0.060 g, 0.124 mmol) in isopropanol (1.0 mL) and tetrahydrofuran (0.5 mL) was added 3-azidooxetane (3.0 M in MTBE) (0.494 mL, 0.247 mmol), DIEA (4.32 µl, 0.025 mmol) and copper(I) iodide (3.53 mg, 0.019 mmol). The resulting reaction mixture was heated with microwave at 80° C. for 30 min then was evaporated down under vacuum. The residue was dissolved methanol (1.0 mL) after which was added NaOH (6.0 N) (0.165 mL, 0.988 mmol). The resulting reaction mixture was heated with microwave at 120° C. for 30 min after which was added HCl (6.0 N) (0.165 mL, 0.988 mmol), evaporated down under vacuum and purified by reverse phase HPLC (formic acid modifier) to give the title compound (16.5 mg, 0.029 mmol, 23.40% yield). LC/MS: m/z 571.3 (M+H)⁺, 1.04 min (ret. time).

The compounds in Table 18 were prepared by a method similar to the one described for the preparation of 2,2-dimethyl-3-(4-methyl-3-(((R)-4-methyl-1,1-dioxido-3,4-dihydro-2H-benzo[b][1,4,5]oxathiazepin-2-yl)methyl)phenyl)-3-((1-(oxetan-3-yl)-1H-1,2,3-triazol-4-yl)methoxy)propanoic acid. As is appreciated by those skilled in the art, these analogous examples may involve variations in general reaction conditions.

TABLE 18

| Ex # | Structure | Name | LCMS [M + H]⁺ | Retention Time (min) |
|---|---|---|---|---|
| Example 105 | 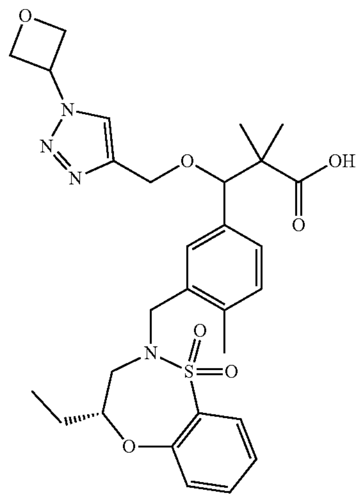 [SMILES: CC[C@@H]1CN(Cc2cc(C(OCc3cn(C4COC4)nn3)C(C)(C)C(=O)O)ccc2C)S(=O)(=O)c2ccccc2O1] | 3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-((1-(oxetan-3-yl)-1H-1,2,3-triazol-4-yl)methoxy)propanoic acid | 585.3 | 1.09 |

Example 106

3-(3-(((R)-4-ethyl-1,1-dioxido-3,4-dihydro-2H-benzo[b][1,4,5]oxathiazepin-2-yl)methyl)-4-methylphenyl)-3-((1-(2-methoxyethyl)-1H-1,2,3-triazol-4-yl)methoxy)-2,2-dimethylpropanoic Acid

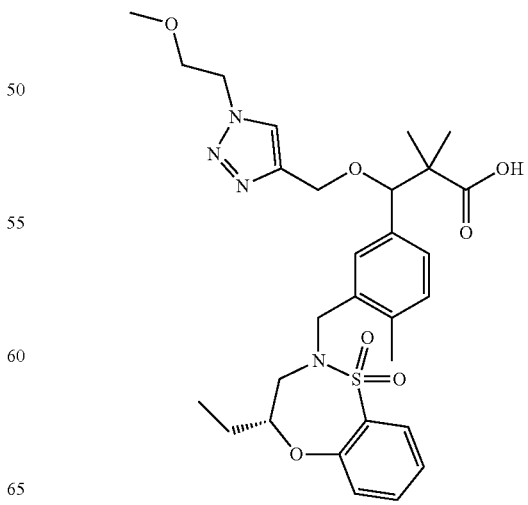

To the mixture of 1-bromo-2-methoxyethane (0.056 mL, 0.600 mmol) in N,N-dimethylformamide (1.0 mL) was added sodium azide (39.0 mg, 0.600 mmol). The resulting reaction mixture was stirred at 80° C. for 5.5 h. The reaction mixture was cooled to ambient temperature after which was added isopropanol (1.0 mL), tetrahydrofuran (1.0 mL), methyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-(prop-2-yn-1-yloxy)propanoate (100 mg, 0.200 mmol), DIEA (6.99 µl, 0.040 mmol), water (0.6 mL) and copper(I) iodide (5.72 mg, 0.030 mmol). The resulting reaction mixture was heated with microwave at 80° C. for 30 min then was evaporated down under vacuum. The residue was dissolved in methanol (4.0 mL) after which was added NaOH (6.0 N) (0.334 mL, 2.002 mmol). The resulting reaction mixture was heated with microwave at 120° C. for 60 min after which was added more NaOH (6.0 N) (0.067 mL, 0.400 mmol). The resulting reaction mixture was heated with microwave at 120° C. for 60 min and heated again with microwave at 130° C. for 60 min after which was added HCl (6.0 N) (0.400 mL, 2.402 mmol), evaporated down under vacuum, purified by reverse phase HPLC (formic acid modifier) to give the title compound (51.6 mg, 0.088 mmol, 43.9% yield). LC/MS: m/z 587.4 (M+H)+, 1.12 min (ret. time).

The compounds in Table 19 were prepared by a method similar to the one described for the preparation of 3-(3-(((R)-4-ethyl-1,1-dioxido-3,4-dihydro-2H-benzo[b][1,4,5]oxathiazepin-2-yl)methyl)-4-methylphenyl)-3-((1-(2-methoxyethyl)-1H-1,2,3-triazol-4-yl)methoxy)-2,2-dimethylpropanoic acid. As is appreciated by those skilled in the art, these analogous examples may involve variations in general reaction conditions.

Example 108

(R)-3-(3-(((R)-2-Ethyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)methoxy)propanoic Acid Hydrochloride

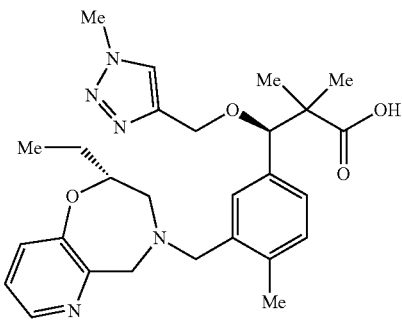 [SMILES: CC[C@@H]1CN(Cc2cc([C@@H](OCc3cn(C)nn3)C(C)(C)C(=O)O)ccc2C)Cc2ncccc2O1]

(R)-1-(((3-Fluoropyridin-2-yl)methyl)amino)butan-2-ol

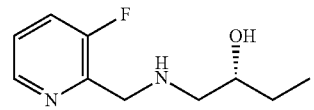

To a solution of (R)-1-aminobutan-2-ol (3.70 g, 41.5 mmol) in methanol (150 mL) was added 3-fluoropicolinaldehyde (4.67 g, 37.4 mmol) followed by magnesium sulfate (4.50 g, 37.4 mmol) and the reaction mixture was stirred at 0° C. for 1 hr. The reaction mixture was filtered through

TABLE 19

| Ex # | Structure | Name | LCMS [M + H]+ | Retention Time (min) |
|---|---|---|---|---|
| Example 107 | | 3-(3-(((R)-4-ethyl-1,1-dioxido-3,4-dihydro-2H-benzo[b][1,4,5]oxathiazepin-2-yl)methyl)-4-methylphenyl)-3-((1-(2-(2-methoxyethoxy)ethyl)-1H-1,2,3-triazol-4-yl)methoxy)-2,2-dimethylpropanoic acid | 631.4 | 1.12 | celite and washed with methanol (300 ml). Sodium borohydride (1.413 g, 37.4 mmol) was added in two portions to the filtrate and the reaction mixture was stirred at ambient temperature for 30 min. The reaction mixture was quenched with 10% sodium bicarbonate solution and the methanol evaporated under reduced pressure. The remaining aqueous phase was extracted with ethyl acetate (3×125 mL) and the combined organic extracts were washed with brine, dried over sodium sulfate, filtered and the solvent evaporated under reduced pressure. The crude residue was purified by silica gel chromatography (0-100%/3:1 ethyl acetate:ethanol/hexanes) to afford a yellow oil (R)-1-(((3-fluoropyridin-2-yl)methyl)amino)butan-2-ol (5.3 g, 24.06 mmol, 58.0% yield). $^1$H NMR (CHCl$_3$-d) δ: 8.36-8.45 (m, 1H), 7.37-7.45 (m, 1H), 7.22-7.32 (m, 1H), 4.10-4.16 (m, 2H), 3.68-3.77 (m, 1H), 2.89 (m, 1H), 2.64 (m, 1H), 1.43-1.55 (m, 2H), 0.90-1.02 (m, 3H). LC-MS: m/z 199.2 (M+H)$^+$ (R)-Tert-butyl 2-ethyl-2,3-dihydropyrido[2,3-f][1,4]oxazepine-4(5H)-carboxylate

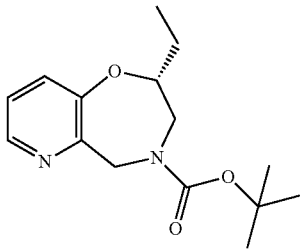 [SMILES: CC[C@@H]1CN(C(=O)OC(C)(C)C)Cc2ncccc2O1]

To a solution of (R)-1-(((3-fluoropyridin-2-yl)methyl)amino)butan-2-ol (5.20 g, 26.2 mmol) in dimethyl sulfoxide (100 mL) was added potassium tert-butoxide (3.68 g, 32.8 mmol) and the reaction mixture was stirred at 90° C. for 45 min. The reaction mixture was cooled to ambient temperature to afford a deep red-colored solution. Boc-anhydride (6.09 mL, 26.2 mmol) was added and the reaction mixture was allowed to stir for 18 hr. The reaction mixture was diluted with ethyl acetate (500 mL) and the organic phase washed with water (4×200 mL), brine, dried over sodium sulfate, filtered and the solvent evaporated under reduced pressure. The crude residue was purified by silica gel chromatography (0-50% ethyl acetate/hexanes) to afford an orange oil (R)-tert-butyl 2-ethyl-2,3-dihydropyrido[2,3-f][1,4]oxazepine-4(5H)-carboxylate (4.84 g, 17.39 mmol, 66.3% yield). $^1$H NMR (DMSO-d$_6$) δ: 8.17 (m, 1H), 7.36 (m, 1H), 7.24 (m, 1H), 4.49-4.76 (m, 2H), 3.93 (br. s., 1H), 3.47-3.74 (m, 2H), 1.52-1.66 (m, 2H), 1.36 (br. s., 4H), 1.25 (s, 5H), 0.96-1.07 (m, 3H). LC-MS: m/z 279.2 (M+H)+.

(R)-2-Ethyl-2,3,4,5-tetrahydropyrido[2,3-f][1,4]oxazepine, hydrochloride

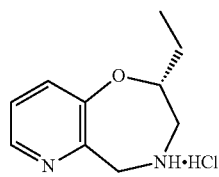

To a solution of (R)-tert-butyl 2-ethyl-2,3-dihydropyrido[2,3-f][1,4]oxazepine-4(5H)-carboxylate (4.84 g, 17.39 mmol) in 1,4-dioxane (20 mL), at ambient temperature, was added 4N HCl in dioxane (100 mL, 400 mmol) and the reaction mixture was stirred at ambient temperature for 2h. The solvent was evaporated under reduced pressure and azeotroped with diethyl ether (3×) to afford a cream solid (R)-2-ethyl-2,3,4,5-tetrahydropyrido[2,3-f][1,4]oxazepine, hydrochloride (3.55 g, 16.54 mmol, 95% yield). $^1$H NMR (DMSO-d$_6$) δ: 9.95-10.36 (m, 2H), 8.38 (m, 1H), 7.66 (m, 1H), 7.51 (m, 1H), 4.39-4.57 (m, 2H), 4.04-4.18 (m, 1H), 3.47-3.60 (m, 1H), 3.24-3.40 (m, 1H), 1.69 (m, 2H), 1.05 (m, 3H). LC-MS: m/z 179.2 (M+H)$^+$ 3-(((4-Methoxybenzyl)oxy)methyl)-4-methylbenzaldehyde

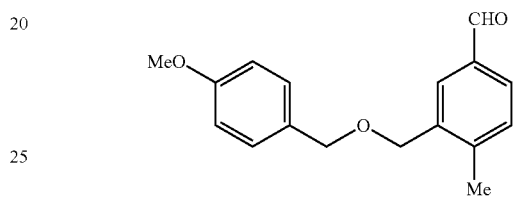

To a solution of 4-bromo-2-(((4-methoxybenzyl)oxy)methyl)-1-methylbenzene (12.6 g, 39.2 mmol) in tetrahydrofuran (THF) (131 ml) at −78° C. was added n-butyllithium (1.6 M in hexanes) (39.2 ml, 62.8 mmol) dropwise. After 60 min at −78° C., DMF (9.11 ml, 118 mmol) was added dropwise. After 2 h at −78° C., the reaction mixture was quenched at −78° C. with 300 mL of saturated aqueous NH$_4$Cl, removed from the bath and stirred for 10 min. The reaction contents were diluted with 20 mL water and partitioned with 300 mL EtOAc. The layers were separated and the aqueous layer was extracted with 1×150 mL EtOAc. The combined organics were dried over Na$_2$SO$_4$, filtered, and concentrated to give an orange oil. Purification by silica gel chromatography (330 g column, 0-25% EtOAc:Hexanes) gave the title compound as a clear, orange oil (7.4 g, 27.4 mmol, 70% yield). LC-MS m/z 241.1 (M-29 (CHO))$^+$, 1.11 min (ret. time). $^1$H NMR (400 MHz, CHLOROFORM-d) δ ppm 2.41 (s, 3H) 3.77-3.86 (m, 3H) 4.58 (d, J=6.53 Hz, 4H) 6.83-7.00 (m, 2H) 7.29-7.37 (m, 3H) 7.74 (dd, J=7.78, 1.76 Hz, 1H) 7.90 (d, J=1.25 Hz, 1H) 10.00 (s, 1H).

Methyl (R)-3-hydroxy-3-(3-(((4-methoxybenzyl)oxy)methyl)-4-methylphenyl)-2,2-dimethyl-propanoate

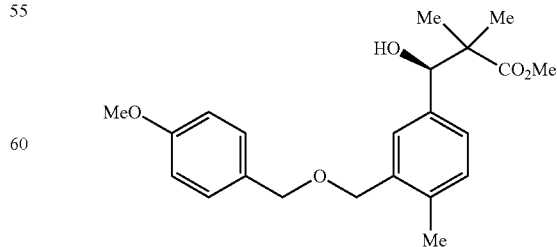

To a suspension of tosyl-L-valine (5.72 g, 21.09 mmol) in dichloromethane (DCM) (59.7 ml) at 0° C. was added borane tetrahydrofuran complex (21.09 ml, 21.09 mmol) dropwise. Vigorous bubbling occurred initially. After ~5 min, bubbling ceased and the suspension dissolved to give a clear, colorless solution. The solution was stirred for 30 min at 0° C., then warmed to ambient temperature and stirred for an additional 1 h. The mixture was subsequently cooled to −78° C. and a solution of 3-(((4-methoxybenzyl)oxy)methyl)-4-methylbenzaldehyde (5.7 g, 21.09 mmol) in dichloromethane (DCM) (26.0 ml) was added dropwise. After 5 min, ((1-methoxy-2-methylprop-1-en-1-yl)oxy)trimethylsilane (5.57 ml, 27.4 mmol) was added dropwise and the resulting reaction mixture was allowed to remain stirring at −78° C. After 2 h at −78° C., the reaction was quenched with 20 mL MeOH and 100 mL saturated aqueous NH$_4$Cl, warmed to ambient temperature, and stirred vigorously for 20 min. The resulting layers were separated and the aqueous layer was extracted with 3×50 mL DCM. The combined organics were dried over Na$_2$SO$_4$, filtered and concentrated to give a thick, pale yellow oil. Purification by silica gel chromatography (330 g column, 0-70% EtOAc:Hexanes) afforded the title compound as a clear, colorless oil (2.7 g, 7.3 mmol, 34% yield). LC-MS m/z 373.0 (M+H)$^+$, 1.16 min (ret. time). $^1$H NMR (400 MHz, CHLOROFORM-d) δ ppm 1.14 (s, 3H) 1.17 (s, 3H) 2.33 (s, 3H) 3.74 (s, 3H) 3.84 (s, 3H) 4.48-4.52 (m, 2H) 4.53 (s, 2H) 4.90 (s, 1H) 6.89-6.94 (m, 2H) 7.14-7.17 (m, 2H) 7.31 (d, J=8.78 Hz, 3H).

Methyl (R)-3-(3-(((4-methoxybenzyl)oxy)methyl)-4-methylphenyl)-2,2-dimethyl-3-(prop-2-yn-1-yloxy)propanoate

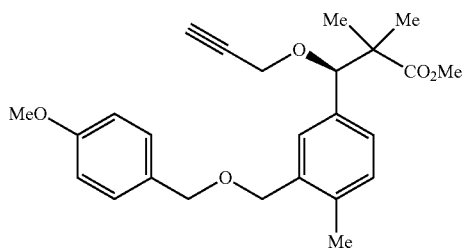 [SMILES: C#CCO[C@H](c1ccc(C)c(COCc2ccc(OC)cc2)c1)C(C)(C)C(=O)OC]

To a solution of methyl (R)-3-hydroxy-3-(3-(((4-methoxybenzyl)oxy)methyl)-4-methylphenyl)-2,2-dimethylpropanoate (4.8 g, 12.89 mmol) and 3-bromoprop-1-yne (1.831 ml, 19.33 mmol, ~80% in toluene) in N,N-dimethylformamide (DMF) (25.8 ml) at 0° C. was added sodium hydride (0.773 g, 19.33 mmol, 60% dispersion in mineral oil). After 2 h, the reaction was quenched with 50 mL water and diluted with 100 mL EtOAc. The resulting layers were separated and the aqueous layer was extracted with 1×50 mL EtOAc. The combined organics were sequentially washed with 4×50 mL water and 1×50 mL brine. The combined organics were dried over Na$_2$SO$_4$, filtered and concentrated to give a pale-yellow oil. Purification by silica gel chromatography (220 g column, 0-30% EtOAc:Hexanes) afforded the title compound as a colorless semi-solid (4.3 g, 10.5 mmol, 81% yield). LC-MS m/z 433.3 (M+Na)$^+$, 1.36 min (ret. time). $^1$H NMR (400 MHz, CHLOROFORM-d) δ ppm 1.06 (s, 3H) 1.18 (s, 3H) 2.34 (s, 3H) 2.37 (t, J=2.38 Hz, 1H) 3.70-3.74 (m, 3H) 3.81-3.89 (m, 4H) 4.09-4.18 (m, 1H) 4.53 (d, J=4.02 Hz, 4H) 4.86 (s, 1H) 6.83-6.96 (m, 2H) 7.12-7.17 (m, 2H) 7.28 (s, 1H) 7.31 (d, J=8.78 Hz, 2H).

Methyl-(R)-3-(3-(hydroxymethyl)-4-methylphenyl)-2,2-dimethyl-3-(prop-2-yn-1-yloxy)propanoate

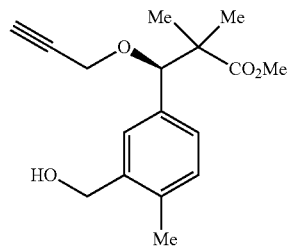 [SMILES: C#CCO[C@H](c1ccc(C)c(CO)c1)C(C)(C)C(=O)OC]

To a solution of methyl (R)-3-(3-(((4-methoxybenzyl)oxy)methyl)-4-methylphenyl)-2,2-dimethyl-3-(prop-2-yn-1-yloxy)propanoate (6.5 g, 15.83 mmol) in acetonitrile (72.0 ml) and water (7.20 ml) was added ceric ammonium nitrate (26.0 g, 47.5 mmol). The resulting solution was allowed to stir at ambient temperature. After 20 min, the reaction mixture was partitioned with 300 mL EtOAc and 300 mL water, and the resulting layers were separated. The aqueous layer was extracted with 3×100 mL EtOAc and the combined organics were dried over Na$_2$SO$_4$, filtered and concentrated to give a thick, orange oil. Purification by silica gel chromatography (220 g column, 0-50% EtOAc:Hexanes) gave the title compound as a thick, clear, pale yellow oil (3.9 g, 13.4 mmol, 85% yield). LC-MS m/z 313.1 (M+Na)$^+$, 0.94 min (ret. time). $^1$H NMR (400 MHz, CHLOROFORM-d) δ ppm 1.06 (s, 3H) 1.18 (s, 3H) 1.63 (br. s., 1H) 2.36-2.38 (m, 3H) 3.73 (s, 3H) 3.85 (dd, J=15.81, 2.26 Hz, 1H) 4.15 (dd, J=15.81, 2.51 Hz, 1H) 4.73 (s, 2H) 4.87 (s, 1H) 7.08-7.21 (m, 2H) 7.28 (s, 1H).

Methyl (R)-3-(3-(hydroxymethyl)-4-methylphenyl)-2,2-dimethyl-3-(0-methyl-1H-1,2,3-triazol-4-yl)methoxy)propanoate

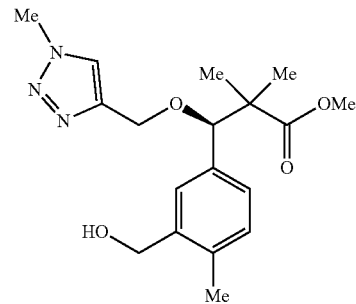 [SMILES: COC(=O)C(C)(C)[C@H](OCc1cn(C)nn1)c1ccc(C)c(CO)c1]

To a solution of methyl (R)-3-(3-(hydromethyl)-4-methylphenyl)-2,2-dimethyl-3-(prop-2-yn-1-yloxy)propanoate (1.1 g, 3.79 mmol) in water (14.57 ml) was added sequentially DIPEA (0.132 ml, 0.758 mmol), copper(I) iodide (0.144 g, 0.758 mmol), iodomethane (0.472 ml, 7.58 mmol) and sodium azide (0.493 g, 7.58 mmol). The resulting reaction mixture was heated to 70° C. After 45 min, the reaction mixture was cooled to ambient temperature and partitioned with 200 mL EtOAc and 150 mL saturated aqueous NaHCO$_3$. The resulting layers were separated and the aqueous layer was extracted with 3×50 mL EtOAc. The combined organics were dried over Na$_2$SO$_4$, filtered and concentrated to give a green oil. Purification by silica gel chromatography (40 g column, 0-90% EtOAc:Hexanes) afforded a thick, orange/red oil. Subsequent purification by chiral SFC (Chiralpak IG 20×250 mm, 5u column, 20% EtOH co-solvent) afforded the title compound as a thick, orange/red oil (1.2 g, 3.5 mmol, 91% yield). LC-MS m/z 348.2 (M+H)+, 0.78 min (ret. time). 1H NMR (400 MHz, CHLOROFORM-cab ppm 1.06 (s, 3H) 1.18 (s, 3H) 2.38 (s, 3H) 3.69 (s, 3H) 4.18 (d, J=4.77 Hz, 2H) 4.80 (br. s., 3H) 5.32 (s, 3H) 7.19 (br. s., 3H) 7.28 (s, 1H).

Methyl-(R)-3-(3-(chloromethyl)-4-methylphenyl)-2,
2-dimethyl-3-(0-methyl-1H-1,2,3-triazol-4-yl)
methoxy)propanoate

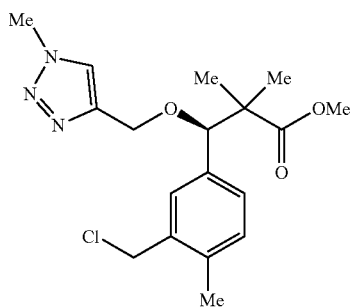 [SMILES: COC(=O)C(C)(C)[C@H](OCc1cn(C)nn1)c1ccc(C)c(CCl)c1]

To a solution of methyl (R)-3-(3-(hydromethyl)-4-methylphenyl)-2,2-dimethyl-3-((1-methyl-1H-1,2,3-triazol-4-yl)methoxy)propanoate (683 mg, 1.966 mmol) in dichloromethane (DCM) (9830 µl) was added thionyl chloride (287 µl, 3.93 mmol). After 10 min at ambient temperature, the reaction mixture was concentrated to give the title compound as a pale yellow semi-solid, which was carried forward without further purification. LC-MS m/z 366.1 (M+H)+, 1.06 min (ret. time).

Methyl-(R)-3-(3-(((R)-2-ethyl-2,3-dihydropyrido[2,
3-f][1,4]oxazepin-4(5H)-yl)methyl)-4-methylphenyl)-2,2-dimethyl-3-((1-methyl-1H-1,2,3-triazol-4-yl)methoxy)propanoate

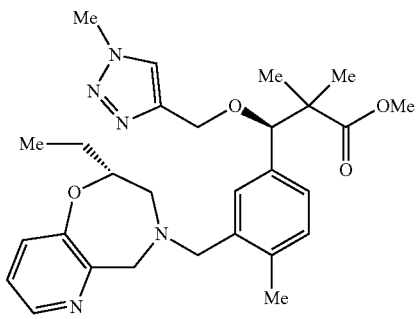 [SMILES: CC[C@@H]1CN(Cc2cc([C@@H](OCc3cn(C)nn3)C(C)(C)C(=O)OC)ccc2C)Cc2ncccc2O1]

To a solution of methyl (R)-3-(3-(chloromethyl)-4-methylphenyl)-2,2-dimethyl-3-((1-methyl-1H-1,2,3-triazol-4-yl)methoxy)propanoate (360 mg, 0.984 mmol) and (R)-2-ethyl-2,3,4,5-tetrahydropyrido[2,3-f][1,4]oxazepine-hydrochloride (211 mg, 0.984 mmol) in acetonitrile (3690 µl) and tetrahydrofuran (THF) (1230 µl) was added $K_2CO_3$ (408 mg, 2.95 mmol) and sodium iodide (73.7 mg, 0.492 mmol). The resulting reaction mixture was heated to 80° C. After 45 min, the reaction contents were cooled to ambient temperature and partitioned with 30 mL EtOAc, 15 mL saturated aqueous $NH_4Cl$ and 5 mL water. The resulting layers were separated and the aqueous layer was extracted with 3×10 mL EtOAc. The combined organics were dried over $Na_2SO_4$, filtered and concentrated to give a yellow oil. Purification by silica gel chromatography (24 g column, 0-80% EtOAc:Hexanes) afforded the title compound as an orange oil (480 mg, 0.95 mmol, 96% yield). LC-MS m/z 508.4 (M+H)+, 0.73 min (ret. time).

(R)-3-(3-(((R)-2-Ethyl-2,3-dihydropyrido[2,3-f][1,4]
oxazepin-4(5H)-yl)methyl)-4-methylphenyl)-2,2-
dimethyl-3-((1-methyl-1H-1,2,3-triazol-4-yl)
methoxy)propanoic Acid Hydrochloride

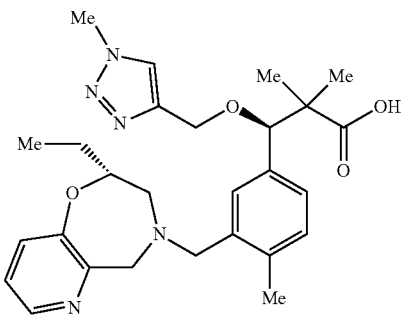 [SMILES: CC[C@@H]1CN(Cc2cc([C@@H](OCc3cn(C)nn3)C(C)(C)C(=O)O)ccc2C)Cc2ncccc2O1]

To a solution of methyl (R)-3-(3-(((R)-2-ethyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)methoxy)propanoate (480 mg, 0.946 mmol) in methanol (9456 µl) was added a solution of 1 M aqueous NaOH (9456 µl, 9.46 mmol). The resulting reaction mixture was heated to 100° C. After 1 h, the reaction contents were cooled to ambient temperature and concentrated. Purification by reverse-phase HPLC (10-80% $CH_3CN$+0.1% TFA:$H_2O$+0.1% TFA) and concentration of the product-containing fractions gave a colorless oil. Treatment with 2 mL of 6 N aqueous HCl followed by lyophilization afforded the hydrochloride salt of the title compound as a white solid (499.7 mg, 0.94 mmol, 100% yield). LC-MS m/z 494.4 (M+H)+, 0.66 min (ret. time). 1H NMR (400 MHz, METHANOL-$d_4$) δ ppm 1.05 (s, 3H) 1.12-1.22 (m, 6H) 1.73-1.93 (m, 2H) 2.53 (s, 3H) 3.79-3.86 (m, 2H) 4.16 (s, 3H) 4.36-4.46 (m, 1H) 4.49-4.64 (m, 2H) 4.65-4.69 (m, 2H) 4.81 (s, 2H) 4.89-4.94 (m, 1H) 7.42 (s, 2H) 7.66-7.69 (m, 1H) 7.70-7.74 (m, 1H) 7.85-7.94 (m, 1H) 8.10-8.22 (m, 1H) 8.36-8.47 (m, 1H).

The compounds in Table 20 were prepared by a method similar to the one described for the preparation of (R)-3-(3-(((R)-2-ethyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)methoxy)propanoic acid. As is appreciated by those skilled in the art, these analogous examples may involve variations in general reaction conditions.

TABLE 20

| Ex # | Structure | Name | LCMS [M + 1] | Retention Time (min) | 1H NMR |
|---|---|---|---|---|---|
| Ex 109 | 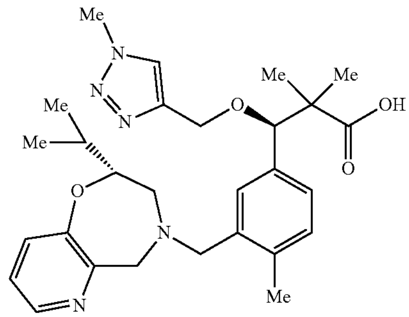 [SMILES: Cc1ccc([C@@H](OCc2cn(C)nn2)C(C)(C)C(=O)O)cc1CN1Cc2ncccc2O[C@H](C(C)C)C1] | (R)-3-(3-(((R)-2-isopropyl-2,3-dihydropyrido[2,3-f][1,4]-oxazepin-4(5H)-yl)methyl)-4-methylphenyl)-2,2-dimethyl-3-((1-methyl-1H-1,2,3-triazol-4-yl)methoxy) propanoic acid hydrochloride | 508.4 | 0.71 | $^1$H NMR (400 MHz, METHANOL-$d_4$) δ ppm 1.05 (s, 3 H) 1.12-1.18 (m, 9 H) 2.06-2.12 (m, 1 H) 2.56 (s, 3 H) 3.85-4.03 (m, 2 H) 4.20 (s, 3 H) 4.39-4.48 (m, 1 H) 4.51-4.66 (m, 2 H) 4.74 (d, J = 11.04 Hz, 2 H) 4.82 (s, 2 H) 4.90-4.96 (m, 1 H) 7.40-7.46 (m, 2 H) 7.74 (s, 1 H) 7.77-7.82 (m, 1 H) 7.96-8.04 (m, 1 H) 8.30 (s, 1 H) 8.43-8.51 (m, 1 H) |

Example 110

(R)-3-(3-(((R)-2-Ethyl-7-methyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)methoxy)propanoic Acid Trifluoroacetate

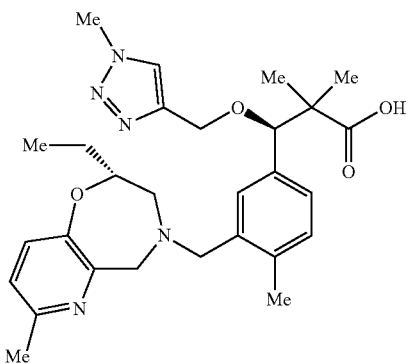 [SMILES: CC[C@@H]1CN(Cc2cc([C@@H](OCc3cn(C)nn3)C(C)(C)C(=O)O)ccc2C)Cc2nc(C)ccc2O1]

(R)-1-(((6-Chloro-3-fluoropyridin-2-yl)methyl)amino)butan-2-ol

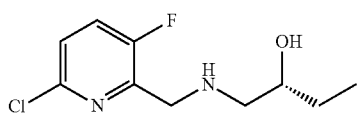

To a solution of 6-chloro-3-fluoropicolinaldehyde (5 g, 31.3 mmol) in methanol (50 mL) was added under an atmosphere of nitrogen to a mixture of (R)-1-aminobutan-2-ol (3.35 g, 37.6 mmol) and sodium hydroxide (10 mL, 31.3 mmol). The resulting reaction mixture was stirred at ambient temperature for 16 h. Following this duration, the reaction contents were cooled to 0° C. and NaBH$_4$ (1.423 g, 37.6 mmol) was added in equal portions over 5 min. The reaction mixture was then warmed to ambient temperature and stirred for 2 h. Following this duration, the reaction mixture was concentrated and purified by silica gel chromatography (0-50% EtOAc:Petroleum ether) to give the title compound as a colorless liquid (2 g, 6.5 mmol, 21% yield). LC-MS m/z 233.0 (M+H)$^+$, 2.8 min (ret. time).

(R)-tert-Butyl 7-chloro-2-ethyl-2,3-dihydropyrido[2,3-f][1,4]oxazepine-4(5H)-carboxylate To a solution of (R)-1-(((6-chloro-3-fluoropyridin-2-yl)methyl)amino)butan-2-ol (2 g, 8.60 mmol) in dimethyl sulfoxide (DMSO) (20 mL) under an atmosphere of N2 was added potassium tert-butoxide (1.447 g, 12.89 mmol) at ambient temperature. The resulting reaction mixture was then heated to 90° C. and stirred for 2 h. Following this duration, the reaction contents were cooled to 0° C. and Boc-anhydride (2.395 mL, 10.31 mmol) and TEA (1.438 mL, 10.31 mmol) were added sequentially. The resulting reaction mixture was warmed to ambient temperature and stirred for 2 h. Following this duration, the reaction contents were poured into ice cold water (50 mL) and extracted with EtOAc (2×50 mL). The organic layer was separated, dried over Na$_2$SO$_4$ and concentrated to obtain a yellow oil. Purification by silica gel chromatography (0-15% EtOAc:Petroleum ether) afforded the title compound as a yellow solid (1.0 g, 2.88 mmol, 34% yield). LC-MS m/z 313.0 (M+H)$^+$, 3.9 min (ret. time).

tert-Butyl (R)-2-ethyl-7-methyl-2,3-dihydropyrido[2,3-f][1,4]oxazepine-4(5H)-carboxylate

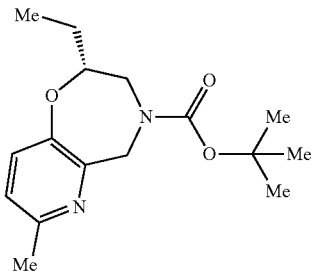 [SMILES: CC[C@@H]1CN(C(=O)OC(C)(C)C)Cc2nc(C)ccc2O1]

Anhydrous 1,4-dioxane (9831 µL) was added to a mixture of tert-butyl (R)-7-chloro-2-ethyl-2,3-dihydropyrido[2,3-f][1,4]oxazepine-4(5H)-carboxylate (492 mg, 1.573 mmol), 2,4,6-trimethyl-1,3,5,2,4,6-trioxatriborinane (592 mg, 4.72 mmol), PdCl$_2$(dppf) (57.5 mg, 0.079 mmol), and potassium carbonate (652 mg, 4.72 mmol) under an atmosphere of argon. The resulting reaction mixture was heated in a microwave reactor at 120° C. for 30 min. Following this duration, the reaction contents were filtered. The filtrate was diluted with water and extracted twice with EtOAc. The organic layer was separated, dried over sodium sulfate, filtered, and concentrated. The crude material was purified by silica gel chromatography (40 g column, 0-60% EtOAc:Hexanes) to afford the title compound as a yellow oil (460 mg, 1.09 mmol, 70% yield). LC-MS m/z 293.1 (M+H)$^+$, 0.71 min (ret. time). $^1$H NMR (CHLOROFORM-d) δ ppm 7.20 (d, 1H), 6.98 (d, 1H), 4.79 (d, 1H), 4.50 (m, 1H), 3.65-4.06 (m, 2H), 3.38 (br. s., 1H), 2.42-2.55 (s, 3H), 1.52-1.77 (m, 3H), 1.40 (br. s., 9H), 1.11 (t, 3H).

(R)-2-Ethyl-7-methyl-2,3,4,5-tetrahydropyrido[2,3-f][1,4]oxazepine Hydrochloride

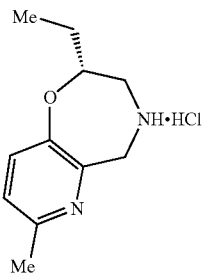

A solution of 4 N HCl in 1,4-dioxane (4370 µl) was added to tert-butyl (R)-2-ethyl-7-methyl-2,3-dihydropyrido[2,3-f][1,4]oxazepine-4(5H)-carboxylate (319.4 mg, 1.092 mmol) and stirred at ambient temperature. After 1 h, the reaction contents were concentrated by heating at 50° C. under a nitrogen stream for 18 h, providing the title compound as a white solid (281.7 mg, 1.23 mmol, 113% yield) which was carried forward without further purification. LC-MS m/z 194.1 (M+H)$^+$, 0.35 min (ret. time). $^1$H NMR (400 MHz, METHANOL-d4) δ ppm 7.88 (d, 1H), 7.63 (d, 1H), 4.71 (d, 2H), 4.15-4.29 (m, 1H), 3.64-3.82 (m, 1H), 3.45-3.62 (m, 1H), 2.68 (s, 3H), 1.70-1.93 (m, 2H), 1.18 (m, 3H).

(R)-Methyl-3-(3-(hydroxymethyl)-4-methylphenyl)-2,2-dimethyl-3-(0-methyl-1H-1,2,3-triazol-4-yl)methoxy)propanoate

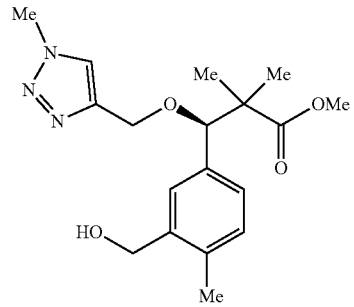 [SMILES: COC(=O)C(C)(C)[C@H](OCc1cn(C)nn1)c1ccc(C)c(CO)c1]

To a solution of methyl 3-(3-(hydroxymethyl)-4-methylphenyl)-2,2-dimethyl-3-(prop-2-yn-1-yloxy)propanoate (950 mg, 3.27 mmol) in tert-butanol (13 ml) and water (13 ml) was added sodium azide (425 mg, 6.54 mmol), copper(I) iodide (125 mg, 0.654 mmol), DIPEA (114 µl, 0.654 mmol) and iodomethane (1018 µl, 16.36 mmol). The resulting reaction mixture was heated to 70° C. After 45 min, the reaction contents were cooled to ambient temperature and partitioned with 100 mL EtOAc and 50 mL saturated aqueous NaHCO$_3$. The resulting layers were separated and the aqueous layer was extracted with 3×15 mL EtOAc. The combined organics were dried over Na$_2$SO$_4$, filtered and concentrated to give a dark orange oil. Purification by silica gel chromatography (40 g column, 0-90% EtOAc:Hexanes) afforded an orange semi-solid (1.1 g, 3.3 mmol). The racemic mixture was subsequently separated by chiral SFC (Chiralpak IG 20×250 mm, 5u column, 25% EtOH co-solvent) to afford the title compound as an orange semi-solid (445.5 mg, 1.3 mmol, 39% yield). LC-MS m/z 348.1 (M+H)$^+$, 0.78 min (ret. time).

(R)-Methyl-3-(3-(chloromethyl)-4-methylphenyl)-2,2-dimethyl-3-(0-methyl-1H-1,2,3-triazol-4-yl)methoxy)propanoate

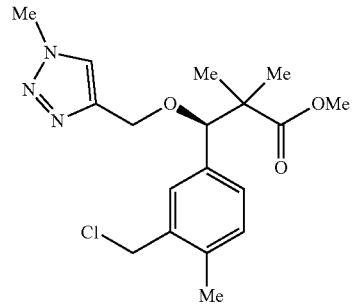 [SMILES: COC(=O)C(C)(C)[C@H](OCc1cn(C)nn1)c1ccc(C)c(CCl)c1]

To a solution of (R)-methyl-3-(3-(hydroxymethyl)-4-methylphenyl)-2,2-dimethyl-3-((1-methyl-1H-1,2,3-triazol-4-yl)methoxy)propanoate (56.0 mg, 0.161 mmol) in dichloromethane (DCM) (806 µl) was added thionyl chloride (23.53 µl, 0.322 mmol), giving a clear, orange solution. After 10 min at ambient temperature, the reaction mixture was concentrated to give the title compound as an orange oil, which was carried forward without further purification.

(R)-Methyl-3-(3-(((R)-2-ethyl-7-methyl-2,3-dihydropyrido[2,3-f][1,4]oxazepin-4(5H)-yl)methyl)-4-methylphenyl)-2,2-dimethyl-3-(0-methyl-1H-1,2,3-triazol-4-yl)methoxy)propanoate

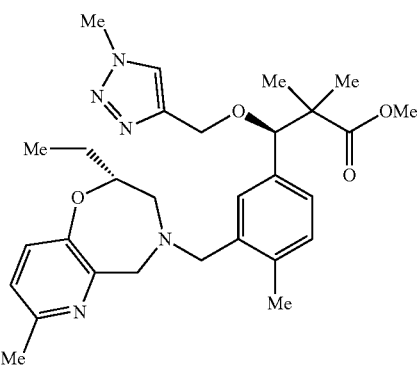 [SMILES: CC[C@@H]1CN(Cc2cc([C@@H](OCc3cn(C)nn3)C(C)(C)C(=O)OC)ccc2C)Cc2nc(C)ccc2O1]

To a solution of (R)-methyl-3-(3-(chloromethyl)-4-methylphenyl)-2,2-dimethyl-3-((1-methyl-1H-1,2,3-triazol-4-yl)methoxy)propanoate (59 mg, 0.161 mmol) and (R)-2-ethyl-7-methyl-2,3,4,5-tetrahydropyrido[2,3-f][1,4]oxazepine-hydrochloride (36.9 mg, 0.161 mmol) in acetonitrile (605 μl) and tetrahydrofuran (THF) (202 μl) was added $K_2CO_3$ (66.9 mg, 0.484 mmol) and sodium iodide (12.09 mg, 0.081 mmol). The resulting reaction mixture was warmed to 80° C. After 45 min, the reaction contents were cooled to ambient temperature and partitioned with 10 mL EtOAc, 10 mL saturated aqueous $NH_4Cl$ and 5 mL water. The layers were separated and the aqueous layer was extracted with 3×10 mL EtOAc. The combined organics were dried over $Na_2SO_4$, filtered and concentrated to give a yellow oil. Purification by silica gel chromatography (12 g column, 0-80% EtOAc: Hexanes) afforded the title compound as an orange oil (54.4 mg, 0.10 mmol, 65% yield). LC-MS m/z 522.3 $(M+H)^+$, 0.79 min (ret. time).

(R)-3-(3-(((R)-2-Ethyl-7-methyl-2,3-dihydropyrido [2,3-f][1,4]oxazepin-4(5H)-yl)methyl)-4-methylphenyl)-2,2-dimethyl-3-((1-methyl-1H-1,2,3-triazol-4-yl)methoxy)propanoic Acid Trifluoroacetate

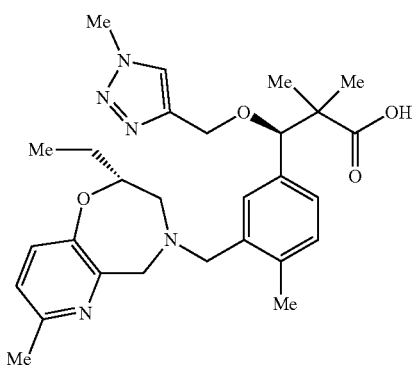 [SMILES: CC[C@@H]1CN(Cc2cc([C@@H](OCc3cn(C)nn3)C(C)(C)C(=O)O)ccc2C)Cc2nc(C)ccc2O1]

To a solution of (R)-methyl-3-(3-(((R)-2-ethyl-7-methyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)methoxy)propanoate (54.4 mg, 0.104 mmol) in methanol (1043 μl) was added a 1 M solution of aqueous NaOH (1043 μl, 1.043 mmol). The resulting reaction mixture was warmed to 100° C. After 45 min, the reaction contents were cooled to ambient temperature and purified directly by reverse-phase HPLC (10-80% $CH_3CN$+0.1% TFA:$H_2O$+0.1% TFA) to afford the trifluoroacetic acid salt of the title compound as a white solid (51.4 mg, 0.08 mmol, 79% yield). LC-MS m/z 508.3 $(M+H)^+$, 0.69 min (ret. time). $^1$H NMR (400 MHz, METHANOL-$d_4$) δ ppm 1.05 (s, 3H) 1.12-1.20 (m, 6H) 1.60-1.76 (m, 1H) 1.77-1.88 (m, 1H) 2.48 (d, J=5.77 Hz, 6H) 3.62-3.70 (m, 2H) 4.08 (s, 3H) 4.11-4.17 (m, 1H) 4.40-4.59 (m, 5H) 4.62-4.71 (m, 1H) 4.78 (s, 1H) 7.38 (s, 3H) 7.55 (s, 1H) 7.57-7.63 (m, 1H) 7.89 (s, 1H).

1-(((3-Fluoropyridin-2-yl)methyl)amino)-3-methylbutan-2-ol

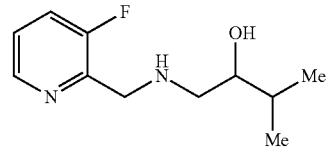 [SMILES: CC(C)C(O)CNCc1ncccc1F]

To a solution of 3-fluoropicolinaldehyde (18 g, 144 mmol) in methanol (200 mL) was added 1-amino-3-methylbutan-2-ol (15.96 g, 155 mmol) and a solution of 1M aqueous sodium hydroxide (28.8 mL, 28.8 mmol). The resulting reaction mixture was stirred under an atmosphere of nitrogen for 16 hr at ambient temperature. Following this duration, sodium borohydride (6.53 g, 173 mmol) was added in equal portions over 15 min and the resulting reaction mixture was stirred at ambient temperature for 4 h. Following this duration, the methanol solvent was evaporated and the resulting mixture was diluted with water (100 ml) and extracted with 10% MeOH in DCM (3×150 ml). The combined organic layers were washed with saturated aqueous sodium chloride (1000 mL), dried over $Na_2SO_4$, filtered and concentrated under reduced pressure. Purification by silica gel chromatography (95% EtOAc in petroleum ether) provided the title compound as a yellow gum (16 g, 44.1 mmol, 30.6% yield). LC-MS m/z 213.1 $(M+H)^+$, 0.98 min (ret. time).

(R)-tert-Butyl 2-isopropyl-2,3-dihydropyrido[2,3-f][1,4]oxazepine-4(5H)-carboxylate

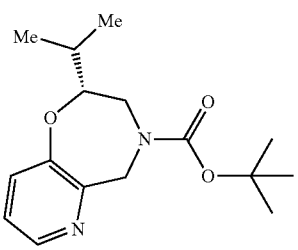 [SMILES: CC(C)[C@@H]1CN(C(=O)OC(C)(C)C)Cc2ncccc2O1]

To a stirred solution of 1-(((3-fluoropyridin-2-yl)methyl)amino)-3-methylbutan-2-ol (16 g, 75 mmol) in dimethyl sulfoxide (DMSO) (150 mL) was added potassium tert-butoxide (10.15 g, 90 mmol) in one portion at ambient temperature. The resulting reaction mixture was warmed to 90° C. and stirred for 2 h. Following this duration, the reaction mixture was cooled back to ambient temperature and triethylamine (11.44 g, 113 mmol) and di-tert-butyldicarbonate (19.74 g, 90 mmol) were added sequentially. The resulting mixture was then allowed to stir for 16 h at ambient temperature. Following this duration, it was diluted with ice water (750 mL) and extracted with diethyl ether (2×500 mL). The combined organic layers were washed with saturated aqueous NaCl (250 mL), dried over $Na_2SO_4$, filtered and concentrated under reduced pressure to get provide a thick, orange oil. Purification by silica gel chromatography (10% EtOAc in petroleum ether) provided racemic tert-butyl 2-isopropyl-2,3-dihydropyrido[2,3-f][1,4]oxazepine-4(5H)-carboxylate as an off-white gum (4.4 g, 14.3 mmol, 18.9% yield). Subsequent chiral SFC chromatography (Chiralpak IE (30×250 mm, 5 u) column, 90:10 Hexane:IPA) afforded the title compound as a white solid (2.1 g, 6.48 mmol). LC-MS m/z 293.1 (M+H)$^+$, 2.86 min (ret. time).

(R)-2-Isopropyl-2,3,4,5-tetrahydropyrido[2,3-f][1,4]oxazepine Hydrochloride

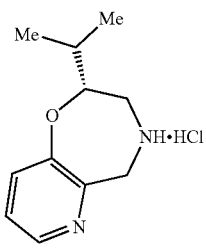

To a solution of (R)-tert-butyl 2-isopropyl-2,3-dihydropyrido[2,3-f][1,4]oxazepine-4(5H)-carboxylate (2.1 g, 7.18 mmol) in 1,4-dioxane (20 mL) at 0° C. was added a solution of 4M hydrochloric acid in 1,4-dioxane (8.98 mL, 35.9 mmol) dropwise over 5 min under an atmosphere of nitrogen. The resulting reaction mixture was stirred at ambient temperature for 3 hr. Following this duration, the reaction mixture was concentrated under reduced pressure. The resulting crude material was triturated with diethyl ether (20 ml), and the resulting solid was isolated and dried to afford the title compound as an off-white solid (1.8 g, 6.9 mmol, 96% yield). LC-MS m/z 193.2 (M+H)$^+$, 1.99 min (ret. time).

3-(Bromomethyl)picolinonitrile

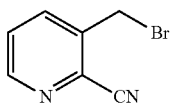

To a 500 mL single-neck round bottom flash fitted with a reflux condenser and a nitrogen outlet was added 10.1 g (86 mmol) 3-methylpicolinonitrile, 200 mL dimethyl carbonate, 18.2 g (103 mmol) N-bromosuccinimide and 2.1 g (8.5 mmol) benzoyl peroxide. The resulting reaction mixture was heated to 87° C. and stirred for 5 h. Following this duration, the reaction mixture was cooled to ambient temperature and filtered, and the solid was rinsed with $Et_2O$. DCM was subsequently added to the filtrate and the resulting mixture was filtered. The combined organics were concentrated and the resulting semi-solid was purified by silica gel chromatography (2×330 g column, 5-35% EtOAc/Hexane) followed by reverse-phase HPLC (Waters Xbridge Prep C18 10 μm OBD, 50×250 mm column) to afford the title compound as a yellow solid (6.3 g, 32.0 mmol, 37% yield). LC-MS m/z 196.8 (M+H)$^+$, 0.60 min (ret. time).

Ethyl 2-((2-cyanopyridin-3-yl)methyl)butanoate

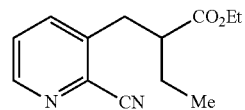

A 1000 mL 3-neck round bottom flash fitted with a 125 mL addition funnel and a temperature probe was flushed with nitrogen and dried using a heat gun. LDA (2M in THF/heptane/ethylbenzene, 18.3 mL, 36.6 mmol) and 46 mL THF were added followed by cooling with a dry ice/acetone bath. Ethyl butyrate (3.5 g, 30.5 mmol) dissolved in 46 mL THF was added over 24 min via the addition funnel while maintaining the internal temperature below −70.9° C. The reaction mixture was stirred for 45 min. Following this duration, 3-(bromomethyl)picolinonitrile (6.0 g, 30.5 mmol) dissolved in 80 mL THF was added to the enolate over 25 min while keeping the internal temperature below −70.8° C. The addition funnel was rinsed with 6 mL THF. After 1 h, the reaction mixture was quenched with 2.6 mL AcOH in 11 mL THF (internal temperature was maintained below −67.4° C.) and then warmed to 0° C. Saturated aqueous $NH_4Cl$ (177 mL) was added (temperature was maintained below 8.4° C.) followed by EtOAc (177 mL). The reaction mixture was warmed to ambient temperature and water was added to dissolve the solids present in the aqueous layer. The layers were separated and the aqueous layer was washed with 70 mL EtOAc. The combined organic layers were washed with saturated aqueous NaCl, dried over $Na_2SO_4$, filtered, and concentrated. Purification by silica gel chromatography (330 g column, 5-70% EtOAc/Hex) afforded the title compound as a pale-yellow oil (5.0 g, 21.5 mmol, 70% yield). LC-MS m/z 233.1 (M+H)$^+$, 0.88 min (ret. time).

2-((2-(Aminomethyl)pyridin-3-yl)methyl)butan-1-ol

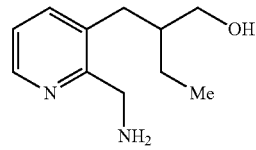 [SMILES: CCC(CO)Cc1cccnc1CN]

A 1 L round bottom flask fitted with an addition funnel and a temperature probe was dried by flushing with nitrogen and heating with a heat gun. THF (160 mL) and LAH (33 mL, 64.4 mmol, 2M in THF) were added followed by cooling with an ice (aq) bath. Ethyl 2-((2-cyanopyridin-3-yl)methyl)butanoate (5.0 g, 21.5 mmol) was dissolved in 160 mL THF and added via an addition funnel over 49 min while maintaining the internal temperature below 5.2° C. The brown reaction mixture was warmed to ambient temperature and stirred for 90 min. The reaction mixture was cooled with an ice (aq) bath and slowly quenched with 11 mL saturated aqueous Na$_2$SO$_4$ while keeping the internal temperature below 15° C. The resulting yellow reaction mixture was warmed to ambient temperature and filtered, and the aqueous layer was washed with 3× EtOAc. The organic layer was concentrated to give the title compound as a yellow oil (3.96 g), which was used without further purification. LC-MS m/z 195.2 (M+H)$^+$, 0.28 min (ret. time).

tert-Butyl ((3-(2-(hydroxymethyl)butyl)pyridin-2-yl)methyl)carbamate

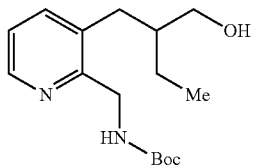 [SMILES: CCC(CO)Cc1cccnc1CNC(=O)OC(C)(C)C]

To a 500 mL round bottom flask containing 3.96 g (20.4 mmol) of 2-((2-(aminomethyl)pyridin-3-yl)methyl)butan-1-ol was added 160 mL DCM and 2.89 g (20.4 mmol) BOC$_2$O. After stirring for 4 h at ambient temperature, the reaction mixture was concentrated and the resulting crude yellow oil was purified using silica gel chromatography (330 g column, 20-90% EtOAc/Hex) to give the title compound as a clear yellow oil (3.2 g, 11.0 mmol, 54% yield). LC-MS m/z 295.2 (M+H)$^+$, 0.47 min (ret. time).

2-((2-(((tert-Butoxycarbonyl)amino)methyl)pyridin-3-yl)methyl)butyl Methanesulfonate

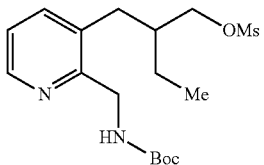 [SMILES: CCC(COS(C)(=O)=O)Cc1cccnc1CNC(=O)OC(C)(C)C]

To a 500 mL (3) neck round bottom flask fitted with a temperature probe was added 3.24 g (11.0 mmol) tert-butyl ((3-(2-(hydroxymethyl)butyl)pyridin-2-yl)methyl)carbamate dissolved in 160 mL DCM and 2.3 mL (16.5 mmol) TEA. The reaction mixture was cooled with an ice(aq) bath followed by the addition of MsCl (1.1 mL, 14.3 mmol) over 7 min. The temperature was held between 3.8 and 6.9° C. during the MsCl addition. The resulting reaction mixture was warmed to ambient temperature and stirred for 1 h. The reaction mixture was concentrated in vacuo (water bath temperature was kept below 26° C.) and the crude material was purified using silica gel chromatography (330 g column, 30-90% EtOAc/Hex) to afford the title compound as a colorless oil (4.05 g, 10.9 mmol, 99% yield). LC-MS m/z 373.2 (M+H)$^+$, 0.58 min (ret. time).

(S)-tert-Butyl 6-ethyl-5,6,7,9-tetrahydro-8H-pyrido[2,3-c]azepine-8-carboxylate

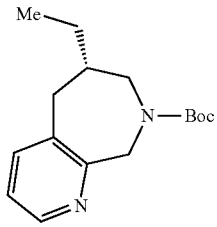 [SMILES: CC[C@H]1Cc2cccnc2CN(C(=O)OC(C)(C)C)C1]

To a 250 mL 3-neck round bottom flask fitted with a temperature probe was added 2.5 g of KOtBu and 36 mL DMF. The reaction mixture was cooled with an ice (aq) bath. 2-((2-(((tert-Butoxycarbonyl)amino)methyl)pyridin-3-yl)methyl)butyl methanesulfonate (4.05 g) in 46 mL of DMF was added dropwise over 20 min (internal temperature: 2.1-5.8° C.), followed by an 11 mL DMF flask rinse. The reaction mixture was subsequently warmed to ambient temperature. After 1 h, the reaction mixture was transferred to a 1 L 3-neck round bottom flask fitted with a temperature probe and then cooled with an ice(aq) bath. Water (210 mL) and EtOAc (210 mL) were added slowly while keeping the temperature below 21° C. The reaction mixture was then warmed to ambient temperature and the layers were separated. The aqueous layer was extracted with 70 mL EtOAc. The combined organic layers were washed with water (70 mL), brine (159 mL), dried over Na$_2$SO$_4$, filtered and concentrated. Purification by silica gel chromatography (330 g column, 10%-90% EtOAc/Hex) afforded racemic tert-butyl 6-ethyl-5,6,7,9-tetrahydro-8H-pyrido[2,3-c]azepine-8-carboxylate (3.0 g, 11 mmol, 100% yield). Chiral SFC (Chiralpak IF, 20×250 mm, 5u column) provided the title compound as a thick, pale yellow oil (1.2 g, 4.4 mmol). LC-MS m/z 277.2 (M+H)$^+$, 0.61 min (ret. time).

(S)-6-Ethyl-6,7,8,9-tetrahydro-5H-pyrido[2,3-c]azepine Hydrochloride

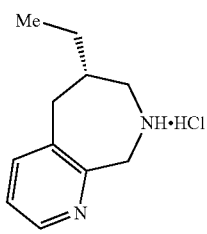

To a solution of tert-butyl (S)-6-ethyl-5,6,7,9-tetrahydro-8H-pyrido[2,3-c]azepine-8-carboxylate (875 mg, 3.17 mmol) in diethyl ether (10 mL), with a minimum amount of DCM for solubility, was added hydrochloric acid (4N in dioxane) (30 mL, 120 mmol) and the reaction mixture was stirred at ambient temperature for 2 h. The reaction mixture was diluted with Et$_2$O, the solid filtered, washed with Et$_2$O and dried under vacuo to afford the title compound as a light yellow solid (503.9 g, 2.4 mmol, 75% yield). LC-MS m/z 177.0 (M+H)+, 0.24 min (ret. time).

The compounds in Table 21 were prepared by a method similar to the one described for the preparation of (R)-3-(3-(((R)-2-ethyl-7-methyl-2,3-dihydropyrido[2,3-f][1,4]oxazepin-4(51-1)-yl)methyl)-4-methylphenyl)-2,2-dimethyl-3-((1-methyl-1H-1,2,3-triazol-4-yl)methoxy)propanoic acid. As is appreciated by those skilled in the art, these analogous examples may involve variations in general reaction conditions.

TABLE 21

| Ex # | Structure | Name | LCMS [M + 1] | Retention Time (min) | 1H NMR |
|---|---|---|---|---|---|
| Ex 111 | 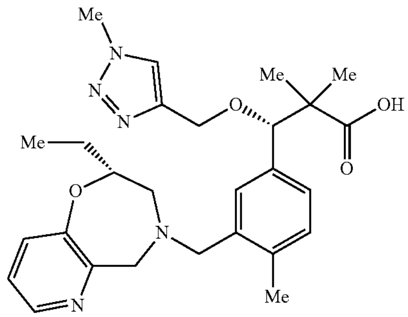 [SMILES: CC[C@@H]1CN(Cc2cc([C@H](OCc3cn(C)nn3)C(C)(C)C(=O)O)ccc2C)Cc2ncccc2O1] | (S)-methyl 3-(3-(((R)-2-ethyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)-methoxy)-propanoic acid, trifluoroacetate | 494.4 | 0.67 | $^1$H NMR (400 MHz, METHANOL-$d_4$) δ ppm 1.05 (s, 3 H) 1.13 (s, 3 H) 1.20 (t, J = 7.40 Hz, 3 H) 1.71-1.81 (m, 1 H) 1.82-1.92 (m, 1 H) 2.50 (s, 3 H) 3.67-3.84 (m, 2 H) 4.05 (s, 3 H) 4.24-4.36 (m, 1 H) 4.45 (d, J = 12.30 Hz, 2 H) 4.58 (br. s., 3 H) 4.72 (s, 1 H) 4.81 (s, 1 H) 7.39 (s, 2 H) 7.43-7.48 (m, 1 H) 7.58-7.66 (m, 2 H) 7.87 (s, 1 H) 8.17-8.26 (m, 1 H) |
| Ex 112 | 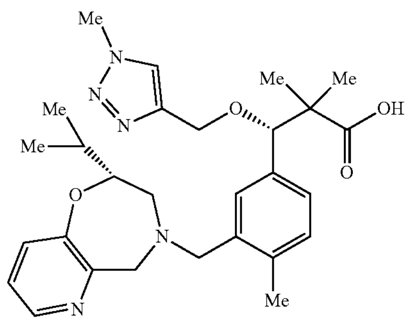 [SMILES: Cc1ccc([C@H](OCc2cn(C)nn2)C(C)(C)C(=O)O)cc1CN1Cc2ncccc2O[C@H](C(C)C)C1] | (S)-3-(3-(((R)-2-isopropyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)-methoxy)propanoic acid, trifluoroacetate | 508.3 | 0.72 | $^1$H NMR (400 MHz, METHANOL-$d_4$) δ ppm 1.05 (s, 3 H) 1.12 (s, 3 H) 1.15-1.20 (m, 6 H) 1.99-2.14 (m, 1 H) 2.51 (s, 3 H) 3.86 (d, J = 6.02 Hz, 2 H) 4.05 (s, 3 H) 4.25 (d, J = 5.52 Hz, 1 H) 4.44 (q, J = 11.80 Hz, 2 H) 4.51-4.57 (m, 1 H) 4.61 (br. s., 2 H) 4.72 (d, J = 14.31 Hz, 1 H) 4.81 (s, 1 H) 7.40 (s, 2 H) 7.43 (dd, J = 8.16, 4.89 Hz, 1 H) 7.58-7.66 (m, 2 H) 7.86 (s, 1 H) 8.19 (d, J = 4.27 Hz, 1 H) |

Example 113

(R)-3-((1-Ethyl-1H-1,2,3-triazol-4-yl)methoxy)-3-(3-(((R)-2-ethyl-2,3-dihydropyrido[2,3-f][1,4]oxazepin-4(5H)-yl)methyl)-4-methylphenyl)-2,2-dimethylpropanoic Acid, Trifluoroacetate

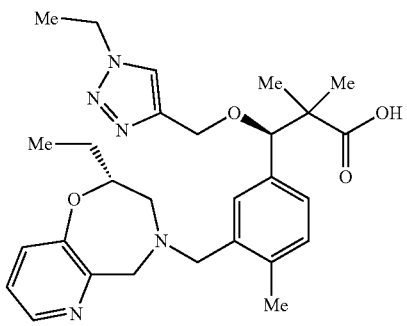 [SMILES: CC[C@@H]1CN(Cc2cc([C@@H](OCc3cn(CC)nn3)C(C)(C)C(=O)O)ccc2C)Cc2ncccc2O1]

Methyl 3-(3-(chloromethyl-4-methylphenyl)-2,2-dimethyl-3-(prop-2-yn-1-yloxy)propanoate

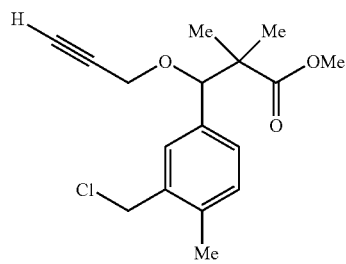 [SMILES: C#CCOC(c1ccc(C)c(CCl)c1)C(C)(C)C(=O)OC]

To a solution of methyl 3-(3-(hydroxymethyl)-4-methylphenyl)-2,2-dimethyl-3-(prop-2-yn-1-yloxy)-propanoate (556 mg, 1.915 mmol) in dichloromethane (DCM) (9574 μl) was added thionyl chloride (279 μl, 3.83 mmol), giving a clear orange solution. After 10 min at ambient temperature, concentrated the reaction contents to give an orange oil (630.7 mg), which was carried forward without further purification. LC-MS m/z 331.0 (M+Na)$^+$, 1.23 min (ret. time). $^1$H NMR (400 MHz, CHLOROFORM-d) δ ppm 1.06 (s, 3H) 1.19 (s, 3H) 2.39 (s, 1H) 2.45 (s, 3H) 3.73 (s, 3H) 3.86 (d, J=15.81 Hz, 1H) 4.16 (d, J=15.81 Hz, 1H) 4.63 (s, 2H) 4.85 (s, 1H) 7.19 (s, 1H) 7.24 (s, 1H) 7.29 (s, 1H).

Methyl-3-(3-(((R)-2-ethyl-2,3-dihydropyrido[2,3-f]
[1,4]oxazepin-4(5H)-yl)methyl)-4-methylphenyl)-2,
2-dimethyl-3-(prop-2-yn-1-yloxy)propanoate

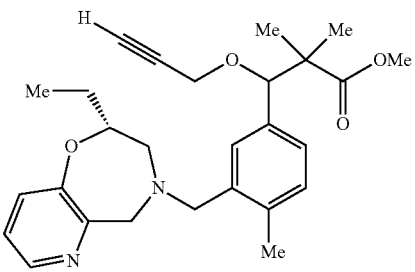 [SMILES: C#CCOC(c1ccc(C)c(CN2Cc3ncccc3O[C@H](CC)C2)c1)C(C)(C)C(=O)OC]

To a solution of methyl 3-(3-(chloromethyl)-4-methylphenyl)-2,2-dimethyl-3-(prop-2-yn-1-yloxy)propanoate (212.5 mg, 0.688 mmol) and (R)-2-ethyl-2,3,4,5-tetrahydropyrido[2,3-f][1,4]oxazepine-hydrochloride (148 mg, 0.688 mmol) in acetonitrile (2581 µl) and tetrahydrofuran (THF) (860 µl) was added $K_2CO_3$ (285 mg, 2.064 mmol) and sodium iodide (51.6 mg, 0.344 mmol). The resulting reaction mixture was heated to 80° C. After 45 min, the reaction contents were cooled to ambient temperature and partitioned with 50 mL EtOAc, 50 mL saturated aqueous $NH_4Cl$ and 10 mL water. The resulting layers were separated and the aqueous layer was extracted with 3×10 mL EtOAc. The combined organics over dried over $Na_2SO_4$, filtered and concentrated to give a yellow oil. Purification by silica gel chromatography (24 g column, 0-50% EtOAc:Hexanes) afforded the title compound as a thick, clear, colorless oil (287.3 mg, 0.64 mmol, 93% yield). LC-MS m/z 451.2 (M+H)+, 0.87 min (ret. time). ¹H NMR (400 MHz, CHLOROFORM-d) δ ppm 0.98-1.09 (m, 6H) 1.15 (d, J=4.77 Hz, 3H) 1.39-1.50 (m, 1H) 1.59 (s, 3H) 1.62-1.74 (m, 1H) 2.36-2.39 (m, 1H) 2.78-2.97 (m, 2H) 3.60-3.71 (m, 2H) 3.72 (s, 3H) 3.86 (br. s., 2H) 4.04-4.10 (m, 1H) 4.13-4.20 (m, 2H) 4.83 (d, J=4.27 Hz, 1H) 7.04-7.11 (m, 1H) 7.12-7.20 (m, 3H) 7.34 (d, J=7.78 Hz, 1H) 8.24 (d, J=3.76 Hz, 1H).

(R)-Methyl-3-((1-ethyl-1H-1,2,3-triazol-4-yl)
methoxy)-3-(3-(((R)-2-ethyl-2,3-dihydropyrido-[2,3-
f][1,4]oxazepin-4(5H)-yl)methyl)-4-methylphenyl)-
2,2-dimethylpropanoate

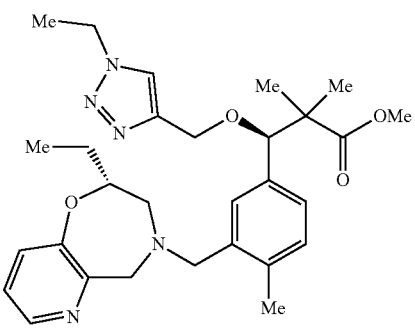 [SMILES: CC[C@@H]1CN(Cc2cc([C@@H](OCc3cn(CC)nn3)C(C)(C)C(=O)OC)ccc2C)Cc2ncccc2O1]

To a solution of methyl 3-(3-(((R)-2-ethyl-2,3-dihydropyrido[2,3-f][1,4]oxazepin-4(5H)-yl)methyl)-4-methylphenyl)-2,2-dimethyl-3-(prop-2-yn-1-yloxy)propanoate in tert-butanol (2349 µl) and water (2349 µl) was added sodium azide (79 mg, 1.212 mmol), copper(I) iodide (23.09 mg, 0.121 mmol), DIPEA (21.17 µl, 0.121 mmol), and ethyl iodide (98 µl, 1.212 mmol). The resulting reaction mixture was heated to 70° C. After 50 min, the reaction contents were cooled to ambient temperature and partitioned with 10 mL EtOAc and 10 mL saturated aqueous $NaHCO_3$. The resulting layers were separated and the aqueous layer was extracted with 3×5 mL EtOAc. The combined organics were dried over $Na_2SO_4$, filtered and concentrated to give a dark green oil. Purification by silica gel chromatography (24 g column, 0-90% EtOAc:Hexanes) afforded a thick, pale yellow oil (223.2 mg). The diastereomeric mixture was separated by chiral reverse-phase HPLC (Chiralpak AS 20×250 mm, 5u column, heptene+0.1% isopropylamine: EtOH+0.1% isopropylamine (80:20)) to give the title compound as a white solid (76.1 mg, 0.15 mmol, 24% yield). LC-MS m/z 522.3 (M+H)+, 0.78 min (ret. time). ¹H NMR (400 MHz, CHLOROFORM-d) δ ppm 1.01 (d, J=15.31 Hz, 3H) 1.03-1.08 (m, 3H) 1.12 (d, J=6.78 Hz, 3H) 1.40-1.49 (m, 1H) 1.55 (t, J=7.40 Hz, 3H) 1.67 (d, J=7.03 Hz, 1H) 2.35 (d, J=2.51 Hz, 3H) 2.80-2.99 (m, 2H) 3.60-3.67 (m, 4H) 3.68-3.73 (m, 1H) 3.80-3.90 (m, 1H) 4.03-4.17 (m, 2H) 4.39 (q, J=7.28 Hz, 3H) 4.57 (d, J=12.55 Hz, 1H) 4.71 (s, 1H) 7.09-7.21 (m, 4H) 7.34 (dt, J=7.91, 1.44 Hz, 1H) 7.49 (s, 1H) 8.18-8.28 (m, 1H).

(R)-3-(0-Ethyl-1H-1,2,3-triazol-4-yl)methoxy)-3-(3-
(((R)-2-ethyl-2,3-dihydropyrido[2,3-f][1,4]oxazepin-
4(5H)-yl)methyl)-4-methylphenyl)-2,2-dimethylpropanoic Acid, Trifluoroacetate

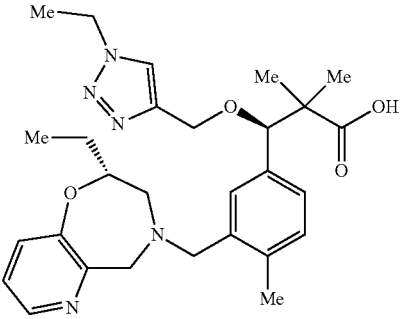 [SMILES: CC[C@@H]1CN(Cc2cc([C@@H](OCc3cn(CC)nn3)C(C)(C)C(=O)O)ccc2C)Cc2ncccc2O1]

To a solution of (R)-methyl-3-((1-ethyl-1H-1,2,3-triazol-4-yl)methoxy)-3-(3-(((R)-2-ethyl-2,3-dihydropyrido-[2,3-f][1,4]oxazepin-4(5H)-yl)methyl)-4-methylphenyl)-2,2-dimethylpropanoate (65.6 mg, 0.126 mmol) in methanol (1258 µl) was added a solution of 1 M aqueous NaOH (1258 µl, 1.258 mmol). The resulting reaction mixture was heated to 100° C. After 1 h, the reaction contents were cooled to ambient temperature and directly purified by reverse-phase HPLC (10-80% $CH_3CN$+0.1% TFA:$H_2O$+0.1% TFA) to give the trifluoroacetic acid salt of the title compound as a white solid (62.2 mg, 0.10 mmol, 80% yield). LC-MS m/z 508.3 (M+H)+, 0.70 min (ret. time). ¹H NMR (400 MHz, METHANOL-d₄) δ ppm 1.05 (s, 3H) 1.12-1.20 (m, 6H) 1.49 (t, J=7.28 Hz, 3H) 1.67-1.78 (m, 1H) 1.83 (s, 1H) 2.48 (s, 3H) 3.68-3.73 (m, 2H) 4.12-4.24 (m, 1H) 4.39 (q, J=7.45 Hz, 2H) 4.44-4.53 (m, 2H) 4.56 (br. s., 2H) 4.72 (d, J=18.32 Hz, 2H) 4.78 (s, 1H) 7.37 (s, 2H) 7.47-7.52 (m, 1H) 7.56 (s, 1H) 7.65 (d, J=8.03 Hz, 1H) 7.92 (s, 1H) 8.34 (d, J=4.52 Hz, 1H).

(R)-2-Ethyl-2,3,4,5-tetrahydrobenzo[f][1,4] oxazepine Hydrochloride

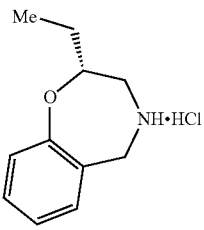

(R)-2-Ethyl-2,3,4,5-tetrahydrobenzo[f][1,4]oxazepine hydrochloride of the invention was made using compounds described in WO 2016/202253 on page 146, published Dec. 22, 2016, and incorporated herein by reference.

The compounds in Table 22 were prepared by a method similar to the one described for the preparation of (R)-3-((1-ethyl-1H-1,2,3-triazol-4-yl)methoxy)-3-(3-(((R)-2-ethyl-2,3-dihydropyrido[2,3-f][1,4]oxazepin-4(5H)-yl)methyl)-4-methylphenyl)-2,2-dimethylpropanoic acid. As is appreciated by those skilled in the art, these analogous examples may involve variations in general reaction conditions.

TABLE 22

| Ex # | Structure | Name | LCMS [M + 1] | Retention Time (min) | 1H NMR |
|---|---|---|---|---|---|
| Ex 114 | 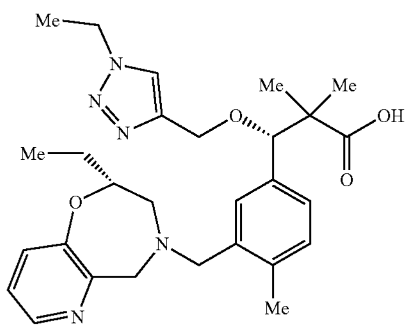 [SMILES: CC[C@@H]1CN(Cc2cc([C@H](OCc3cn(CC)nn3)C(C)(C)C(=O)O)ccc2C)Cc2ncccc2O1] | (S)-methyl 3-((1-ethyl-1H-1,2,3-triazol-4-yl)-methoxy)-3-(3-(((R)-2-ethyl-2,3-dihydropyrido[2,3-f][1,4]oxazepin-4(5H)-yl)methyl)-4-methylphenyl)-2,2-dimethylpropanoic acid, trifluoroacetate | 508.3 | 0.71 | $^1$H NMR (400 MHz, METHANOL-$d_4$) δ ppm 1.06 (s, 3 H) 1.13 (s, 3 H) 1.20 (s, 3 H) 1.49 (t, J = 7.40 Hz, 3 H) 1.71-1.81 (m, 1 H) 1.82-1.93 (m, 1 H) 2.49 (s, 3 H) 3.66-3.84 (m, 2 H) 4.38 (d, J = 7.28 Hz, 4 H) 4.46 (d, J = 2.76 Hz, 2 H) 4.54-4.60 (m, 2 H) 4.67-4.75 (m, 1 H) 4.81 (s, 1 H) 7.38 (s, 2 H) 7.41-7.48 (m, 1 H) 7.62 (s, 2 H) 7.91 (s, 1 H) 8.17-8.23 (m, 1 H) |
| Ex 115 | 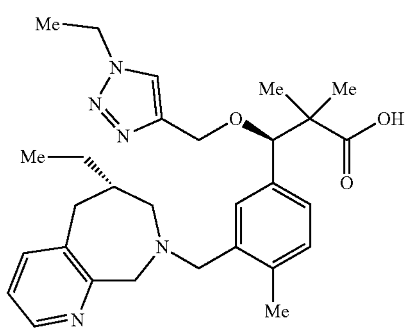 [SMILES: CC[C@H]1Cc2cccnc2CN(Cc2cc([C@@H](OCc3cn(CC)nn3)C(C)(C)C(=O)O)ccc2C)C1] | (R)-methyl 3-((1-ethyl-1H-1,2,3-triazol-4-yl)-methoxy)-3-(3-(((S)-6-ethyl-6,7-dihydro-5H-pyrido[2,3-c]azepin-8(9H)-yl)methyl)-4-methylphenyl)-2,2-dimethylpropanoic acid, trifluoroacetate | 506.3 | 0.65 | $^1$H NMR (400 MHz, METHANOL-$d_4$) δ ppm 0.98-1.08 (m, 7 H) 1.16 (s, 3 H) 1.50 (s, 5 H) 1.90-2.06 (m, 1 H) 2.39-2.51 (m, 3 H) 3.03-3.10 (m, 2 H) 3.46-3.53 (m, 1 H) 3.57-3.73 (m, 1 H) 4.32-4.43 (m, 2 H) 4.44-4.55 (m, 3 H) 4.57-4.65 (m, 1 H) 4.73-4.79 (m, 1 H) 7.37-7.40 (m, 2 H) 7.43-7.48 (m, 1 H) 7.52-7.57 (m, 1 H) 7.81-7.87 (m, 1 H) 7.91-7.94 (m, 1 H) 8.39-8.45 (m, 1 H) |
| Ex 116 | 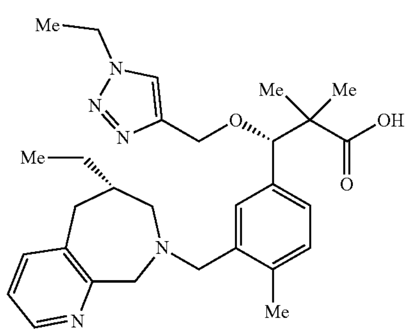 [SMILES: CC[C@H]1Cc2cccnc2CN(Cc2cc([C@H](OCc3cn(CC)nn3)C(C)(C)C(=O)O)ccc2C)C1] | (S)-methyl 3-((1-ethyl-1H-1,2,3-triazol-4-yl)-methoxy)-3-(3-(((S)-6-ethyl-6,7-dihydro-5H-pyrido[2,3-c]azepin-8(9H)-yl)methyl)-4-methylphenyl)-2,2-dimethylpropanoic acid, trifluoroacetate | 506.3 | 0.66 | $^1$H NMR (400 MHz, METHANOL-$d_4$) δ ppm 1.02-1.10 (m, 6 H) 1.13 (s, 3 H) 1.50 (t, J = 7.40 Hz, 5 H) 2.10-2.24 (m, 1 H) 2.49 (s, 3 H) 2.97-3.17 (m, 2 H) 3.46-3.52 (m, 1 H) 3.66-3.81 (m, 1 H) 4.29-4.59 (m, 7 H) 4.80 (s, 1 H) 7.39 (s, 3 H) 7.61 (s, 1 H) 7.74-7.83 (m, 1 H) 7.90 (s, 1 H) 8.21-8.32 (m, 1 H) |

TABLE 22-continued

| Ex # | Structure | Name | LCMS [M + 1] | Retention Time (min) | 1H NMR |
|---|---|---|---|---|---|
| Ex 117 | 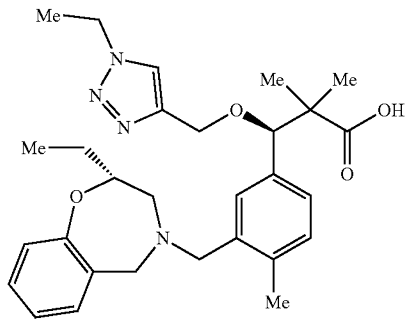 [SMILES: CC[C@@H]1CN(Cc2cc([C@@H](OCc3cn(CC)nn3)C(C)(C)C(=O)O)ccc2C)Cc2ccccc2O1] | (R)-methyl 3-((1-ethyl-1H-1,2,3-triazol-4-yl)-methoxy)-3-(3-(((R)-2-ethyl-2,3-dihydrobenzo[f][1,4]oxazepin-4(5H)-yl)methyl)-4-methylphenyl)-2,2-dimethylpropanoic acid, trifluoroacetate | 507.3 | 0.74 | $^1$H NMR (400 MHz, METHANOL-$d_4$) δ ppm 1.05 (s, 3 H) 1.11-1.21 (m, 6 H) 1.49 (s, 3 H) 1.66-1.74 (m, 1 H) 1.74-1.87 (m, 1 H) 2.37-2.52 (m, 3 H) 3.55-3.69 (m, 2 H) 4.32-4.42 (m, 2 H) 4.45-4.60 (m, 6 H) 4.65-4.74 (m, 1 H) 4.79 (s, 1 H) 7.14-7.21 (m, 2 H) 7.27-7.33 (m, 1 H) 7.36 (s, 2 H) 7.42-7.49 (m, 1 H) 7.54-7.59 (m, 1 H) 7.92 (s, 1 H) |
| Ex 118 | 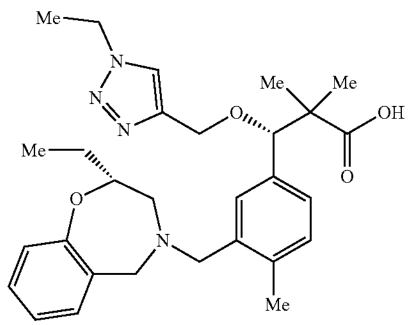 [SMILES: CC[C@@H]1CN(Cc2cc([C@H](OCc3cn(CC)nn3)C(C)(C)C(=O)O)ccc2C)Cc2ccccc2O1] | (S)-methyl 3-((1-ethyl-1H-1,2,3-triazol-4-yl)-methoxy)-3-(3-(((R)-2-ethyl-2,3-dihydrobenzo[f][1,4]oxazepin-4(5H)-yl)methyl)-4-methylphenyl)-2,2-dimethylpropanoic acid, trifluoroacetate | 507.3 | 0.74 | $^1$H NMR (400 MHz, METHANOL-$d_4$) δ ppm 1.05 (s, 3 H) 1.13 (s, 3 H) 1.19 (t, J = 7.40 Hz, 3 H) 1.50 (t, J = 7.40 Hz, 3 H) 1.66-1.76 (m, 1 H) 1.76-1.86 (m, 1 H) 2.47 (br. s., 3 H) 3.63-3.69 (m, 2 H) 4.03-4.21 (m, 1 H) 4.33-4.51 (m, 5 H) 4.69 (d, J = 13.80 Hz, 3 H) 4.81 (s, 1 H) 7.02-7.13 (m, 1 H) 7.17 (d, J = 7.78 Hz, 1 H) 7.19-7.25 (m, 1 H) 7.38 (s, 2 H) 7.42 (br. s., 1 H) 7.60 (br. s., 1 H) 7.91 (s, 1 H) |

Example 119

(R)-3-(3-(((S)-4-Ethyl-1,1-dioxido-4,5-dihydrobenzo[f][1,2]thiazepin-2(3H)-yl)methyl)-4-methylphenyl)-2,2-dimethyl-3-((1-methyl-1H-1,2,3-triazol-4-yl)methoxy)propanoic Acid (R)-Methyl 3-(3-(chloromethyl)-4-methylphenyl)-2,2-dimethyl-3-((1-methyl-1H-1,2,3-triazol-4-yl)methoxy)propanoate

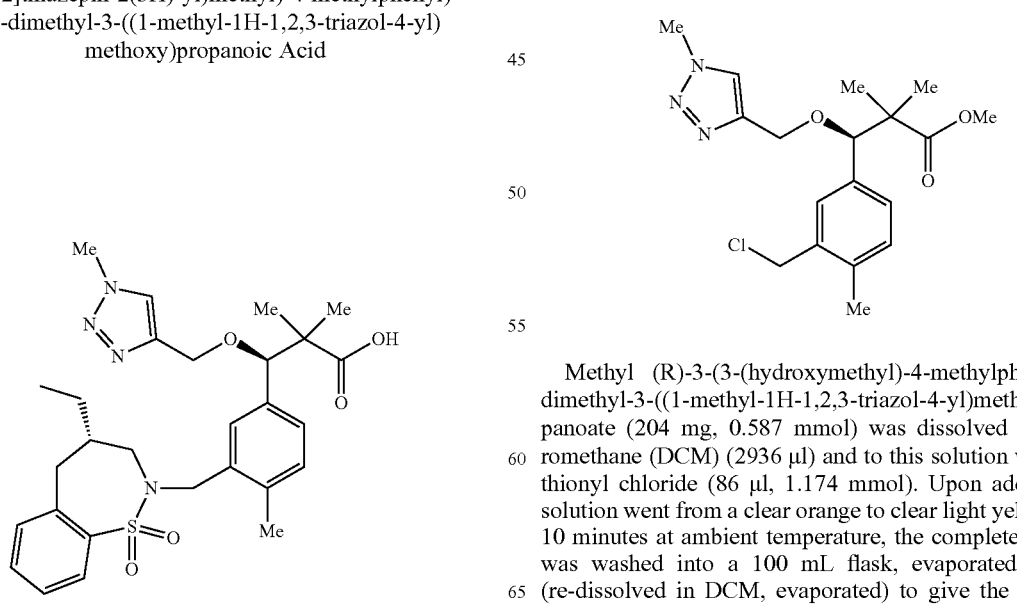

Methyl (R)-3-(3-(hydroxymethyl)-4-methylphenyl)-2,2-dimethyl-3-((1-methyl-1H-1,2,3-triazol-4-yl)methoxy)propanoate (204 mg, 0.587 mmol) was dissolved in dichloromethane (DCM) (2936 μl) and to this solution was added thionyl chloride (86 μl, 1.174 mmol). Upon addition, the solution went from a clear orange to clear light yellow. After 10 minutes at ambient temperature, the completed reaction was washed into a 100 mL flask, evaporated, then 3× (re-dissolved in DCM, evaporated) to give the title compound (198 mg, 0.541 mmol, 92% yield) as a resin solid. LC-MS m/z 366.2 (M+H)$^+$, 1.04 min (ret. time)

(R)-3-(3-(((S)-4-Ethyl-1,1-dioxido-4,5-dihydrobenzo[f][1,2]thiazepin-2(3H)-yl)methyl)-4-methylphenyl)-2,2-dimethyl-3-((1-methyl-1H-1,2,3-triazol-4-yl)methoxy)propanoic Acid

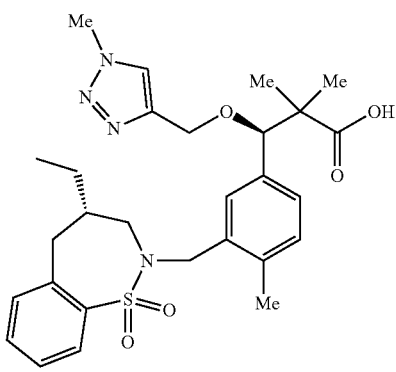 [SMILES: CC[C@H]1Cc2ccccc2S(=O)(=O)N(Cc2cc([C@@H](OCc3cn(C)nn3)C(C)(C)C(=O)O)ccc2C)C1]

Into a 2 mL uW tube was placed (S)-4-ethyl-2,3,4,5-tetrahydrobenzo[f][1,2]thiazepine 1,1-dioxide (18.47 mg, 0.082 mmol), methyl (R)-3-(3-(chloromethyl)-4-methylphenyl)-2,2-dimethyl-3-((1-methyl-1H-1,2,3-triazol-4-yl)methoxy)propanoate (25 mg, 0.068 mmol), and acetonitrile (550 µl), followed by sodium hydride (5.47 mg, 0.137 mmol, 60% wt.). The reaction was heated to 140° C. for a 1 minute hold time in a microwave reactor. To then hydrolyze the methyl ester, NaOH 1 M aqueous (683 µl, 0.683 mmol) was added and the reaction was again heated to 140° C. for a 1 minute hold time in a microwave reactor. The reaction was purified with preparative reversed phase HPLC under acidic (0.1% v/v TFA) conditions to give the title compound (24.8 mg, 67.1% yield). LC-MS m/z 541.3 (M+H)+, 1.17 min (ret. time). $^1$H NMR (400 MHz, DMSO-d$_6$) δ=7.89 (s, 1H), 7.87-7.82 (m, 1H), 7.63-7.57 (m, 1H), 7.55-7.50 (m, 1H), 7.50-7.44 (m, 1H), 7.26-7.22 (m, 1H), 7.22-7.12 (m, 2H), 4.68-4.63 (m, 1H), 4.38-4.19 (m, 3H), 4.01 (s, 3H), 3.78-3.53 (m, 2H), 3.38-3.21 (m, 1H), 2.94 (m, 2H), 2.27 (s, 3H), 1.92-1.79 (m, 1H), 1.26-1.11 (m, 2H), 0.99-0.91 (m, 3H), 0.90-0.80 (m, 6H)

The compounds in Table 23 were prepared by a method similar to the one described for the preparation of (R)-3-(3-(((S)-4-Ethyl-1,1-dioxido-4,5-dihydrobenzo[f][1,2]thiazepin-2(3H)-yl)methyl)-4-methylphenyl)-2,2-dimethyl-3-((1-methyl-1H-1,2,3-triazol-4-yl)methoxy)propanoic acid. As is appreciated by those skilled in the art, these analogous examples may involve variations in general reaction conditions.

TABLE 23

| Ex # | Structure | Name | LCMS [M +1] | Retention Time (min) |
|---|---|---|---|---|
| Ex 120 | 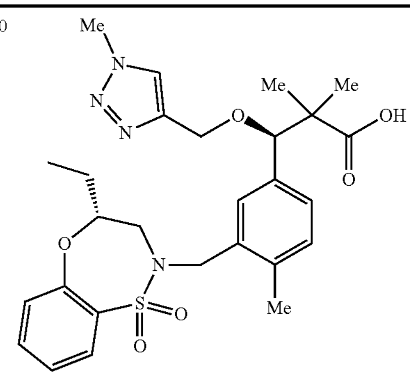 | (R)-3-(3-(((R)-4-Ethyl-1,1-dioxido-3,4-dihydro-2H-benzo[b][1,4,5]oxathiazepin-2-yl)methyl)-4-methylphenyl)-2,2-dimethyl-3-((1-methyl-1H-1,2,3-triazol-4-yl)methoxy)propanoic acid | 543.3 | 1.09 |
| Ex 121 | 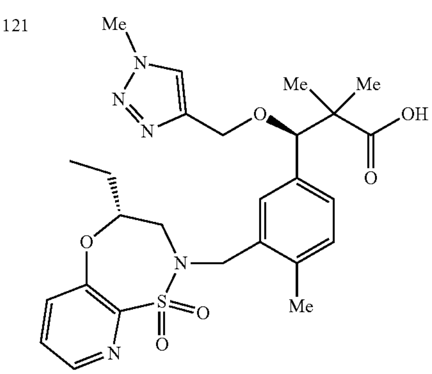 | (R)-3-(3-(((R)-4-Ethyl-1,1-dioxido-3,4-dihydro-2H-pyrido[3,2-b][1,4,5]oxathiazepin-2-yl)methyl)-4-methylphenyl)-2,2-dimethyl-3-((1-methyl-1H-1,2,3-triazol-4-yl)methoxy)propanoic acid | 544.3 | 0.93 |

What is claimed is:

1. A compound which is (R)-3-(3-(((R)-2-Ethyl-2,3-dihydropyrido[2,3-f][1,4]oxazepin-4(5H)-yl)methyl)-4-methylphenyl)-2,2-dimethyl-3-((1-methyl-1H-1,2,3-triazol-4-yl)methoxy)propanoic acid, or a pharmaceutically acceptable salt thereof.

2. A pharmaceutical composition comprising a compound of claim 1 and a pharmaceutically acceptable excipient.

3. A compound which is (R)-3-((1-Ethyl-1H-1,2,3-triazol-4-yl)methoxy)-3-(3-(((R)-2-ethyl-2,3-dihydropyrido[2,3-f][1,4]oxazepin-4(5H)-yl)methyl)-4-methylphenyl)-2,2-dimethylpropanoic acid, or a pharmaceutically acceptable salt thereof.

4. A pharmaceutical composition comprising a compound of claim 3 and a pharmaceutically acceptable excipient.

* * * * *